(12) United States Patent
Del'Guidice et al.

(10) Patent No.: US 12,286,632 B2
(45) Date of Patent: *Apr. 29, 2025

(54) RATIONALLY-DESIGNED SYNTHETIC PEPTIDE SHUTTLE AGENTS FOR DELIVERING POLYPEPTIDE CARGOS FROM AN EXTRACELLULAR SPACE TO THE CYTOSOL AND/OR NUCLEUS OF A TARGET EUKARYOTIC CELL, USES THEREOF, METHODS AND KITS RELATING TO SAME

(71) Applicant: Feldan Bio Inc., Québec (CA)

(72) Inventors: Thomas Del'Guidice, Québec (CA); Jean-Pascal Lepetit-Stoffaes, Québec (CA); David Guay, Québec (CA)

(73) Assignee: Feldan Bio Inc., Québec (CA)

(*) Notice: Subject to any disclaimer, the term of this patent is extended or adjusted under 35 U.S.C. 154(b) by 191 days.

This patent is subject to a terminal disclaimer.

(21) Appl. No.: 18/062,234

(22) Filed: Dec. 6, 2022

(65) Prior Publication Data

US 2023/0348537 A1    Nov. 2, 2023

Related U.S. Application Data

(63) Continuation of application No. 16/341,681, filed as application No. PCT/CA2017/051205 on Oct. 11, 2017, now Pat. No. 11,629,170, which is a continuation of application No. 15/666,139, filed on Aug. 1, 2017, now Pat. No. 9,982,267.

(60) Provisional application No. 62/535,015, filed on Jul. 20, 2017, provisional application No. 62/407,232, filed on Oct. 12, 2016.

(51) Int. Cl.
| | |
|---|---|
| C07K 7/08 | (2006.01) |
| A61K 39/395 | (2006.01) |
| C07K 14/00 | (2006.01) |
| C07K 14/47 | (2006.01) |
| C07K 16/00 | (2006.01) |
| C07K 16/18 | (2006.01) |
| C07K 16/46 | (2006.01) |
| C07K 17/06 | (2006.01) |
| C12N 9/22 | (2006.01) |
| C12N 15/11 | (2006.01) |
| C12N 15/62 | (2006.01) |
| C12N 15/87 | (2006.01) |
| C12N 15/90 | (2006.01) |
| C12Q 1/68 | (2018.01) |
| A61K 38/00 | (2006.01) |

(52) U.S. Cl.
CPC ............ *C12N 15/62* (2013.01); *A61K 39/395* (2013.01); *C07K 7/08* (2013.01); *C07K 14/00* (2013.01); *C07K 14/4705* (2013.01); *C07K 16/00* (2013.01); *C07K 16/18* (2013.01); *C07K 16/46* (2013.01); *C07K 17/06* (2013.01); *C12N 9/22* (2013.01); *C12N 15/11* (2013.01); *C12N 15/90* (2013.01); *A61K 38/00* (2013.01); *C07K 2319/01* (2013.01); *C07K 2319/02* (2013.01); *C07K 2319/03* (2013.01); *C07K 2319/09* (2013.01); *C07K 2319/10* (2013.01); *C07K 2319/70* (2013.01); *C12N 2310/20* (2017.05)

(58) Field of Classification Search
CPC ...... C07K 7/08; C07K 14/00; C07K 14/4705; C07K 16/00; C07K 16/18; C07K 16/46; C07K 17/06
See application file for complete search history.

(56) References Cited

U.S. PATENT DOCUMENTS

| | | |
|---|---|---|
| 7,084,248 B2 | 8/2006 | Summerton |
| 7,579,318 B2 | 8/2009 | Divita et al. |
| 8,242,081 B2 | 8/2012 | Divita et al. |
| 9,738,687 B2 | 8/2017 | Guay et al. |

(Continued)

FOREIGN PATENT DOCUMENTS

| | | |
|---|---|---|
| CA | 3040645 A1 | 10/2020 |
| WO | WO-2015038662 A1 | 3/2015 |

(Continued)

OTHER PUBLICATIONS

Kawczyński, M.T., et al. (2013 Ph.D. Interdiscip. J.: pp. 31-36) (Year: 2013).*

(Continued)

*Primary Examiner* — Marsha Tsay
(74) *Attorney, Agent, or Firm* — WILSON SONSINI GOODRICH & ROSATI

(57) ABSTRACT

The present description relates to methods for delivering polypeptide cargos from an extracellular space to the cytosol and/or nucleus of a target eukaryotic cell. The methods involve contacting the cell with the polypeptide cargo in the presence of a peptide shuttle agent at a concentration sufficient to increase the polypeptide cargo's transduction efficiency. Also described here are parameters that may be used in the rational design of such synthetic peptide shuttle agents, peptide shuttle agents that satisfy one or more of these design parameters, as well as methods and compositions relating to the use of the synthetic peptide shuttle agents for delivery of a variety of polypeptide cargos (such as transcription factors, antibodies, CRISPR-associated nucleases and functional genome editing complexes) from an extracellular space to the cytosol and/or nucleus of target eukaryotic cells. Applications and targets for genome-editing NK cells for improved immunotherapy are also described.

20 Claims, 58 Drawing Sheets

Specification includes a Sequence Listing.

(56) References Cited

U.S. PATENT DOCUMENTS

| | | | |
|---|---|---|---|
| 9,982,267 | B2 | 5/2018 | Del'Guidice et al. |
| 10,633,421 | B2 | 4/2020 | Guay et al. |
| 11,629,170 | B2 | 4/2023 | Del'Guidice et al. |
| 12,060,387 | B2 | 8/2024 | Guay et al. |
| 2003/0104622 | A1 | 6/2003 | Robbins et al. |
| 2007/0054401 | A1 | 3/2007 | Prochiantz et al. |
| 2015/0071903 | A1 | 3/2015 | Liu et al. |
| 2022/0204561 | A1 | 6/2022 | Guay et al. |
| 2023/0383291 | A1 | 11/2023 | Lepetit-Stoffaes et al. |
| 2023/0399661 | A1 | 12/2023 | Guay et al. |
| 2024/0197896 | A1 | 6/2024 | Soultan et al. |

FOREIGN PATENT DOCUMENTS

| | | | |
|---|---|---|---|
| WO | WO-2015089462 | A1 | 6/2015 |
| WO | WO-2016052442 | A1 | 4/2016 |
| WO | WO-2016161516 | A1 | 10/2016 |
| WO | WO-2017049407 | A1 | 3/2017 |
| WO | WO-2017175072 | A1 | 10/2017 |
| WO | WO-2018053632 | A1 | 3/2018 |
| WO | WO-2018068135 | A1 | 4/2018 |
| WO | WO-2020016242 | A1 | 1/2020 |
| WO | WO-2020210916 | A1 | 10/2020 |
| WO | WO-2022077121 | A1 | 4/2022 |
| WO | WO-2022082315 | A1 | 4/2022 |
| WO | WO-2022204806 | A1 | 10/2022 |

OTHER PUBLICATIONS

Aguila et al.: SALL4 is a robust stimulator for the expansion of hematopoietic stem cells. Blood 118(3):576-585 (2011).

Ain et al.: Effects of protein transduction domain (PTD) selection and position for improved intracellular delivery of PTD-Hsp27 fusion protein formulations. Arch. Pharm. Res. 39:1266-1274 (2016).

Akinci et al.: Reprogramming of pancreatic exocrine cells towards a beta (beta) cell character using Pdx1, Ngn3 and MafA. Biochem J. 442(3):539-550 (2012).

Akishiba et al., Cytosolic antibody delivery by lipid-sensitive endosomolytic peptide. Nat Chem. Aug. 2017;9(8):751-761 (2017). doi: 10.1038/nchem.2779. Epub May 22, 2017. PMID: 28754944.

Akishiba et al., Inducible Membrane Permeabilization by Attenuated Lytic Peptides: A New Concept for Accessing Cell Interiors through Ruffled Membranes. Mol Pharm. 16(6):2540-2548 (2019).

Alford et al.: Toxicity of organic fluorophores used in molecular imaging: literature review. Mol Imaging. 8(6):341-354 (2009).

Amand, Helene L. et al. Functionalization with C-terminal cysteine enhances transfection efficiency of cell-penetrating peptides through dimer formation. Biochemical and Biophysical Research Communications 418(3):469-474 (2012).

Andreu, David. et al. Shortened cecropin A-melittin hybrids Significant size reduction retains potent antibiotic activity. FEBS Letters 296(2):190-194 (1992).

Aoukaty et al.: Role for glycogen synthase kinase-3 in NK cell cytotoxicity and X-linked lymphoproliferative disease. J Immunol 174:4551-4558 (2005).

Barrangou et al.: CRISPR-Cas Systems: Prokaryotes Upgrade to Adaptive Immunity. Mod. Cell 54(2):234-244 (2014).

Bejarano et al.: Motif trap:A rapid method to clone motifs that can target proteins to defined subcellular localisations. J Cell Sci. 112(Pt 23):4207-4211 (1999).

Bikard, David. et al. Programmable repression and activation of bacterial gene expression using an engineered CRISPR-Cas system. Nucleic Acids Res 41(15):7429-7437 (2013).

Boman, H G. et al. Antibacterial and antimalarial properties of peptides that are cecropin-melittin hybrids. FEBS Letters 259(1):103-106 (1989).

Braud et al.: HLA-E binds to natural killer cell receptors CD94/NKG2A, B and C. Nature 391:795-799 (1998).

Brock et al.: Efficient cell delivery mediated by lipid-specific endosomal escape of supercharged branched peptides; Traffic; 19:421-435 (2018).

Buganim et al.: The Developmental Potential of iPSCs Is Greatly Influenced by Reprogramming Factor Selection. Cell stem cell. 15:295-309 (2014).

Burstein, David. et al. New CRISPR-Cas systems from Uncultivated Microbes. Nature 542(7640):237-241 (2017).

Cardarelli et al.: Quantitative Analysis of Tat Peptide Binding to Import Carriers Reveals Unconventional Nuclear Transport Properties. The Journal of Biological Chemistry. 286(14):12292-12299 (2011).

Chan et al.: Enhancement of MSH receptor- and GAL4-mediated gene transfer by switching the nuclear import pathway. Gene Ther 8(2):166-171 (2001).

Chan et al.: Enhancement of polylysine-mediated transferrinfection by nuclear localization sequences: polylysine does not function as a nuclear localization sequence. Hum Gene Ther. 10(10):1695-1702 (1999).

Chance, Deborah L, and Thomas P. Mawhinney. Observations of, and Insights into, Cystic Fibrosis Mucus Heterogeneity in the Pre-Modulator Era: Sputum Characteristics, DNA and Glycoprotein Content, and Solubilization Time. Journal of Respiration 1(1):8-29 (2021).

Chang et al., CD13 (aminopeptidase N) can associate with tumor-associated antigen L6 and enhance the motility of human lung cancer cells. Int J Cancer. 116(2):243-252 (2005).

Chang et al.: Cellular Internalization of Fluorescent Proteins via Arginine-rich Intracellular Delivery Peptide in Plant Cells; Plant Cell Physiol.; 46(3):482-488 (2005).

Cong, Le. et al. Multiplex Genome Engineering using CRISPR/Cas systems. Science 339(6121): pp. 819-823 (2013).

Cooper et al.: The biology of human natural killer-cell subsets. Trends Immunol 22:633-640 (Abstract) (2001).

Cornut et al., The amphipathic alpha-helix concept. Application to the de novo design of ideally amphipathic Leu, Lys peptides with hemolytic activity higher than that of melittin. FEBS Lett. 349(1):29-33 (1994).

Co-pending U.S. Appl. No. 18/553,178, inventors Soultan; Al-Halifa et al., filed Sep. 28, 2023.

Cox, David Benjamin Turitz. et al. Therapeutic Genome Editing: Prospects and Challenges. Nature Medicine 21(2):121-131 (2015).

Crombez et al.: A New Potent Secondary Amphipathic Cell-penetrating Peptide for siRNA Delivery Into Mammalian Cells. Molecular Therapy. 17(1): 95-103 (2009).

De Kruijf et al.: HLA-E and HLA-G expression in classical HLA class I-negative tumors is of prognostic value for clinical outcome of early breast cancer patients. J Immunol 185:7452-7459 (2010).

Delconte et al.:, CIS is a potent checkpoint in NK cell-mediated tumor immunity. Nat Immunol. 17(7):816-824 (2016).

Del'Guidice et al.: Intrabody Delivery—The Feldan Shuttle Technology: A Peptide-Based Method to Deliver Antibodies. Drug Development & Delivery. 18(1):28-32 (2018).

Del'Guidice, Thomas. et al. Membrane Permeabilizing Amphiphilic Peptide Delivers Recombinant Transcription Factor and CRISPR-Cas9/Cpf1 ribonucleoproteins in Hard-to-modify Cells. PLOS One 13(4):e0195558, 1-26 (2018).

Denman et al.: Membrane-bound IL-21 promotes sustained ex vivo proliferation of human natural killer cells. PLoS One 7:e30264 (2012).

Deshayes et al.: Structural polymorphism of non-covalent peptide-based delivery systems: Highway to cellular uptake. Biochimica et Biophysica Acta 1798:2304-2314 (2010).

Dolfini et al.: The short isoform of NF-YA belongs to the embryonic stem cell transcription factor circuitry. Stem Cells. 30(11):2450-2459 (2012).

Drin, Guillaume. et al. Studies on the internalization mechanism of cationic cell-penetrating peptides. Journal of Biological Chemistry 278(33):31192-31201 (2003).

Ebina et al.: Transcription factor-mediated reprogramming toward hematopoietic stem cells. EMBO Journal. 34(6):694-709 (2015).

Eisenberg, David. et al. The helical hydrophobic moment: a measure of the amphiphilicity of a helix. Nature 299(5881):371-374 (1982). Abstract Only.

(56) References Cited

OTHER PUBLICATIONS

El-Andaloussi, Samir. et al. A novel cell-penetrating peptide, M918, for efficient delivery of proteins and peptide nucleic acids. Molecular Therapy 15(10):1820-1826 (2007).
Elmquist, Anna. et al. VE-cadherin-derived cell-penetrating peptide, pVEC, with carrier functions. Experimental Cell Research 269(2):237-244 (2001).
El-Sayed, Ayman. et al. Delivery of macromolecules using arginine-rich cell-penetrating peptides: ways to overcome endosomal entrapment. The AAPS Journal 11(1):13-22 (2009).
Erazo-Oliveras, Alfredo. et al. Protein delivery into live cells by incubation with an endosomolytic agent. Nature Methods 11(8):861-867 (2014).
Erazo-Oliveras, et al.; "Improving the Endosomal Escape of Cell-Penetrating Peptides and Their Cargos: Strategies and Challenges"; Pharmaceuticals; vol. 5, pp. 1177-1209 (2012).
Fanara et al.: Quantitative analysis of nuclear localization signal (NLS)-importin alpha interaction through fluorescence depolarization. Evidence for auto-inhibitory regulation of NLS binding. J Biol Chem. 275(28):21218-21223 (2000).
Farkhani, Samad Mussa. et al. Cell penetrating peptides: efficient vectors for delivery of nanoparticles, nanocarriers, therapeutic and diagnostic molecules. Peptides 57:78-94 (2014).
Fasoli et al.: Mechanistic insight into CM18-Tat11 peptide membrane-perturbing action by whole-cell patch-clamp recording. Molecules. 19(7):9228-9239 (2014).
Fawell, Stephen. et al. Tat-mediated delivery of heterologous proteins into cells. Proceedings of the National Academy of Sciences 91(2):664-668 (1994).
Firas et al.: Transcription factor-mediated reprogramming: epigenetics and therapeutic potential. Immunology and Cell Biology. 93(3):284-289 (2015).
Fominaya, J. et al. A chimeric fusion protein containing transforming growth factor-α mediates gene transfer via binding to the EGF receptor. Gene Therapy 5(4):521-530 (1998).
Fominaya, Jesus, and Winfried Wels. Target Cell-specific DNA Transfer Mediated by a Chimeric Multidomain Protein. Novel non-viral gene delivery system. Journal of Biological Chemistry 271(18):10560-10568 (1996).
Fonoudi et al.: ISL1 protein transduction promotes cardiomyocyte differentiation from human embryonic stem cells. PLoS One 8(1):e55577 (2013).
Ford et al.: Protein transduction: an alternative to genetic intervention? Gene Ther. 8(1):1-4 (2001).
Forman, Henry Jay. et al. Glutathione: Overview Of Its Protective Roles, Measurement, And Biosynthesis. Molecular Aspects of Medicine 30(1-2):1-12 (2009). Published online Aug. 30, 2008.
Fujita et al.: Applications of Engineered DNA-Binding Molecules Such as TAL Proteins and the CRISPR/Cas System in Biology Research. International Journal of Molecular Sciences. 16(10):23143-23164 (2015).
Gao, Feng. et al. DNA-guided genome editing using the Natronobacterium gregoryi Argonaute. Nature Biotechnology 34(7):768-773 (2016).
Gentilucci, Luca. et al. Chemical Modifications Designed to Improve Peptide Stability: Incorporation of Non-natural Amino Acids, Pseudopeptide Bonds, and Cyclization. Current Pharmaceutical Design 16(28):3185-3203 (2010).
Giguère et al.: Machine learning assisted design of highly active peptides for drug discovery. PLoS Comput Biol. 11(4):e1004074 (2015).
Gilbert et al., CRISPR-Mediated modular RNA-guided regulation of transcription in Eukaryotes. Cell 154(2): 442-451 (2013).
Gilmore et al.: v-rel oncoproteins in the nucleus and in the cytoplasm transform chicken spleen cells. J Virol 62(3):703-714 (1988).
Giustarini, Daniela. et al. Assessment Of Glutathione/Glutathione Disulphide Ratio And S-Glutathionylated Proteins In Human Blood, Solid Tissues, And Cultured Cells. Free Radical Biology and Medicine 112:360-375 (2017).
Glover, Dominic J. et al. Multifunctional protein nanocarriers for targeted nuclear gene delivery in nondividing cells. The FASEB Journal 23(9):2996-3006 (2009).
Gomez-Cabrero et al.: Use of transduction proteins to target trabecular meshwork cells: outflow modulation by profilin I. Molecular Vision. 11:1071-1082 (2005).
Gordon et al.: The transcription factors T-bet and Eomes control key checkpoints of natural killer cell maturation. Immunity. 36(1):55-67 (2012).
Gottschalk, Sparrow. et al. A novel DNA-peptide complex for efficient gene transfer and expression in mammalian cells. Gene Therapy 3(5):448-457 (1996).
Gould et al.: A conserved tripeptide sorts proteins to peroxisomes. J Cell Biol 108(5):1657-1664 (1989).
Green, Maurice, and Paul M. Loewenstein. Autonomous functional domains of chemically synthesized human immunodeficiency virus tat trans-activator protein. Cell 55(6):1179-1188 (1988).
Grimes et al.: Endocytosis of activated TrkA: evidence that nerve growth factor induces formation of signaling endosomes. J Neurosci 16(24):7950-7964 (1996).
Guo et al., High LIFr expression stimulates melanoma cell migration and is associated with unfavorable prognosis in melanoma. Oncotarget. 6(28):25484-25498(2015).
Guo, Zhang-Yan. et al. Predictive value of HLA-G and HLA-E in the Prognosis of Colorectal Cancer Patients. Cellular Immunology 293:10-16 (2016). Published Online Oct. 28, 2014.
Hallbrink, Mattias. et al. Cargo delivery kinetics of cell-penetrating peptides. Biochimica et Biophysica Acta 1515(2):101-109 (2001).
Herce, Henry D, and Angel E. Garcia. Molecular dynamics simulations suggest a mechanism for translocation of the HIV-1 TAT peptide across lipid membranes. Proceedings of the National Academy of Sciences 104(52):20805-20810 (2007).
Ho, Alan. et al. Synthetic protein transduction domains: enhanced transduction potential in vitro and in vivo. Cancer Research 61(2):474-477 (2001).
Horng et al.: NKG2D signaling is coupled to the interleukin 15 receptor signaling pathway. Nat Immunol 8:1345-1352 (2007).
Hou et al.: Transdermal delivery of proteins mediated by non-covalently associated arginine-rich intracellular delivery peptides; Experimental Dermatology; 16:999-1006 (2007).
Hsu et al. Development and applications of CRISPR-Cas9 for genome engineering. Cell 157(6):1262-1278 (2014).
Hurt et al.: The first twelve amino acids (less than half of the pre-sequence) of an imported mitochondrial protein can direct mouse cytosolic dihydrofolate reductase into the yeast mitochondrial matrix. Embo J. 4(8):2061-2068 (1985).
Ichii, Hirohito. et al. Bcl6 acts as an Amplifier for the Generation and Proliferative Capacity of Central Memory CD8+ T cells. Journal of Immunology 173(2):883-891 (2004).
IL Patent Application No. IL265920 Office Action dated Jul. 25, 2022.
Ilfeld, Brian M, and Tony L. Yaksh. The end of postoperative pain-a fast-approaching possibility? and, if so, will we be ready?. Regional Anesthesia & Pain Medicine 34(2):85-87 (2009).
Irie et al.: Molecular cloning and characterization of Amida, a novel protein which interacts with a neuron-specific immediate early gene product arc, contains novel nuclear localization signals, and causes cell death in cultured cells. J Biol Chem 275(4):2647-2653 (2000).
Ishigami, Sumiya. et al. Human Leukocyte antigen (HLA)-E and HLA-F Expression in Gastric Cancer. Anticancer Research 35(4):2279-2285 (2015).
Iwasaki et al.: Cellular uptake and in vivo distribution of polyhistidine peptides. Journal of Controlled Release. 210:115-124 (2015).
Jinek et al.: Bacterial Immunity A Programmable Dual-RNA-Guided DNA Endonuclease in Adaptive. Science. 337(6096):816-821 (2012).
Järver et al., Peptide nanoparticle delivery of charge-neutral splice-switching morpholino oligonucleotides. Nucleic Acid Ther. 25(2):65-77 (2015).
Kabouridis: Biological applications of protein transduction technology. Trends in Biotechnology. 21(11):498-503 (2003).

(56) References Cited

OTHER PUBLICATIONS

Kadkhodayan et al.: Generation of GFP Native Protein for Detection of Its Intracellular Uptake by Cell-Penetrating Peptides. Folia Biologica (Praha). 62, 103-109 (2016).
Kakudo, Tomoyuki. et al. Transferrin-modified liposomes equipped with a pH-sensitive fusogenic peptide: an artificial viral-like delivery system. Biochemistry 43(19):5618-5628 (2004).
Karniely et al.: Single translation—dual destination: mechanisms of dual protein targeting in eukaryotes. EMBO Rep 6(5):420-425 (2005).
Kato et al.: Max: functional domains and interaction with c-Myc. Genes Dev. 6(1):81-92 (1992).
Keller et al.: Relationships between Cargo, Cell Penetrating Peptides and Cell Type for Uptake of Non-Covalent Complexes into Live Cells. Pharmaceuticals. 6: 184-203 (2013) doi:10.3390/ph6020184.
Keller et al.: Transduction of Proteins into Leishmania Tarentolae by Formation of Non-Covalent Complexes with Cell-Penetrating Peptides. Journal of Cellular Biochemistry. 115:243-252 (2014).
Kichler, Antoine. et al. Cationic amphipathic histidine-rich peptides for gene delivery. Biochimica et Biophysica Acta 1758(3):301-307 (2006).
Kichler, Antoine. et al. Histidine-rich amphipathic peptide antibiotics promote efficient delivery of DNA into mammalian cells. Proceedings of the National Academy of Sciences 100(4):1564-1568 (2003).
Kirwan et al.: Killer cell Ig-like receptor-dependent signaling by Ig-like transcript 2 (ILT2/CD85j/LILRB1/LIR-1). J Immunol 175:5006-5015 (2005).
Kleinschmidt et al.: Identification of domains involved in nuclear uptake and histone binding of protein N1 of Xenopus laevis. EMBO J, 7(6):1605-1614 (1988).
Kohler et al.: Adenoviral E1A protein nuclear import is preferentially mediated by importin alpha3 in vitro. Virology 289(2):186-191 (2001).
Krishnamurthy, Anuradha. et al. Bispecific Antibodies for Cancer Therapy: a review. Pharmacology & therapeutics 185:122-134 (2018). Published Online Dec. 18, 2017.
Krishnamurthy, Sateesh. et al. Engineered Amphiphilic Peptides Enable Delivery Of Proteins And CRISPR-Associated Nucleases To Airway Epithelia. Nature Communications 10(1):4906, 1-12 (2019).
Kumar, Sumit. et al., PEGylation and Cell-Penetrating Peptides: Glimpse into the Past and Prospects in the Future. Current Topics in Medicinal Chemistry 20(5):337-348 (2020).
Kurzawa et al.: PEP and CADY-mediated delivery of fluorescent peptides and proteins into living cells. Biochimica et Biophysica Acta. 1798: 2274-2285 (2010).
Kwon, Ester J. et al. A truncated HGP peptide sequence that retains endosomolytic activity and improves gene delivery efficiencies. Molecular Pharmaceutics 7(4):1260-1265 (2010).
Kwon et al., Antitumor effect of a transducible fusogenic peptide releasing multiple proapoptotic peptides by caspase-3. Mol Cancer Ther. 7(6):1514-1522 (2008).
Lamiable, Alexis. et al. PEP-FOLD3: faster de novo structure prediction for linear peptides in solution and in complex. Nucleic Acids Research 44(W1):W449-W454 (2016).
Lanford et al.: Induction of nuclear transport with a synthetic peptide homologous to the SV40 T antigen transport signal. Cell 46(4):575-582 (1986).
Lee et al.: Activatable Cell Penetrating Peptide—Peptide Nucleic Acid Conjugate via Reduction of Azobenzene PEG Chains. J. Am. Chem. Soc. 136:12868-12871 (2014).
Lee, et al.; "Delivery of macromolecules into live cells by simple co-incubation with a peptide"; ChemBioChem; vol. 11, No. 3, pp. 325-330 (Feb. 15, 2010).
Lee, Ni. et al. HLA-E is a Major ligand for the Natural Killer Inhibitory Receptor CD94/NKG2A. Proceedings of the National Academy of Sciences of the United States of America 95(9):5199-5204 (1998).
Levy et al.: Human leukocyte antigen-E protein is overexpressed in primary human colorectal cancer. Int J Oncol 32:633-641 (2008).
Li et al.: Delivery of intracellular-acting biologics in pro-apoptotic therapies. Current Pharmaceutical Design. 17(3):293-319 (2011).
Li, Weijun. et al. GALA: a designed synthetic pH-responsive amphipathic peptide with applications in drug and gene delivery. Advanced Drug Delivery Reviews 56(7):967-985 (2004).
Lin et al.: B lymphocyte-induced maturation protein 1 (BLIMP-1) attenuates autoimmune diabetes in NOD mice by suppressing Th1 and Th17 cells. Diabetologia 56(1):136-146 (2013).
Lin et al.: HLA-G expression in human ovarian carcinoma counteracts NK cell function. Annals of Oncology. 18:1804-1809 (2007).
Liou, et al.; "Protein transduction in human cells is enhanced by cell-penetrating peptides fused with an endosomolytic HA2 sequence"; Peptides; vol. 37, pp. 273-284 (2012).
Liu et al, Cell-Penetrating Peptide-Mediated Delivery of TALEN Proteins via Bioconjugation for Genome Engineering, PLOS One, 2014, vol. 9(1), pp. 1-7.
Liu et al.: E3 ubiquitin ligase Cbl-b in innate and adaptive immunity. Cell Cycle 13:1875-1884 (2014).
Liu et al.: Intracellular delivery of quantum dots mediated by a histidine- and arginine-rich HR9 cell-penetrating peptide through the direct membrane translocation mechanism; Biomaterials; 32:3520-3537 (2011).
Liu et al.: Systemic genetic transfer of p21WAF-1 and GM-CSF utilizing of a novel oligopeptide-based EGF receptor targeting polyplex. Cancer Gene Ther. 10(7):529-539 (2003).
Lo et al.: An endosomolytic Tat peptide produced by incorporation of histidine and cysteine residues as a nonviral vector for DNA transfection. ScienceDirect, Biomaterials. 29:2408-2414 (2008).
Loeser et al.: Spontaneous tumor rejection by cbl-b-deficient CD8+ T cells. J Exp Med 204:879-891 (2007).
London, Erwin. Diphtheria toxin: membrane interaction and membrane translocation. Biochimica et Biophysica Acta 1113(1):25-51 (1992).
Lord-Dufour et al.: Evidence for transcriptional regulation of the glucose-6-phosphate transporter by HIF-1alpha: Targeting G6PT with mumbaistatin analogs in hypoxic mesenchymal stromal cells. Stem cells. 27:489-497 (2009).
Lorieau, Justin L. et al. The complete influenza hemagglutinin fusion domain adopts a tight helical hairpin arrangement at the lipid: water interface. Proceedings of the National Academy of Sciences 107(25):11341-11346 (2010).
Lu et al.: Recombinant HoxB4 fusion proteins enhance hematopoietic differentiation of human embryonic stem cells. Stem Cells Dev 16(4):547-559 (2007).
Luan, Liang. et al. Peptide amphiphiles with multifunctional fragments promoting cellular uptake and endosomal escape as efficient gene vectors. Journal of Materials Chemistry B 3(6):1068-1078 (2015). Published Online Dec. 17, 2014.
Lutz-Nicoladoni et al.: Modulation of Immune Cell Functions by the E3 Ligase Cbl-b. Front Oncol 5:58 (2015).
Mack et al.: Aminooxypentane-RANTES induces CCR5 internalization but inhibits recycling: a novel inhibitory mechanism of HIV infectivity. J Exp Med, 187(8):1215-1224 (1998).
Maeng et al.: Effects of single nucleotide polymorphisms on treatment outcomes and toxicity in patients treated with sunitinib. Anticancer Res 33(10):4619-4626 (2013).
Mahlum, Eric. et al. Engineering a noncarrier to a highly efficient carrier peptide for noncovalently delivering biologically active proteins into human cells. Analytical Biochemistry 365(2):215-221 (2007).
Makarova et al.: Unification of Cas protein families and a simple scenario for the origin and evolution of CRISPR-Cas systems. Biol Direct. 6:38 (2011).
Makarova, Kira S. et al. Evolution and Classification of the CRISPR-Cas Systems. Nature reviews. Microbiology 9(6):467-477 (2011).
Makkerh et al.: Comparative mutagenesis of nuclear localization signals reveals the importance of neutral and acidic amino acids. Curr Biol. Aug. 1, 1996;6(8):1025-1027. doi:10.1016/s0960-9822(02)00648-6.
Martinez-Fong et al.: Neurotensin-SPDP-poly-L-lysine conjugate: a nonviral vector for targeted gene delivery to neural cells. Brain Res Mol Brain Res. 69(2):249-262 (1999).

(56) References Cited

OTHER PUBLICATIONS

Matalon et al.: (2016). Dephosphorylation of the adaptor LAT and phospholipase C-gamma by SHP-1 inhibits natural killer cell cytotoxicity. Sci Signal 9:ra54 (2016).
Maurer et al.: Macrophage inflammatory protein-1. Int J Biochem Cell Biol. 36(10): 1882-1886 (2004).
McKay et al.: Secretin-mediated gene delivery, a specific targeting mechanism with potential for treatment of biliary and pancreatic disease in cystic fibrosis. Mol Ther 5(4): 447-454 (2002).
Midoux, Patrick. et al. Membrane permeabilization and efficient gene transfer by a peptide containing several histidines. Bioconjugate Chemistry 9(2):260-267 (1998).
Milenkovic et al.: Identification of the signal directing Tim9 and Tim10 into the intermembrane space of mitochondria. Mol Biol Cell 20(10):2530-2539 (2009).
Mitchell, Dennis J. et al. Polyarginine Enters Cells More Efficiently Than Other Polycationic Homopolymers. The Journal of Peptide Research 56(5):318-325 (2000).
Miyoshi et al.: [Structure and regulation of human thyroid-stimulating hormone (TSH) gene]. Nihon Rinsho 52(4) [Abstract] (1994).
Moede et al.: Identification of a nuclear localization signal, RRMKWKK, in the homeodomain transcription factor PDX-1. FEBS Lett 461(3):229-234 (1999).
Mol, A. R. et al. NetWheels: A Web Application to Create High Quality Peptide Helical Wheel and Net Projections. Posted Sep. 14, 2018.
Montrose, Kristopher. et al. Xentry, a new class of cell-penetrating peptide uniquely equipped for delivery of drugs. Scientific Reports 3(1):1661, 1-7 (2013).
Moreland et al.: Amino acid sequences that determine the nuclear localization of yeast histone 2B. Mol Cell Biol 7(11):4048-4057 (1987).
Morris et al., A non-covalent peptide-based carrier for in vivo delivery of DNA mimics. Nucleic Acids Res. 2007;35(7):e49, pp. 1-10 (2007).
Morris, M C. et al. Combination of a new generation of PNAs with a peptide-based carrier enables efficient targeting of cell cycle progression. Gene Therapy 11(9):757-764 (2004).
Morris, May C. et al. A peptide carrier for the delivery of biologically active proteins into mammalian cells. Nature Biotechnology 19(12):1173-1176 (2001).
Moulton HM: In vivo delivery of morpholino oligos by cell-penetrating peptides. Curr. Pharm. Des. 19(16):2963-9 (2013).
Mussbach et al.: Transduction of Peptides and Proteins Into Live Cells by Cell Penetrating Peptides. Journal of Cellular Biochemistry. 112: 3824-3833 (2011).
Nagahara, et al. Transduction of Full-length TAT Fusion Proteins Into Mammalian Cells: TAT-p27kip1 Induces Cell Migration. Nature Medicine 4(12):1449-1452 (1998).
Nakanishi et al.: Interaction of the Vp3 nuclear localization signal with the importin alpha 2/beta heterodimer directs nuclear entry of infecting simian virus 40. J Virol, 76(18):9368-9377 (2002).
Nitzki, Frauke et al., Patched Knockout Mouse Models of Basal Cell Carcinoma. Journal of Skin Cancer. 2012:907543 pp. 1-11 (2012).
Nomura et al., Improved cytosolic delivery of macromolecules through dimerization of attenuated lytic peptides. Bioorg Med Chem Lett. 30(17):127362, pp. 1-5 (2020).
O'Keefe, Donald O. Characterization of a full-length, active-site mutant of diphtheria toxin. Archives of Biochemistry and Biophysics 296(2):678-684 (1992).
Paolino et al.: The E3 ligase Cbl-b and TAM receptors regulate cancer metastasis via natural killer cells. Nature 507:508-512 (2014).
Parameswaran et al.: Repression of GSK3 restores NK cell cytotoxicity in AML patients. Nat Commun 7:11154 (2016).
Parente, Roberta A. et al. Mechanism of leakage of phospholipid vesicle contents induced by the peptide GALA. Biochemistry 29(37):8720-8728 (1990).
Patel et al.: Glycogen Synthase Kinase 3: A Kinase for All Pathways? Curr Top Dev Biol 123:277-302 (2017).
Paul et al.: Gene transfer using a novel fusion protein, GAL4/invasin.Hum Gene Ther,8(10):1253-1262 (1997).
PCT/CA2017/051205 International Search Report and Written Opinion dated Jan. 24, 2018.
PCT/CA2020/050517 International Preliminary Report on Patentability dated Oct. 28, 2021.
PCT/CA2020/050517 International Search Report and Written Opinion dated Jul. 17, 2020.
PCT/CA2021/051458 International Search Report and Written Opinion dated Jan. 25, 2022.
PCT/CA2021/051490 International Search Report and Written Opinion mailed on Jan. 24, 2022.
PCT/CA2022/050472 International Search Report and Written Opinion dated Jul. 4, 2022.
PCT/CA2022/050472 Invitation to Pay Additional Fees dated May 5, 2022.
PCT/IB2017/000512 International Search Report and Written Opinion dated Jul. 26, 2017.
Perez, F. et al. Antennapedia homeobox as a signal for the cellular internalization and nuclear addressing of a small exogenous peptide. Journal of Cell Science 102(Pt 4):717-722 (1992).
Pimenta et al.: Alpha1-antichymotrypsin and kallistatin hydrolysis by human cathepsin D.J Protein Chem, 19(5):411-418 (2000).
Poli et al.: CD56bright natural killer (NK) cells: an important NK cell subset. Immunology 126:458-465 (2009).
Premsirut et al., A Rapid and Scalable System for Studying Gene Function in Mice Using Conditional RNA Interference. Cell. 145:145-158 (2011).
Prieve et al.: Nuclear localization and formation of beta-catenin-lymphoid enhancer factor 1 complexes are not sufficient for activation of gene expression. Mol Cell Biol, 19(6):4503-4515 (1999).
Rajagopalan et al.: Recombinant fusion proteins TAT-Mu, Mu and Mu-Mu mediate efficient non-viral gene delivery. J Gene Med, 9(4):275-286 (2007).
Ramakrishna et al. Gene disruption by cell-penetrating peptide-mediated delivery of Cas9 protein and guide RNA. Genome Research 24:1020-1027 (2014).
Ramsey, Joshua D, and Nicholas H. Flynn. Cell-penetrating peptides transport therapeutics into cells. Pharmacology & Therapeutics 154:78-86 (2015).
Regalado: Who owns the biggest biotech discover of the century?. MIT Technology Review. 4 pages (2014).
Riddell et al.: Reprogramming committed murine blood cells to induced hematopoietic stem cells with defined factors. Cell, 157:549-564 (2014).
Salomone et al.: High-Yield nontoxic gene transfer through conjugation of the CM18-Tat11 chimeric peptide with nanosecond electric pulses. Molecular Pharmaceutics. 9 pages (2014) available at: http://pubs.acs.org.
Salomone et al.: In vitro efficient transfection by CM18-Tat11 hybrid peptide: a new tool for gene-delivery applications. PLoS One 8(7):e70108, 11 pages (2013).
Salomone, Fabrizio. et al. A novel chimeric cell-penetrating peptide with membrane-disruptive properties for efficient endosomal escape. Journal of Controlled Release 163(3):293-303 (2012).
Sampson et al.: Exploiting CRISPR/Cas systems for biotechnology. Bioessays. 36(1):34-38 (2014).
Sato et al.: Peptide-membrane interactions and mechanisms of membrane destruction by amphipathic α-helical antimicrobial peptides. Biochimica et Biophysica Acta 1758:1245-1256 (2006).
Schiffer, Marianne, and Allen B. Edmundson. Use of Helical Wheels to represent the Structures of Proteins and to Identify Segments with Helical Potential. Biophysical Journal 7(2):121-135 (1967).
Schneider et al.: A novel peptide, Plaeidgielty, for the targeting of alpha9beta1-integrins.FEBS Lett. 429(3):269-273 (1998).
Schreiber et al.: The human poly(ADP-ribose) polymerase nuclear localization signal is a bipartite element functionally separate from DNA binding and catalytic activity. EMBO J. 11(9):3263-3269 (1992).

(56) References Cited

OTHER PUBLICATIONS

Schuster, Martin J. et al. Multicomponent DNA carrier with a vesicular stomatitis virus G-peptide greatly enhances liver-targeted gene expression in mice. Bioconjugate Chemistry 10(6):1075-1083 (1999).
Scott et al.: Characterization and prediction of protein nucleolar localization sequences. Nucleic Acids Res, 38(21):7388-7399 (2010).
Shaw, Paul A. et al. Comparison of protein transduction domains in mediating cell delivery of a secreted CRE protein. Biochemistry 47(4):1157-1166 (2008).
Shawe-Taylor et al.: Kernel methods for pattern analysis. Cambridge University Press. 12 pages (2004).
Shen, Yimin. et al. Improved PEP-FOLD approach for peptide and miniprotein structure prediction. Journal of Chemical Theory and Computation 10(10):4745-4758 (2014).
Shoya et al.: Two proline-rich nuclear localization signals in the amino- and carboxyl-terminal regions of the Borna disease virus phosphoprotein. J .Virol, 72(12):9755-9762 (1998).
Simeoni et al.: Insight into the mechanism of the peptide-based gene delivery system MPG: implications for delivery of siRNA into mammalian cells. Nucleic Acids Research, 31(11): 27170-2724 (2003).
Somasekaram et al.: Intracellular localization of human cytidine deaminase. Identification of a functional nuclear localization signal. J Biol Chem. 274(40):28405-28412 (1999).
Stojanovski et al.: Mechanisms of protein sorting in mitochondria. Cold Spring Harbor Perspect Biol, 4(10):a011320, 18 pages (2012).
Sudbeck et al.: Two independent nuclear localization signals are present in the DNA-binding high-mobility group domains of SRY and SOX9. J Biol Chem. 272(44):27848-27852 (1997).
Summerton JE: Endo-Porter: A novel reagent for safe, effective delivery of substances into cells. Ann NY Acad Sci. 1058:62-75 (2005).
Sun et al.: PTD4-apoptin protein therapy inhibits tumor growth in vivo. Int J cancer. 124(12):2973-2981 (2009).
Sung et al.: Efficient myogenic differentiation of human adipose-derived stem cells by the transduction of engineered MyoD protein. Biochem Biophys Res Commun. 437(1):156-161 (2013).
Takahashi, Kazutoshi, and Shinya Yamanaka. Induction of Pluripotent Stem Cells From Mouse Embryonic and Adult Fibroblast Cultures by Defined Factors. Cell 126(4):663-676 (2006).
Takeda et al.: NUP98-HOXA9 induces long-term proliferation and blocks differentiation of primary human CD34+ hematopoietic cells. Cancer Res. 66(13):6628-6637 (2006).
Tan et al.: Increased levels of FoxA1 transcription factor in pluripotent P19 embryonal carcinoma cells stimulate neural differentiation. Stem Cells Dev. 19(9):1365-1374 (2010).
Tan, Ying-Xia. et al. Truncated peptides from melittin and its analog with high lytic activity at endosomal pH enhance branched polyethylenimine-mediated gene transfection. The Journal of Gene Medicine 14(4):241-250 (2012).
Tansi et al.: Internalization of near-infrared fluorescently labeled activatable cell-penetrating peptide and of proteins into human fibrosarcoma cell line HT-1080. Journal of Cellular Biochemistry. (2015) doi: 10.1002/jcb.25075.
Theriault, Olivier. et al. Differential modulation of Nav1. 7 and Nav1. 8 channels by antidepressant drugs. European Journal of Pharmacology 764:395-403 (2015).
Thevenet, Pierre. et al. PEP-FOLD: an updated de novo structure prediction server for both linear and disulfide bonded cyclic peptides. Nucleic Acids Research 40(W1):W288-W293 (2012).
Turecek, Peter L. et al. PEGylation of Biopharmaceuticals: A Review of Chemistry and Nonclinical Safety Information of Approved Drugs. Journal of Pharmaceutical Sciences 105(2):460-475 (2016).
Uherek, Christoph. et al. A modular DNA carrier protein based on the structure of diphtheria toxin mediates target cell-specific gene delivery. Journal of Biological Chemistry 273(15):8835-8841 (1998).
Ul Ain et al., Effects of protein transduction domain (PTD) selection and position for improved intracellular delivery of PTD-Hsp27 fusion protein formulations. Arch Pharm Res. 39(9):1266-1274 (2016).
U.S. Appl. No. 15/094,365 Applicant Initiated Interview Summary dated Jan. 11, 2017.
U.S. Appl. No. 15/094,365 Office Action dated Dec. 15, 2016.
U.S. Appl. No. 15/094,365 Restriction Requirement dated Aug. 2, 2016.
U.S. Appl. No. 15/486,155 Final Office Action dated Feb. 4, 2019.
U.S. Appl. No. 15/486,155 Final Office Action dated Sep. 25, 2019.
U.S. Appl. No. 15/486,155 Office Action dated Apr. 2, 2018.
U.S. Appl. No. 15/486,155 Office Action dated May 24, 2019.
U.S. Appl. No. 15/666,139 First Action Interview Office Action dated Feb. 2, 2018.
U.S. Appl. No. 16/341,681 Office Action dated Dec. 3, 2021.
U.S. Appl. No. 16/341,681 Final Office Action dated Jun. 15, 2022.
U.S. Appl. No. 16/341,681 Restriction Requirement dated Jun. 3, 2021.
U.S. Appl. No. 16/797,867 Office Action dated Nov. 3, 2023.
U.S. Appl. No. 17/604,328 Office Action dated Sep. 27, 2024.
Varkouhi, Amir K. et al. Endosomal escape pathways for delivery of Biologicals. Journal of Controlled Release 151(3):220-228 (2011). Published Online Nov. 13, 2010.
Veach, Ruth Ann. et al. Receptor/transporter-independent targeting of functional peptides across the plasma membrane. Journal of Biological Chemistry 279(12):11425-11431 (2004). Published Online Dec. 29, 2003.
Veronese, Francesco M, and Anna Mero. The Impact Of PEGylation On Biological Therapies. BioDrugs 22(5):315-329 (2008).
Vives, Eric. et al. A Truncated HIV-1 Tat Protein Basic Domain Rapidly Translocates through the Plasma Membrane and Accumulates in the Cell Nucleus. Journal of Biological Chemistry 272(25):16010-16017 (1997).
Wagstaff et al.: Histone-mediated transduction as an efficient means for gene delivery. Mol Ther. 15(4):721-731 (2007).
Wan: An Overall Comparison of Small Molecules and Large Biologics in ADME Testing. ADMET & DMPK 4(1):1-22; doi: 10.5599/admet.4.1.276 (2016).
Warr et al.: FOXO3A directs a protective autophagy program in haematopoietic stem cells. Nature 494(7437):323-327 (2013).
Welch et al.: RanBP3 contains an unusual nuclear localization signal that is imported preferentially by importin-alpha3. Mol Cell Biol. 19(12):8400-8411 (1999).
Wiedenheft et al.: RNA-guided complex from a bacterial immune system enhances target recognition through seed sequence interactions. PNAS USA 108:10092-10097 (2011).
Witzel et al.: Androgen receptor expression is a predictive marker in chemotherapy-treated patients with endocrine receptor-positive primary breast cancers. J Cancer Res Clin Oncol., 139(5):809-816 (2013).
Wu et al.: Rescuing lymphocytes from HLA-G immunosuppressive effects mediated by the tumor microenvironment. Oncotarget 6(35):37385-97 (2015).
Wu et al.: The quaking I-5 protein (QKI-5) has a novel nuclear localization signal and shuttles between the nucleus and the cytoplasm. J Biol Chem. 274(41):29202-29210 (1999).
Wyman, Tara B. et al. Design, synthesis, and characterization of a cationic peptide that binds to nucleic acids and permeabilizes bilayers. Biochemistry 36(10):3008-3017 (1997).
Ye et al.: Human leukocyte antigen G expression: as a significant prognostic indicator for patients with colorectal cancer. Mod Pathol 20:375-383 (2007).
Yie et al.: Expression of HLA-G is associated with prognosis in esophageal squamous cell carcinoma. Am J Clin Pathol 128:1002-1009 (2007).
Yie et al.: Expression of human leucocyte antigen G (HLA-G) is associated with prognosis in non-small cell lung cancer. Lung Cancer 58:267-274 (2007).
Yie et al.: Expression of human leukocyte antigen G (HLA-G) correlates with poor prognosis in gastric carcinoma. Ann Surg Oncol 14:2721-2729 (2007).

(56) References Cited

OTHER PUBLICATIONS

Yu et al.: A constitutive nuclear localization signal from the second zinc-finger of orphan nuclear receptor TR2. J Endocrinol. 159(1):53-60 (1998).
Yuan et al., Development of siRNA payloads to target KRAS-mutant cancer. Cancer Discov. 4(10): 1182-1197 (2014).
Zahid et al., Cell-type specific penetrating peptides: therapeutic promises and challenges. Molecules. 20;20(7):13055-13070 (2015).
Zetsche et al.: Cpf1 Is a Single RNA-Guided Endonuclease of a Class 2 CRISPR-Cas System. Cell. 25. pii: S0092-8674(15)01200-3[ http://dx.doi.org/10.1016/j.cell.2015.09.038] (2015).
Zhen et al.: Impact of HLA-E gene polymorphism on HLA-E expression in tumor cells and prognosis in patients with stage III colorectal cancer. Med Oncol 30:482 (2013).
Zhou, Hongyan. et al. Generation of induced pluripotent stem cells using recombinant proteins. Cell Stem Cell 4(5):381-384 (2009).

\* cited by examiner

Fig. 20
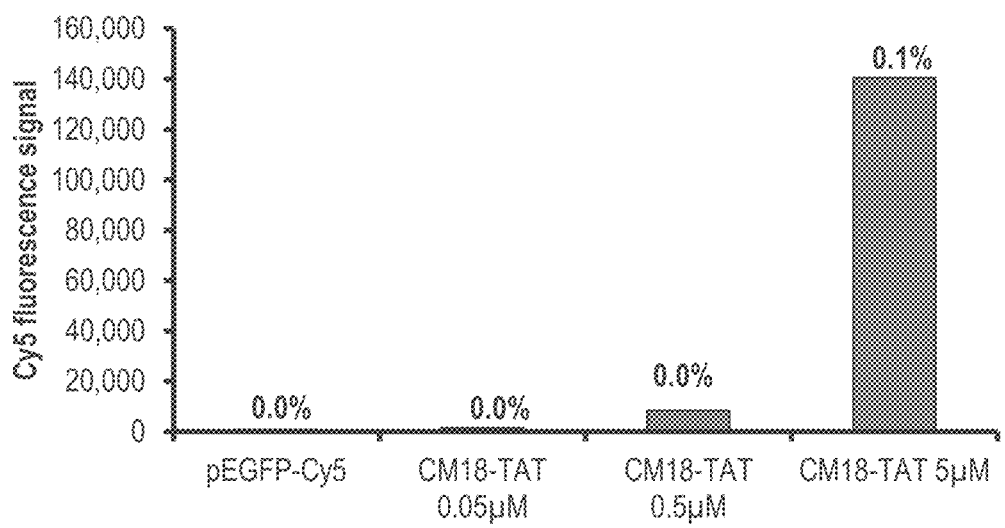
Fig. 21A
Fig. 21B
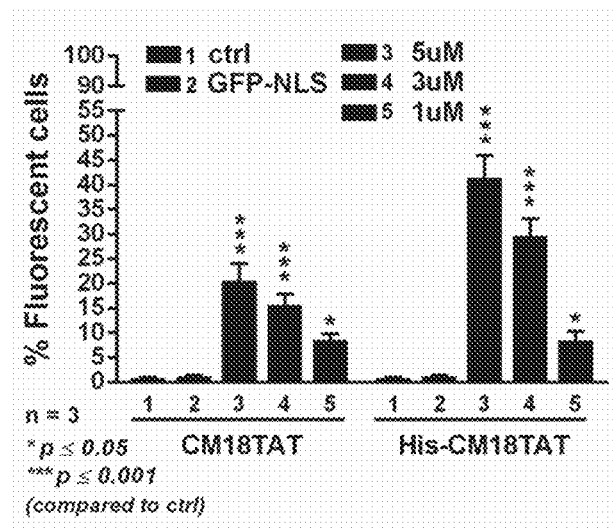
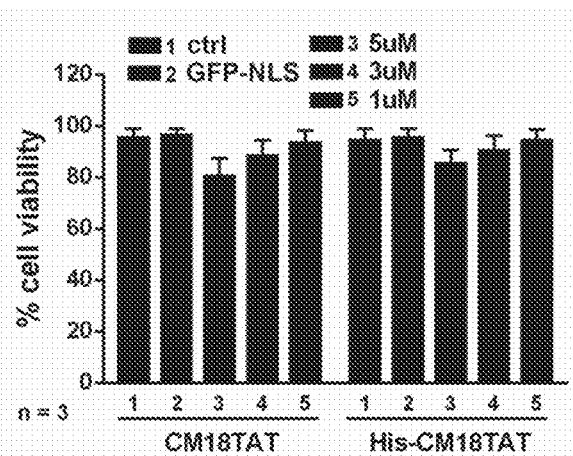

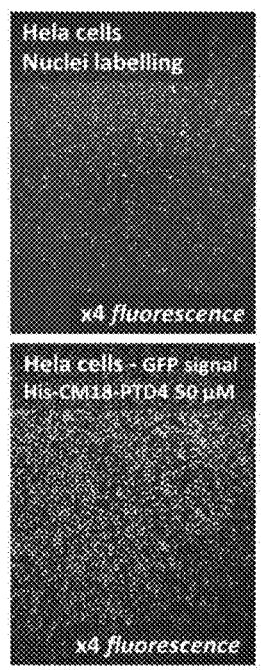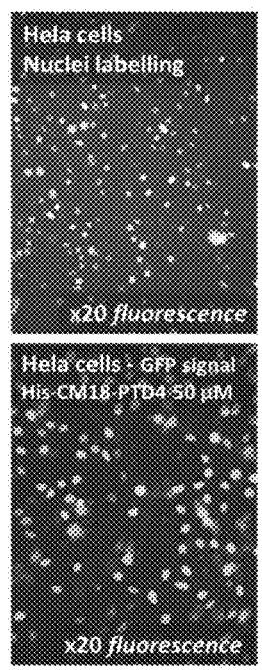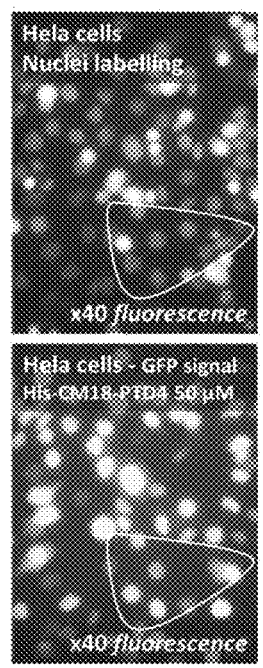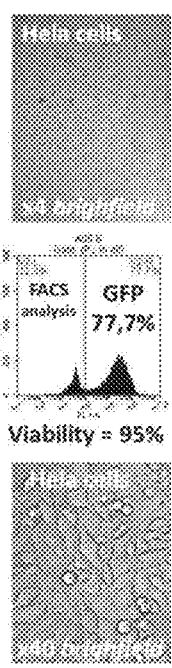
Fig. 23A  Fig. 23B  Fig. 23C  Fig. 23D
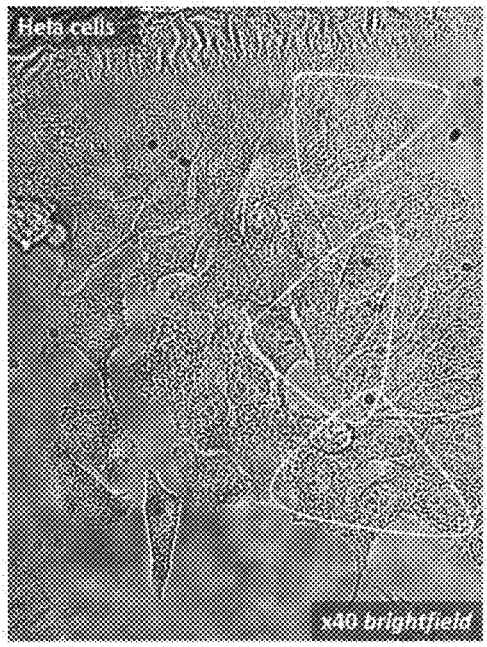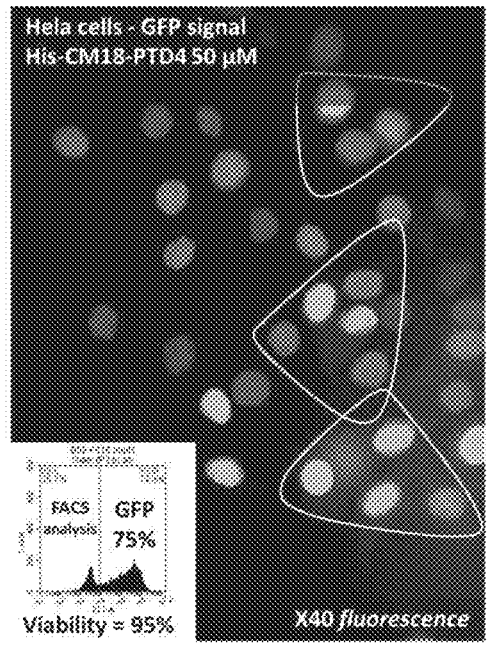
Fig. 24A  Fig. 24B Fig. 25A
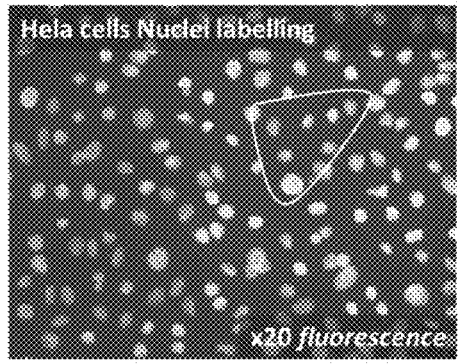
Fig. 25B
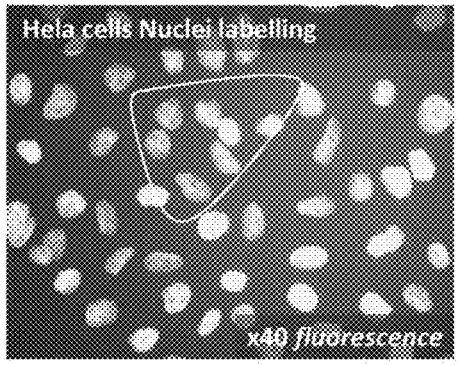
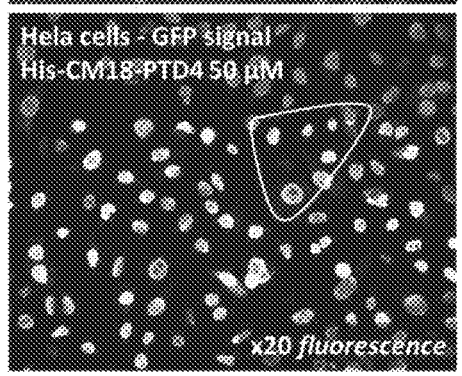
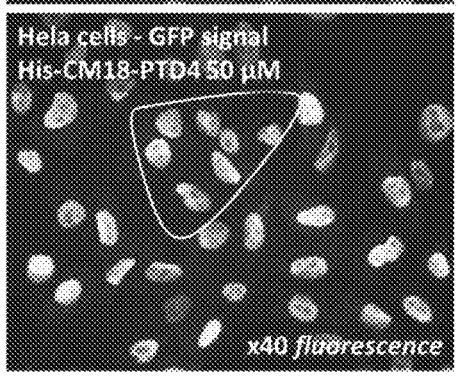
Fig. 26A
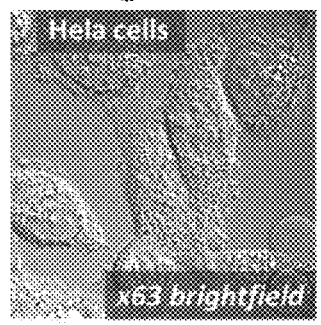
Fig. 26C
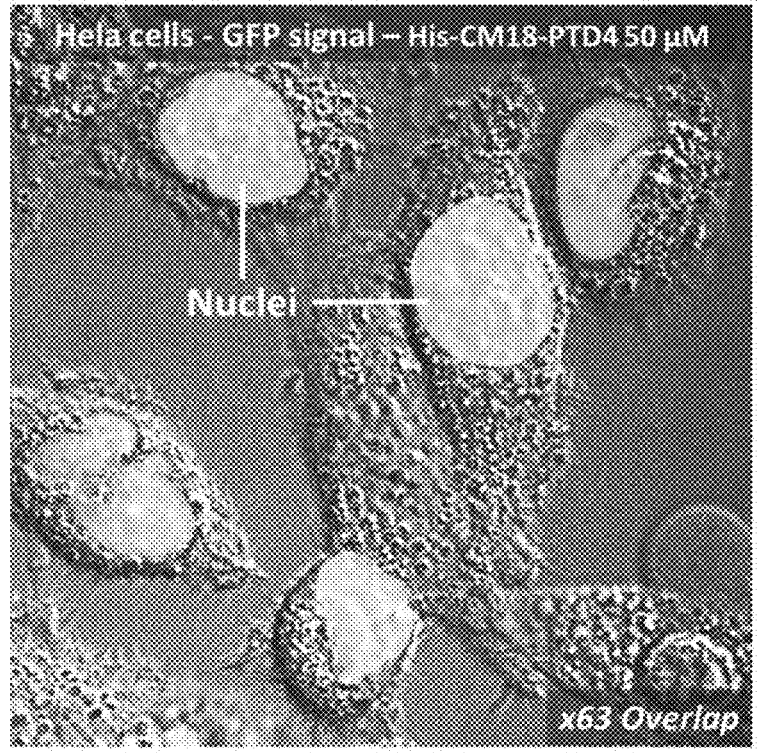
Fig. 26B
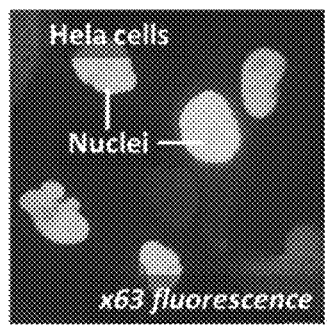

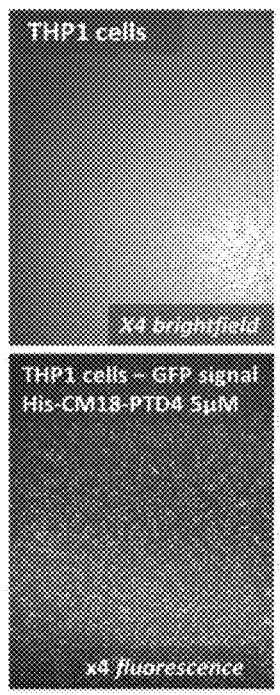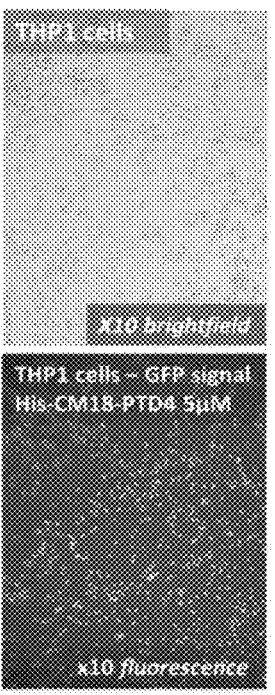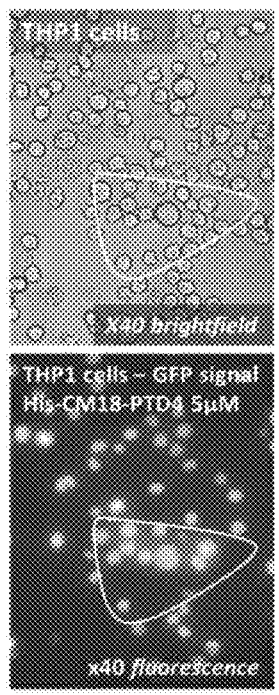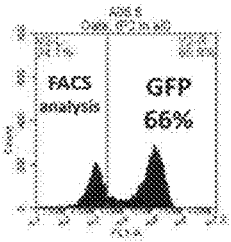
Fig. 32A   Fig. 32B   Fig. 32C   Fig. 32D
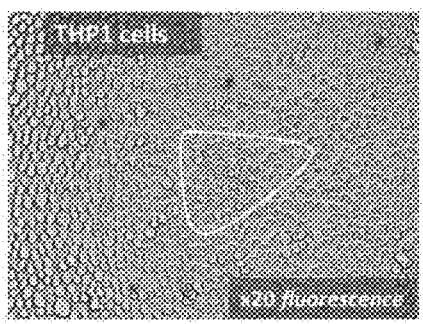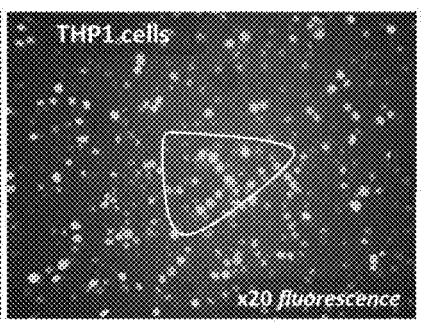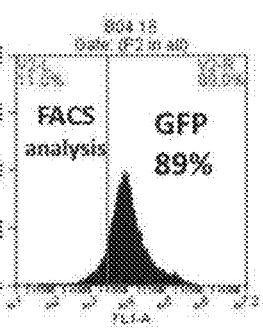
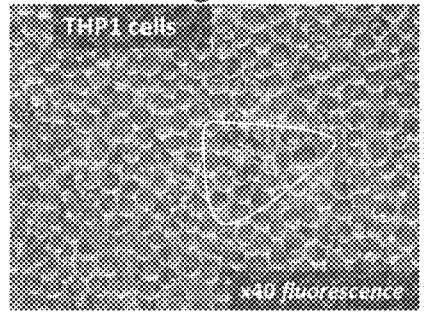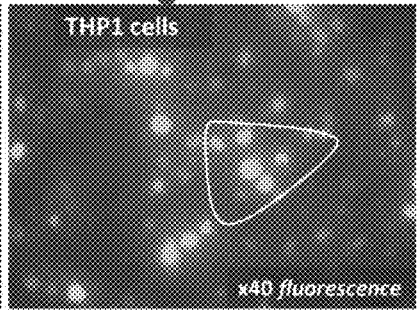
Fig. 33A   Fig. 33C
Fig. 33B   Fig. 33D

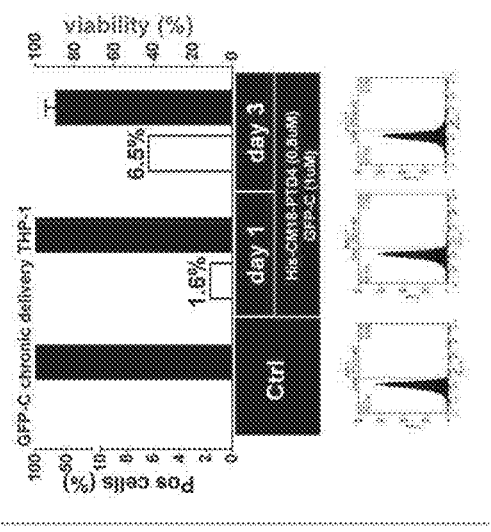
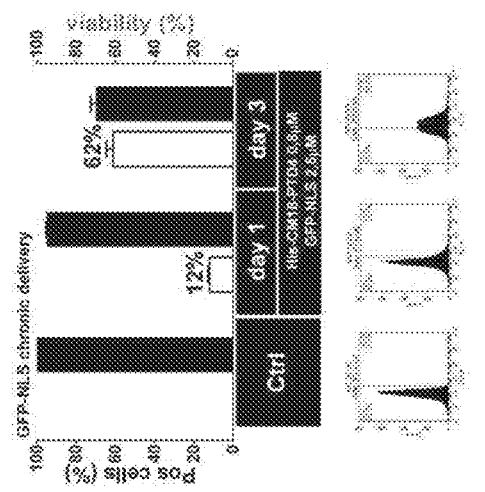
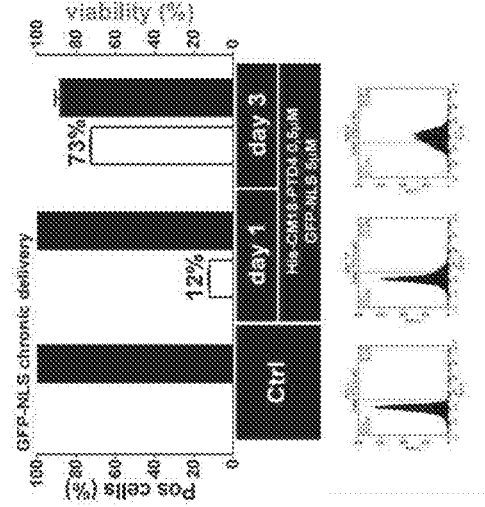
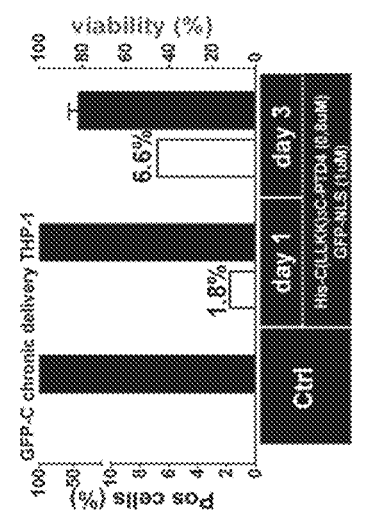
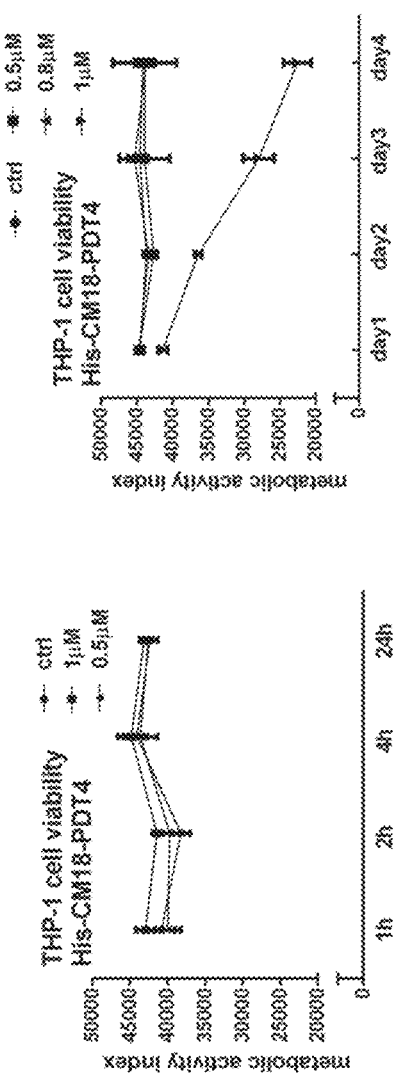
Fig. 35A  Fig. 35B  Fig. 35C  Fig. 35D  Fig. 35E  Fig. 35F

 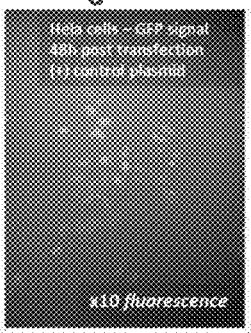  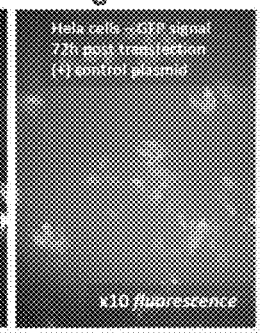
 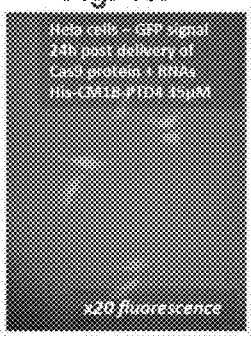 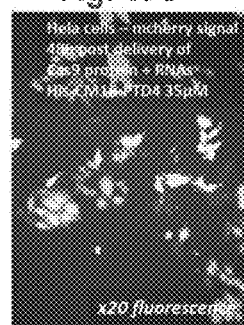 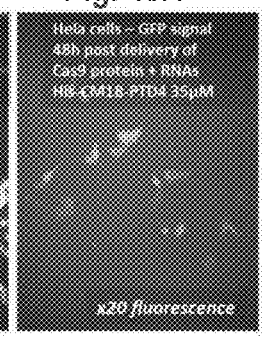
Fig. 40A  Fig. 40B  Fig. 40C  Fig. 40D
Fig. 40E  Fig. 40F  Fig. 40G  Fig. 40H
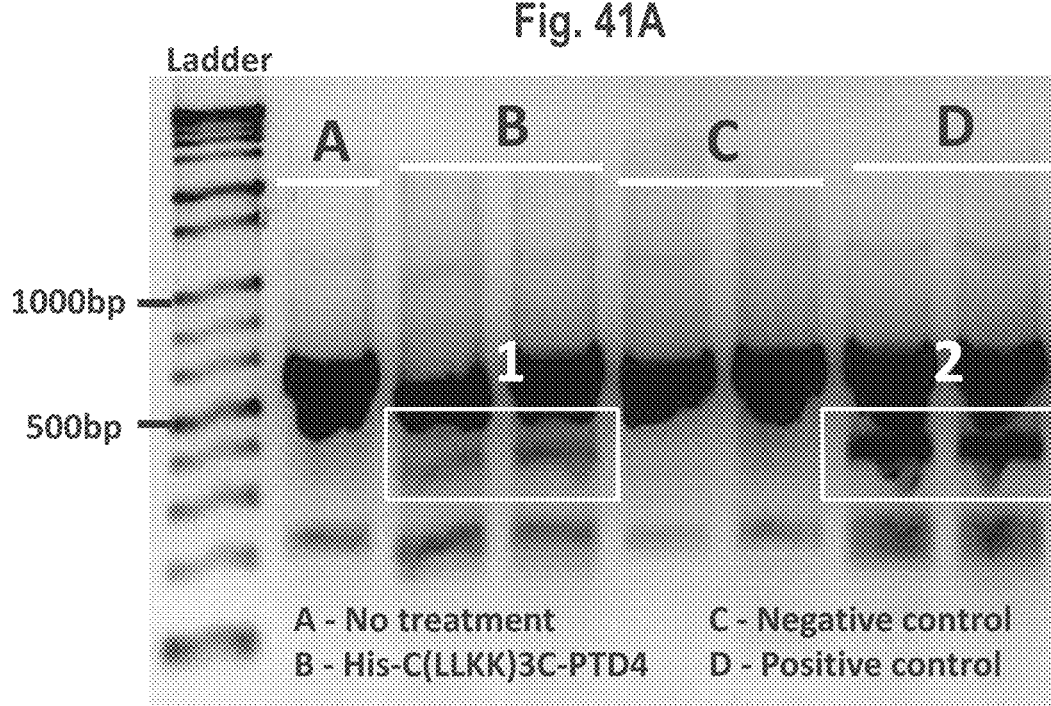
Fig. 41A Fig. 44
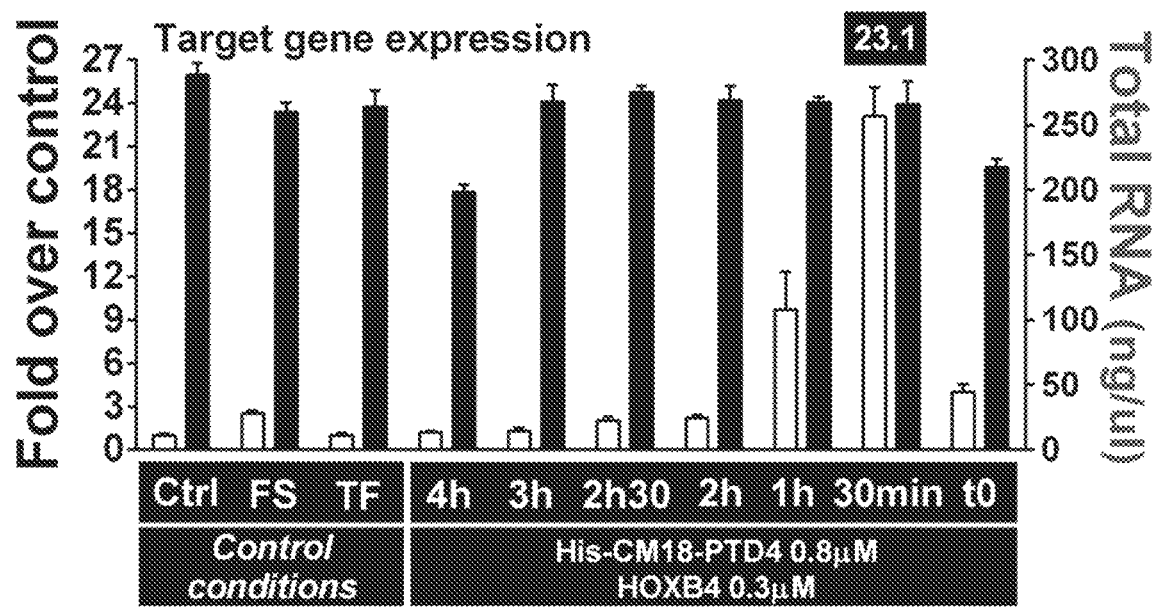
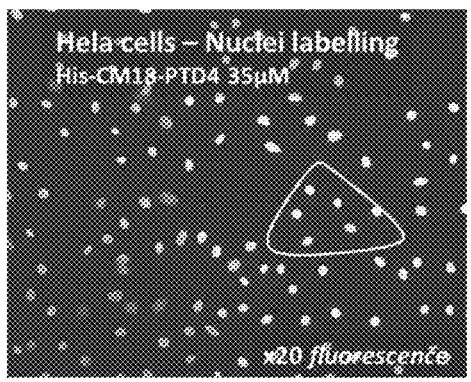
Fig. 45A
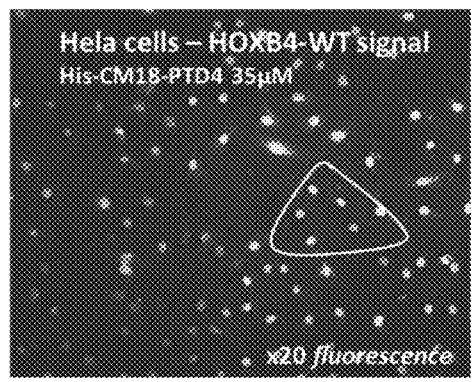
Fig. 45B
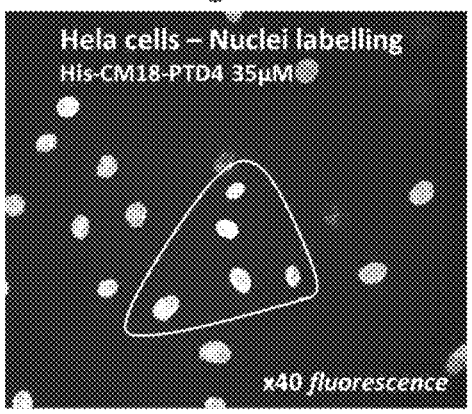
Fig. 45C
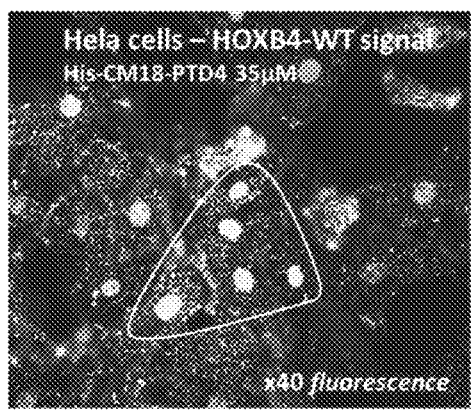
Fig. 45D

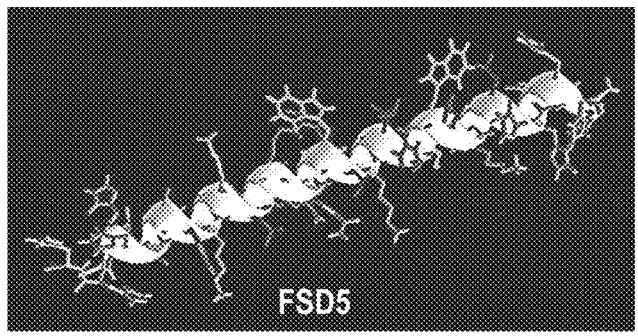
Fig. 49C FSD5
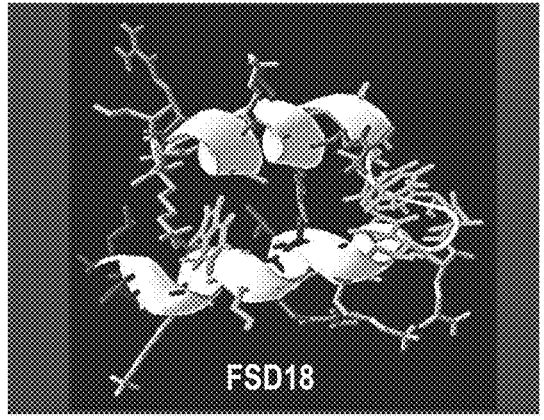
Fig. 49D FSD18
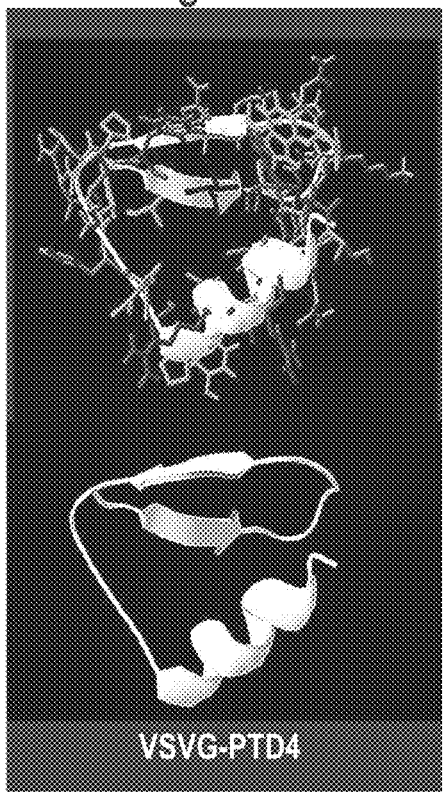
Fig. 49E VSVG-PTD4
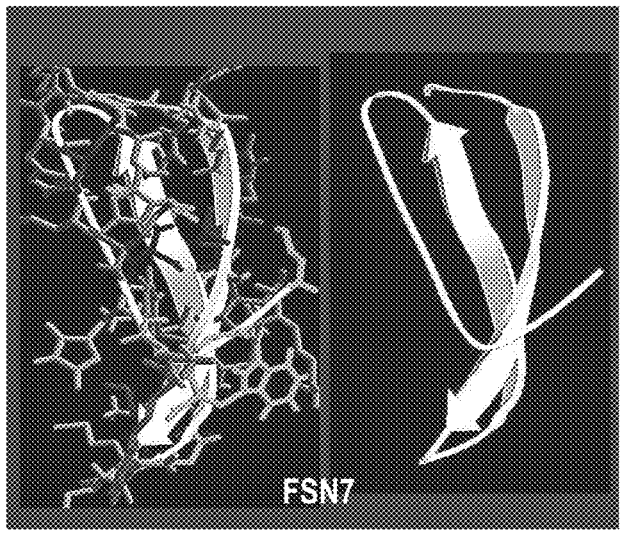
Fig. 49F FSN7

Fig. 49G

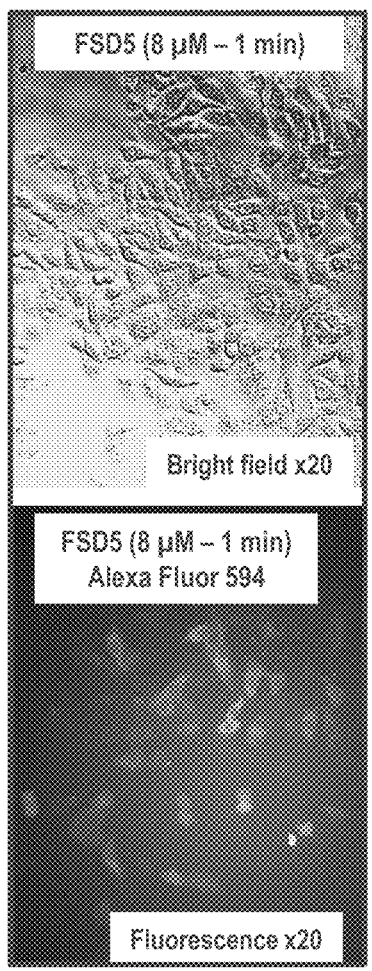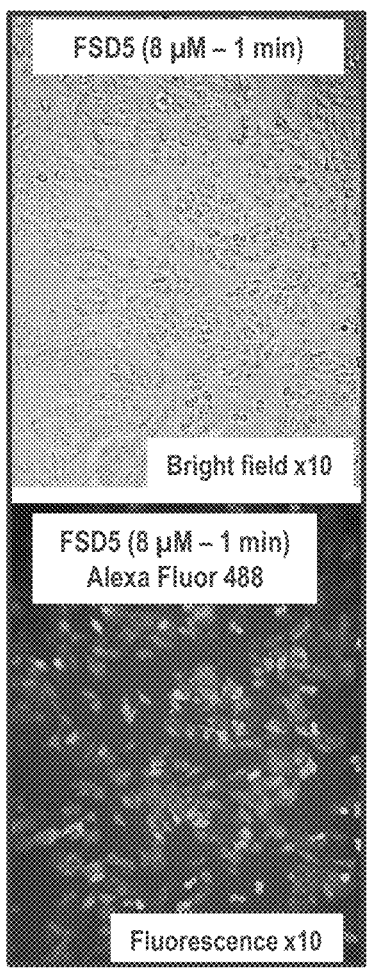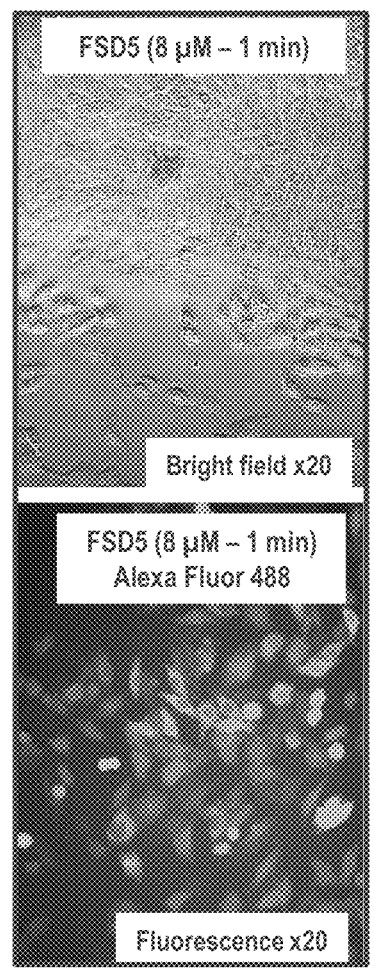

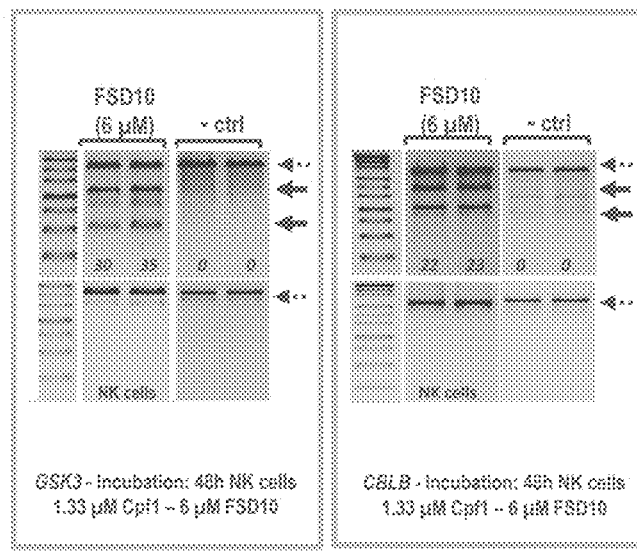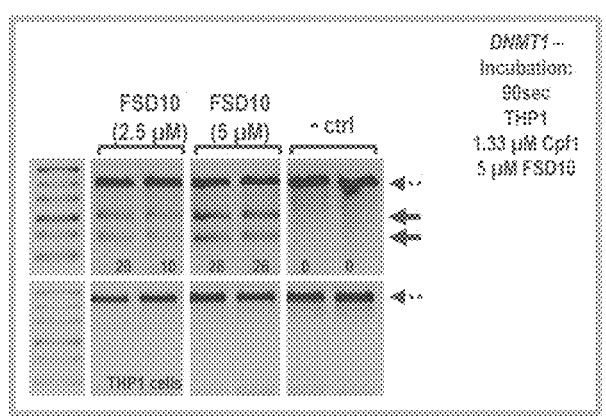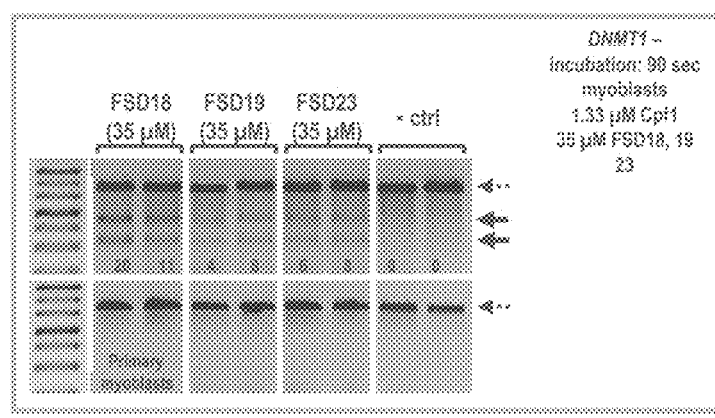

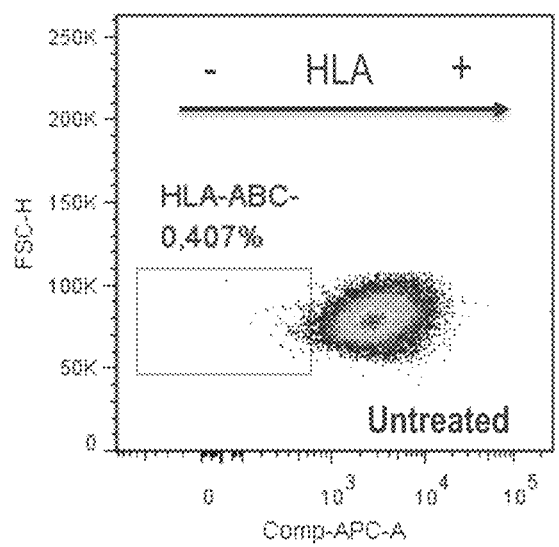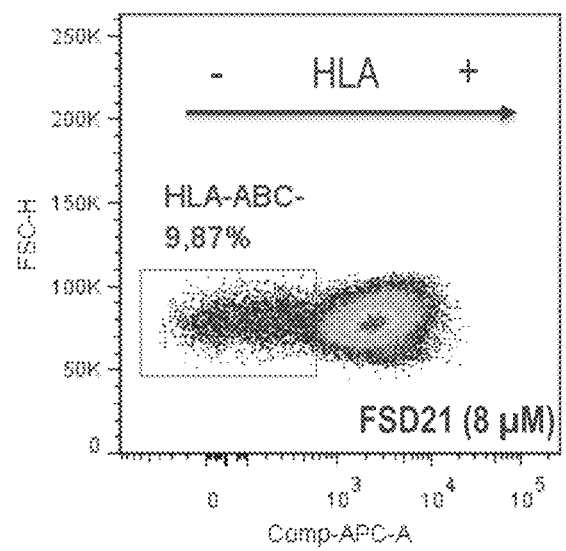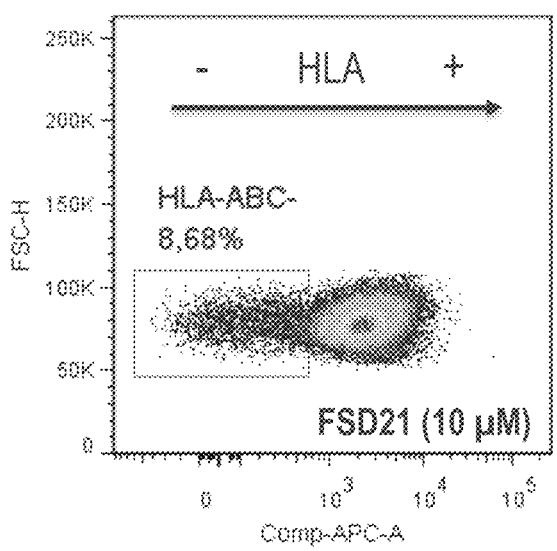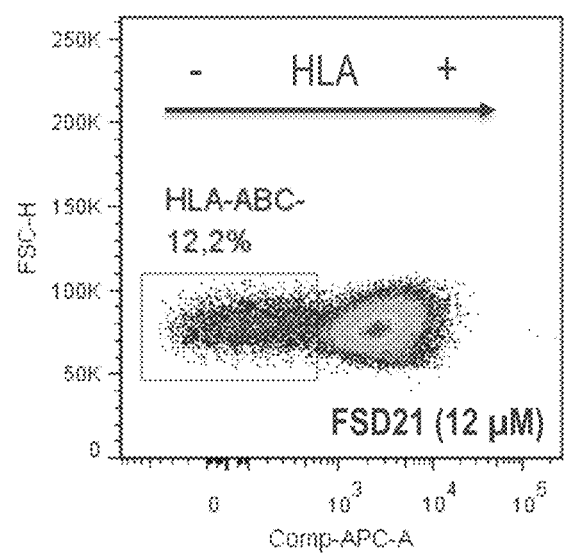

Untreated crRNA E crRNA G crRNA J crRNA E + G + J

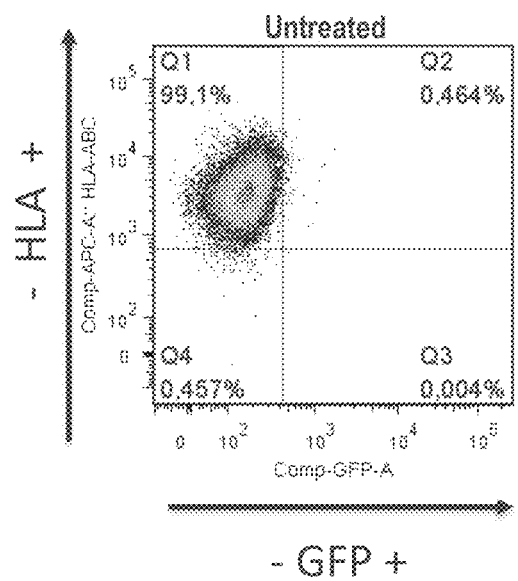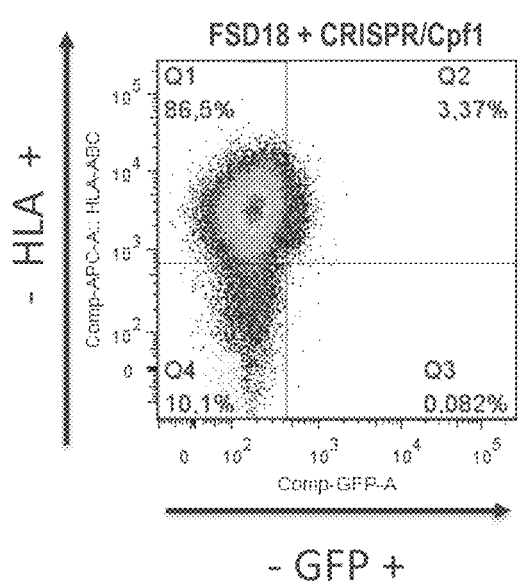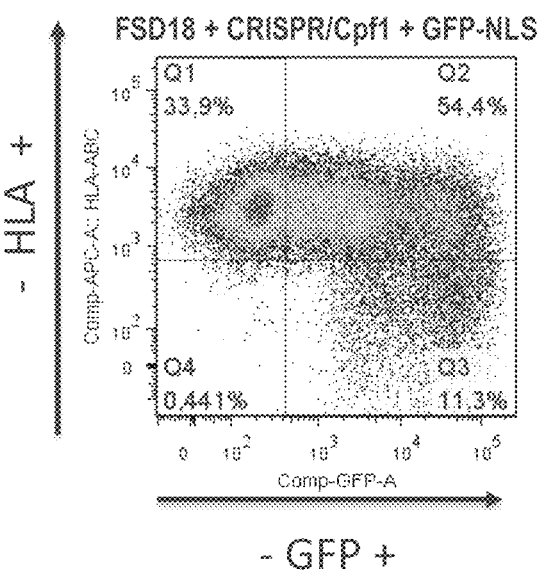

FACS sorting for GFP-negative cells

FACS sorting for GFP-positive cells

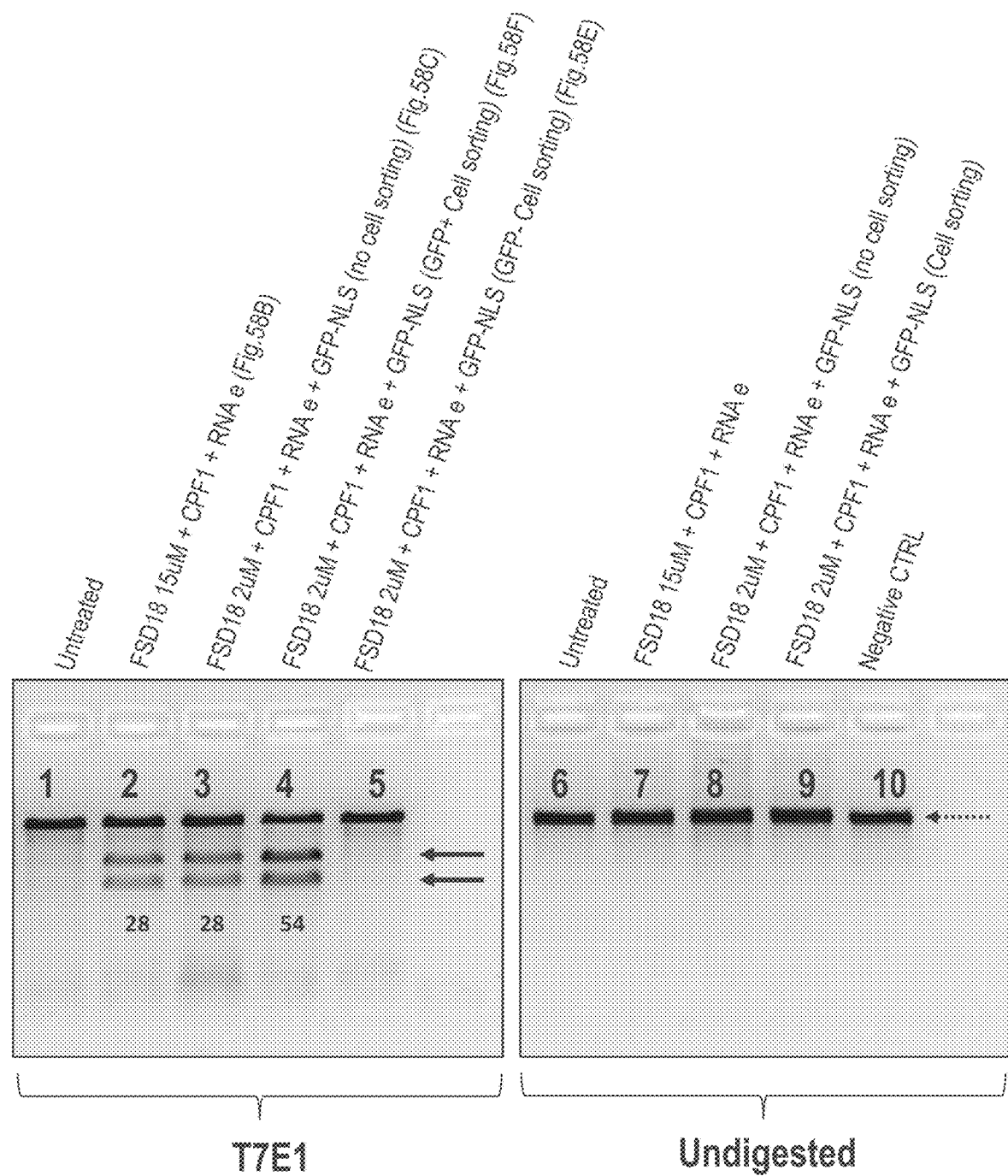

Untreated

Untreated

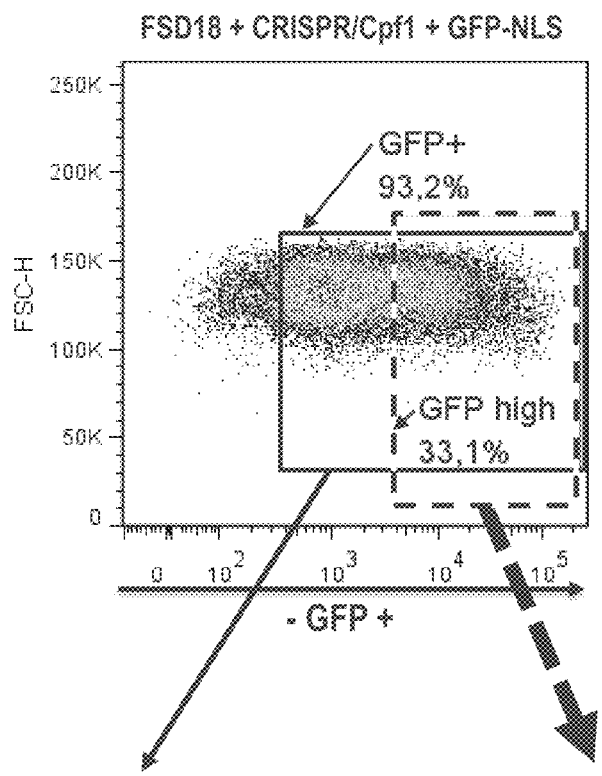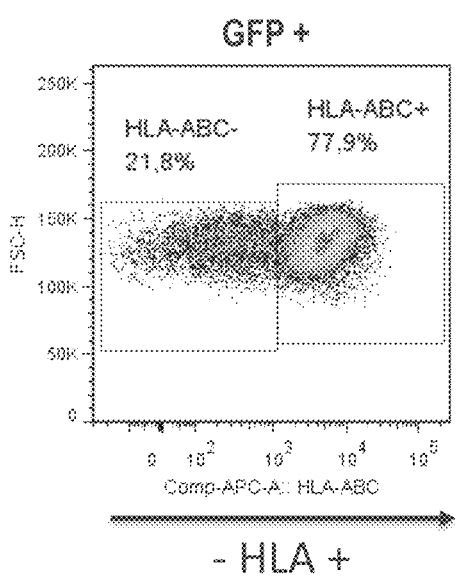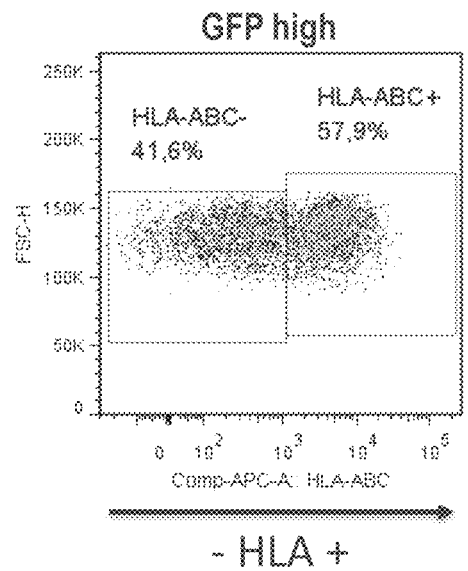

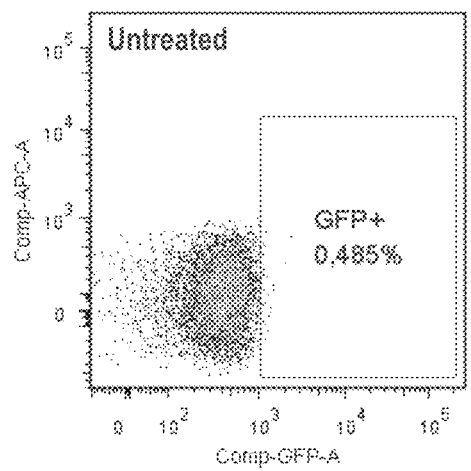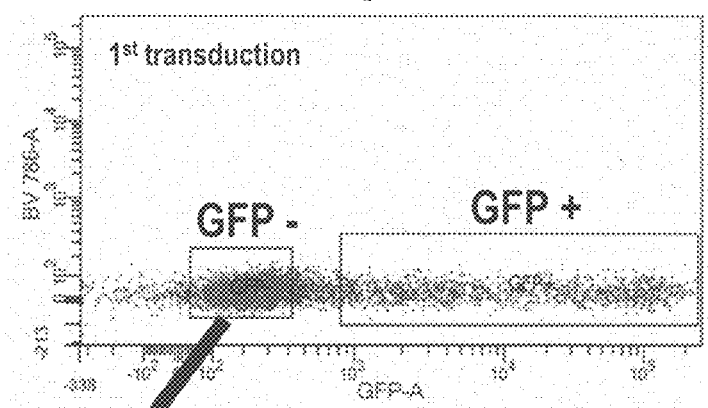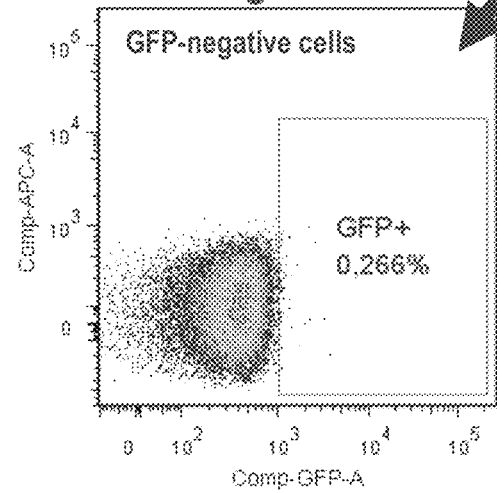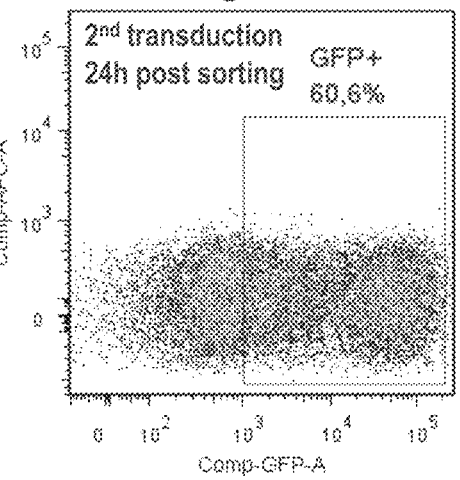

RATIONALLY-DESIGNED SYNTHETIC PEPTIDE SHUTTLE AGENTS FOR DELIVERING POLYPEPTIDE CARGOS FROM AN EXTRACELLULAR SPACE TO THE CYTOSOL AND/OR NUCLEUS OF A TARGET EUKARYOTIC CELL, USES THEREOF, METHODS AND KITS RELATING TO SAME

CROSS-REFERENCE

This application is a continuation of U.S. application Ser. No. 16/341,681, filed on Apr. 12, 2019, pursuant to 35 U.S.C. § 371 as a United States National Phase Application of International Application No. PCT/CA2017/051205 filed on Oct. 11, 2017, which is a Continuation of U.S. application Ser. No. 15/666,139 filed Aug. 1, 2017, now U.S. Pat. No. 9,982,267, issued May 29, 2018, which claims benefit of U.S. Provisional Patent Application No. 62/535,015 filed on Jul. 20, 2017, and U.S. Provisional Patent Application No. 62/407,232 filed on Oct. 12, 2016 all of which are incorporated herein by reference in their entirety.

The present description relates to synthetic peptide shuttle agents useful for delivering a variety of polypeptide cargos from an extracellular space to the cytosol and/or nucleus of target eukaryotic cells. More specifically, the present description relates to parameters useful in the rational design of such synthetic peptide shuttle agents.

BACKGROUND

Cell delivery technologies to transport large molecules inside eukaryotic cells have a wide range of applications, particularly in the biopharmaceutical industry. While some soluble chemical substances (e.g., small molecule drugs) may passively diffuse through the eukaryotic cell membrane, larger cargos (e.g., biologics, polynucleotides, and polypeptides) require the help of shuttle agents to reach their intracellular targets.

Areas that would greatly benefit from advances in cell delivery technologies include the fields of genome editing and cell therapy, which have made enormous leaps over the last two decades. Deciphering the different growth factors and molecular cues that govern cell expansion, differentiation and reprogramming open the door to many therapeutic possibilities for the treatment of unmet medical needs. For example, induction of pluripotent stem cells directly from adult cells, direct cell conversion (trans-differentiation), and genome editing (Zinc finger nuclease, TALEN and CRISPR-associated endonuclease technologies) are examples of methods that have been developed to maximize the therapeutic value of cells for clinical applications. Presently, the production of cells with high therapeutic activity usually requires ex vivo manipulations, mainly achieved by viral transduction, raising important safety and economical concerns for human applications. The ability to directly deliver active proteins such as transcription factors or artificial nucleases, inside these cells, may advantageously circumvent the safety concerns and regulatory hurdles associated with more risky gene transfer methods. In particular, methods of directly delivering active genome editing complexes in immune cells in order to improve immunotherapy would be highly desirable.

Protein transduction approaches involving fusing a recombinant protein cargo directly to a cell-penetrating peptide (e.g., HIV transactivating protein TAT) require large amounts of the recombinant protein and often fail to deliver the cargo to the proper subcellular location, leading to massive endosomal trapping and eventual degradation. Several endosomal membrane-disrupting peptides have been developed to try to facilitate the escape of endosomally-trapped cargos to the cytosol. However, many of these endosomolytic peptides have been used to alleviate endosomal entrapment of cargos that have already been delivered intracellularly, and do not by themselves aid in the initial step of shuttling the cargos intracellularly across the plasma membrane (Salomone et al., 2012; Salomone et al., 2013; Erazo-Oliveras et al., 2014; Fasoli et al., 2014).

In particular, Salomone et al., 2012 described a chimeric peptide $CM_{18}$-$TAT_{11}$, resulting from the fusion of the $Tat_{11}$ cell penetrating motif to the CM18 hybrid (residues 1-7 of Cecropin-A and 2-12 of Melittin). This peptide was reported to be rapidly internalized by cells (due to its TAT motif) and subsequently responsible for destabilizing the membranes of endocytic vesicles (due to the membrane disruptive abilities of the CM18 peptide). Although the peptide $CM_{18}$-$TAT_{11}$ fused to the fluorescent label Atto-633 (molecular weight of 774 Da; 21% of the MW of the peptide) was reported to facilitate the escape of endosomally trapped $TAT_{11}$-EGFP to the cytosol (see FIG. 3 of Salomone et al., 2012), the $CM_{18}$-$TAT_{11}$ peptide (alone or conjugated to Atto-633) was not shown to act as a shuttle agent that can increase delivery of a polypeptide cargo from an extracel/ular space to inside of the cell—i.e., across the plasma membrane. In fact, Salomone et al., 2012 compared co-treatment (simultaneous treatment of $TAT_{11}$-EGFP and $CM_{18}$-$TAT_{11}$-Atto-633) versus time-shifted treatment (i.e., incubation of cells with $TAT_{11}$-EGFP alone, fluorescence imaging, and then incubation of the same cells with the $CM_{18}$-$TAT_{11}$-Atto-633 peptide alone, and again fluorescence imaging), and the authors reported that "both yielded the same delivery results" (see page 295 of Salomone et al., 2012, last sentence of first paragraph under the heading "2.9 Cargo delivery assays"). In other words, Salomone et al., 2012 described that the peptide $CM_{18}$-$TAT_{11}$ (alone or conjugated to Atto-633) had no effect on delivery of a polypeptide cargo from an extracellular space to inside of the cell (i.e., protein transduction). Thus, there remains a need for improved shuttle agents capable of increasing the transduction efficiency of polypeptide cargos, and delivering the cargos to the cytosol and/or nucleus of target eukaryotic cells.

The present description refers to a number of documents, the content of which is herein incorporated by reference in their entirety.

SUMMARY

A plurality of different peptides was screened with the goal of identifying polypeptide-based shuttle agents that can deliver independent polypeptide cargos intracellularly to the cytosol/nucleus of eukaryotic cells. On one hand, these large-scale screening efforts led to the surprising discovery that certain domain-based peptide shuttle agents increase the transduction efficiency of polypeptide cargos in eukaryotic cells, by increasing the number and/or proportion of cells that ultimately internalize the polypeptide cargos, and also enable the internalized cargos to gain access to the cytosol/nuclear compartment (thus avoiding or reducing cargo endosomal entrapment). These domain-base shuttle agents comprise an endosome leakage domain (ELD) operably linked to a cell penetrating domain (CPD), and optionally one or more histidine-rich domains. On the other hand, the above screening efforts also revealed some peptides having no or low polypeptide cargo transduction activity, excessive toxicity, and/or other undesirable properties (e.g., poor solubility and/or stability). These empirical data (both positive and negative) were used herein to identify physiochemical properties of successful, less successful, and failed peptides in order to arrive at a set of design parameters that enable the rational design and/or identification of peptides having protein transduction activity.

Accordingly, the present description relates to methods for delivering polypeptide cargos from an extracellular space to the cytosol and/or nucleus of a target eukaryotic cell by contacting the cell with the polypeptide cargo in the presence of a peptide shuttle agent as described herein, at a concentration sufficient to increase the polypeptide cargo's transduction efficiency, as compared to in the absence of the shuttle agent. More particularly, the present description relates to parameters that may be used in the rational design of such synthetic peptide shuttle agents, peptide shuttle agents that satisfy one or more of these design parameters, as well as methods and compositions relating to the use of the synthetic peptide shuttle agents for delivery of a variety of polypeptide cargos from an extracellular space to the cytosol and/or nucleus of target eukaryotic cells. The present description also relates to machine-learning or computer-assisted approaches that may be used to generate peptide variants that respect one or more of the design parameters described herein.

The present description also relates to co-transducing a polypeptide cargo of interest and a marker protein as a means to identify and/or enrich transduced cells. It was surprisingly discovered that a strikingly high proportion of target eukaryotic cells that were successfully transduced with a polypeptide cargo of interest, were also successfully transduced with a marker protein. Conversely, a strikingly high proportion of cells that were not transduced with the polypeptide cargo of interest, were also not transduced with the marker protein. Isolating cells positive for the marker protein (e.g., via FACS) resulted in a significant increase in the proportion of cells that were successfully transduced with the polypeptide cargo of interest, and the correlation was found to be concentration dependent in that cell populations exhibiting the highest fluorescence of the marker protein also tended to exhibit the highest proportion of transduction with the polypeptide cargo of interest. It was also discovered that cells that were unsuccessfully transduced following a first round of transduction with a polypeptide cargo of interest, may be isolated and re-transduced with the polypeptide cargo of interest in subsequent rounds of transduction. Thus, in some aspects, the present description relates to methods comprising co-transduction of a polypeptide cargo of interest with a marker protein, wherein the marker protein may be used to isolate or enrich cells transduced with a polypeptide cargo of interest. In some embodiments, the present description also relates to methods comprising repeated successive transduction experiments performed on, for example, cells that were not successfully transduced with a marker protein following a first or previous transduction reaction. Such methods present attractive approaches for increasing transduction efficiency in valuable cell populations (e.g., patient-derived cells for cell therapy), and/or in cell populations that are inherently more difficult to transduce.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one". The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, "protein" or "polypeptide" or "peptide" means any peptide-linked chain of amino acids, which may or may not comprise any type of modification (e.g., chemical or post-translational modifications such as acetylation, phosphorylation, glycosylation, sulfatation, sumoylation, prenylation, ubiquitination, etc.). For further clarity, protein/polypeptide/peptide modifications are envisaged so long as the modification does not destroy the protein transduction activity of the shuttle agents described herein As used herein, a "domain" or "protein domain" generally refers to a part of a protein having a particular functionality or function. Some domains conserve their function when separated from the rest of the protein, and thus can be used in a modular fashion. The modular characteristic of many protein domains can provide flexibility in terms of their placement within the shuttle agents of the present description. However, some domains may perform better when engineered at certain positions of the shuttle agent (e.g., at the N- or C-terminal region, or therebetween). The position of the domain within its endogenous protein is sometimes an indicator of where the domain should be engineered within the shuttle agent and of what type/length of linker should be used. Standard recombinant DNA techniques can be used by the skilled person to manipulate the placement and/or number of the domains within the shuttle agents of the present description in view of the present disclosure. Furthermore, assays disclosed herein, as well as others known in the art, can be used to assess the functionality of each of the domains within the context of the shuttle agents (e.g., their ability to facilitate cell penetration across the plasma membrane, endosome escape, and/or access to the cytosol). Standard methods can also be used to assess whether the domains of the shuttle agent affect the activity of the cargo to be delivered intracellularly. In this regard, the expression "operably linked" as used herein refers to the ability of the domains to carry out their intended function(s) (e.g., cell penetration, endosome escape, and/or subcellular targeting) within the context of the shuttle agents of the present description. For greater clarity, the expression "operably linked" is meant to define a functional connection between two or more domains without being limited to a particular order or distance between same.

As used herein, the term "synthetic" used in expressions such as "synthetic peptide" or "synthetic polypeptide" is intended to refer to non-naturally occurring molecules that can be produced in vitro (e.g., synthesized chemically and/or produced using recombinant DNA technology). The purities of various synthetic preparations may be assessed by, for example, high-performance liquid chromatography analysis and mass spectroscopy. Chemical synthesis approaches may be advantageous over cellular expression systems (e.g., yeast or bacteria protein expression systems), as they may preclude the need for extensive recombinant protein purification steps (e.g., required for clinical use). In contrast, longer synthetic polypeptides may be more complicated and/or costly to produce via chemical synthesis approaches and such polypeptides may be more advantageously produced using cellular expression systems. In some embodiments, the peptides or shuttle agent of the present description may be chemically synthesized (e.g., solid- or liquid phase peptide synthesis), as opposed to expressed from a recombinant host cell. In some embodiments, the peptides or shuttle agent of the present description may lack an N-terminal methionine residue. A person of skill in the art may adapt a synthetic peptide or shuttle agent of the present description by using one or more modified amino acids (e.g., non-naturally-occurring amino acids), or by chemically modifying the synthetic peptide or shuttle agent of the present description, to suit particular needs of stability or other needs.

The expression "polypeptide-based" when used here in the context of a shuttle agent of the present description, is intended to distinguish the presently described shuttle agents from non-polypeptide or non-protein-based shuttle agents such as lipid- or cationic polymer-based transduction agents, which are often associated with increased cellular toxicity and may not be suitable for use in human therapy.

As used herein, the term "independent" is generally intended refer to molecules or agents which are not covalently bound to one another. For example, the expression "independent polypeptide cargo" is intended to refer to a polypeptide cargo to be delivered intracellularly that is not covalently bound (e.g., not fused) to a shuttle agent of the present description. In some aspects, having shuttle agents that are independent of (not fused to) a polypeptide cargo may be advantageous by providing increased shuttle agent versatility—e.g., not being required to re-engineer a new fusion protein for different polypeptide cargoes, and/or being able to readily vary the ratio of shuttle agent to cargo (as opposed to being limited to a 1:1 ratio in the case of a fusion protein).

As used herein, the expression "is or is from" or "is from" comprises functional variants of a given protein domain (e.g., CPD or ELD), such as conservative amino acid substitutions, deletions, modifications, as well as variants or function derivatives, which do not abrogate the activity of the protein domain.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:
FIG. 1A shows the results of a fluorescence microscopy experiment, while
FIG. 1B shows the results of a flow cytometry experiment.

FIG. 20 shows the results of DNA transfection efficiency experiment in which plasmid DNA (pEGFP) was labeled with a Cy5™ dye was co-incubated with 0, 0.05, 0.5, or 5 μM of CM18-TAT-Cys (labeled "CM18-TAT"), prior to being exposed to HEK293A cells. Flow cytometry analysis allowed quantification of Cy5™ emission (corresponding to DNA intracellular delivery; y-axis) and GFP emission (corresponding to successful nuclear delivery of DNA; percentage indicated above each bar).

FIGS. 21A and 21B show the results of a GFP-NLS transduction efficiency experiment in which the GFP-NLS cargo protein (5 μM) was co-incubated with 1, 3, or 5 μM of CM18-TAT-Cys (labeled "CM18TAT"), of His-CM18-TAT (labeled "His-CM18TAT"), prior to being exposed to HeLa cells. Cells were evaluated by flow cytometry and the percentage of fluorescent (GFP-positive) cell is shown in FIG. 21A, and corresponding cell toxicity data is shown in FIG. 21B.

FIG. 22A shows a comparison of GFP-NLS transduction efficiencies using different transduction protocols (Protocol A vs. B). FIG. 22B shows the effect of using different concentrations of the shuttle His-CM18-PTD4 when using Protocol B.

FIGS. 23-26 are microscopy images showing the results of transduction experiments in which GFP-NLS (FIG. 23, 24A, 24B, 25 and 26) or FITC-labeled anti-tubulin antibody (FIGS. 24C and 24D) cargo protein was intracellularly delivered with the shuttle His-CM18-PTD4 in HeLa cells. The bright field and fluorescence images of living cells are shown in FIGS. 23, 24 and 26. In FIG. 25, the cells were fixed, permeabilized and subjected to immuno-labelling with an anti-GFP antibody and a fluorescent secondary antibody. White triangle windows indicate examples of areas of co-labelling between nuclei (DAPI) and GFP-NLS signals. FIG. 26 shows images captured by confocal microscopy.

In FIGS. 29A and 29D-29F, cells were exposed to the cargo/shuttle agent for 10 seconds. In panel I, cells were exposed to the cargo/shuttle agent for 1 minute. In FIGS. 29B, 29C, 29G and 29H, cells were exposed to the cargo/shuttle agent for 1, 2, or 5 min. "Relative fluorescence intensity (FL1-A)" or "Signal intensity" corresponds to the mean of all fluorescence intensities from each cell with a GFP fluorescent signal after GFP-NLS fluorescent protein delivery with the shuttle agent. FIG. 29D shows the results of a control experiment in which only single-domain peptides (ELD or CDP) or the peptide His-PTD4 (His-CPD) were used for the GFP-NLS transduction, instead of the multi-domain shuttle agents.

FIG. 30A: TAT-KALA, FIG. 30B: His-CM18-PTD4, FIG. 30C: His-C (LLKK)$_3$C-PTD4, FIG. 30D: PTD4-KALA, FIG. 30E: EB1-PTD4, and FIG. 30F: His-CM18-PTD4-His. The insets in the bottom row panels show the results of corresponding flow cytometry analyses, indicating the percentage of cells exhibiting GFP fluorescence.

FIGS. 32A-32D shows microscopy images of THP-1 cells transduced with GFP-NLS cargo protein using the shuttle His-CM18-PTD4. Images captured under at 4×,10× and 40× magnifications are shown in FIGS. 32A-32C, respectively. White triangle windows in FIG. 32C indicate examples of areas of co-labelling between cells (bright field) and GFP-NLS fluorescence. FIG. 32D shows the results of corresponding flow cytometry analyses, indicating the percentage of cells exhibiting GFP fluorescence.

FIGS. 33A-33D show microscopy images of THP-1 cells transduced with GFP-NLS cargo protein using the shuttle His-CM18-PTD4. White triangle windows indicate examples of areas of co-labelling between cells (bright field; FIGS. 33A and 33B), and GFP-NLS fluorescence (FIG. 33C and FIG. 33D).

In FIG. 34B, "Relative fluorescence intensity (FL1-A)" corresponds to the mean of all fluorescence intensities from each cell with a GFP fluorescent signal after GFP-NLS fluorescent protein delivery with the shuttle agent.

FIGS. 35A-35F shows the results of transduction efficiency experiments in which THP-1 cells were exposed daily to GFP-NLS cargo in the presence of a shuttle agent for 2.5 hours. His-CM18-PTD4 was used in FIGS. 35A-35E, and His-C(LLKK)$_3$C-PTD4 was used in FIG. 35F. GFP-NLS transduction efficiency was determined by flow cytometry at Day 1 or Day 3, and the results are expressed as the percentage of GFP fluorescent cells ("Pos cells (%)"), as well as corresponding cell viability data ("viability (%)") in FIGS. 35A-35C and 35F. FIG. 35D shows the metabolic activity index of the THP-1 cells after 1, 2, 4, and 24 h, and FIG. 35E shows the metabolic activity index of the THP-1 cells after 1 to 4 days, for cells exposed to the His-CM18-PTD4 shuttle.

FIGS. 40A-40H show fluorescence microscopy images of HeLa cells expressing mCherry™ and GFP, indicating CRISPR/Cas9-NLS-mediated cleavage of plasmid surrogate DNA. In panels A-D, HeLa cells were co-transfected with three plasmids: the plasmid surrogate as described in the brief description of FIGS. 39A-39E, and two other expression plasmids encoding the Cas9-NLS protein and crRNA1-tracrRNAs, respectively. CRISPR/Cas9-mediated cleavage of the plasmid surrogate at the STOP codon, and subsequent DNA repair by the cell, enables expression of GFP (FIGS. 40B and 40D) in addition to mCherry™ (FIGS. 40A and 40C). In FIGS. 40E-40H, HeLa cells were transfected with the plasmid surrogate and then transduced with an active CRISPR/Cas9-NLS complex using the shuttle His-CM18-PTD4. CRISPR/Cas9-NLS-mediated cleavage of the plasmid surrogate at the STOP codon, and subsequent DNA repair by the cell, enables expression of GFP (FIGS. 40F and 40H) in addition to mCherry™ (panels 40E and 40G).

FIG. 41A (lanes A to D) shows the products of a DNA cleavage assay (T7E1 assay) separated by agarose gel electrophoresis, which is used to measure CRISPR/Cas9-mediated cleavage of cellular genomic DNA. HeLa cells were transduced with a CRISPR-Cas9-NLS complex programmed to cleave the PPIB gene. The presence of the cleavage product framed in white boxes 1 and 2, indicates cleavage of the PPIB gene by the CRISPR-Cas9-NLS complex, which was delivered intracellularly using the shuttle His-C(LLKK)₃C-PTD4 (FIG. 41A, lane B) or with a lipidic transfection agent used as a positive control (FIG. 41A, lane D). This cleavage product is absent in negative controls (FIG. 41A, lanes A and C).

FIGS. 42-44 show the transcriptional activity of THP-1 cells that have been transduced with the transcription factor HOXB4 using different concentrations of the shuttle His-CM18-PTD4 and different cargo/shuttle exposure times. Successful intra-nuclear delivery of HOXB4 was determined by monitoring mRNA levels of a target gene by real-time PCR, and the results are normalized against those in the negative control (HOXB4 without shuttle agent) and expressed as "Fold over control" (left bars). Total cellular RNA (ng/µL) was quantified and used a marker for cell viability (right bars). "0" or "Ctrl" means "no treatment"; "TF" means "Transcription Factor alone"; "FS" means "shuttle alone".

FIGS. 45A-45D show fluorescence microscopy images of HeLa cells transduced with wild-type HOXB4 cargo using the shuttle His-CM18-PTD4. After a 30-minute incubation to allow transduced HOXB4-WT to accumulate in the nucleus, the cells were fixed, permeabilized and HOXB4-WT was labelled using a primary anti-HOXB4 monoclonal antibody and a fluorescent secondary antibody (FIGS. 45B and 45D). Nuclei were labelled with DAPI (FIGS. 45A and 45C). White triangle windows indicate examples of areas of co-labelling between nuclei and HOXB4-compare FIG. 45A vs 45B (×20 magnification), and FIG. 45C vs 45D (×40 magnification).

FIG. 46A shows the results with the shuttle agents: His-CM18-PTD4, His-CM18-PTD4-His, and His-C(LLKK)3C-PTD4 in HeLa cells. FIG. 46B shows the results with His-CM18-PTD4-His and His-CM18-L2-PTD4 in Jurkat cells. Negative controls (lane 4 in panels A and B) show amplified HPTR DNA sequence after incubation of the cells with the CRISPR/Cas9 complex without the presence of the shuttle agent. Positive controls (lane 5 in panels A and B) show the amplified HPTR DNA sequence after incubation of the cells with the Cas9/RNAs complex in presence of a commercial lipidic transfection agent.

FIG. 48B shows the stereotaxic coordinates of the injection site (black arrows) from the rat brain atlas of Franklin and Paxinos. The injection of GFP-NLS in presence of His-CM18-PTD4 was performed on the left part of the brain, and the negative control (injection of GFP-NLS alone), was done on the contralateral site. The black circle and connected black lines in FIG. 48B show the areas observed in the fluorescent pictures (FIGS. 48A, 48C and 48D)

FIGS. 49C-49F show predicted 3-dimensional models of the structures of the peptides FSD5, FSD18, VSVG-PTD4, and a peptide having two beta-sheets and no alpha helices, respectively.

FIG. 49G shows a multiple sequence alignment of the peptides His-CM18-PTD4; EB1-PTD4; His-C(LLKK)₃C-PTD4; FSD5; FSD10; FSD19; FSD20; FSD21; FSD44; FSD46; and FSD63, along with "Consistency" scores for each residue position. For the alignment, histidine-rich domains were voluntarily excluded.

FIGS. 50A-50C show microscopy images of live HeLa cells successfully transduced by the shuttle agent FSD5 with fluorescently labelled antibodies as cargos. FIG. 50A shows the cytoplasmic transduction of a Goat Anti-Rabbit IgG H&L (Alexa Fluor® 594) antibody visualized by bright field (upper panel) and fluorescence microscopy (lower panel) at 20× magnification. FIGS. 50B and 50C show the cytoplasmic transduction of a Goat Anti-Mouse IgG H&L (Alexa Fluor®488) antibody visualized by bright field (upper panels) and fluorescence microscopy (lower panels) at 10× and 20× magnifications, respectively.

FIGS. 52F-52I show the results of the cleavage of a targeted genomic GSK3 (FIG. 52F), CBLB (FIG. 52G) and DNMT1 (FIG. 52H-1) DNA sequence with the CRISPR/Cpf1-NLS and a single guide crRNA in the absence ("-ctrl") or presence of the shuttle agents FSD10, FSD18, FSD19 or FSD23 used at different concentrations, exposure times, and in different types of cells: NK (FIG. 52F-G); THP-1 (FIG. 52H) and primary myoblasts (FIG. 52I), after separation by agarose gel electrophoresis. Cells were incubated with CRISPR/Cpf1 complexes and FSD at the indicated times and concentrations. Thin dashed arrows indicate the bands corresponding to the target gene, and thicker solid arrows indicate the bands corresponding to the CRISPR system-mediated cleavage products of these target genes, which indicate the successful transduction of fully functional CRISPR/Cpf1-NLS genome editing complexes.

Figure 52A:
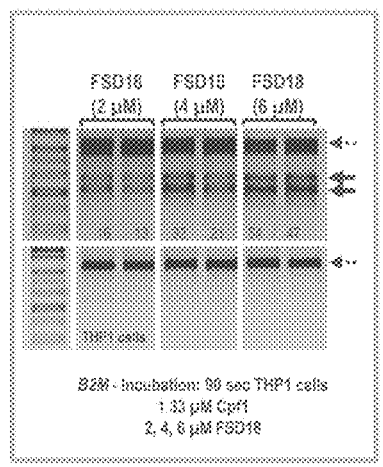
FIGS. 52A-52E show the results of the cleavage of a targeted genomic B2MDNA sequence with the CRISPR/Cas9-NLS and the crRNA/tracrRNA, or with the CRISPR/Cpf1-NLS and a single guide RNA in the absence ("-ctrl") or presence of the shuttle agents FSD10, FSD18, FSD19, FSD21, FSD23 or FSD43 used at different concentrations, exposure times, and in different types of cells: THP-1 (FIG. 52A); NK (FIG. 52B-D) and HeLa (FIG. 52E), after separation by agarose gel electrophoresis. Cells were incubated with CRISPR/Cpf1 complexes and FSD shuttle agents at the indicated times and concentrations. Thin dashed arrows indicate the bands corresponding to the target gene, and thicker solid arrows indicate the bands corresponding to the CRISPR system-mediated cleavage products of this target gene, which indicate the successful transduction of fully functional CRISPR/Cas9-NLS genome editing complexes. An imaging software was used to quantify the relative signal intensities of each of the different bands directly on gels. The sum of all the bands in a given lane corresponds to 100% of the signal, and the numerical value in italics at the bottom of each lane is the sum of the relative signals (%) of only the two cleavage product bands (thick solid arrows).
Figure 52B:
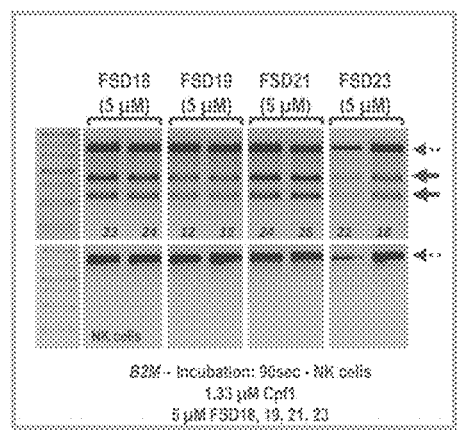
Figure 52C:
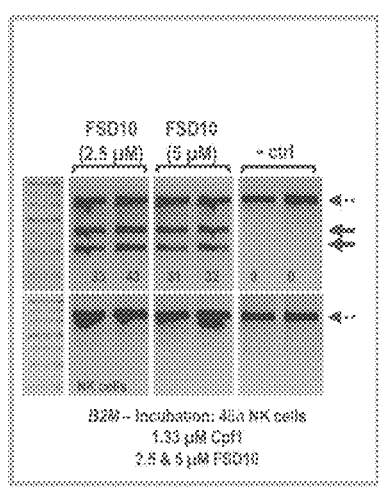

or presence of the shuttle agents FSD10, FSD21, FSD22 or FSD23 used at different concentrations, exposure times, and in NK cells (FIG. 52F-52G) and NK-92 cells (FIG. 52H), after separation by agarose gel electrophoresis. Cells were incubated with CRISPR/Cpf1 complexes for the indicated incubation times and concentrations. Thin dashed arrows indicate the bands corresponding to the target gene, and thicker solid arrows indicate the bands corresponding to the CRISPR system-mediated cleavage products of this target gene, which indicate the successful transduction of fully functional CRISPR/Cpf1-NLS genome editing complexes.

FIGS. 53A-53G show the results of the cleavage of the targeted genomic HPRT, DNMT1 and B2M DNA sequences with CRISPR systems. The two genomic HPRT (FIG. 53A) and DNMT1 (FIG. 53B) DNA sequences or two DNA loci on the genomic B2M exon 2 (FIG. 53C-D) were targeted in HeLa cells using CRISPR/Cas9-NLS and CRISPR/Cpf1-NLS genome editing complexes designed for those purposes, which were transduced using the shuttle agent peptide FSD18. The two DNA loci on the genomic B2M exon 2 (FIG. 53E-G) were targeted in NK cells with the CRISPR/Cpf1-NLS and single guide crRNA-1, crRNA-2 or both, in the absence ("-ctrl") or presence of the shuttle agents FSD10 (FIG. 53E), FSD21 (FIG. 53F) or FSD23 (FIG. 53G) used at different concentrations and exposure times after separation by agarose gel electrophoresis. Thin dashed arrows indicate the bands corresponding to the target gene, and thicker solid arrows indicate the bands corresponding to the CRISPR/Cpf1-mediated cleavage products in presence of the crRNA-1 or crRNA2 or both (crRNA1+2) for the B2M exon 2, which indicate the successful transduction of fully functional CRISPR/Cpf1-NLS genome editing complexes.

FIGS. 54A-54D show the results of flow cytometry assays in which T cells were treated with increasing concentrations of the shuttle agent FSD21 (8 µM in FIG. 54B, 10 µM in FIG. 54C, and 12 µM in FIG. 54D), 1.33 µM of CRISPR/Cpf1-NLS system and 2 µM of single guide crRNA targeting a B2M genomic DNA sequence. HLA-positive and HLA-negative (B2M knock-out) cells were identified 72 hours after treatment by using an APC-labeled Mouse Anti-Human HLA-ABC antibody. Left-shifted cell populations indicated successful inactivation of cell surface HLA receptors, resulting from inactivation of the B2M gene.

FIGS. 55A-55D show the results of flow cytometry assays in which T cells were treated with increasing concentrations of the shuttle agent FSD18 (8 µM in FIG. 55B, 10 µM in FIG. 55C, and 12 µM in FIG. 55D), 1.33 µM of CRISPR/Cpf1-NLS system and 2 µM of single guide crRNA targeting a B2M DNA sequence. HLA-positive and HLA-negative (B2M knock-out) cells were identified 72 hours after treatment by using an APC-labeled Mouse Anti-Human HLA-ABC antibody. Left-shifted cell populations indicated successful inactivation of cell surface HLA receptors, resulting from inactivation of the B2M gene.

Figure 56A:
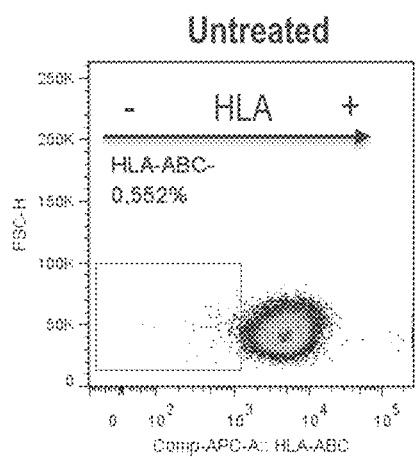
Figure 56B:
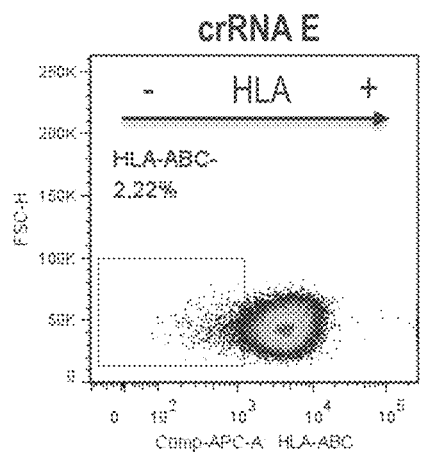
Figure 56C:
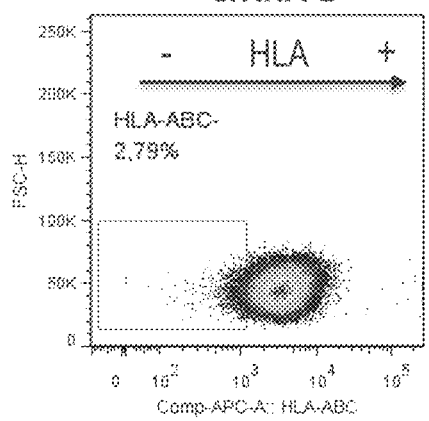
Figure 56D:
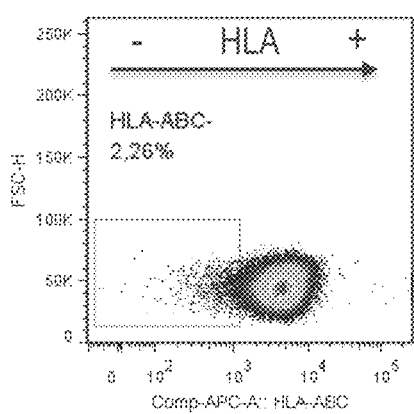
Figure 56E:
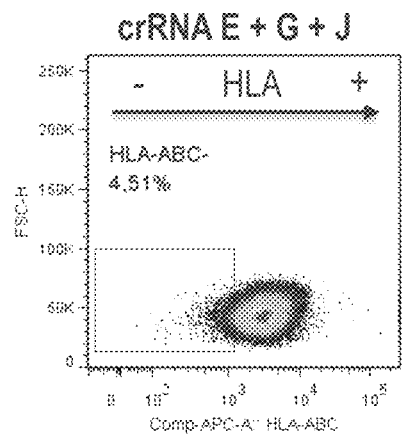

FIGS. 56A-56E show the results of flow cytometry assays in which THP-1 cells were treated (FIG. 56B-56E) or not ("untreated", FIG. 56A) with a mixture of 1.33 µM of CRISPR/Cpf1-NLS system, 2 µM of one or three guide crRNA each targeting different sites within the B2M genomic DNA sequence and 3 µM of FSD18. HLA-positive and HLA-negative (B2M knock-out) cells were identified 48 hours after treatment by using an APC-labeled Mouse Anti-Human HLA-ABC antibody in untreated cells (FIG. 56A), crRNA E treated cells (FIG. 56B), crRNA G treated cells (FIG. 56C), crRNA J treated cells (FIG. 56D) and crRNA E+G+J treated cells (FIG. 56E). Left-shifted cell populations indicated successful inactivation of cell surface HLA receptors, resulting from inactivation of the B2M gene.

Figure 57A:
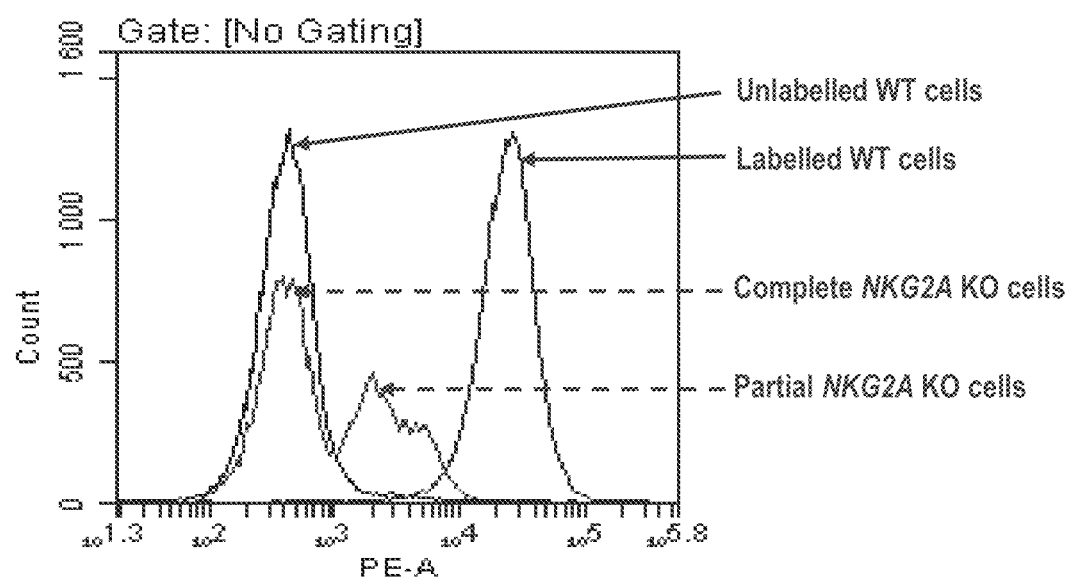
Figure 57B:
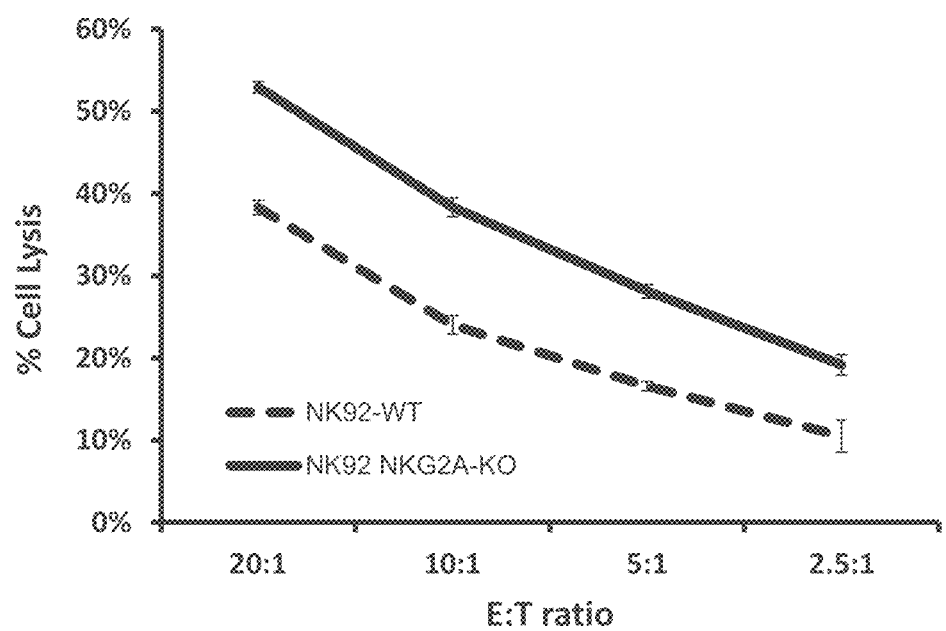

FIGS. 57A and 57B show the results of experiments in which NK-92 cells were genome-edited to determine whether inactivation of the endogenous NKG2A gene could increase their ability to kill target HeLa cells. Briefly, NK-92 cells were transduced with a CRISPR/Cpf1-NLS genome editing complex designed to cleave the NKG2A gene using the shuttle agent peptide FSD23. After transduction, NK-92 cells were immunolabelled with a phycoerythrin (PE)-labelled anti-NKG2A antibody and then analyzed by flow cytometry as shown in FIG. 57A, to verify successful inactivation of NKG2A. As controls, unlabelled wild-type NK-92 cells ("unlabelled WT cells") had no antibody signal, and labelled wild-type NK-92 cells ("labelled WT cells") had full immunolabelling signal. For NKG2A-KO NK-92 cells, two cell populations (peaks) were observed: one with a complete knock-out of NKG2A receptor expression on the cell surface ("Complete NKG2A KO cells"), and the other with a partial lack of expression ("Partial NKG2A KO cells"). FIG. 57B shows the results of cytotoxicity assays in which target HeLa cells previously loaded with an intracellular fluorescent dye (calcein) were exposed to either wild-type (solid line) or genome edited NKG2A-KO (dotted line) effector NK-92 cells, at different Effector:Target ratios (E:T ratio). Cytotoxicity was evaluated by the relative release of intracellular calcein into the extracellular space resulting from disruption of the cell membranes of the target HeLa cells (% cell lysis").

Figure 58D:
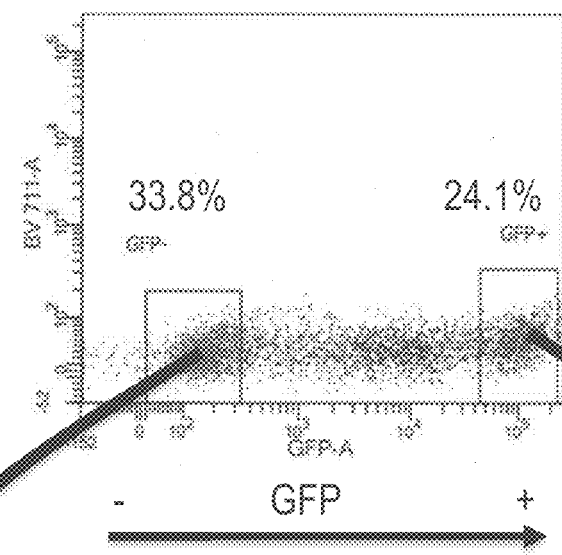
Figure 58E:
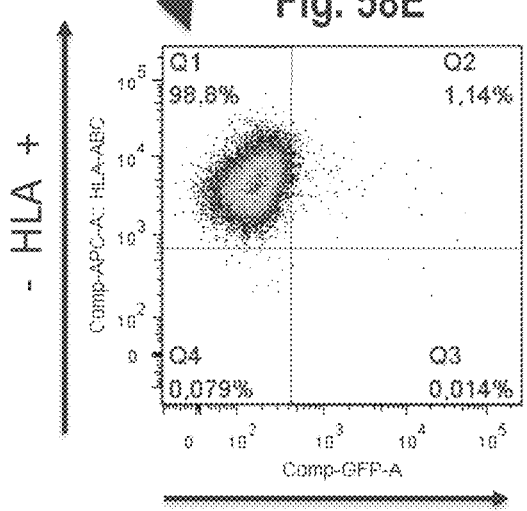
Figure 58F:
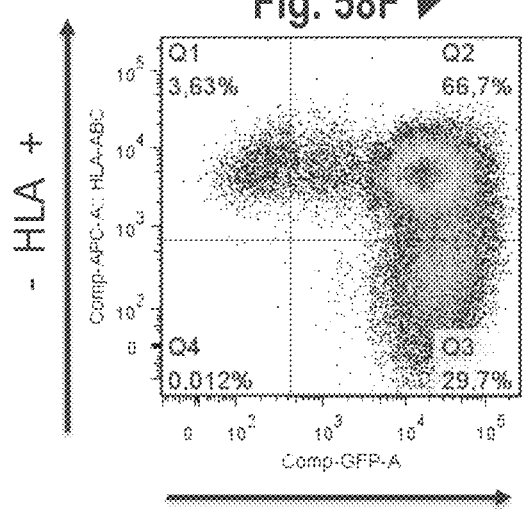

FIGS. 58A-58F show the results of flow cytometry assays in which T cells were treated (FIG. 58A-58F) or not ("untreated", FIG. 58A) with a mixture of GFP-NLS, a CRISPR/Cpf1-NLS complex designed to cleave the B2M genomic DNA sequence, and the shuttle agent FSD18. FIGS. 58B and 58C show the results of a two-dimensional flow cytometry analysis 5 h after treatment based on GFP fluorescence (x-axis) and cell surface HLA expression (y-axis). Fluorescence-activated cell sorting (FIG. 58D) of cells based on their GFP-fluorescence into a GFP-negative fraction (FIG. 58E) and a GFP-positive fraction (FIG. 58F) resulted in an increase in the proportion of genome-edited (HLA-negative) cells to 29.7% in the GFP-positive fraction (FIG. 58F). Each cell fraction was then subjected to a standard T7E1 cleavage assay followed by agarose gel electrophoresis to evaluate the effectiveness of the genome editing. The results are shown in FIG. 58G, wherein thin dashed arrows indicate the bands corresponding to the target gene, and thicker solid arrows indicate the bands corresponding to the CRISPR system-mediated cleavage products of this target gene. The values at the bottom of lanes 2, 3 and 4 correspond to the relative signal intensities (%) of the cleavage product bands (solid arrows) in that lane.

Figure 59A:
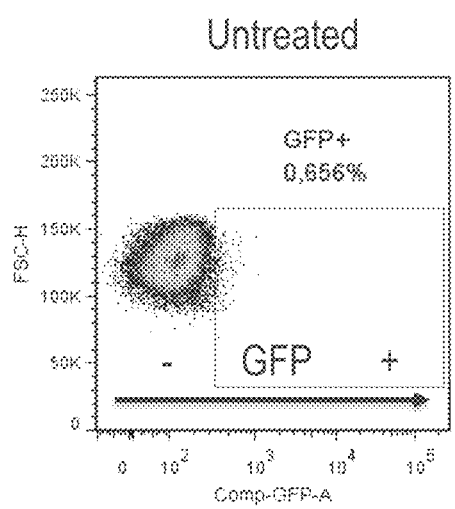
Figure 59B:
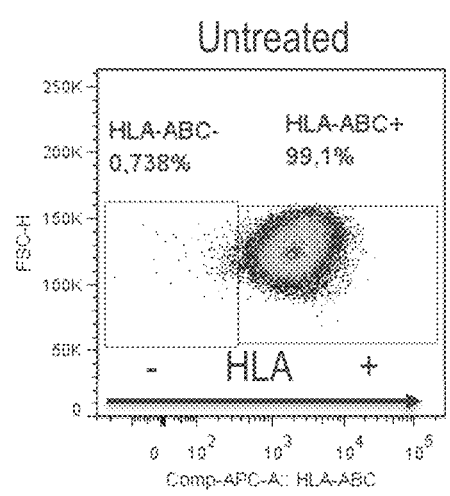

FIGS. 59A-59E show the results of flow cytometry assays in which T cells were treated (FIG. 59C-59E) or not ("untreated", FIGS. 59A and 59B) with a mixture GFP-NLS, a CRISPR/Cpf1-NLS complex designed to cleave the endogenous B2M gene, and the shuttle agent FSD18. FIGS. 59A and 59B, show the results of "untreated" negative control cells not exposed to the peptide shuttle agent, GFP, nor CRISPR/Cpf1, which were analyzed by flow cytometry for GFP fluorescence (FIG. 59A) and cell surface HLA expression (FIG. 59B). T cells were co-transduced with both GFP-NLS and CRISPR/Cpf1 via the peptide FSD18, and the resulting GFP fluorescence distribution is shown in FIG. 59C. The two gates shown in FIG. 59C indicate the fraction of cells that were considered to be GFP-positive ("GFP+"; 93.2%; solid gate) and the sub-fraction of cells that were considered as exhibiting high GFP fluorescence ("GFP high"; 33.1%; dotted gate). Fluorescence-activated cell sorting was performed to quantify the level of cell surface HLA expression in cells considered to be GFP-positive (FIG. 59D) as compared to cells considered as exhibiting high GFP fluorescence (FIG. 59E). The above co-transduction experiment was repeated using 12 μM or 15 μM FSD18, followed by fluorescence-activated cell sorting into GFP-positive and GFP-negative cell fractions. Each fraction was subjected to a standard T7E1 cleavage assay, and the different samples were subjected to agarose gel electrophoresis.

FIG. 60 shows the results of a flow cytometry analysis in which T cells were subjected to a first transduction (FIG. 60B) or not ("untreated", FIG. 60A) with the cargo GFP-NLS using the peptide FSD18. The first transduction resulted in a GFP-NLS transduction efficiency of 55.4% (FIG. 60B). Fluorescence-activated cell sorting was performed to isolate GFP-negative cells (FIG. 60C) following the first transduction, and this GFP-negative cell population was subjected to a second transduction with GFP-NLS using the peptide FSD18. The results from this second transduction are shown in FIG. 60D, in which the GFP-NLS transduction efficiency was found to be 60.6%.

SEQUENCE LISTING

This application contains a Sequence Listing in computer readable form amended Feb. 24, 2022 having a size of about 5 MB. The computer readable form is incorporated herein by reference.

| SEQ ID NO: | Description |
| --- | --- |
| 1 | CM18 |
| 2 | Diphtheria toxin T domain (DT) |
| 3 | GALA |
| 4 | PEA |
| 5 | INF-7 |
| 6 | LAH4 |
| 7 | HGP |
| 8 | H5WYG |
| 9 | HA2 |
| 10 | EB1 |
| 11 | VSVG |
| 12 | Pseudomonas toxin |
| 13 | Melittin |
| 14 | KALA |
| 15 | JST-1 |
| 16 | SP |
| 17 | TAT |
| 18 | Penetratin (Antennapedia) |
| 19 | pVEC |
| 20 | M918 |
| 21 | Pep-1 |
| 22 | Pep-2 |
| 23 | Xentry |
| 24 | Arginine stretch |
| 25 | Transportan |
| 26 | SynB1 |
| 27 | SynB3 |
| 28 | E1a |
| 29 | SV40 T-Ag |
| 30 | c-myc |
| 31 | Op-T-NLS |
| 32 | Vp3 |
| 33 | Nucleoplasmin |
| 34 | Histone 2B NLS |
| 35 | Xenopus N1 |
| 36 | PARP |
| 37 | PDX-1 |
| 38 | QKI-5 |
| 39 | HCDA |
| 40 | H2B |
| 41 | v-Rel |
| 42 | Amida |
| 43 | RanBP3 |
| 44 | Pho4p |
| 45 | LEF-1 |
| 46 | TCF-1 |
| 47 | BDV-P |
| 48 | TR2 |
| 49 | SOX9 |
| 50 | Max |
| 51 | Mitochondrial signal sequence from Tim9 |
| 52 | Mitochondrial signal sequence from Yeast cytochrome c oxidase subunit IV |
| 53 | Mitochondrial signal sequence from 18S rRNA |
| 54 | Peroxisome signal sequence—PTS1 |
| 55 | Nucleolar signal sequence from BIRC5 |
| 56 | Nucleolar signal sequence from RECQL4 |
| 57 | CM18-TAT |
| 58 | CM18-Penetratin |
| 59 | His-CM18-TAT |
| 60 | GFP |
| 61 | TAT-GFP |
| 62 | GFP-NLS |
| 63 | C(LLKK)3C |
| 64 | G(LLKK)3G |
| 65 | PTD4 |
| 66 | TAT-CM18 |
| 67 | TAT-KALA |
| 68 | His-CM18-PTD4 |
| 69 | His-CM18-9Arg |
| 70 | His-CM18-Transportan |
| 71 | His-LAH4-PTD4 |
| 72 | His-C(LLKK)3C-PTD4 |
| 73 | mCherryTM-NLS |
| 74 | Cas9-NLS |
| 75 | crRNA (Example 13.3) |
| 76 | tracrRNA (Example 13.3) |
| 77 | Feldan tracrRNA (Example 13.5, 13.6) |
| 78 | PPIB crRNA (Example 13.5) |
| 79 | Dharmacon tracrRNA (Example 13.5) |
| 80 | HOXB4-WT |
| 81 | His-PTD4 |
| 82 | PTD4-KALA |
| 83 | 9Arg-KALA |
| 84 | Pep1-KALA |
| 85 | Xentry-KALA |
| 86 | SynB3-KALA |
| 87 | VSVG-PTD4 |
| 88 | EB1-PTD4 |
| 89 | JST-PTD4 |
| 90 | CM18-PTD4 |
| 91 | 6Cys-CM18-PTD4 |
| 92 | CM18-L1-PTD4 |
| 93 | CM18-L2-PTD4 |
| 94 | CM18-L3-PTD4 |
| 95 | His-CM18-TAT |
| 96 | His-CM18-PTD4-6Cys |
| 97 | 3His-CM18-PTD4 |
| 98 | 12His-CM18-PTD4 |
| 99 | HA-CM18-PTD4 |
| 100 | 3HA-CM18-PTD4 |
| 101 | CM18-His-PTD4 |
| 102 | His-CM18-PTD4-His |
| 103 | HPRT crRNA (Example 13.6) |
| 104-129 | FSD1-FSD26 |
| 130-137 | FSN1-FSN8 |
| 138-153 | FSD27-FSD42 |
| 154 | Short DNA template |
| 155 | Cpf1-NLS |

-continued

| SEQ ID NO: | Description |
|---|---|
| 156 | GFP coding DNA template |
| 157 | DNMT1 crRNA |
| 158 | LKLWXRXLKXXXXG motif |
| 159 | RRXXAKXA motif |
| 160 | B2M crRNA (Cas9) |
| 161 | B2M exon 2 crRNA-1 (Cpf1) |
| 162 | B2M exon 2 crRNA-2 (Cpf1) |
| 163 | CBLB crRNA |
| 164 | GSK3 crRNA |
| 165 | NKG2A crRNA |
| 166 | B2M crRNA-E |
| 167 | B2M crRNA-J |
| 168 | B2M crRNA-G |
| 169-242 | FSD43-FSD116 |
| 243-10 242 | Computer-generated peptide variants that respect design parameters described herein |
| 10 243 | GGS |
| 10 244 | |

DETAILED DESCRIPTION

Large-scale screening efforts led to the discovery that domain-based peptide shuttle agents, comprising an endosome leakage domain (ELD) operably linked to a cell penetrating domain (CPD), and optionally one or more histidine-rich domains, can increase the transduction efficiency of an independent polypeptide cargo in eukaryotic cells, such that the cargo gains access to the cytosol/nuclear compartment (e.g., see Examples 1-15). Conversely, the above screening efforts also revealed some peptides having no or low polypeptide cargo transduction power, excessive toxicity, and/or other undesirable properties (e.g., poor solubility and/or stability).

Based on these empirical data (both positive and negative), the amino acid sequences and properties of successful, less successful, and failed peptides were compared in order to better understand the physicochemical properties common to the more successful shuttle agents. This comparison involved two main approaches: First, manually stratifying the different screened peptides according to their transduction performance, based on our complied biological characterization data; and second, a more simplified "transduction score" approach, which considered only the transduction efficiency and cellular toxicity of the different peptides, for a given polypeptide cargo and cell line.

For manual stratification, the screened peptides were evaluated individually according to their transduction performance, with due consideration to, for example: their solubility/stability/ease of synthesis; their ability to facilitate escape of endosomally-trapped calcein (e.g., see Example 2); their ability to deliver one or more types of independent polypeptide cargos intracellularly, as evaluated by flow cytometry (e.g., see Examples 3-6 and 8-15) in different types of cells and cell lines (e.g., primary, immortalized, adherent, suspension, etc.) as well as under different transduction protocols; their ability to deliver polypeptide cargos to the cytosol and/or nucleus, as evaluated by fluorescence microscopy (e.g., for fluorescently labelled cargos), increased transcriptional activity (e.g., for transcription factor cargos), or genome editing capabilities (e.g., for nuclease cargos or genome-editing complexes such as CRISPR/Cas9 or CRISPR/Cpf1) (e.g., see Examples 3-6 and 8-15), and toxicity towards different types of cells and cell lines (e.g., primary, immortalized, adherent, suspension, etc.), under different transduction protocols.

For the "transduction score" approach, each peptide was assigned a score corresponding to a given cell line and fluorescently-labelled polypeptide cargo, which combines both transduction efficiency and cellular toxicity data into a single numerical value. The transduction scores were calculated by simply multiplying the highest percentage transduction efficiency observed by flow cytometry for a given peptide, cargo and cell type by the percentage cellular viability for the peptide in the tested cell line. The peptides were then sorted according to their transduction scores as a screening tool to stratify peptides as successful, less successful, or failed shuttle agents.

The above-mentioned manual curation and "transduction score"-based analyses revealed a number of parameters that are generally shared by successful domain-based shuttle agents (e.g. see Example A). These parameters were then successfully used to manually design new peptide shuttle agents having polypeptide cargo transduction activity, which lack and/or are not based on known putative CPDs and/or ELDs (e.g., see Example B). Furthermore, it was observed that peptides satisfying the most number of design parameters had generally the highest transduction scores, while peptides satisfying the least number of design parameters had generally the lowest transduction scores. The design parameters described herein were further validated by testing a plurality of synthetic peptides whose amino acid sequences were generated using a machine learning algorithm (e.g., see Example C.1), the algorithm having been "trained" using transduction efficiency and cellular toxicity data of domain-based peptides (but not the design parameters described herein). Interestingly, the peptides generated by the machine learning algorithm demonstrating the highest transduction scores were generally peptides that satisfied all of the design parameters described herein, thereby substantiating their use in actively designing and/or predicting the transduction activity of new peptide shuttle agents (e.g., tailored to particular polypeptide cargos and/or types of cells). Furthermore, computer-assisted random peptide sequence generation followed by descriptors filtering was used to generate a list of 10 000 peptide variants that respect nearly all of the design parameters described herein (see Example C.2).

Rationally-designed peptide shuttle agents are shown herein to facilitate escape of an endosomally trapped fluorescent dye, suggesting endosomolytic activity (e.g., see Example D). Furthermore, the ability of rationally-designed peptide shuttle agents to transduce a variety of polypeptide cargos (e.g., fluorescent proteins, transcription factors, antibodies, as well as entire CRISPR-associated genome editing complexes, with or without a DNA template) in a variety of different cell types (both adherent and suspension) is also shown herein (e.g., see Examples E-G).

Rational Design Parameters and Peptide Shuttle Agents

In some aspects, the present description relates to a method for delivering a polypeptide cargo from an extracellular space to the cytosol and/or nucleus of a target eukaryotic cell. The method comprises contacting the target eukaryotic cell with the polypeptide cargo in the presence of a shuttle agent at a concentration sufficient to increase the transduction efficiency of said polypeptide cargo, as compared to in the absence of the shuttle agent. In some aspects, the shuttle agent relates to a peptide that satisfies one or more of the following parameters:

(1) In some embodiments, the shuttle agent is a peptide at least 20 amino acids in length. For example, the peptide may comprise a minimum length of 20, 21, 22, 23, 24, 25, 26, 27, 28, 29, or 30 amino acid residues, and a maximum length of 35, 36, 37, 38, 39, 40, 41, 42, 43, 44, 45, 46, 47, 48, 49, 50, 51, 52, 53, 54, 55, 60, 65, 70, 75, 80, 85, 90, 95, 100, 105, 110, 115, 120, 125, 130, 135, 140, 145, or 150 amino acid residues. In some embodiments, shorter peptides (e.g., in the 20-50 amino acid range) may be particularly advantageous because they may be more easily synthesized and purified by chemical synthesis approaches, which may be more suitable for clinical use (as opposed to recombinant proteins that must be purified from cellular expression systems). While numbers and ranges in the present description are often listed as multiples of 5, the present description should not be so limited. For example, the maximum length described herein should be understood as also encompassing a length of 56, 57, 58 . . . 61, 62, etc., in the present description, and that their non-listing herein is only for the sake of brevity. The same reasoning applies to the % of identities listed herein.

(2) In some embodiments, the peptide shuttle agent comprises an amphipathic alpha-helical motif. As used herein, the expression "alpha-helical motif" or "alpha-helix", unless otherwise specified, refers to a right-handed coiled or spiral conformation (helix) having angle of rotation between consecutive amino acids of 100 degrees and/or an alpha-helix having 3.6 residues per turn. As used herein, the expression "comprises an alpha-helical motif" or "an amphipathic alpha-helical motif" and the like, refers to the three-dimensional conformation that a peptide (or segment of a peptide) of the present description is predicted to adopt when in a biological setting based on the peptide's primary amino acid sequence, regardless of whether the peptide actually adopts that conformation when used in cells as a shuttle agent. Furthermore, the peptides of the present description may comprise one or more alpha-helical motifs in different locations of the peptide. For example, the shuttle agent FSD5 is predicted to adopt an alpha-helix over the entirety of its length (see FIG. 49C), while the shuttle agent FSD18 is predicted to comprise two separate alpha-helices towards the N and C terminal regions of the peptide (see FIG. 49D). In some embodiments, the shuttle agents of the present description are not predicted to comprise a beta-sheet motif, for example as shown in FIGS. 49E and 49F. Methods of predicting the presence of alpha-helices and beta-sheets in proteins and peptides are well known in the art. For example, one such method is based on 3D modeling using PEP-FOLD™, an online resource for de novo peptide structure prediction (http://bioserv.rpbs.univ-paris-diderot.fr/services/PEP-FOLD/) (Lamiable et al., 2016; Shen et al., 2014; Thevenet et al., 2012). Other methods of predicting the presence of alpha-helices in peptides and protein are known and readily available to the skilled person.

As used herein, the expression "amphipathic" refers to a peptide that possesses both hydrophobic and hydrophilic elements (e.g., based on the side chains of the amino acids that comprise the peptide). For example, the expression "amphipathic alpha helix" or "amphipathic alpha-helical motif" refers to a peptide predicted to adopt an alpha-helical motif having a non-polar hydrophobic face and a polar hydrophilic face, based on the properties of the side chains of the amino acids that form the helix.

(3) In some embodiments, peptide shuttle agents of the present description comprise an amphipathic alpha-helical motif having a positively-charged hydrophilic outer face, such as one that is rich in R and/or K residues. As used herein, the expression "positively-charged hydrophilic outer face" refers to the presence of at least three lysine (K) and/or arginine (R) residues clustered to one side of the amphipathic alpha-helical motif, based on alpha-helical wheel projection (e.g., see FIG. 49A, left panel). Such helical wheel projections may be prepared using a variety of programs, such as the online helical wheel projection tool available at: http://rzlab.ucr.edu/scripts/wheel/wheel.cgi. In some embodiments, the amphipathic alpha-helical motif may comprise a positively-charged hydrophilic outer face that comprises: (a) at least two, three, or four adjacent positively-charged K and/or R residues upon helical wheel projection; and/or (b) a segment of six adjacent residues comprising three to five K and/or R residues upon helical wheel projection, based on an alpha helix having angle of rotation between consecutive amino acids of 100 degrees and/or an alpha-helix having 3.6 residues per turn.

In some embodiments, peptide shuttle agents of the present description comprise an amphipathic alpha-helical motif comprising a hydrophobic outer face, the hydrophobic outer face comprising: (a) at least two adjacent L residues upon helical wheel projection; and/or (b) a segment of ten adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn.

Figure 49A:
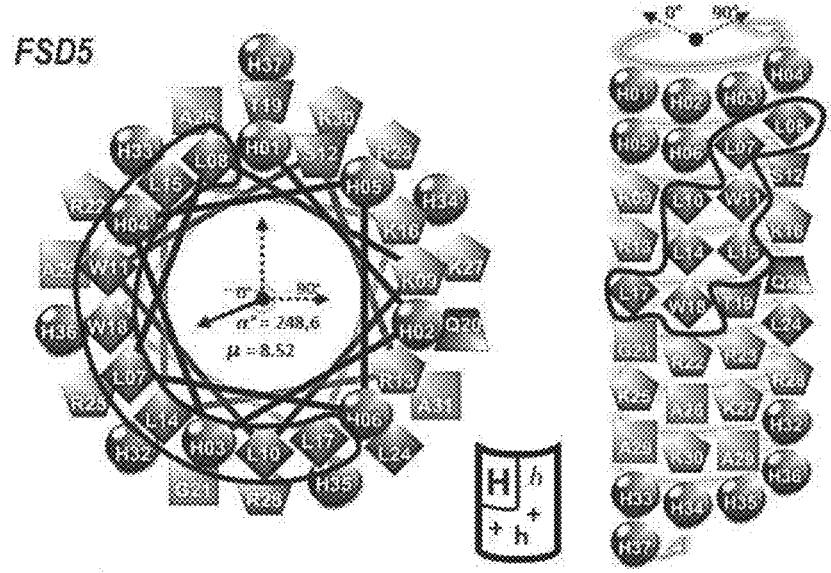
FIGS. 49A and 49B show helical wheel (left panels) and "open cylinder" (right panels) representations of the peptides FSD5 and VSVG-PTD4, respectively. The geometrical shape of each amino acid residue corresponds to its biochemical property based on the residue's side chain (i.e., hydrophobicity, charge, or hydrophilicity). One of the main differences between the two opened cylindrical representations of FSD5 and VSVG-PTD4 is the presence of a highly hydrophobic core in FSD5 (outlined in FIG. 49A, left and right panels), which is not present in VSVG-PTD4. The cylinder in the lower middle panels of FIGS. 49A and 49B represent simplified versions of the opened cylindrical representations in the right panels, in which: "H" represents the high hydrophobic surface area; "h" represents low hydrophobic surface area; "+" represents positively charged residues; and "h" represent hydrophilic residues.

(4) In some embodiments, peptide shuttle agents of the present description comprise an amphipathic alpha-helical motif having a highly hydrophobic core composed of spatially adjacent highly hydrophobic residues (e.g., L, I, F, V, W, and/or M). In some embodiments, the highly hydrophobic core may consist of spatially adjacent L, I, F, V, W, and/or M amino acids representing 12 to 50% of the amino acids of the peptide, calculated while excluding any histidine-rich domains (see below), based on an open cylindrical representation of the alpha-helix having 3.6 residues per turn, as shown for example in FIG. 49A, right panel. In some embodiments, the highly hydrophobic core may consist of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%, 40%, or 45% of the amino acids of the peptide. More particularly, highly hydrophobic core parameter may be calculated by first arranging the amino acids of the peptide in an opened cylindrical representation, and then delineating an area of contiguous highly hydrophobic residues (L, I, F, V, W, M), as shown in FIG. 49A, right panel. The number of highly hydrophobic residues comprised in this delineated highly hydrophobic core is then divided by the total amino acid length of the peptide, excluding any histidine-rich domains (e.g., N- and/or C-terminal histidine-rich domains). For example, for the peptide shown in FIG. 49A, there are 8 residues in the delineated highly hydrophobic core, and 25 total residues in the peptide (excluding the terminal 12 histidines). Thus, the highly hydrophobic core is 32% (8/25).

(5) Hydrophobic moment relates to a measure of the amphiphilicity of a helix, peptide, or part thereof, calculated from the vector sum of the hydrophobicities of the side chains of the amino acids (Eisenberg et al., 1982). An online tool for calculating the hydrophobic moment of a polypeptide is available from: http://rzlab.ucr.edu/scripts/wheel/wheel.cgi. A high hydrophobic moment indicates strong amphiphilicity, while a low hydrophobic moment indicates poor amphiphilicity. In some embodiments, peptide shuttle agents of the present description may consist of or comprise a peptide or alpha-helical domain having have a hydrophobic moment ($\mu$) of 3.5 to 11. In some embodiments, the shuttle agent may be a peptide comprising an amphipathic alpha-helical motif having a hydrophobic moment between a lower limit of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, 10.5, 10.6, 10.7, 10.8, 10.9, or 11.0. In some embodiments, the shuttle agent may be a peptide having a hydrophobic moment between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9, 10.0, 10.1, 10.2, 10.3, 10.4, or 10.5. In some embodiments, the hydrophobic moment is calculated excluding any histidine-rich domains that may be present in the peptide.

(6) In some embodiments, peptide shuttle agents of the present description may have a predicted net charge of at least+4 at physiological pH, calculated from the side chains of K, R, D, and E residues. For example, the net charge of the peptide may be at least+5, +6, +7, at least+8, at least+9, at least+10, at least+11, at least+12, at least+13, at least +14, or at least+15 at physiological pH. These positive charges are generally conferred by the greater presence of positively-charged lysine and/or arginine residues, as opposed to negatively charged aspartate and/or glutamate residues.

(7) In some embodiments, peptide shuttle agents of the present description may have a predicted isoelectric point ($\mu$I) of 8 to 13, preferably from 10 to 13. Programs and methods for calculating and/or measuring the isoelectric point of a peptide or protein are known in the art. For example, pI may be calculated using the Prot Param software available at: http://web.expasy.org/protparam/

(8) In some embodiments, peptide shuttle agents of the present description may be composed of 35 to 65% of hydrophobic residues (A, C, G, I, L, M, F, P, W, Y, V). In particular embodiments, the peptide shuttle agents may be composed of 36% to 64%, 37% to 63%, 38% to 62%, 39% to 61%, or 40% to 60% of any combination of the amino acids: A, C, G, I, L, M, F, P, W, Y, and V.

(9) In some embodiments, peptide shuttle agents of the present description may be composed of 0 to 30% of neutral hydrophilic residues (N, Q, S, T). In particular embodiments, the peptide shuttle agents may be composed of 1% to 29%, 2% to 28%, 3% to 27%, 4% to 26%, 5% to 25%, 6% to 24%, 7% to 23%, 8% to 22%, 9% to 21%, or 10% to 20% of any combination of the amino acids: N, Q, S, and T.

(10) In some embodiments, peptide shuttle agents of the present description may be composed of 35 to 85% of the amino acids A, L, K and/or R. In particular embodiments, the peptide shuttle agents may be composed of 36% to 80%, 37% to 75%, 38% to 70%, 39% to 65%, or 40% to 60% of any combination of the amino acids: A, L, K, or R.

(11) In some embodiments, peptide shuttle agents of the present description may be composed of 15 to 45% of the amino acids A and/or L, provided there being at least 5% of L in the peptide. In particular embodiments, the peptide shuttle agents may be composed of 15% to 40%, 20% to 40%, 20 to 35%, or 20 to 30% of any combination of the amino acids: A and L, provided there being at least 5% of L in the peptide.

(12) In some embodiments, peptide shuttle agents of the present description may be composed of 20 to 45% of the amino acids K and/or R. In particular embodiments, the peptide shuttle agents may be composed of 20% to 40%, 20 to 35%, or 20 to 30% of any combination of the amino acids: K and R.

(13) In some embodiments, peptide shuttle agents of the present description may be composed of 0 to 10% of the amino acids D and/or E. In particular embodiments, the peptide shuttle agents may be composed of 5 to 10% of any combination of the amino acids: D and E.

(14) In some embodiments, the absolute difference between the percentage of A and/or L and the percentage of K and/or R in the peptide shuttle agent may be less than or equal to 10%. In particular embodiments, the absolute difference between the percentage of A and/or L and the percentage of K and/or R in the peptide shuttle agent may be less than or equal to 9%, 8%, 7%, 6%, or 5%.

(15) In some embodiments, peptide shuttle agents of the present description may be composed of 10% to 45% of the amino acids Q, Y, W, P, I, S, G, V, F, E, D, C, M, N, T, or H (i.e., not A, L, K, or R). In particular embodiments, the peptide shuttle agents may be composed of 15 to 40%, 20% to 35%, or 20% to 30% of any combination of the amino acids: Q, Y, W, P, I, S, G, V, F, E, D, C, M, N, T, and H.

In some embodiments, peptide shuttle agents of the present description respect at least one, at least two, at least three, at least four, at least five, at least six, at least seven, at least eight, at least nine, at least ten, at least eleven, at least twelve, at leave thirteen, at least fourteen, or all of parameters (1) to (15) described herein. In particular embodiments, peptide shuttle agents of the present description respect all of parameters (1) to (3), and at least six, at least seven, at least eight, at least nine, at least ten, at least eleven, or all of parameters (4) to (15) described herein.

In some embodiments, where a peptide shuttle agent of the present description comprises only one histidine-rich domain, the residues of the one histidine-rich domain may be included in the calculation/assessment of parameters (1) to (15) described herein. In some embodiments, where a peptide shuttle agent of the present description comprises more than one histidine-rich domain, only the residues of one of the histidine-rich domains may be included in the calculation/assessment of parameters (1) to (15) described herein. For example, where a peptide shuttle agent of the present description comprises two histidine-rich domains: a first histidine-rich domain towards the N terminus, and a second histidine-rich domain towards the C terminus, only the first histidine-rich domain may be included in the calculation/assessment of parameters (1) to (15) described herein.

In some embodiments, a machine-learning or computer-assisted design approach may be implemented to generate peptides that respect one or more of parameters (1) to (15)

described herein. Some parameters, such as parameters (1) and (5)-(15), may be more amenable to implementation in a computer-assisted design approach, while structural parameters, such as parameters (2), (3) and (4), may be more amenable to a manual design approach. Thus, in some embodiments, peptides that respect one or more of parameters (1) to (15) may be generated by combining computer-assisted and manual design approaches. For example, multiple sequence alignment analyses of a plurality of peptides shown herein (and others) to function as effective shuttle agents revealed the presence of some consensus sequences—i.e., commonly found patterns of alternance of hydrophobic, cationic, hydrophilic, alanine and glycine amino acids. The presence of these consensus sequences are likely to give rise to structural parameters (2), (3) and (4) being respected (i.e., amphipathic alpha-helix formation, a positively-charged face, and a highly hydrophobic core of 12%-50%). Thus, these and other consensus sequences may be employed in machine-learning and/or computer-assisted design approaches to generate peptides that respect one or of parameters (1)-(15).

Accordingly, in some embodiments, peptide shuttle agents described herein may comprise or consist of the amino acid sequence of:

(a) [X1]-[X2]-(linker)-[X3]-[X4]     (Formula 1);

(b) [X1]-[X2]-[linker]-[X4]-[X3]     (Formula 2);

(c) [X2]-[X1]-[linker]-[X3]-[X4]     (Formula 3);

(d) [X2]-[X1]-[linker]-[X4]-[X3]     (Formula 4);

(e) [X3]-[X4]-[linker]-[X1]-[X2]     (Formula 5);

(f) [X3]-[X4]-[linker]-[X2]-[X1]     (Formula 6);

(g) [X4]-[X3]-[linker]-[X1]-[X2]     (Formula 7); or (h) [X4]-[X3]-[linker]-[X2]-[X1]     (Formula 8), wherein:
[X1] is selected from: 2[Φ]-1[+]-2[Φ]-1[ζ]-1[+]-; 2[Φ]-1[+]-2[Φ]-2[+]-; 1[+]-1[Φ]-1[+]-2[Φ]-1[ζ]-1[+]-; and 1[+]-1[Φ]-1[+]-;
[X2] is selected from: -2[Φ]-1[+]-2[Φ]-2[ζ]; -2[Φ]-1[+]-2[ζ]-2[+]-; -2[Φ]-1[+]-2[Φ]-1[+]-1[ζ]-; -2[Φ]-1[+]-2[Φ]-1[ζ]-1[+]-; -2[Φ]-2[+]-1[ζ]-2[+]-; -2[Φ]-2[+]-1[Φ]-2[ζ]-; -2[Φ]-2[+]-1[Φ]-1[+]-1[ζ]-; and -2[Φ]-2[+]-1[Φ]-1[Φ-1[+]-;
[X3] is selected from: -4[+]-A-; -3[+]-G-A-; -3[+]-A-A-; -2[+]-1[Φ]-1[+]-A-; -2[+]-1[Φ]-G-A-; -2[+]-1[Φ]-A-A-; or -2[+]-A-1[+]-A; -2[+]-A-G-A; -2[+]-A-A-A-; -1[Φ]-3[+]-A-; -1[Φ]-2[+]-G-A-; -1[Φ]-2[+]-A-A-; -1[Φ]-1[+]-1[Φ]-1[+]-A; -1[Φ]-1 [+]-1 [ζ]-G-A; -1 [ζ]-1 [+]-1[Φ]-A-A; -1 [Φ]-1 [+]-A-1 [+]-A; -1 [ζ]-1 [+]-A-G-A; -1 [ζ]-1 [+]-A-A-A; -A-1[+]-A-1[+]-A; -A-1[+]-A-G-A; and -A-1[+]-A-A-A;
[X4] is selected from: -1[ζ]-2A-1[+]-A; -1[ζ]-2A-2[+]; -1[+]-2A-1[+]-A; -1[ζ]-2A-1[+]-1[ζ]-A-1[+]; -1[ζ]-A-1[ζ]-A-1[+]; -2[+]-A-2[+]; -2[+]-A-1[+]-A; -2[+]-A-1[+]-1[ζ]-A-1[+]; -2[+]-1[ζ]-A-1[+]; -1[+]-1[ζ]-A-1[+]-A; -1[+]-1[g-A-2[+]; -1[+]-1[ζ]-A-1[+]-1[ζ]-A-1[+]; -1[+]-2[ζ]-A-1[+]; -1[+]-2[ζ]-2[+]; -1[+]-2[ζ]-1[+]-A; -1[+]-2[Φ-1[+]-1[ζ]-A-1[+]; -1[+]-2[Φ-1[ζ]-A-1[+]; -3[ζ]-2[+]; -3[Φ-1[+]-A; -3[Φ-1[+]-1[ζ]-A-1[+]; -1[ζ]-2A-1[+]-A; -1[ζ]-2A-2[+]; -1[ζ]-2A-1[+]-

1[Q-A-1[+]; -2[+]-A-1[+]-A; -2[+]-1[Φ-1[+]-A; -1[+]-1[ζ]-A-1[+]-A; -1[+]-2A-1[+]-1[ζ]-A-1[+]; and -1[[ζ]-A-1[ζ]-A-1[+]; and
[linker] is selected from: —Gn—; —Sn—; —(GnSn)n—; —(GnSn)nGn—; —(GnSn)nSn—; —(GnSn)nGn(GnSn)n—; and -(GnSn)nSn(GnSn)n—;
wherein: [Φ] is an amino acid which is: Leu, Phe, Trp, lie, Met, Tyr, or Val; [+] is an amino acid which is: Lys or Arg; [ζ] is an amino acid which is: Gln, Asn, Thr, or Ser; A is the amino acid Ala; G is the amino acid Gly; S is the amino acid Ser; and n is an integer from i to 20,1 to 19,1 to 18,1 to 17,1 to 16,1 to 15,1 to 14,1 to 13,1 to 12,1 to 1 11 to 10,1 to 9,1 to 8,1 to 7,1 to 6,1 to 5,1 to 1 to 4, or 1 to 3.

In some embodiments, peptide shuttle agents of the present description may comprise or consist of any one of the amino acid sequences of SEQ ID NOs: 104, 105, 107, 108, 110-131, 133-135, 138, 140, 142, 145, 148, 151, 152, 169-242, and 243-10 242. In some embodiments, peptide shuttle agents of the present description may comprise the amino acid sequence motifs of SEQ ID NOs: 158 and/or 159, which were found in each of peptides FSD5, FSD16, FSD18, FSD19, FSD20, FSD22, and FSD23. In some embodiments, peptide shuttle agents of the present description may comprise the amino acid sequence motif of SEQ ID NO: 158 operably linked to the amino acid sequence motif of SEQ ID NO: 159. In some embodiments, peptide shuttle agents of the present description may comprise or consist of a peptide which is at least 50%, 55%, 60%, 65%, 70%, 75%, 80%, 85%, 90%, or 95% identical to the amino acid sequence of any one of SEQ ID NOs: 104,105,107,108,110-131,133-135,138,140,142,145,148,151,152, 169-242, and 243-10 242, or a functional variant of any one of SEQ ID NOs: 104, 105, 107, 108, 110-131, 133-135, 138, 140, 142, 145, 148, 151, 152, 169-242, and 243-10 242. As used herein, a "functional variant" refers to a peptide having polypeptide cargo transduction activity, which differs from the reference peptide by one or more conservative amino acid substitutions. As used herein, a "conservative amino acid substitution" is one in which one amino acid residue is replaced with another amino acid residue having a similar side chain. Families of amino acid residues having similar side chains have been well defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, peptide shuttle agents of the present description may comprise or consist of the amino acid sequence of any one of SEQ ID NOs: 57-59, 66-72, or 82-102, or a functional variant thereof having at least 65%, 66%, 67%, 68%, 69%, 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to any one of SEQ ID NOs: 57-59, 66-72, or 82-102. In some embodiments, peptide shuttle agents of the present description do not comprise one or more of the amino acid sequences of any one of SEQ ID NOs: 57-59, 66-72, or 82-102.

In some embodiments, shuttle agents of the present description may comprise oligomers (e.g., dimers, trimers, etc.) of peptides described herein. Such oligomers may be constructed by covalently binding the same or different types of shuttle agent monomers (e.g., using disulfide bridges to link cysteine residues introduced into the monomer sequences). In some embodiments, shuttle agents of the present description may comprise an N-terminal and/or a C-terminal cysteine residue.

Histidine-Rich Domains

In some embodiments, peptide shuttle agents of the present description may further comprise one or more histidine-rich domains. In some embodiments, the histidine-rich domain may be a stretch of at least 2, at least 3, at least 4, at least 5, or at least 6 amino acids comprising at least 30%, at least 35%, at least 40%, at least 45%, at least 50%, at least 55%, at least 60%, at least 65%, at least 70%, at least 75%, at least 80%, at least 85%, or at least 90% histidine residues. In some embodiments, the histidine-rich domain may comprise at least 2, at least 3, at least 4 at least 5, at least 6, at least 7, at least 8, or at least 9 consecutive histidine residues. Without being bound by theory, the histidine-rich domain in the shuttle agent may act as a proton sponge in the endosome through protonation of their imidazole groups under acidic conditions of the endosomes, providing another mechanism of endosomal membrane destabilization and thus further facilitating the ability of endosomally-trapped cargos to gain access to the cytosol. In some embodiments, the histidine-rich domain may be located at or towards the N and/or C terminus of the peptide shuttle agent.

Linkers

In some embodiments, peptide shuttle agents of the present description may comprise one or more suitable linkers (e.g., flexible polypeptide linkers). In some embodiments, such linkers may separate two or more amphipathic alpha-helical motifs (e.g., see the shuttle agent FSD18 in FIG. 49D). In some embodiments, linkers can be used to separate two more domains (CPDs, ELDs, or histidine-rich domains) from one another. In some embodiments, linkers may be formed by adding sequences of small hydrophobic amino acids without rotatory potential (such as glycine) and polar serine residues that confer stability and flexibility. Linkers may be soft and allow the domains of the shuttle agents to move. In some embodiments, prolines may be avoided since they can add significant conformational rigidity. In some embodiments, the linkers may be serine/glycine-rich linkers (e.g., GGS, GGSGGGS (SEQ ID NO: 10 243), GGSGGGSGGGS (SEQ ID NO: 10 244), or the like). In some embodiments, the use shuttle agents comprising a suitable linker may be advantageous for delivering an independent polypeptide cargo to suspension cells, rather than to adherent cells. In some embodiments, the linker may comprise or consist of: —Gn—; —Sn—; —(GnSn)n—; —(GnSn)nGn—; —(GnSn)nSn—; -(GnSn)nGn(GnSn)n—; or -(GnSn)nSn(GnSn)n—, wherein G is the amino acid Gly; S is the amino acid Ser; and n is an integer from 1 to 5.

Endosome Leakage Domains (ELDs)

In some aspects, peptide shuttle agents of the present description may comprise an endosome leakage domain (ELD) for facilitating endosome escape and access to the cytoplasmic compartment. As used herein, the expression "endosome leakage domain" refers to a sequence of amino acids which confers the ability of endosomally-trapped macromolecules to gain access to the cytoplasmic compartment. Without being bound by theory, endosome leakage domains are short sequences (often derived from viral or bacterial peptides), which are believed to induce destabilization of the endosomal membrane and liberation of the endosome contents into the cytoplasm. As used herein, the expression "endosomolytic peptide" is intended to refer to this general class of peptides having endosomal membrane-destabilizing properties. Accordingly, in some embodiments, synthetic peptide or polypeptide-based shuttle agents of the present description may comprise an ELD which is an endosomolytic peptide. The activity of such peptides may be assessed for example using the calcein endosome escape assays described in Example 2.

In some embodiments, the ELD may be a peptide that disrupts membranes at acidic pH, such as pH-dependent membrane active peptide (PMAP) or a pH-dependent lytic peptide. For example, the peptides GALA and INF-7 are amphiphilic peptides that form alpha helixes when a drop in pH modifies the charge of the amino acids which they contain. More particularly, without being bound by theory, it is suggested that ELDs such as GALA induce endosomal leakage by forming pores and flip-flop of membrane lipids following conformational change due to a decrease in pH (Kakudo, Chaki et al., 2004, Li, Nicol et al., 2004). In contrast, it is suggested that ELDs such as INF-7 induce endosomal leakage by accumulating in and destabilizing the endosomal membrane (El-Sayed, Futaki et al., 2009). Accordingly, in the course of endosome maturation, the concomitant decline in pH causes a change in the conformation of the peptide and this destabilizes the endosome membrane leading to the liberation of the endosome contents. The same principle is thought to apply to the toxin A of *Pseudomonas* (Varkouhi, Scholte et al., 2011). Following a decline in pH, the conformation of the domain of translocation of the toxin changes, allowing its insertion into the endosome membrane where it forms pores (London 1992, O'Keefe 1992). This eventually favors endosome destabilization and translocation of the complex outside of the endosome. The above described ELDs are encompassed within the ELDs of the present description, as well as other mechanisms of endosome leakage whose mechanisms of action may be less well defined.

In some embodiments, the ELD may be an antimicrobial peptide (AMP) such as a linear cationic alpha-helical antimicrobial peptide (AMP). These peptides play a key role in the innate immune response due to their ability to strongly interact with bacterial membranes. Without being bound by theory, these peptides are thought to assume a disordered state in aqueous solution, but adopt an alpha-helical secondary structure in hydrophobic environments. The latter conformation thought to contribute to their typical concentration-dependent membrane-disrupting properties. When accumulated in endosomes at certain concentrations, some antimicrobial peptides may induce endosomal leakage.

In some embodiments, the ELD may be an antimicrobial peptide (AMP) such as Cecropin-A/Melittin hybrid (CM series) peptide. Such peptides are thought to be among the smallest and most effective AMP-derived peptides with membrane-disrupting ability. Cecropins are a family of antimicrobial peptides with membrane-perturbing abilities against both Gram-positive and Gram-negative bacteria. Cecropin A (CA), the first identified antibacterial peptide, is composed of 37 amino acids with a linear structure. Melittin (M), a peptide of 26 amino acids, is a cell membrane lytic factor found in bee venom. Cecropin-melittin hybrid peptides have been shown to produce short efficient antibiotic peptides without cytotoxicity for eukaryotic cells (i.e., non-hemolytic), a desirable property in any antibacterial agent. These chimeric peptides were constructed from various combinations of the hydrophilic N-terminal domain of Cecropin A with the hydrophobic N-terminal domain of Melittin, and have been tested on bacterial model systems. Two 26-mers, CA(1-13)M(1-13) and CA(1-8) M(1-18) (Boman et al., 1989), have been shown to demonstrate a wider spectrum and improved potency of natural Cecropin A without the cytotoxic effects of melittin.

In an effort to produce shorter CM series peptides, the authors of Andreu et al., 1992 constructed hybrid peptides such as the 26-mer (CA(1-8)M(1-18)), and compared them with a 20-mer (CA(1-8)M(1-12)), a 18-mer (CA(1-8)M(1-10)) and six 15-mers ((CA(1-7)M(1-8), CA(1-7)M(2-9), CA(1-7)M(3-10), CA(1-7)M(4-11), CA(1-7)M(5-12), and CA(1-7)M(6-13)). The 20 and 18-mers maintained similar activity comparatively to CA(1-8)M(1-18). Among the six 15-mers, CA(1-7)M(1-8) showed low antibacterial activity, but the other five showed similar antibiotic potency compared to the 26-mer without hemolytic effect. Accordingly, in some embodiments, synthetic peptide or polypeptide-based shuttle agents of the present description may comprise an ELD which is or is from CM series peptide variants, such as those described above.

In some embodiments, the ELD may be the CM series peptide CM18 composed of residues 1-7 of Cecropin-A (KWKLFKKIGAVLKVLTTG) fused to residues 2-12 of Melittin (YGRKKRRQRRR), [C(1-7)M(2-12)]. When fused to the cell penetrating peptide TAT, CM18 was shown to independently cross the plasma membrane and destabilize the endosomal membrane, allowing some endosomally-trapped cargos to be released to the cytosol (Salomone et al., 2012). However, the use of a CM18-TAT11 peptide fused to a fluorophore (atto-633) in some of the authors' experiments, raises uncertainty as to the contribution of the peptide versus the fluorophore, as the use of fluorophores themselves have been shown to contribute to endosomolysis—e.g., via photochemical disruption of the endosomal membrane (Erazo-Oliveras et al., 2014).

In some embodiments, the ELD may be CM18 having the amino acid sequence of SEQ ID NO: 1, or a variant thereof having at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identity to SEQ ID NO: 1 and having endosomolytic activity.

In some embodiments, the ELD may be a peptide derived from the N terminus of the HA2 subunit of influenza hemagglutinin (HA), which may also cause endosomal membrane destabilization when accumulated in the endosome.

In some embodiments, synthetic peptide or polypeptide-based shuttle agents of the present description may comprise an ELD which is or is from an ELD set forth in Table I, or a variant thereof having endosome escape activity and/or pH-dependent membrane disrupting activity.

TABLE I

Examples of endosome leakage domains

| Name | Amino acid sequence | SEQ ID NO: | Reference(s) |
|---|---|---|---|
| CM18 | KWKLFKKIGAVLKVLTTG | 1 | (Salomone, Cardarelli et al., 2012) |
| Diphtheria toxin T domain (DT) | VGSSLSCINLDWDVIRDKTKTKIESLKEHGPIKNK MSESPNKTVSEEKAKQYLEEFHQTALEHPELSEL KTVIGINPVFAGANYMWAVNVAQVIDSETADNL EKTTAALSILPGIGSVMGIADGAVHHNTEEIVAQSI ALSSLMVAQAIPLVGELVDIGFAAYNFVESIIN LFQVVHNSYNRPAYSPG | 2 | (Uherek, Fominaya et al., 1998, Glover, Ng et al., 2009) |
| GALA | WEAALAEALAEALAEHLAEALAEALEALAA | 3 | (Parente, Nir et al., 1990) (Li, Nicol et al., 2004) |
| PEA | VLAGNPAKHDLDIKPTVISHRLHFPEGGSLAALTA HQACHLPLETFTRHRQPRGWEQLEQCGYPVQRL VALYLAARLSWNQVDQVIRNALASPGSGG DLGEAIREQPEQARLALT | 4 | (Fominaya and Wels 1996) |
| INF-7 | GLFEAIEGFIENGWEGMIDGWYGC | 5 | (El-Sayed, Futaki et al., 2009) |
| LAH4 | KKALLALALHHLAHLALHLALALKKA | 6 | (Kichler, Mason et al., 2006) Kichler et al., 2003 |
| HGP | LLGRRGWEVLKYWWNLLQYWSQEL | 7 | Kwon et al., 2010 |
| H5WYG | GLFHAIAHFIHGGWHGLIHGWYG | 8 | (Midoux, Kichler et al., 1998) |
| HA2 | GLFGAIAGFIENGWEGMIDGWYG | 9 | (Lorieau, Louis et al., 2010) |
| EB1 | LIRLWSHLIHIWFQNRRLKWKKK | 10 | (Amand, Norden et al., 2012) |
| VSVG | KFTIVFPHNQKGNWKNVPSNYHYCP | 11 | (Schuster, Wu et al., 1999) |
| Pseudomonas toxin | EGGSLAALTAHQACHLPLETFTRHRQPRGWEQL EQCGYPVQRLVALYLAARLSWNQVDQVIRNALAS PGSGGDLGEAIREQPEQARLALTLAAAESERFVR QGTGNDEAGAANAD | 12 | (Fominaya, Uherek et al., 1998) |

TABLE I-continued

Examples of endosome leakage domains

| Name | Amino acid sequence | SEQ ID NO: | Reference(s) |
|---|---|---|---|
| Melittin | GIGAVLKVLTTGLPALISWIKRKRQQ | 13 | Tan, Chen et al., 2012) |
| KALA | WEAKLAKALAKALAKHLAKALAKALKACEA | 14 | (Wyman, Nicol et at, 1997) |
| JST-1 | GLFEALLELLESLWELLLEA | 15 | (Gottschalk, Sparrow et al., 1996) |
| C(LLKK)$_3$C | CLLKKLLKKLLKKC | 63 | (Luan et al., 2014) |
| G(LLKK)$_3$G | GLLKKLLKKLLKKG | 64 | (Luan et al., 2014) |

In some embodiments, shuttle agents of the present description may comprise one or more ELD or type of ELD. More particularly, they can comprise at least 2, at least 3, at least 4, at least 5, or more ELDs. In some embodiments, the shuttle agents can comprise between 1 and 10 ELDs, between 1 and 9 ELDs, between 1 and 8 ELDs, between 1 and 7 ELDs, between 1 and 6 ELDs, between 1 and 5 ELDs, between 1 and 4 ELDs, between 1 and 3 ELDs, etc.

In some embodiments, the order or placement of the ELD relative to the other domains (CPD, histidine-rich domains) within the shuttle agents of the present description may be varied provided the shuttling ability of the shuttle agent is retained.

In some embodiments, the ELD may be a variant or fragment of any one those listed in Table I, and having endosomolytic activity. In some embodiments, the ELD may comprise or consist of the amino acid sequence of any one of SEQ ID NOs: 1-15, 63, or 64, or a sequence which is at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identical to any one of SEQ ID NOs: 1-15, 63, or 64, and having endosomolytic activity.

In some embodiments, shuttle agents of the present description do not comprise one or more of the amino acid sequence of any one of SEQ ID NOs: 1-15, 63, or 64.

Cell Penetration Domains (CPDs)

In some aspects, the shuttle agents of the present description may comprise a cell penetration domain (CPD). As used herein, the expression "cell penetration domain" refers to a sequence of amino acids which confers the ability of a macromolecule (e.g., peptide or protein) containing the CPD to be transduced into a cell.

In some embodiments, the CPD may be (or may be from) a cell-penetrating peptide or the protein transduction domain of a cell-penetrating peptide. Cell-penetrating peptides can serve as carriers to successfully deliver a variety of cargos intracellularly (e.g., polynucleotides, polypeptides, small molecule compounds or other macromolecules/compounds that are otherwise membrane-impermeable). Cell-penetrating peptides often include short peptides rich in basic amino acids that, once fused (or otherwise operably linked) to a macromolecule, mediate its internalization inside cells (Shaw, Catchpole et al., 2008). The first cell-penetrating peptide was identified by analyzing the cell penetration ability of the HIV-1 trans-activator of transcription (Tat) protein (Green and Loewenstein 1988, Vives, Brodin et al., 1997). This protein contains a short hydrophilic amino acid sequence, named "TAT", which promotes its insertion within the plasma membrane and the formation of pores. Since this discovery, many other cell-penetrating peptides have been described. In this regard, in some embodiments, the CPD can be a cell-penetrating peptide as listed in Table II, or a variant thereof having cell-penetrating activity.

TABLE II

Examples of cell-penetrating peptides

| Name | Amino acid sequence | SEQ ID NO: | Reference(s) |
|---|---|---|---|
| SP | AAVALLPAVLLALLAP | 16 | (Mahlum, Mandal et al., 2007) |
| TAT | YGRKKRRQRRR | 17 | (Green and Loewenstein 1988, Fawell, Seery et al., 1994, Vives, Brodin et al., 1997) |
| Penetratin (Antennapedia) | RQIKIWFQNRRMKWKK | 18 | (Perez, Joliot et al., 1992) |
| pVEC | LLIILRRRIRKQAHAHSK | 19 | (Elmquist, Lindgren et al., 2001) |
| M918 | MVTVLFRRLRIRRACGPPRVRV | 20 | (El-Andaloussi, Johansson et al., 2007) |
| Pep-1 | KETWWETWWTEWSQPKKKRKV | 21 | (Morris, Depollier et al., 2001) |
| Pep-2 | KETWFETWFTEWSQPKKKRKV | 22 | (Morris, Chaloin et al., 2004) |
| Xentry | LCLRPVG | 23 | (Montrose, Yang et al., 2013) |

TABLE II-continued

Examples of cell-penetrating peptides

| Name | Amino acid sequence | SEQ ID NO: | Reference(s) |
|---|---|---|---|
| Arginine stretch | RRRRRRRR | 24 | (Zhou, Wu et al., 2009) |
| Transportan | WTLNSAGYLLGKINLKALAALAKKIL | 25 | (Hallbrink, Floren et al., 2001) |
| SynB1 | RGGRLSYSRRRFSTSTGR | 26 | (Drin, Cottin et al., 2003) |
| SynB3 | RRLSYSRRRF | 27 | (Drin, Cottin et al., 2003) |
| PTD4 | YARAAARQARA | 65 | (Ho et al, 2001) |

Without being bound by theory, cell-penetrating peptides are thought to interact with the cell plasma membrane before crossing by pinocytosis or endocytosis. In the case of the TAT peptide, its hydrophilic nature and charge are thought to promote its insertion within the plasma membrane and the formation of a pore (Herce and Garcia 2007). Alpha helix motifs within hydrophobic peptides (such as SP) are also thought to form pores within plasma membranes (Veach, Liu et al., 2004).

In some embodiments, shuttle agents of the present description may comprise one or more CPD or type of CPD. More particularly, they may comprise at least 2, at least 3, at least 4, or at least 5 or more CPDs. In some embodiments, the shuttle agents can comprise between 1 and 10 CPDs, between 1 and 6 CPDs, between 1 and 5 CPDs, between 1 and 4 CPDs, between 1 and 3 CPDs, etc.

In some embodiments, the CPD may be TAT having the amino acid sequence of SEQ ID NO: 17, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to SEQ ID NO: 17 and having cell penetrating activity; or Penetratin having the amino acid sequence of SEQ ID NO: 18, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 85%, 86%, 87%, 88%, 89%, 90%, 91%, 92%, 93%, 94%, or 95% identity to SEQ ID NO: 18 and having cell penetrating activity.

In some embodiments, the CPD may be PTD4 having the amino acid sequence of SEQ ID NO: 65, or a variant thereof having at least 70%, 71%, 72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, or 95% identity to SEQ ID NO: 65.

In some embodiments, the order or placement of the CPD relative to the other domains (ELD, histidine-rich domains) within the shuttle agents of the present description may be varied provided the shuttling ability of the shuttle agent is retained.

In some embodiments, the CPD may be a variant or fragment of any one those listed in Table II, and having cell penetrating activity. In some embodiments, the CPD may comprise or consist of the amino acid sequence of any one of SEQ ID NOs: 16-27 or 65, or a sequence which is at least 70%, 71%, 72%, 73%, 74%, 75%, 76%, 77%, 78%, 79%, 80%, 81%, 82%, 83%, 84%, 85%, 86%, 87%, 88%, 89%, 85%, 90%, 91%, 92%, 93%, 94%, or 95% identical to any one of SEQ ID NOs: 16-27 or 65, and having cell penetrating activity.

In some embodiments, shuttle agents of the present description do not comprise any one of the amino acid sequences of SEQ ID NOs: 16-27 or 65.

Cargos

In some aspects, peptide shuttle agents of the present description may be useful for delivering a polypeptide cargo (e.g., an independent polypeptide cargo) from an extracellular space to the cytosol and/or nucleus of a target eukaryotic cell, wherein the synthetic peptide shuttle agent is used at a concentration sufficient to increase the transduction efficiency of said polypeptide cargo, as compared to in the absence of said synthetic peptide shuttle agent. In some embodiments, the polypeptide cargo may be fused to one or more CPDs to further facilitate intracellular delivery. In some embodiments, the CPD fused to the polypeptide cargo may be the same or different from a CPD that may be present in the shuttle agent of the present description. Such fusion proteins may be constructed using standard recombinant technology. In some embodiments, the independent polypeptide cargo may be fused, complexed with, or covalently bound to a second biologically active cargo (e.g., a biologically active polypeptide or compound). Alternatively or simultaneously, the polypeptide cargo may comprise a subcellular targeting domain.

In some embodiments, the polypeptide cargo must be delivered to the nucleus for it to carry out its intended biological effect. One such example is when the cargo is a polypeptide intended for nuclear delivery (e.g., a transcription factor). In this regard, studies on the mechanisms of translocation of viral DNA have led to the identification of nuclear localization signals (NLSs). The NLS sequences are recognized by proteins (importins a and R), which act as transporters and mediators of translocation across the nuclear envelope. NLSs are generally enriched in charged amino acids such as arginine, histidine, and lysine, conferring a positive charge which is partially responsible for their recognition by importins. Accordingly, in some embodiments, the polypeptide cargo may comprise an NLS for facilitating nuclear delivery, such as one or more of the NLSs as listed in Table III, or a variant thereof having nuclear targeting activity. Of course, it is understood that, in certain embodiments, the polypeptide cargo may comprise its natural NLS.

TABLE III

Nuclear localizaion signals

| Name | Amino acid sequence | SEQ ID NO: | Reference(s) |
|---|---|---|---|
| E1a | KRPRP | 28 | (Kohler, Gorlich et al., 2001) |
| SV40 T-Ag | PKKKRKV | 29 | (Lanford, Kanda et al., 1986) |
| c-myc | PAAKRVKLD | 30 | (Makkerh, Dingwall et al., 1996) |
| Op-T-NLS | SSDDEATADSQHAAPPKKKRKV | 31 | (Chan and Jans 1999) |
| Vp3 | KKKRK | 32 | (Nakanishi, Shum et al., 2002) |
| Nucleoplasmin | KRPAATKKAGQAKKKK | 33 | (Fanara, Hodel et al., 2000) |
| Histone 2B NLS | DGKKRKRSRK | 34 | (Moreland, Langevin et al., 1987) |
| Xenopus N1 | VRKKRKTEEESPLKDKDAKKSKQE | 35 | (Kleinschmidt and Seiter 1988) |
| PARP | KRKGDEVDGVDECAKKSKK | 36 | (Schreiber, Molinete et al., 1992) |
| PDX-1 | RRMKWKK | 37 | (Moede, Leibiger et al., 1999) |
| QKI-5 | RVHPYQR | 38 | (Wu, Zhou et al., 1999) |
| HCDA | KRPACTLKPECVQQLLVCSQEAKK | 39 | (Somasekaram, Jarmuz et al., 1999) |
| H2B | GKKRSKA | 40 | (Moreland, Langevin et al., 1987) |
| v-Rel | KAKRQR | 41 | (Gilmore and Temin 1988) |
| Amida | RKRRR | 42 | (Irie, Yamagata et al., 2000) |
| RanBP3 | PPVKRERTS | 43 | (Welch, Franke et al., 1999) |
| Pho4p | PYLNKRKGKP | 44 | (Welch, Franke et al., 1999) |
| LEF-1 | KKKKRKREK | 45 | (Prieve and Waterman 1999) |
| TCF-1 | KKKRRSREK | 46 | (Prieve and Waterman 1999) |
| BDV-P | PRPRKIPR | 47 | (Shoya, Kobayashi et al., 1998) |
| TR2 | KDCVINKHHRNRCQYCRLQR | 48 | (Yu, Lee et al., 1998) |
| SOX9 | PRRRK | 49 | (Sudbeck and Scherer 1997) |
| Max | PQSRKKLR | 50 | (Kato, Lee et al., 1992) |

Once delivered to the cytoplasm, recombinant proteins are exposed to protein trafficking system of eukaryotic cells. Indeed, all proteins are synthetized in the cell's cytoplasm and are then redistributed to their final subcellular localization by a system of transport based on small amino acid sequences recognized by shuttle proteins (Karniely and Pines 2005, Stojanovski, Bohnert et al., 2012). In addition to NMSs, other localization sequences can mediate subcellular targeting to various organelles following intracellular delivery of the polypeptide cargos of the present description. Accordingly, in some embodiments, polypeptide cargos of the present description may comprise a subcellular localization signal for facilitating delivery of the shuttle agent and cargo to specific organelles, such as one or more of the sequences as listed in Table IV, or a variant thereof having corresponding subcellular targeting activity.

TABLE IV

Subcellular localization signals

| Name | Amino acid sequence | SEQ ID NO: | Reference(s) |
|---|---|---|---|
| Mitochondrial signal sequence from Tim9 | NLVERCFTD | 51 | (Milenkovic, Ramming et al., 2009) |
| Mitochondrial signal sequence from Yeast cytochrome c oxidase subunit IV | MLSLRQSIRFFK | 52 | (Hurt, Pesold-Hurt et al., 1985) |
| Mitochondrial signal sequence from 18S rRNA | MLISRCKWSRFPGNQR | 53 | (Bejarano and Gonzalez 1999) |

TABLE IV-continued

Subcellular localization signals

| Name | Amino acid sequence | SEQ ID NO: | Reference(s) |
|---|---|---|---|
| Peroxisome signal sequence-PTS1 | SKL | 54 | (Gould, Keller et al., 1989) |
| Nucleolar signal sequence from BIRC5 | MQRKPTIRRKNLRLRRK | 55 | (Scott, Boisvert et al., 2010) |
| Nucleolar signal sequence from RECQL4 | KQAWKQKWRKK | 56 | (Scott, Boisvert et al., 2010) |

In some embodiments, the cargo can be a biologically active compound such as a biologically active (recombinant) polypeptide (e.g., a transcription factor, a cytokine, or a nuclease) intended for intracellular delivery. As used herein, the expression "biologically active" refers to the ability of a compound to mediate a structural, regulatory, and/or biochemical function when introduced in a target cell.

In some embodiments, the cargo may be a recombinant polypeptide intended for nuclear delivery, such as a transcription factor. In some embodiments, the transcription factor can be HOXB4 (Lu, Feng et al., 2007), NUP98-HOXA9 (Takeda, Goolsby et al., 2006), Oct3/4, Sox2, Sox9, Klf4, c-Myc (Takahashi and Yamanaka 2006), MyoD (Sung, Mun et al., 2013), Pdx1, Ngn3 and MafA (Akinci, Banga et al., 2012), Blimp-1 (Lin, Chou et al., 2013), Eomes, T-bet (Gordon, Chaix et al., 2012), FOXO3A (Warr, Binnewies et al., 2013), NF-YA (Dolfini, Minuzzo et al., 2012), SALL4 (Aguila, Liao et al., 2011), ISL1 (Fonoudi, Yeganeh et al., 2013), FoxA1 (Tan, Xie et al., 2010), Nanog, Esrrb, Lin28 (Buganim et al., 2014), HIF1-alpha (Lord-Dufour et al., 2009), Hlf, Runx1t1, Pbx1, Lmo2, Zfp37, Prdm5 (Riddell et al., 2014), or Bcl-6 (Ichii, Sakamoto et al., 2004).

In some embodiments, the cargo may be a recombinant polypeptide intended for nuclear delivery, such as a nuclease useful for genome editing technologies. In some embodiments, the nuclease may be an RNA-guided endonuclease, a CRISPR endonuclease, a type I CRISPR endonuclease, a type II CRISPR endonuclease, a type III CRISPR endonuclease, a type IV CRISPR endonuclease, a type V CRISPR endonuclease, a type VI CRISPR endonuclease, CRISPR associated protein 9 (Cas9), Cpf1 (Zetsche et al., 2015), CasX and/or CasY (Burstein et al., 2016) a zinc-finger nuclease (ZFN), a Transcription activator-like effector nuclease (TALEN) (Cox et al., 2015), a homing endonuclease, a meganuclease, a DNA-guided nuclease such as Natronobacterium gregoryi Argonaute (NgAgo; Gao et al., 2016), or any combination thereof. In some embodiments, the nuclease may be a catalytically dead endonuclease, such as a catalytically dead CRISPR associated protein 9 (dCas9), dCpf1, dCasX, dCasY, or any combination thereof. Other nucleases not explicitly mentioned here may nevertheless be encompassed in the present description. In some embodiments, the nuclease may be fused to a nuclear localization signal (e.g., Cas9-NLS; Cpf1-NLS; ZFN-NLS; TALEN-NLS). In some embodiments, the nuclease may be complexed with a nucleic acid (e.g., one or more guide RNAs, a crRNA, a tracrRNAs, or both a crRNA and a tracrRNA). In some embodiments, the nuclease may possess DNA or RNA— binding activity, but may lack the ability to cleave DNA.

In some embodiments, the shuttle agents of the present description may be used for intracellular delivery (e.g., nuclear delivery) of one or more CRISPR endonucleases, for example one or more of the CRISPR endonucleases described below.

Type I and its subtypes A, B, C, D, E, F and I, including their respective Cas1, Cas2, Cas3, Cas4, Cas6, Cas7 and Cas8 proteins, and the signature homologs and subunits of these Cas proteins including Cse1, Cse2, Cas7, Cas5, and Cas6e subunits in E. coli (type I-E) and Csy1, Csy2, Csy3, and Cas6f in Pseudomonas aeruginosa (type I-F) (Wiedenheft et al., 2011; Makarova et al, 2011). Type 11 and its subtypes A, B, C, including their respective Cas1, Cas2 and Cas9 proteins, and the signature homologs and subunits of these Cas proteins including Csn complexes (Makarova et al, 2011). Type III and its subtypes A, B and MTH326-like module, including their respective Cas1, Cas2, Cas6 and Cas10 proteins, and the signature homologs and subunits of these Cas proteins including Csm and CMR complexes (Makarova et al, 2011). Type IV represents the Csf3 family of Cas proteins. Members of this family show up near CRISPR repeats in Acidithiobacillus ferrooxidans ATCC 23270, Azoarcus sp. (strain EbNI), and Rhodoferax ferrireducens (strain DSM 15236/ATCC BAA-621/T118). In the latter two species, the CRISPR/Cas locus is found on a plasmid. Type V and it subtypes have only recently been discovered and include Cpf1, C2cl, and C2c3. Type VI includes the enzyme C2c2, which reported shares little homology to known sequences.

In some embodiments, the shuttle agents of the present description may be used in conjunction with one or more of the nucleases, endonucleases, RNA-guided endonuclease, CRISPR endonuclease described above, for a variety of applications, such as those described herein. CRISPR systems interact with their respective nucleic acids, such as DNA binding, RNA binding, helicase, and nuclease motifs (Makarova et al, 2011; Barrangou & Marraffini, 2014). CRISPR systems may be used for different genome editing applications including:

a Cas-mediated genome editing method conducting to non-homologous end-joining (NHEJ) and/or Homologous-directed recombination (HDR) (Cong et al, 2013);

a catalytically dead Cas (dCas) that can repress and/or activate transcription initiation when bound to promoter sequences, to one or several gRNA(s) and to a RNA polymerase with or without a complex formation with others protein partners (Bikard et al, 2013);

a catalytically dead Cas (dCas) that can also be fused to different functional proteins domains as a method to bring enzymatic activities at specific sites of the genome including transcription repression, transcription activation, chromatin remodeling, fluorescent reporter, histone modification, recombinase system acetylation, methylation, ubiquitylation, phosphorylation, sumoylation, ribosylation and citrullination (Gilbert et al, 2013).

The person of ordinary skill in the art will understand that the present shuttle agents, although exemplified with Cas9 and Cpf1 in the present examples, may be used with other nucleases as described herein. Thus, nucleases such as Cpf1, Cas9, and variants of such nucleases or others, are encompassed by the present description. It should be understood that, in one aspect, the present description may broadly cover any cargo having nuclease activity, such an RNA-guided endonuclease, or variants thereof (e.g., those that can bind to DNA or RNA, but have lost their nuclease activity; or those that have been fused to a transcription factor).

In some embodiments, the polypeptide cargo may be a cytokine such as a chemokine, an interferon, an interleukin, a lymphokine, or a tumour necrosis factor. In some embodiments, the polypeptide cargo may be a hormone or growth factor. In some embodiments, the cargo may be an antibody (e.g., a labelled antibody, a therapeutic antibody, an anti-apoptotic antibody, an antibody that recognizes an intracellular antigen). In some embodiments, the cargo may be a detectable label (fluorescent polypeptide or reporter enzyme) that is intended for intracellular delivery, for example, for research and/or diagnostic purposes.

In some embodiments, the cargo may be a globular protein or a fibrous protein. In some embodiments, the cargo may have a molecule weight of any one of about 5, 10, 15, 20, 25, 30, 35, 40, 45, to 50 to about 150, 200, 250, 300, 350, 400, 450, 500 kDa or more. In some embodiments, the cargo may have a molecule weight of between about 20 to 200 kDa.

In some embodiments, the polypeptide cargo may be a peptide cargo, such as peptide that recognizes an intracellular molecule.

In some embodiments, the polypeptide cargo may be an enzyme and/or an enzyme inhibitor.

In some embodiments, peptide shuttle agents of the present description may be useful for delivering a polypeptide cargo from an extracellular space to the cytosol and/or nucleus of different types of target eukaryotic cells, wherein the synthetic peptide shuttle agent is used at a concentration sufficient to increase the transduction efficiency of said polypeptide cargo, as compared to in the absence of said synthetic peptide shuttle agent. The target eukaryotic cells may be an animal cell, a mammalian cell, or a human cell. In some embodiments, the target eukaryotic cells may be a stem cell (e.g., embryonic stem cells, pluripotent stem cells, induced pluripotent stem cells, neural stem cells, mesenchymal stem cells, hematopoietic stem cells, peripheral blood stem cells), a primary cell (e.g., myoblast, fibroblast), or an immune cell (e.g., NK cell, T cell, dendritic cell, antigen presenting cell). It will be understood that cells that are often resistant or not amenable to protein transduction may be interesting candidates for the synthetic peptides or polypeptide-based shuttle agents of the present description.

Non-Toxic, Metabolizable Shuttle Agents

In some embodiments, the shuttle agents of the present description may be non-toxic to the intended target eukaryotic cells at concentrations up to 50 µM, 45 µM, 40 µM, 35 µM, 30 µM, 25 µM, 20 µM, 15 µM, 10 µM, 9 µM, 8 µM, 7 µM, 6 µM, 5 µM, 4 µM, 3 µM, 2 µM, 1 µM, 0.5 µM 0.1 µM, or 0.05 µM. Cellular toxicity of shuttle agents of the present description may be measured using any suitable method. Furthermore, transduction protocols may be adapted (e.g., concentrations of shuttle and/or cargo used, shuttle/cargo exposure times, exposure in the presence or absence of serum), to reduce or minimize toxicity of the shuttle agents, and/or to improve/maximize transfection efficiency.

In some embodiments, shuttle agents of the present description may be readily metabolizable by intended target eukaryotic cells. For example, the shuttle agents may consist entirely or essentially of peptides or polypeptides, for which the target eukaryotic cells possess the cellular machinery to metabolize/degrade. Indeed, the intracellular half-life of the synthetic peptides and polypeptide-based shuttle agents of the present description is expected to be much lower than the half-life of foreign organic compounds such as fluorophores. However, fluorophores can be toxic and must be investigated before they can be safely used clinically (Alford et al., 2009). In some embodiments, shuttle agents of the present description may be suitable for clinical use. In some embodiments, the shuttle agents of the present description may avoid the use of domains or compounds for which toxicity is uncertain or has not been ruled out.

Cocktails

In some embodiments, the present description relates to a composition comprising a cocktail of at least 2, at least 3, at least 4, or at least 5 different types of the synthetic peptides or polypeptide-based shuttle agents as defined herein. In some embodiments, combining different types of synthetic peptides or peptide shuttle agents (e.g., different shuttle agents comprising different types of domains) may provide increased versatility for delivering different polypeptide cargos intracellularly. Furthermore, without being bound by theory, combining lower concentrations of different types of shuttle agents may help reduce cellular toxicity associated with using a single type of shuttle agent (e.g., at higher concentrations).

Methods, Kits, Uses and Cells

In some embodiments, the present description relates to methods for delivering a polypeptide cargo from an extracellular space to the cytosol and/or nucleus of a target eukaryotic cell. The methods comprise contacting the target eukaryotic cell with the polypeptide cargo in the presence of a shuttle agent at a concentration sufficient to increase the transduction efficiency of said polypeptide cargo, as compared to in the absence of said shuttle agent. In some embodiments, contacting the target eukaryotic cell with the polypeptide cargo in the presence of the shuttle agent results in an increase in the transduction efficiency of said polypeptide cargo by at least 10-fold, 20-fold, 30-fold, 40-fold, 50-fold, or 100-fold, as compared to in the absence of said shuttle agent.

In some embodiments, the present description relates to a method for increasing the transduction efficiency of a polypeptide cargo to the cytosol of a target eukaryotic cell. As used herein, the expression "increasing transduction efficiency" refers to the ability of a shuttle agent of the present description to improve the percentage or proportion of a population of target cells into which a cargo of interest (e.g., a polypeptide cargo) is delivered intracellularly across the plasma membrane. Immunofluorescence microscopy, flow cytometry, and other suitable methods may be used to assess cargo transduction efficiency. In some embodiments, a shuttle agent of the present description may enable a transduction efficiency of at least 25%, 30%, 35%, 40%, 45%, 50%, 55%, 60%, 65%, 70%, 75%, 80%, or 85%, for example as measure by immunofluorescence microscopy, flow cytometry, FACS, and other suitable methods. In some embodiments, a shuttle agent of the present description may enable one of the aforementioned transduction efficiencies together wish a cell viability of at least 25%, 30%, 35%, 40%, 45%, 50%, 55%, 60%, 65%, 70%, 75%, 80%, 85%, 90%, or 95%, for example as measure by the assay described in Example 3.3a, or by another suitable assay known in the art.

In addition to increasing target cell transduction efficiency, shuttle agents of the present description may facilitate the delivery of a cargo of interest (e.g., a polypeptide cargo) to the cytosol of target cells. In this regard, efficiently delivering an extracellular cargo to the cytosol of a target cell using peptides can be challenging, as the cargo often becomes trapped in intracellular endosomes after crossing the plasma membrane, which may limit its intracellular availability and may result in its eventual metabolic degradation. For example, use of the protein transduction domain from the HIV-1 Tat protein has been reported to result in massive sequestration of the cargo into intracellular vesicles. In some aspects, shuttle agents of the present description may facilitate the ability of endosomally-trapped cargo to escape from the endosome and gain access to the cytoplasmic compartment. In this regard, the expression "to the cytosol" in the phrase "increasing the transduction efficiency of an independent polypeptide cargo to the cytosol," is intended to refer to the ability of shuttle agents of the present description to allow an intracellularly delivered cargo of interest to escape endosomal entrapment and gain access to the cytoplasmic compartment. After a cargo of interest has gained access to the cytosol, it may be subsequently targeted to various subcellular compartments (e.g., nucleus, nucleolus, mitochondria, peroxisome). In some embodiments, the expression "to the cytosol" is thus intended to encompass not only cytosolic delivery, but also delivery to other subcellular compartments that first require the cargo to gain access to the cytoplasmic compartment.

In some embodiments, the methods of the present description are in vitro methods. In other embodiments, the methods of the present description are in vivo methods.

In some embodiments, the methods of the present description may comprise contacting the target eukaryotic cell with the shuttle agent, or composition as defined herein, and the polypeptide cargo. In some embodiments, the shuttle agent, or composition may be pre-incubated with the polypeptide cargo to form a mixture, prior to exposing the target eukaryotic cell to that mixture. In some embodiments, the type of shuttle agent may be selected based on the amino acid sequence of the polypeptide cargo to be delivered intracellularly. In other embodiments, the type of shuttle agent may be selected to take into account the amino acid sequence of the polypeptide cargo to be delivered intracellularly, the type of cell, the type of tissue, etc.

In some embodiments, the method may comprise multiple treatments of the target cells with the shuttle agent, or composition (e.g., 1, 2, 3, 4 or more times per day, and/or on a pre-determined schedule). In such cases, lower concentrations of the shuttle agent, or composition may be advisable (e.g., for reduced toxicity). In some embodiments, the cells may be suspension cells or adherent cells. In some embodiments, the person of skill in the art will be able to adapt the teachings of the present description using different combinations of shuttles, domains, uses and methods to suit particular needs of delivering a polypeptide cargo to particular cells with a desired viability.

In some embodiments, the methods of the present description may apply to methods of delivering a polypeptide cargo intracellularly to a cell in vivo. Such methods may be accomplished by parenteral administration or direct injection into a tissue, organ, or system.

In some embodiments, the shuttle agent, or composition, and the polypeptide cargo may be exposed to the target cell in the presence or absence of serum. In some embodiments, the method may be suitable for clinical or therapeutic use.

In some embodiments, the present description relates to a kit for delivering a polypeptide cargo from an extracellular space to the cytosol and/or nucleus of a target eukaryotic cell. In some embodiments, the present description relates to a kit for increasing the transduction efficiency of a polypeptide cargo to the cytosol of a target eukaryotic cell. The kit may comprise the shuttle agent, or composition as defined herein, and a suitable container.

In some embodiments, the target eukaryotic cells may be an animal cell, a mammalian cell, or a human cell. In some embodiments, the target eukaryotic cells may be a stem cell (e.g., embryonic stem cells, pluripotent stem cells, induced pluripotent stem cells, neural stem cells, mesenchymal stem cells, hematopoietic stem cells, peripheral blood stem cells), a primary cell (e.g., myoblast, fibroblast), or an immune cell (e.g., NK cell, T cell, dendritic cell, antigen presenting cell). In some embodiments, the present description relates to an isolated cell comprising a synthetic peptide or polypeptide-based shuttle agent as defined herein. In some embodiments, the cell may be a protein-induced pluripotent stem cell. It will be understood that cells that are often resistant or not amenable to protein transduction may be interesting candidates for the synthetic peptides or polypeptide-based shuttle agents of the present description.

In some embodiments, the present description relates to a method for producing a synthetic peptide shuttle agent that delivers a polypeptide cargo from an extracellular space to the cytosol and/or nucleus of a target eukaryotic cell, the method comprising synthesizing a peptide which is:

(1) a peptide at least 20 amino acids in length comprising
(2) an amphipathic alpha-helical motif having
(3) a positively-charged hydrophilic outer face, and a hydrophobic outer face, wherein at least five of the following parameters (4) to (15) are respected:
(4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
(5) the peptide has a hydrophobic moment ($\mu$) of 3.5 to 11;
(6) the peptide has a predicted net charge of at least+4 at physiological pH;
(7) the peptide has an isoelectric point ($\mu$I) of 8 to 13;
(8) the peptide is composed of 35% to 65% of any combination of the amino acids: A, C, G, I, L, M, F, P, W, Y, and V;
(9) the peptide is composed of 0% to 30% of any combination of the amino acids: N, Q, S, and T;
(10) the peptide is composed of 35% to 85% of any combination of the amino acids: A, L, K, or R;
(11) the peptide is composed of 15% to 45% of any combination of the amino acids: A and L, provided there being at least 5% of L in the peptide;
(12) the peptide is composed of 20% to 45% of any combination of the amino acids: K and R;
(13) the peptide is composed of 0% to 10% of any combination of the amino acids: D and E;
(14) the difference between the percentage of A and L residues in the peptide (% A+L), and the percentage of K and R residues in the peptide (% K+R), is less than or equal to 10%; and

(15) the peptide is composed of 10% to 45% of any combination of the amino acids: Q, Y, W, P, I, S, G, V, F, E, D, C, M, N, T, and H.

In some embodiments, the present description relates to a method for identifying a shuttle agent that delivers a polypeptide cargo from an extracellular space to the cytosol and/or nucleus of a target eukaryotic cell, the method comprising: (a) synthesizing a peptide which is the peptide as defined herein; (b) contacting the target eukaryotic cell with the polypeptide cargo in the presence of said peptide; (c) measuring the transduction efficiency of the polypeptide cargo in the target eukaryotic cell; and (d) identifying the peptide as being a shuttle agent that transduces the polypeptide cargo, when an increase in the transduction efficiency of said polypeptide cargo in the target eukaryotic cell is observed.

In some embodiments, the present description relates to a genome editing system comprising: (a) the shuttle agent as defined herein; (b) a CRISPR-associated endonuclease; and (c) one or more guide RNAs. In some embodiments, the genome editing system may further comprise a linear DNA template for controlling the genome editing.

Genome Editing for Improved Cell Therapy

In some embodiments, the shuttle agents, synthetic peptides, compositions, and methods described herein may be used for transducing genome-editing complexes (e.g., the CRISPR-based genome editing complexes) to genetically engineer cells for improved cell therapy, as compared to native cells or unengineered cells. Such improvements may include, for example, reducing the immunogenicity of the engineered cells and/or improving the activity/efficacy of the engineered cells.

Particularly attractive immune cells for genome engineering may be natural killer (NK) cells, given their natural ability to recognize and kill tumor cells. Accordingly, in some embodiments, the present description relates to the use of the shuttle agents, synthetic peptides, compositions, and methods described herein for transducing genome-editing complexes (e.g., the CRISPR-based genome editing complexes) to genetically engineer NK (or other immune cells that would benefit from the same modifications) for improved cell-based immunotherapy. For example, the present description may relate to the intracellular delivery of one or more CRISPR-based genome editing complexes that comprise a guide RNA and/or linear DNA template targeting the CBLB gene, c-CBL gene, GSK3 gene, ILT2 gene, CISH gene, NKG2a gene, B2M gene, or any combination thereof. Such gene targets may potentiate NK-mediated cellular cytotoxicity following knockout, as discussed below.

1. NKG2A (KLRC1, CD159A, Killer Cell Lectin-Like Receptor C1)

CD94/NKG2A acts as an MHC class-I specific NK inhibitory receptor (Braud et al., 1998; Lee et al., 1998). It is expressed by a subset of NK cells known as $CD56^{bright}$ $CD16^{dim}$(10% of peripheral NK), which are typically less cytotoxic (Cooper et al., 2001; Poli et al., 2009). NKG2A ligands are the non-classical MHC class-I HLA-E molecules that are expressed in every human cell. The recognition of HLA-E by the NKG2A receptor is part of the "self-tolerance" mechanism (also including KIR receptors), resulting in negative modulation of NK cell cytotoxicity (Lee et al., 1998).

There exists clinical evidence demonstrating the role of non-classical HLA class I, mainly HLA-E and HLA-G (see ILT-2 target), in evading immune surveillance resulting in higher cancer relapses and decrease overall survival following surgery (de Kruijf et al., 2010; Levy et al., 2008; Ye et al., 2007a; Yie et al., 2007b; Yie et al., 2007c; Yie et al., 2007d; Guo et al., 2015; Ishigami et al., 2015; Zhen et al., 2013). The use of NKG2A-KO NK cells during adoptive cell therapy may counteract the presence of HLA-E molecules (membrane-bound or solubles) in tumor microenvironment. In addition, NK cells expanded from IL15 or IL21-expressing K562 feeder cells lead to a high percentage of $NKG2A^{pos}$ cells (Denman et al., 2012), and it may be desirable to knockout this inhibitory receptor during the expansion process. Furthermore, the results in Example G.9 demonstrate that NKG2A-KO NK92 cells are significantly more cytotoxic against IFN-gamma-treated HeLa cells.

2. ILT2 (Ig-Like transcript 2 gene)

ILT2 is an inhibitory receptor expressed on several immune cells, including NK cells (Kirwan et al., 2005). The ligands for this receptor are HLA-G molecules, which are naturally expressed only in thymus and trophoblasts. However, many tumors gain the capacity to express HLA-G to escape immune cell attack by inhibition through ILT2 receptor activation. In fact, $NKL^{ILT2}$-cells are more potent than parental NKL against HLA-G-overexpressing K562 cells (Wu et al., 2015). Moreover, overexpression of HLA-G in OVCAR-3 cancer cells impaired NK cell-mediated cytotoxicity (Lin et al., 2007). As for HLA-E, expression of HLA-G on cancer cells is generally associated with poor prognosis.

3. c-Cbl and Cbl-b (Casitas B-lineage lymphoma proto-oncogene family).

These genes (from the Casitas B-lineage lymphoma proto-oncogene, Cbl family) encode for E3 ligases, which are function in the protein ubiquitylation pathway (regulation of cellular protein content). E3 ligases catalyze the formation of a covalent bond between Ub (ubiquitin) and specific lysine residues on targeted proteins (more than thousand E3 ligases in mammalians). Cbl family members are involved in negative regulation of signaling by receptor tyrosine kinases on immune cells by binding and ubiquitylating phosphorylated receptor and adaptors (Liu et al., 2014; utz-Nicoladoni, 2015). One demonstrated that both c-cbl and Cbl-b ubiquitylate phosphorylated LAT adaptor. Phosphorylation of LAT following NK cell activation is required to recruit other mediators, especially PLC-<<<and siRNA-mediated c-cbl and Cbl-b knockdown increased NK cell activity against B cell lymphoma 721.221-Cw4 (Matalon et al., 2016).

Others identified TAM (Tyro3, Axl, Mer) receptors as targets for Cbl-b ubiquitylation (Paolino et al., 2014). However, assuming that TAM receptors are proposed to negatively regulate NK cells, Cbl-b knockout should rather be associated to a decrease in NK cell activity. Therefore, TAM receptors may be considered as a good target to enhance NK cells but unlikely via Cbl-b knockout.

In vivo studies demonstrated that $Cbl-b^{-/-}$ mice prevent primary tumor growth (Loeser et al., 2007). In addition, NK cells isolated from these mice have increased proliferation and IFN-production when activated (Paolino et al., 2014).

4. GSK3B (Glycogen Synthase Kinase Beta)

GSK3b is a Ser/Thr kinase involved in several cellular functions, such as proliferation, apoptosis, inflammatory response, stress, and others (Patel et al., 2017). Inhibition of GSK3b (using small inhibitors) in NK cells leads to increase cytotoxicity (likely through IFN-g, TNF-<production, 2B4 stimulation and up-regulation of LFA-1) against AML (OCI-AML3) (Parameswaran et al., 2016; Aoukaty et al., 2005). We have recently demonstrated that the GSK3<inhibitor, SB216763, enhances the cytotoxic activity of NK92 against HeLa cells (data not shown). This effect is increased by co-incubation with IL-15.

5. CISH (Cytokine-inducible SH2-containing protein)

CIS protein is a member of the suppressor of cytokine signaling (SOCS) proteins, which bind to phosphorylated JAKs and inhibit JAK-STAT signaling pathways. Recently, Cish$^{-/-}$ mice demonstrated that CIS is a key suppressor of IL15 signaling in NK cells (Delconte et al., 2016). Following IL15 exposure, these cells have prolonged IL15 responses, an elevated IFN-g production, and an increased cytotoxic potential. Moreover, there is a clear relationship between IL15 responsiveness and NKG2D-dependent cytotoxicity (Horng et al., 2007).

In clinical trials, co-injection of cytokines, such as IL2 and IL15, during adoptive NK-cell therapy is strongly recommended to sustain NK cell activity. However, such a co-injection induces serious side effects to patients. The use of IL15-hypersensitive NK cells (CISH knockout) would benefit the treatment.

In some embodiments, disrupting the B2M gene encoding 32 microglobulin (B2M), a component of MHC class I molecules, may substantially reduce the immunogenicity of every cell expressing MHC class 1. In other aspects, the genome of NK cells can be modified after the delivery of a genome editing system as described herein. More specifically, the cytotoxicity of NK cells can be improved after the delivery of a genome editing system targeting specific putative targets that may potentiate NK-mediated cellular cytotoxicity such as the NKG2A, ILT2, c-Cbl, Cbl-b, GSK3B and CISH genes.

Co-Transduction with a Polypeptide Cargo of Interest and a Marker Protein

The ability of domain-based and rationally-designed peptide shuttle agents to co-transduce two different polypeptide cargos into a population of target eukaryotic cells has been demonstrated herein and in PCT patent application publication No. WO/2016/161516. Example I of the present description shows that co-transducing a polypeptide cargo of interest (e.g., a CRISPR-endonuclease) and an independent marker protein (e.g., GFP) in a population of target eukaryotic cells may not necessarily increase the overall transduction efficiency of the polypeptide cargo of interest. However, it was surprisingly discovered that a strikingly high proportion of target eukaryotic cells that were successfully transduced with the polypeptide cargo of interest, were also successfully transduced with the marker protein. Conversely, a strikingly high proportion of cells that were not transduced with the polypeptide cargo of interest, were also not transduced with the marker protein. Isolating cells positive for the marker protein (e.g., via FACS) resulted in a significant increase in the proportion of cells that were successfully transduced with the polypeptide cargo of interest, and the correlation was found to be concentration dependent in that cell populations exhibiting the highest fluorescence of the marker protein also exhibited the highest proportion of transduction with the polypeptide cargo of interest.

In some aspects, the present description relates to a method for enriching eukaryotic cells transduced with a polypeptide cargo of interest. The method may comprise (a) co-transducing a target eukaryotic cell population with a polypeptide cargo of interest and a marker protein; and (b) isolating or concentrating eukaryotic cells transduced with the marker protein, thereby enriching eukaryotic cells transduced with the polypeptide cargo of interest.

In some embodiments, the marker protein may not be covalently bound to the polypeptide cargo of interest (e.g., the marker protein is independent from the polypeptide cargo of interest), the marker protein may be covalently bound to the polypeptide cargo of interest, the marker protein may be non-covalently bound to the polypeptide cargo of interest (e.g., electrostatically and/or conformationally bound via a protein domain-protein domain interaction), or the marker protein is covalently bound to the polypeptide cargo of interest via a cleavable linker (e.g., a linker peptide comprising an enzyme cleavage site, such as an enzyme expressed in endosomes, lysosomes, or in the cytosol). In some embodiments, the intracellular concentration of the transduced marker protein may be positively correlated with the intracellular concentration of the transduced polypeptide cargo of interest.

In some embodiments, the marker protein may comprise a detectable label. As used herein, "detectable label" refers to a molecule or particle that enables a person of skill in the art to identify and separate cells comprising the label from cells lacking the label. In some embodiments, the marker protein may be a fluorescent protein, a fluorescently-labeled protein, a bioluminescent protein, an isotopically-labelled protein, a magnetically-labeled protein, or another detectable label that enables separation of cells containing the marker protein from cells lacking the marker protein, or enables separation of cells based on the level of intracellular marker protein.

In some embodiments, eukaryotic cells transduced with the marker protein may be isolated or concentrated using flow cytometry, fluorescence-activated cell sorting (FACS), magnetic-activated cell sorting (MACS), or other known cell separation/sorting technologies. Isolating or enriching successfully transduced cells may be particularly advantageous, for example, for polypeptide cargoes such as functional CRISPR-based genome-editing complexes, which may be associated with relatively lower transduction efficiencies.

It was also surprisingly disclosed herein in Example I that cells that were unsuccessfully transduced following a first round of transduction with a polypeptide cargo of interest, may be isolated and re-transduced with the polypeptide cargo of interest in subsequent rounds of transduction. These results suggest that, although the cells unsuccessfully transduced following a first round of transduction with a polypeptide cargo of interest are not necessarily refractory to subsequent transductions.

In some embodiments, the present description relates to a method for enriching eukaryotic cells transduced with a polypeptide cargo of interest, the method comprising: (a) co-transducing a target eukaryotic cell population with a polypeptide cargo of interest and a marker protein; (b) isolating eukaryotic cells transduced with the marker protein from cells lacking the marker protein, thereby producing a marker protein-positive cell population and a marker protein-negative cell population. In some embodiments, steps (a) and (b) may be repeated, one or more times, on the marker protein-negative cell population, on the marker protein-positive cell population, or on both the marker protein-negative and the marker protein-positive cell populations. In some embodiments, the method for enriching eukaryotic cells transduced with a polypeptide cargo of interest may be automated, for example, by isolating cells negative for transduction with the marker protein and re-transducing the marker protein-negative cell population.

In some embodiments, the present description relates to a method for enriching eukaryotic cells transduced with a polypeptide cargo of interest, the method comprising: (a) co-transducing a target eukaryotic cell population with a polypeptide cargo of interest and a marker protein; and (b)

isolating eukaryotic cells transduced with the marker protein based on their intracellular concentration of the marker protein.

In some embodiments, the marker protein described herein may be a protein that stimulates cell proliferation (e.g., a growth factor or a transcription factor), a protein that stimulates cell differentiation, a protein that promotes cell survival, an anti-apoptotic protein, or a protein having another biological activity.

In some embodiments, the polypeptide cargo of interest and the marker protein may be co-transduced by contacting the target eukaryotic cell with the polypeptide cargo and the marker protein in the presence of a peptide transduction agent, wherein the peptide transduction agent is present at a concentration sufficient to increase the transduction efficiency of the polypeptide cargo and the marker protein, as compared to in the absence of said peptide transduction agent. In some embodiments, the peptide transduction agent may be an endosomolytic peptide. In some embodiments, the peptide transduction agent is or comprises a domain-based peptide shuttle agent, or a rationally designed peptide shuttle agent as defined herein, in PCT patent application publication No. WO/2016/161516, and/or U.S. Pat. No. 9,738,687. In some embodiments, the aforementioned domain-based peptide shuttle agent may be a synthetic peptide comprising an endosome leakage domain (ELD) operably linked to a cell penetrating domain (CPD), or an ELD operably linked to a histidine-rich domain and a CPD. In some embodiment, the aforementioned domain-based peptide shuttle agent: (a) comprises a minimum length of 20, 21, 22, 23, 24, 25, 26, 27, 28, 29, or 30 amino acid residues and a maximum length of 35, 40, 45, 50, 55, 65, 70, 75, 80, 85, 90, 95, 100, 105, 110, 115, 120, 125, 130, 135, 140, 145, or 150 amino acid residues; (b) has a predicted net charge of at least+4, +5, +6, +7, +8, +9, +10, +11, +12, +13, +14, or +15 at physiological pH; (c) is soluble in aqueous solution; or (d) any combination of (a) to (c). In some embodiments, the ELD, CPD, histidine-rich domain, linker domain, are as defined herein. In some embodiments, the target eukaryotic cells comprise or consist of animal cells, mammalian cells, human cells, stem cells, primary cells, immune cells, T cells, NK cells, dendritic cells, or other types or sub-types of cells.

In some embodiments, the polypeptide cargo of interest may be: (i) the polypeptide cargo as defined herein; and/or (ii) one or more CRISPR-associated endonucleases alone or with one or more corresponding guide RNA and/or linear DNA templates as defined herein.

Items

In some embodiments, the present description may relate to the following items:

1. A method for delivering a polypeptide cargo from an extracellular space to the cytosol and/or nucleus of a target eukaryotic cell, said method comprising contacting the target eukaryotic cell with the polypeptide cargo in the presence of a shuttle agent at a concentration sufficient to increase the transduction efficiency of said polypeptide cargo, as compared to in the absence of said shuttle agent, wherein said shuttle agent is
   (1) a peptide at least 20 amino acids in length comprising
   (2) an amphipathic alpha-helical motif having
   (3) a positively-charged hydrophilic outer face, and a hydrophobic outer face, wherein at least five of the following parameters (4) to (15) are respected:
   (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
   (5) the peptide has a hydrophobic moment ($\mu$) of 3.5 to 11;
   (6) the peptide has a predicted net charge of at least+4 at physiological pH;
   (7) the peptide has an isoelectric point ($\mu$l) of 8 to 13;
   (8) the peptide is composed of 35% to 65% of any combination of the amino acids: A, C, G, I, L, M, F, P, W, Y, and V;
   (9) the peptide is composed of 0% to 30% of any combination of the amino acids: N, Q, S, and T;
   (10) the peptide is composed of 35% to 85% of any combination of the amino acids: A, L, K, or R;
   (11) the peptide is composed of 15% to 45% of any combination of the amino acids: A and L, provided there being at least 5% of L in the peptide;
   (12) the peptide is composed of 20% to 45% of any combination of the amino acids: K and R;
   (13) the peptide is composed of 0% to 10% of any combination of the amino acids: D and E;
   (14) the difference between the percentage of A and L residues in the peptide (% A+L), and the percentage of K and R residues in the peptide (K+R), is less than or equal to 10%; and
   (15) the peptide is composed of 10% to 45% of any combination of the amino acids: Q, Y, W, P, I, S, G, V, F, E, D, C, M, N, T and H.

2. The method of item 1, wherein the shuttle agent respects at least six, at least seven, at least eight, at least nine, at least ten, at least eleven, or respects all of parameters (4) to (15).

3. The method of item 1 or 2, wherein:
   (i) said shuttle agent is a peptide having a minimum length of 20, 21, 22, 23, 24, 25, 26, 27, 28, 29, or 30 amino acids, and a maximum length of 40, 41, 42, 43, 44, 45, 46, 47, 48, 49, 50, 51, 52, 53, 54, 55, 60, 65, 70, 80, 90, 100, 110, 120, 130, 140, or 150 amino acids;
   (ii) said amphipathic alpha-helical motif has a hydrophobic moment ($\mu$) between a lower limit of 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9,10.0, 10.1,10.2, 10.3,10.4, 10.5,10.6, 10.7,10.8, 10.9, or 11.0;
   (iii) said amphipathic alpha-helical motif comprises a positively-charged hydrophilic outer face comprising: (a) at least two, three, or four adjacent positively-charged K and/or R residues upon helical wheel projection; and/or (b) a segment of six adjacent residues comprising three to five K and/or R residues upon helical wheel projection, based on an alpha helix having angle of rotation between consecutive amino acids of 100 degrees and/or an alpha-helix having 3.6 residues per turn;
   (iv) said amphipathic alpha-helical motif comprises a hydrophobic outer face comprising: (a) at least two adjacent L residues upon helical wheel projection; and/or (b) a segment of ten adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn;

(v) said hydrophobic outer face comprises a highly hydrophobic core consisting of spatially adjacent L, I, F, V, W, and/or M amino acids representing from 12.5%, 13%, 13.5%, 14%, 14.5%, 15%, 15.5%, 16%, 16.5%, 17%, 17.5%, 18%, 18.5%, 19%, 19.5%, or 20%, to 25%, 30%, 35%,40%, or 45% of the amino acids of the peptide;

(vi) said peptide has a hydrophobic moment (μ) between a lower limit of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, and an upper limit of 9.5, 9.6, 9.7, 9.8, 9.9,10.0, 10.1, 10.2,10.3,10.4, or 10.5;

(vii) said peptide has a predicted net charge of between +4, +5, +6, +7, +8, +9, to +10, +11, +12, +13, +14, or +15;

(viii) said peptide has a predicted pI of 10-13; or (ix) any combination of (i) to (viii).

4. The method of any one of items 1 to 3, wherein said shuttle agent respects at least one, at least two, at least three, at least four, at least five, at least six, or all of the following parameters:

(8) the peptide is composed of 36% to 64%, 37% to 63%, 38% to 62%, 39% to 61%, or 40% to 60% of any combination of the amino acids: A, C, G, I, L, M, F, P, W, Y, and V;

(9) the peptide is composed of 1% to 29%, 2% to 28%, 3% to 27%, 4% to 26%, 5% to 25%, 6% to 24%, 7% to 23%, 8% to 22%, 9% to 21%, or 10% to 20% of any combination of the amino acids: N, Q, S, and T;

(10) the peptide is composed of 36% to 80%, 37% to 75%, 38% to 70%, 39% to 65%, or 40% to 60% of any combination of the amino acids: A, L, K, or R;

(11) the peptide is composed of 15% to 40%, 20% to 40%, 20 to 35%, or 20 to 30% of any combination of the amino acids: A and L;

(12) the peptide is composed of 20% to 40%, 20 to 35%, or 20 to 30% of any combination of the amino acids: K and R;

(13) the peptide is composed of 5 to 10% of any combination of the amino acids: D and E;

(14) the difference between the percentage of A and L residues in the peptide (% A+L), and the percentage of K and R residues in the peptide (K+R), is less than or equal to 9%, 8%, 7%, 6%, or 5%; and

(15) the peptide is composed of 15 to 40%, 20% to 35%, or 20% to 30% of any combination of the amino acids: Q, Y, W, P, I, S, G, V, F, E, D, C, M, N, T, and H.

5. The method of any one of items 1 to 4, wherein said peptide comprises a histidine-rich domain.

6. The method of item 5, wherein said histidine-rich domain is:

(i) positioned towards the N terminus and/or towards the C terminus of the peptide;

(ii) is a stretch of at least 3, at least 4, at least 5, or at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, at least 6, at least 7, at least 8, or at least 9 consecutive histidine residues; or (iii) both (i) and (ii).

7. The method of any one of items 1 to 6, wherein said peptide comprises a flexible linker domain rich in serine and/or glycine residues.

8. The method of any one of items 1 to 7, wherein said peptide comprises or consists of the amino acid sequence of: (a) [X1]–[X2]–[linker]–[X3]–[X4](Formula 1); (b) [X1]–[X2]–[linker]–[X4]–[X3](Formula 2); (c) [X2]–[X1]–[linker]–[X3]–[X4](Formula 3); (d) [X2]–[X1]–[linker]–[X4]–[X3](Formula 4); (e) [X3]–[X4]–[linker]–[X1]–[X2](Formula 5); (f) [X3]–[X4]–[linker]–[X2]–[X1](Formula 6); (g) [X4]–[X3]–[linker]–[X1]–[X2](Formula 7); or (h) [X4]–[X3]–[linker]–[X2]–[X1](Formula 8), wherein: [X1]is selected from: 2[Φ]–1[+]–2[Φ]–1[–1[+]–; 2[Φ]–1[+]–2[Φ]–2[+]–; 1[+]–1[Φ]–1[+]–2[Φ]–1[Φ–1[+]–; and 1[+]–1[Φ]–1[+]–2[(V)–2[+]–; [X2]is selected from: –2[Φ]–1[+]–2[Φ]–2[ζ]–; –2[(D)–1[+]–2[Φ]–2[+]–; –2[(t)–1[+]–2[q)]–1[+]–1[ζ]–; –2[Φ]–1[+]–2[Φ]–1[Φ–1[+]–; –2[ζ]–2[+]–1[Φ]–2[+]–; –2[qI]–2[+]–1[Φ]–2[ζ]–; –2[c]–2[+]–1[1]–1[+]–1[Φ]–; and –2[Φ]–2[+]–1[–]–1[Φ–1[+]–; [X3]is selected from: –4[+]–A–; –3[+]–G–A–; –3[+]–A–A–; –2[+]–1[Φ]–1[+]–A–; –2[+]–1[Φ]–G–A–; –2[+]–1[Φ]–A–A–; or –2[+]–A–1[+]–A; –2[+]–A–G–A; –2[+]–A–A–A–; –1[Φ]–3[+]–A–; –1[Φ]–2[+]–G–A–; –1[Φ]–2[+]–A–A–;–1[Φ]–1[+]–1[Φ]–1[+]–A–1[Φ]–1[+]–1[Φ]–G–A;–1[Φ]–i[+]–1[Φ]–A–A; –1[(I]–1[+]–A–1[+]–A; –1[Φ]–1[+]–A–G–A; –1[Φ]–1[+]–A–A–A; –A–1[+]–A–1[+]–A; –A–1[+]–A–G–A; and –A–1[+]–A–A–A; [X4]is selected from: –1[ζ]–2A–1[+]–A; –1[Q–2A–2[+]; –1[+]–2A–1[+]–A; –1[ζ]–2A–1[+]–1[ζ]–A–1[+]; –1[(–A–1[ζ]–A–1[+]; –2[+]–A–2[+]; –2[+]–A–1[+]–A; –2[+]–A–1[+]–1[[ζ]–A–1[+]; –2[+]–1[–A–1 [+]; –1 [+]–1 [ζ]–A–1 [+]–A; –1 [+]–1 [f–A–2[+]; –1 [+]–1 [i;–A–1 [+]–1 [ζ]–A–1 [+]; –1 [+]–2 [Φ]–A–1 [+]; –1 [+]–2[Φ]–2[+]; –1[Φ]2-1 [+]–A; –1 [+]–2[Qj-1 [+]–1 [–A–1 [+]; –1[+]–2[Φ–1[ζ]–A–1 [+]; –3[ζ]–2[+]; –3[ζ]–1[+]–A; –3[ζ]–1[+]–1[ζ]–A–1[+]; –1[ζ]–2A–1[+]–A; –1[ζ]–2A–2[+]; –1[ζ]–2A–1 [+]–1[ζ]–A–1[+]; –2[+]–A–1[+]–A; –2[+]–1[ζ]–1[+]–A; –1[+]–1[ζ]–A–1[+]–A; –1[+]–2A–1[+]–1[ζ]–A–1[+]; and –1[ζ]–A–1[(–A–1[+]; and [linker]is selected from: —Gn—; —Sn—; —(GnSn)n—; —(GnSn)nGn—; —(GnSn)nSn—; —(GnSn)nGn(GnSn)n—; and -(GnSn)nSn(GnSn)n—; wherein: [Φ]is an amino acid which is: Leu, Phe, Trp, IIe, Met, Tyr, or Val; [+]is an amino acid which is: Lys or Arg; [Φ]is an amino acid which is: Gln, Asn, Thr, or Ser; A is the amino acid Ala; G is the amino acid Gly; S is the amino acid Ser; and n is an integer from 1 to 20,1 to 19,1 to 18,1 to 17,1 to 16,1 to 15,1 to 14,1 to 13,1 to 12,1 to 11, 1 to 10, 1 to 9, 1 to 8, 1 to 7, 1 to 6, 1 to 5, 1 to 1 to 4, or 1 to 3.

9. The method of any one of items 1 to 8, wherein:

(i) said peptide is at least 50%, 55%, 60%, 65%, 70%, 75%, 80%, 85%, 90%, or 95% identical to the amino acid sequence of any one of SEQ ID NOs: 104, 105, 107, 108, 110-131, 133-135, 138, 140, 142, 145, 148, 151, 152, 169-242, and 243-10242; or said peptide comprises or consists of a functional variant of any one of SEQ ID NOs: 104, 105,107, 108, 110-131, 133-135, 138,140, 142,145,148,151,152,169-242, and 243-10 242;

(ii) said peptide:

(a) comprises or consists of the amino acid sequence of any one of SEQ ID NOs: 104,105,107,108,110-131,133-135,138,140,142,145,148,151,152,169-242, and 243-10 242;

(b) comprises the amino acid sequence motifs of SEQ ID NOs: 158 and/or 159; or (c) comprises the amino acid sequence motif of SEQ ID NO: 158 operably linked to the amino acid sequence motif of SEQ ID NO: 159; or
(iii) both (i) and (ii).
10. The method of any one of items 1 to 9, wherein the peptide comprises an endosome leakage domain (ELD), and/or a cell penetrating domain (CPD).
11. The method of item 10, wherein:
(i) said ELD is or is from: an endosomolytic peptide; an antimicrobial peptide (AMP); a linear cationic alpha-helical antimicrobial peptide; a Cecropin-A/Melittin hybrid (CM series) peptide; pH-dependent membrane active peptide (PAMP); a peptide amphiphile; a peptide derived from the N terminus of the HA2 subunit of influenza hemagglutinin (HA); CM18; Diphtheria toxin T domain (DT); GALA; PEA; INF-7; LAH4; HGP; H5WYG; HA2; EB1; VSVG; *Pseudomonas* toxin; melittin; KALA; JST-1; C(LLKK)$_3$C; G(LLKK)$_3$G; or any combination thereof;
(ii) said CPD is or is from: a cell-penetrating peptide or the protein transduction domain from a cell-penetrating peptide; TAT; PTD4; Penetratin (Antennapedia); pVEC; M918; Pep-1; Pep-2; Xentry; arginine stretch; transportan; SynB1; SynB3; or any combination thereof; or
(iii) both (i) and (ii).
12. The method of item 10 or 11, wherein said peptide comprises:
(a) an ELD comprising the amino acid sequence of any one of SEQ ID NOs: 1-15, 63, or 64, or a variant or fragment thereof having endosomolytic activity;
(b) a CPD comprising the amino acid sequence of any one of SEQ ID NOs: 16-27 or 65, or a variant or fragment thereof having cell penetrating activity; or
(c) both (a) and (b).
13. The method of any one of items 10 to 12, wherein:
(i) said peptide comprises an ELD which is CM18, KALA, or C(LLKK)3C having the amino acid sequence of SEQ ID NO: 1,14, or 63, or a variant thereof having at least 50%, 55%, 60%, 65%, 70%, 75%, 80%, 85%, 90%, or 95% identity to SEQ ID NO: 1,14, or 63, and having endosomolytic activity;
(ii) wherein said peptide comprises a CPD which is TAT or PTD4 having the amino acid sequence of SEQ ID NO: 17 or 65, or a variant thereof having at least 50%, 55%, 60%, 65%, 70%, 75%, 80%, 85%, 90%, or 95% identity to SEQ ID NO: 17 or 65 and having cell penetrating activity; or
(iii) both (i) and (ii).
14. The method of any one of items 1 to 9, wherein said peptide comprises the amino acid sequence of any one of SEQ ID NOs: 57-59, 66-72, or 82-102, or a functional variant thereof having at least 85%, 90%, or 95% identity to any one of SEQ ID NOs: 57-59, 66-72, or 82-102.
15. The method of any one of items 1 to 14, wherein:
(i) said shuttle agent is completely metabolizable by the target eukaryotic cell; and/or
(ii) contacting the target eukaryotic cell with the polypeptide cargo in the presence of the shuttle agent at said concentration results in an increase in the transduction efficiency of said polypeptide cargo by at least 10-fold, 20-fold, 30-fold, 40-fold, 50-fold, or 100-fold, as compared to in the absence of said shuttle agent.
16. The method of any one of items 1 to 15, which is an in vitro method.
17. A synthetic peptide shuttle agent which is the peptide as defined in any one of items 1 to 15.
18. The synthetic peptide of item 17, which is a peptide between 20 and 100 amino acids in length comprising the amino acid sequence of any one of SEQ ID NOs: 104, 15 0,18 1,11 1,13 1,15 1,17 1,19 2,11 122,123, 124,125, 126,127, 128, 129, 130, 131, 133, 134, 135, 138, 140, 142, 145, 148, 151, 152, 169-242, and 243-10 242; or comprises the amino acid sequence motifs of SEQ ID NOs: 158 and/or 159.
19. The synthetic peptide shuttle agent of item 17 or 18 for use in delivering a polypeptide cargo from an extracellular space to the cytosol and/or nucleus of a target eukaryotic cell in vitro, wherein the synthetic peptide shuttle agent is used at a concentration sufficient to increase the transduction efficiency of said polypeptide cargo, as compared to in the absence of said synthetic peptide shuttle agent..
20. The synthetic peptide shuttle agent of item 17 or 18 for use in delivering a polypeptide cargo from an extracellular space to the cytosol and/or nucleus of a target eukaryotic cell in vivo, wherein the synthetic peptide shuttle agent is used at a concentration sufficient to increase the transduction efficiency of said polypeptide cargo, as compared to in the absence of said synthetic peptide shuttle agent.
21. A composition comprising the shuttle agent as defined in any one of items 1 to 15, or a cocktail of at least 2, at least 3, at least 4, or at least 5 different types of the shuttle agents as defined in any one of items 1 to 15, and a polypeptide cargo to be delivered from an extracellular space to the cytosol and/or nucleus of a target eukaryotic cell.
22. Use of the shuttle agent as defined in any one of items 1 to 15, or the synthetic peptide as defined in item 18, for delivering a polypeptide cargo from an extracellular space to the cytosol and/or nucleus of a target eukaryotic cell, wherein the shuttle agent or synthetic peptide is used at a concentration sufficient to increase the transduction efficiency of said polypeptide cargo, as compared to in the absence of said shuttle agent or synthetic peptide.
23. A kit for delivering a polypeptide cargo from an extracellular space to the cytosol and/or nucleus of a target eukaryotic cell, said kit comprising the shuttle agent as defined in any one of items 1 to 15, or the synthetic peptide as defined in item 18, and a suitable container.
24. The method of any one of items 1 to 16, the synthetic peptide shuttle agent of any one of items 17 to 20, the composition of item 21, the use of item 22, or the kit of item 23, wherein said polypeptide cargo lacks a cell penetrating domain.
25. The method of any one of items 1 to 16, the synthetic peptide shuttle agent of any one of items 17 to 20, the composition of item 21, the use of item 22, or the kit of item 23, wherein said polypeptide cargo comprises a cell penetrating domain.
26. The method of any one of items 1 to 16, 24 or 25, the synthetic peptide shuttle agent of any one of items 17 to 20, 24 or 25, the composition of any one of items 21, 24 or 25, the use of any one of items 22 to 25, wherein said polypeptide cargo comprises a subcellular targeting domain.

27. The method, the synthetic peptide shuttle agent, composition, use, or kit of item 26, wherein said subcellular targeting domain is:
 (a) a nuclear localization signal (NLS);
 (b) a nucleolar signal sequence;
 (c) a mitochondrial signal sequence; or
 (d) a peroxisome signal sequence.
28. The method, the synthetic peptide shuttle agent, composition, use, or kit of item 27, wherein: (a) said NLS is from: E1a, T-Ag, c-myc, T-Ag, op-T-NLS, Vp3, nucleoplasmin, histone 2B, *Xenopus* N1, PARP, PDX-1, QKI-5, HCDA, H2B, v-Rel, Amida, RanBP3, Pho4p, LEF-1, TCF-1, BDV-P, TR2, SOX9, or Max;
 (b) said nucleolar signal sequence is from BIRC5 or RECQL4;
 (c) said mitochondrial signal sequence is from Tim9 or Yeast cytochrome c oxidase subunit IV; or
 (d) said peroxisome signal sequence is from PTS1.
29. The method, the synthetic peptide shuttle agent, composition, use, or kit of any one of items 24 to 29, wherein said polypeptide cargo is complexed with a DNA and/or RNA molecule.
30. The method, the synthetic peptide shuttle agent, composition, use, or kit of any one of items 24 to 29, wherein said polypeptide cargo is a transcription factor, a nuclease, a cytokine, a hormone, a growth factor, an antibody, a peptide cargo, an enzyme, an enzyme inhibitor, or any combination thereof.
31. The method, the synthetic peptide shuttle agent, composition, use, or kit of item 30, wherein:
 (a) said transcription factor is: HOXB4, NUP98-HOXA9, Oct3/4, Sox2, Sox9, Klf4, c-Myc, MyoD, Pdx1, Ngn3, MafA, Blimp-1, Eomes, T-bet, FOX03A, NF-YA, SALL4, ISL1, FoxA1, Nanog, Esrrb, Lin28, HIF1-alpha, Hlf, Runx1t1, Pbx1, Lmo2, Zfp37, Prdm5, Bcl-6, or any combination thereof;
 (b) said nuclease is a catalytically active or catalytically dead: RNA-guided endonuclease, CRISPR endonuclease, type I CRISPR endonuclease, type II CRISPR endonuclease, type Ill CRISPR endonuclease, type IV CRISPR endonuclease, type V CRISPR endonuclease, type VI CRISPR endonuclease, CRISPR associated protein 9 (Cas9), Cpf1, CasY, CasX, zinc-finger nuclease (ZFNs), Transcription activator-like effector nucleases (TALENs), homing endonuclease, meganuclease, DNA-guided nuclease, Natronobacterium gregoryi Argonaute (NgAgo), or any combination thereof;
 (c) said antibody recognizes an intracellular antigen; and/or
 (d) said peptide cargo recognizes an intracellular molecule.
32. The method, the synthetic peptide shuttle agent, composition, use, or kit of any one of items 24 to 31, for use in cell therapy, genome editing, adoptive cell transfer, and/or regenerative medicine.
33. The method, the synthetic peptide shuttle agent, composition, use, or kit of any one of items 24 to 32, wherein said target eukaryotic cell is an animal cell, a mammalian cell, a human cell, a stem cell, a primary cell, an immune cell, a T cell, an NK cell, or a dendritic cell.
34. A eukaryotic cell comprising the shuttle agent as defined in any one of items 1 to 15, the synthetic peptide shuttle agent as defined in item 18, or the composition as defined in item 21.
35. The eukaryotic cell of item 34, which is an animal cell, a mammalian cell, a human cell, a stem cell, a primary cell, an immune cell, a T cell, an NK cell, or a dendritic cell.
36. A method for delivering one or more CRISPR-associated endonucleases alone or with one or more corresponding guide RNA and/or linear DNA templates, to a target eukaryotic cell, said method comprising contacting the target eukaryotic cell with the endonuclease in the presence of a shuttle agent at a concentration sufficient to increase the transduction efficiency of said endonuclease, as compared to in the absence of said shuttle agent, wherein said shuttle agent is as defined in any one of items 1 to 15.
37. The method of item 36, which is an in vitro method, or an in vivo method.
38. The method of item 36 or 37, wherein said one or more endonuclease is: a type I CRISPR endonuclease, a type II CRISPR endonuclease, a type Ill CRISPR endonuclease, a type IV CRISPR endonuclease, a type V CRISPR endonuclease, a type VI CRISPR endonuclease, or any combination thereof.
39. The method of item 36 or 37, wherein said one or more endonuclease is CRISPR associated protein 9 (Cas9), Cpf1, CasX, CasY, or any combination thereof; or a catalytically dead CRISPR associated protein 9 (dCas9), dCpf1, dCasX, dCasY, or any combination thereof.
40. The method of any one of items 36 to 39, wherein said target eukaryotic cell is an animal cell, a mammalian cell, a human cell, a stem cell, a primary cell, an immune cell, a T cell, an NK cell, or a dendritic cell.
41. The method of item 58, wherein said one or more corresponding guide RNA and/or linear DNA template targets one or more genes to reduce the immunogenicity, improve cytotoxicity, and/or otherwise improve the effectiveness of the target eukaryotic cell for cell-based therapy, as compared to a corresponding parent eukaryotic cell that has not been subjected to said method.
42. The method of item 41, wherein said cell-based therapy is cell-based cancer immunotherapy.
43. The method of any one of items 40 to 42, wherein said one or more corresponding guide RNA and/or linear DNA template targets the CBLB gene, c-CBL gene, GSK3 gene, ILT2 gene, CISH gene, NKG2a gene, B2M gene, or any combination thereof.
44. A method for producing a synthetic peptide shuttle agent that delivers a polypeptide cargo from an extracellular space to the cytosol and/or nucleus of a target eukaryotic cell, said method comprising synthesizing a peptide which is:
 (1) a peptide at least 20 amino acids in length comprising
 (2) an amphipathic alpha-helical motif having
 (3) a positively-charged hydrophilic outer face, and a hydrophobic outer face, wherein at least five of the following parameters (4) to (15) are respected:
 (4) the hydrophobic outer face comprises a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
 (5) the peptide has a hydrophobic moment ($\mu$) of 3.5 to 11;
 (6) the peptide has a predicted net charge of at least +4 at physiological pH;

(7) the peptide has an isoelectric point (μI) of 8 to 13;
(8) the peptide is composed of 35% to 65% of any combination of the amino acids: A, C, G, I, L, M, F, P, W, Y, and V;
(9) the peptide is composed of 0% to 30% of any combination of the amino acids: N, Q, S, and T;
(10) the peptide is composed of 35% to 85% of any combination of the amino acids: A, L, K, or R;
(11) the peptide is composed of 15% to 45% of any combination of the amino acids: A and L, provided there being at least 5% of L in the peptide;
(12) the peptide is composed of 20% to 45% of any combination of the amino acids: K and R;
(13) the peptide is composed of 0% to 10% of any combination of the amino acids: D and E;
(14) the difference between the percentage of A and L residues in the peptide (% A+L), and the percentage of K and R residues in the peptide (K+R), is less than or equal to 10%; and
(15) the peptide is composed of 10% to 45% of any combination of the amino acids: Q, Y, W, P, I, S, G, V, F, E, D, C, M, N, T, and H.

45. The method of item 44, wherein the peptide is as defined in any one of items 2 to 15.

46. A method for identifying a shuttle agent that delivers a polypeptide cargo from an extracellular space to the cytosol and/or nucleus of a target eukaryotic cell, said method comprising:
  (a) synthesizing a peptide which is the peptide as defined in any one items 1 to 15 or 18;
  (b) contacting the target eukaryotic cell with the polypeptide cargo in the presence of said peptide;
  (c) measuring the transduction efficiency of the polypeptide cargo in the target eukaryotic cell; and
  (d) identifying the peptide as being a shuttle agent that transduces the polypeptide cargo, when an increase in the transduction efficiency of said polypeptide cargo in the target eukaryotic cell is observed.

47. The method of item 46, wherein said polypeptide cargo is as defined in any one of items 24 to 31.

48. A genome editing system comprising:
  (a) the shuttle agent as defined in any one items 1 to 15 or 18;
  (b) one or more CRISPR-associated endonucleases; and
  (c) one or more guide RNAs.

49. The genome editing system of item 48, further comprising a linear DNA template for controlling the genome editing.

50. The genome editing system of item 48 or 49, wherein said one or more CRISPR-associated endonucleases is: a type I CRISPR endonuclease, a type II CRISPR endonuclease, a type Ill CRISPR endonuclease, a type IV CRISPR endonuclease, a type V CRISPR endonuclease, a type VI CRISPR endonuclease, CRISPR associated protein 9 (Cas9), Cpf1, CasX, CasY, or any combination thereof.

51. A method for enriching eukaryotic cells transduced with a polypeptide cargo of interest, said method comprising:
  (a) co-transducing a target eukaryotic cell population with a polypeptide cargo of interest and a marker protein; and
  (b) isolating or concentrating eukaryotic cells transduced with the marker protein, thereby enriching eukaryotic cells transduced with the polypeptide cargo of interest.

52. The method of item 51, wherein:
  (i) the marker protein is not covalently bound to the polypeptide cargo of interest, the marker protein is covalently bound to the polypeptide cargo of interest, the marker protein is non-covalently bound to the polypeptide cargo of interest, or the marker protein is covalently bound to the polypeptide cargo of interest via a cleavable linker; and/or
  (ii) the marker protein comprises a detectable label, or the marker protein is a fluorescent protein, a fluorescently-labeled protein, a bioluminescent protein, an isotopically-labelled protein, or a magnetically-labeled protein.

53. The method of item 51 or 52, wherein the intracellular concentration of the transduced marker protein is positively correlated with the intracellular concentration of the transduced polypeptide cargo of interest.

54. The method of any one of items 51 to 53, wherein the eukaryotic cells transduced with the marker protein are isolated or concentrated using flow cytometry, fluorescence-activated cell sorting (FACS), or magnetic-activated cell sorting (MACS).

55. The method of any one of items 51 to 54, wherein the eukaryotic cells transduced with the marker protein are isolated or sorted from cells lacking the marker protein, thereby producing a marker protein-positive cell population and/or a marker protein-negative cell population.

56. The method of item 55, further comprising repeating steps (a) and (b), one or more times, on the marker protein-negative cell population, on the marker protein-positive cell population, or on both the marker protein-negative and the marker protein-positive cell populations.

57. The method of any one of items 51 to 56, wherein the eukaryotic cells transduced with the marker protein are isolated or sorted based on their intracellular concentration of the marker protein.

58. The method of any one of items 51 to 57, wherein the marker protein is a protein that stimulates cell proliferation, a protein that stimulates cell differentiation, a protein that promotes cell survival, an anti-apoptotic protein, or a protein having another biological activity.

59. The method of any one of items 51 to 58, wherein the polypeptide cargo of interest and the marker protein are co-transduced by contacting the target eukaryotic cell with the polypeptide cargo and the marker protein in the presence of a peptide transduction agent, wherein the peptide transduction agent is present at a concentration sufficient to increase the transduction efficiency of the polypeptide cargo and the marker protein, as compared to in the absence of said peptide transduction agent.

60. The method of item 59, wherein:
  (a) the peptide transduction agent is an endosomolytic peptide;
  (b) the peptide transduction agent is or comprises the synthetic peptide shuttle agent as defined in item 17 or 18;
  (c) the target eukaryotic cells comprise animal cells, mammalian cells, human cells, stem cells, primary cells, immune cells, T cells, NK cells, or dendritic cells;

(d) the polypeptide cargo of interest is: (i) the polypeptide cargo as defined in any one of items 24 to 31; and/or (ii) one or more CRISPR-associated endonucleases alone or with one or more corresponding guide RNA and/or linear DNA templates as defined in any one of items 38 to 43; or (e) any combination of (a) to (d).

Other objects, advantages and features of the present description will become more apparent upon reading of the following non-restrictive description of specific embodiments thereof, given by way of example only with reference to the accompanying drawings.

EXAMPLES

Example 1

Materials and Methods 1.1 Materials

All chemicals were purchased from Sigma-Aldrich (St. Louis, MO, USA or Oakville, ON, Canada) or equivalent grade from BioShop Canada Inc. (Mississauga, ON, Canada) or VWR (Ville Mont-Royal, QC, Canada), unless otherwise noted. 1.2 Reagents

TABLE 1.1

Reagents

| Material | Company | City, Province-State, Country |
|---|---|---|
| RPMI 1640 media | Sigma-Aldrich | Oakville, ON, Canada |
| DMEM | Sigma-Aldrich | Oakville, ON, Canada |
| Alpha MEM | Stem Cell Technology | Oakville, ON, Canada |
| Fetal bovine serum (FBS) | NorthBio | Toronto, ON, Canada |
| Horse serum | Invitrogen | Burlington, ON, Canada |
| L-glutamine-Penicillin-Streptomycin | Sigma-Aldrich | Oakville, ON, Canada |
| Trypsin-EDTA solution | Sigma-Aldrich | Oakville, ON, Canada |
| Inositol | Sigma-Aldrich | Oakville, ON, Canada |
| Folic acid | Sigma-Aldrich | Oakville, ON, Canada |
| pEGFP-C1 | CLONTECH Laboratories | Palo Alto, CA, USA |
| FITC-Antibody α-tubulin | Abcam ab64503 | Cambridge, MA, USA |
| ITS | Invitrogen/41400-045 | Burlington, ON, Canada |
| FGF 2 | Feldan Bio/1D-07-017 | Quebec, QC, Canada |
| Dexamethasone | Sigma-Aldrich/D8893 | Oakville, ON, Canada |
| Bovine serum albumin (BSA) | Sigma-Aldrich/A-1933 | Oakville, ON, Canada |
| MB1 media | GE Healthcare HyClone | Logan, Utah, USA |
| Calcein | Sigma-Aldrich/C0875 | Oakville, ON, Canada |
| HisTrap ™ FF column | GE Healthcare | Baie d'Urfe, QC, Canada |
| Q Sepharose ™ | GE Healthcare | Baie d'Urfe, QC, Canada |
| SP Sepharose ™ | GE Healthcare | Baie d'Urfe, QC, Canada |
| Amicon Ultra centrifugal filters | EMD Millipore | Etobicoke, ON Canada |
| Label IT ® Cy ®5 kit | Mirus Bio LLC | Madison, WI, USA |
| Calf serum | NorthBio | Toronto, ON, Canada |
| beta-mercaptoethanol | Sigma-Aldrich or Gibco-ThermoFisher | Oakville, ON, Canada |
| IL-2 | Feldan Bio/rhIL-2 Research | Quebec, QC, Canada |
| Resazurin sodium salt | Sigma-Aldrich/R7017-1G | Oakville, ON, Canada |
| Anti-HOXB4 monoclonal antibody | Novus Bio #NBP2-37257 | Oakville, ON, Canada |
| Alexa ™-594 Anti-Mouse | Abcam #150116 | Toronto, ON, Canada |
| Fluoroshield ™ with DAPI | Sigma #F6057 | Oakville, ON, Canada |
| GFP Monoclonal antibody | Feldan Bio #A017 | Quebec, QC, Canada |
| Phusion ™ High-Fidelity DNA polymerase | (NEB #M0530S) | Whitby, ON, Canada |
| Edit-R ™ Synthetic crRNA Positive Controls | (Dharmacon #U-007000-05) | Ottawa, ON, Canada |
| T7 Endonuclease I | (NEB, Cat #M0302S) | Whitby, ON, Canada |
| FastFect ™ transfection reagent | (Feldan Bio #9K-010-0001) | Quebec, QC, Canada |
| Goat Anti-Mouse IgG H&L (Alexa Fluor ®488) | Abcam ab150113 | Toronto, ON, Canada |
| Goat Anti-Rabbit IgG H&L (Alexa Fluor ® 594) | Abcam ab150080 | Toronto, ON, Canada |
| Opti-MEM ™ | Sigma-Aldrich | Oakville, ON, Canada |
| Anti-NUP98 | Abcam #ab50610 | Toronto, ON, Canada |
| PARP (Cleaved) [214/215] Human ELISA Kit | ThermoFisher #KHO0741 | Burlington, ON, Canada |
| Purified Rabbit Anti-Active Caspase-3 | BD Biosciences #559565 | Mississauga, ON, Canada |
| Active Caspace-3 antibody | Cedarlane #AF835 | Burlington, ON, Canada |
| TNF-alpha Antibody | BioVision Inc #3054-100 | Milpitas, CA, USA |
| APC Mouse Anti-Human HLA-ABC | BD Biosciences #555555 | Mississauga, ON, Canada |
| Anti-CD3 | Biolegend#cat: 300438 | San Diego, CA, USA |
| Anti-CD28 | Thermofisher #cat: 16-0289-85 | Burlington, ON, Canada |

1.3 Cell lines eDCu26,T1,M

HeLa, HEK293A, HEK293T, THP-1, CHO, NIH3T3, CA46, Balb3T3, HT2, KMS-12, DOHH2, RECA1, HCC-78, NCI-H196 and HT2 cells were obtained from American Type Culture Collection (Manassas, VA, USA) and cultured following the manufacturer's instructions. Myoblasts are primary human cells kindly provided by Professor J.P. Tremblay (Universite Laval, Quebec, Canada).Table 1.2: Cell lines and culture conditions

TABLE 1.2

Cell lines and culture conditions

| Cell lines | Description | ATCC/others | Culture media | Serum | Additives |
|---|---|---|---|---|---|
| HeLa (adherent cells) | Human cervical carcinoma cells | ATCC ™ CCL-2 | DMEM | 10% FBS | L-glutamine 2 mM<br>Penicillin 100 units<br>Streptomycin 100 µg/mL |
| HEK 293A (adherent cells) | Human embryonic Epithelial kidney cells | ATCC ™ CRL-1573 | DMEM | 10% FBS | L-glutamine 2 mM<br>Penicillin 100 units<br>Streptomycin 100 µg/mL |
| HEK 293T (adherent cells) | Human embryonic Epithelial kidney cells | ATCC ™ CRL-3216 | DMEM | 10% FBS | L-glutamine 2 mM<br>Penicillin 100 units<br>Streptomycin 100 µg/mL |
| THP-1 (suspension cells) | Acute monocytic leukemia | ATCC ™ TIB202 | RPMI 1640 | 10% FBS | β-mercaptoethanol 0.05 mM<br>L-glutamine 2 mM<br>Penicillin 100 units<br>Streptomycin 100 µg/mL |
| Myoblasts (primary adherent cells) | Human (13 months) myoblasts | Kindly provided by Professor J. P. Tremblay | MB1 | 15% FBS | ITS 1x, FGF 2 10 ng/mL,<br>Dexamethasone 0.39 µg/mL,<br>BSA 0.5 mg/mL,<br>MB1 85% |
| CHO (adherent cells) | Chinese hamster ovary cells | ATCC ™ CCL-61 | DMEM | 10% FBS | L-glutamine 2 mM<br>Penicillin 100 units<br>Streptomycin 100 µg/mL |
| NIH3T3 (adherent cells) | Fibroblasts | ATCC ™ CRL-1658 | DMEM | 10% Calf serum | L-glutamine 2 mM<br>Penicillin 100 units<br>Streptomycin 100 µg/mL |
| HT2 (suspension cells) | T lymphocytes | ATCC ™ CRL-1841 | RPMI 1640 | 10% FBS | 200 IU/mL IL-2<br>β-mercaptoethanol 0.05 mM<br>L-glutamine 2 mM<br>Penicillin 100 units<br>Streptomycin 100 µg/mL |
| CA46 (suspension cells) | *Homo sapiens* Burkitt's lymphoma | ATCC ™ CRL-1648 | RPMI 1640 | 20% FBS | L-glutamine 2 mM<br>Penicillin 100 units<br>Streptomycin 100 µg/mL |
| Balb3T3 (adherent cells) | Fibroblasts | ATCC ™ CCL-163 | DMEM | 10% Calf serum | L-glutamine 2 mM<br>Penicillin 100 units<br>Streptomycin 100 µg/mL |
| Jurkat (suspension cells) | Human T cells | ATCC ™ TIB-152 | RPMI 1640 | 10% FBS | L-glutamine 2 mM<br>Penicillin 100 units<br>Streptomycin 100 µg/mL |
| DOHH2 (suspension cells) | Human B cell lymphoma | Gift from Horizon Inc. | RPMI 1640 | 10% FBS | L-glutamine 2 mM<br>Penicillin 100 units<br>Streptomycin 100 µg/mL |
| KMS-12 (suspension cells) | Myeloma bone marrow | Gift from Horizon Inc. | Advanced RPMI 1640 | 10% FBS | L-glutamine 2 mM<br>Penicillin 100 units<br>Streptomycin 100 µg/mL |
| REC-1 (suspension cells) | Human lymph node mantel cell | Gift from Horizon Inc. | RPMI 1640 | 10% FBS | L-glutamine 2 mM<br>Penicillin 100 units<br>Streptomycin 100 µg/mL |
| HCC-78 (adherent cells) | Human adenocarcinoma lung cell | Gift from Horizon Inc. | RPMI 1640 | 20% FBS | L-glutamine 2 mM<br>Penicillin 100 units<br>Streptomycin 100 µg/mL |
| NCI-H196 (adherent cells) | Human small cell lung cancer | Gift from Horizon Inc. | RPMI 1640 | 10% FBS | L-glutamine 2 mM<br>Penicillin 100 units<br>Streptomycin 100 µg/mL |
| NK (suspension cells) | Human normal Peripheral Blood CD56+ lymphocyte | All cells ™ #PB012-PF | RPMI 1640 | 10% FBS | 200 IU/mL IL-2<br>L-glutamine 2 mM<br>Penicillin 100 units<br>Streptomycin 100 µg/mL |
| NK-92 (suspension cells) | Human normal Peripheral Blood CD56+ lymphocyte | Gift from CETC | Alpha MEM | 12.5% FBS<br>12.5% Horse serum | L-glutamine 200 nM<br>IL-2 25000 U/mL<br>Inositol 1M<br>Folic acid 100 nM<br>B-ME 55 mM |
| T cells (suspension cells) | Human normal Peripheral Blood CD3+ lymphocyte | Healthy blood donor | RPMI advanced | 10% FBS | L-glutamine 200 nM<br>IL-2 25000 U/mL<br>Penicillin 100 units<br>Streptomycin 100 µg/mL |

FBS: Fetal bovine serum 1.4 Protein Purification

Fusion proteins were expressed in bacteria (*E. coli* BL21DE3) under standard conditions using an isopropyl p-D-1-thiogalactopyranoside (IPTG) inducible vector containing a T5 promoter. Culture media contained 24 g yeast extract, 12 g tryptone, 4 mL glycerol, 2.3 g $KH_2PO_4$, and 12.5 g $K_2HPO_4$ per liter. Bacterial broth was incubated at 37° C. under agitation with appropriate antibiotic (e.g., ampicillin). Expression was induced at optical density (600 nm) between 0.5 and 0.6 with a final concentration of 1 mM IPTG for 3 hours at 30° C. Bacteria were recuperated following centrifugation at 5000 RPM and bacterial pellets were stored at −20° C.

Bacterial pellets were resuspended in Tris buffer (Tris 25 mM pH 7.5, NaCl 100 mM, imidazole 5 mM) with phenylmethylsulfonyl fluoride (PMSF) 1 mM, and lysed by passing 3 times through the homogenizer Panda 2K™ at 1000 bar. The solution was centrifuged at 15000 RPM, 4° C. for 30 minutes. Supernatants were collected and filtered with a 0.22 µM filtration device.

Solubilized proteins were loaded, using a FPLC (AKTA Explorer 100R), on HisTrap™ FF column previously equilibrated with 5 column volumes (CV) of Tris buffer. The column was washed with 30 column volumes (CV) of Tris buffer supplemented with 0.1% Triton™ X-114 followed with 30 CV of Tris buffer with imidazole 40 mM. Proteins were eluted with 5 CV of Tris buffer with 350 mM Imidazole and collected. Collected fractions corresponding to specific proteins were determined by standard denaturing SDS-PAGE.

Purified proteins were diluted in Tris 20 mM at the desired pH according to the protein's pI and loaded on an appropriate ion exchange column (Q Sepharos™ or SP Sepharose™) previously equilibrated with 5 CV of Tris 20 mM, NaCl 30 mM. The column was washed with 10 CV of Tris 20 mM, NaCl 30 mM and proteins were eluted with a NaCl gradient until 1 M on 15 CV. Collected fractions corresponding to specific proteins were determined by standard denaturing SDS-PAGE. Purified proteins were then washed and concentrated in PBS 1X on Amicon Ultra™ centrifugal filters 10,000 MWCO. Protein concentration was evaluated using a standard Bradford assay.

1.5 Synthetic Peptides and Shuttle Agents

All peptides used in this study were purchased from GLBiochem (Shanghai, China) and their purities were confirmed by high-performance liquid chromatography analysis and mass spectroscopy. In some cases, peptides were synthesized to contain a C-terminal cysteine residue to allow the preparation of peptide dimers. These dimeric peptides were directly synthetized with a disulfide bridge between the C-terminal cysteines of two monomers. The amino acid sequences and characteristics of each of the synthetic peptides and shuttle agents tested in the present examples are summarized in Table 1.3, Table B1, and Table C1.

TABLE 1.3

Synthetic peptides and shuttle agents

| Domain(s) | Peptide or Shuttle agent | Amino acid (a.a.) sequence [SEQ ID NO; not including C-terminal Cys, unless indicated with an *] | a.a. | MW (kDa) | pI | Charge | Hydropathicity index |
|---|---|---|---|---|---|---|---|
| ELD | CM18 | KWKLFKKIGAVLKVLTTG [1] | 18 | 2.03 | 10.60 | 5+/0− | 0.350 |
| | C(LLKK)₃C | CLLKKLLKKLLKKC [63] | 14 | 1.69 | 10.05 | 6+/0− | 0.314 |
| | LAH4 | KKALLALALHHLAHLALHLALALKKA [6] | 26 | 2.78 | 10.48 | 4+/0− | 0.923 |
| | KALA | WEAKLAKALAKALAKHLAKALAKALKACEA [14] | 30 | 3.13 | 9.9 | 7+/2− | 0.283 |
| CPD | TAT-cys | YGRKKRRQRRRC [17] | 12 | 1.66 | 12.01 | 8+/0− | −3.125 |
| | Penetratin-cys | RQIKIWFQNRRMKWKKC [18] | 17 | 2.35 | 11.75 | 7+/0− | −1.482 |
| | PTD4 | YARAAARQARA [65] | 11 | 1.2 | 11.72 | 3+/0− | −0.682 |
| His-PTD4 | His-PTD4 | HHHHHHHYARAAARQARA [81] | 17 | 2.03 | 11.71 | 3+/0− | −1.57 |
| CPD-ELD | TAT-CM18 | YGRKKRRQRRRCKWKLFKKIGAVLKVLTTG [66] | 30 | 3.68 | 12.02 | 13+/0− | −1.041 |
| | TAT-KALA | YGRKKRRQRRRCWEAKLAKALAKALAKHLAKALAKALKACEA [67] | 42 | 4.67 | 11.46 | 15+/2− | −0.768 |
| | PTD4-KALA | YARAAARQARAWEAKLAKALAKALAKHLAKALAKALKACEA [82] | 41 | 4.32 | 10.46 | 10+/2− | 0.024 |
| | 9Arg-KALA | RRRRRRRRRWEAKLAKALAKALAKHLAKALAKALKACEA [83] | 39 | 4.54 | 12.11 | 16+/2− | −0.821 |
| | Pep1-KALA | KETWWETWWTEWSQPKKKRKVWEAKLAKALAKALAKHLAKALAKALKACEA [84] | 51 | 5.62 | 10.01 | 13+/5− | −0.673 |
| | Xentry-KALA | LCLRPVGWEAKLAKALAKALAKHLAKALAKALKACEA [85] | 37 | 3.87 | 9.93 | 8+/2− | 0.441 |
| | SynB3-KALA | RRLSYSRRRFWEAKLAKALAKALAKHLAKALAKALKACEA [86] | 40 | 4.51 | 11.12 | 12+/2− | −0.258 |
| ELD-CPD | CM18-TAT-Cys | KWKLFKKIGAVLKVLTTGYGRKKRRQRRRC [57] | 30 | 3.67 | 12.02 | 13+/0− | −1.04 |
| | CM18-Penetratin-Cys | KWKLEKKIGAVLKVLTTGRQIKIWFQNRRMKWKKC [58] | 35 | 4.36 | 11.36 | 12+/0− | −0.54 |
| | dCM18-TAT-Cys (CM18-TAT-cys dimer) | KWKLFKKIGAVLKVLTTGYGRKKRRQRRRC [57] KWKLFKKIGAVLKVLTTGYGRKKRRQRRRC [57] | 60 | 7.34 | 12.16 | 26+/0− | −1.04 |

TABLE 1.3-continued

Synthetic peptides and shuttle agents

| Domain(s) | Peptide or Shuttle agent | Amino acid (a.a.) sequence [SEQ ID NO; not including C-terminal Cys, unless indicated with an *] | a.a. | MW (kDa) | pI | Charge | Hydro-pathi-city index |
|---|---|---|---|---|---|---|---|
| | dCM18-Penetratin-Cys (CM18-Penetratin-Cys dimer) | KWKLFKKIGAVLKVLTTGRQIKIWFQNRRMKWKKC [58] | 70 | 8.72 | 12.05 | 24+/0- | -0.54 |
| | VSVG-PTD4 | KFTIVFPHNQKGNWKNVPSNYHYCPYARAAARQARA [87] | 36 | 4.2 | 10.3 | 6+/0- | -0.89 |
| | EB1-PTD4 | LIRLWSHLIHIWFQNRRLKWKKKYARAAARQARA [88] | 34 | 4.29 | 12.31 | 10+/0- | -0.647 |
| | JST-PTD4 | GLFEALLELLESLWELLLEAYARAAARQARA [89] | 31 | 3.49 | 4.65 | 5+/3- | 0.435 |
| | CM18-PTD4 | KWKLFKKIGAVLKVLTTGYARAAARQARA [90] | 29 | 3.217 | 11.76 | 8+/0- | -0.041 |
| | 6Cys-CM18-PTD4 | CCCCCCKWKLFKKIGAVLKVLTTGYARAAARQARA [91] | 35 | 3.835 | 9.7 | 8+/0- | 0.394 |
| | CM18-L1-PTD4 | KWKLFKKIGAVLKVLTTGGGSYARAAARQARA [92] | 32 | 3.42 | 11.76 | 8+/0- | -0.087 |
| | CM18-L2-PTD4 | KWKLFKKIGAVLKVLTTGGGSGGGSYARAAARQARA [93] | 36 | 3.68 | 11.76 | 8+/0- | -0.133 |
| | CM18-L3-PTD4 | KWKLFKKIGAVLKVLTTGGGSGGGSGGGSGYARAAARQARA [94] | 41 | 3.99 | 11.76 | 8+/0- | -0.176 |
| His-ELD-CPD | Met-His-CM18-TAT-Cys | MHHHHHHKWKLFKKIGAVLKVLTTGYGRKKRRQRRRC [59*] | 37 | 4.63 | 12.02 | 13+/0- | -1.311 |
| | His-CM18-TAT | HHHHHHKWKLFKKIGAVLKVLTTGYGRKKRRQRRR [95] | 35 | 4.4 | 12.31 | 13+/0- | -1.208 |
| | His-CM18-PTD4 | HHHHHHKWKLFKKIGAVLKVLTTCYARAAARQARA [68] | 35 | 4.039 | 11.76 | 8+/0- | -0.583 |
| | His-CM18-PTD4-6Cys | HHHHHHKWKLFKKIGAVLKVLTTGYARAAARQARACCCCCC [96*] | 41 | 4.659 | 9.7 | 8+/0- | -0.132 |
| | His-CM18-9Arg | HHHHHHKWKLFKKIGAVLKVLTTGRRRRRRRRR [69] | 33 | 4.26 | 12.91 | 14+/0- | -1.618 |
| | His-CM18-Transportan | HHHHHHKWKLFKKIGAVLKVLTTGGWTLNSAGYLLKINLKALAALAKKIL [70] | 50 | 5.62 | 10.6 | 9+/0- | 0.092 |
| | His--PTD4 | HHHHHHKKALLALALHHLAHLALHLALALKKAYARAAARQARA [71] | 43 | 4.78 | 11.75 | 7+/0- | -0.63 |
| | His-C(LLKK)₃C-PTD4 | HHHHHHCLLKKLLKKLLKKCYARAAARQARA [72] | 31 | 3.56 | 11.21 | 9+/0- | -0.827 |
| | 3His-CM18-PTD4 | HHHKWKLFKKIGAVLKVLTTGYARAAARQARA [97] | 32 | 3.63 | 11.76 | 8+/0- | -0.338 |
| | 12His-CM18-PTD4 | HHHHHHHHHHHHKWKLFKKIGAVLKVLTTGYARAAARQARA [98] | 41 | 4.86 | 11.78 | 8+/0- | -0.968 |
| | HA-CM18-PTD4 | HHHAHHHKWKLFKKIGAVLKVLTTGYARAAARQARA [99] | 36 | 4.11 | 11.76 | 8+/0- | -0.517 |
| | 3HA-CM18-PTD4 | HAHHAHHAHKWKLFKKIGAVLKVLTTGYARAAARQARA [100] | 38 | 4.25 | 11.78 | 8+/0- | -0.395 |
| ELD-His-CPD | CM18-His-PTD4 | KWKLFKKIGAVLKVLTTGHHHHHHYARAAARQARA [101] | 35 | 4.04 | 11.76 | 8+/0- | -0.583 |
| His-ELD-CPD-His | His-CM18-PTD4-His | HHHHHHKWKLFKKIGAVLKVLTTGYARAAARQARAHHHHHH [102] | 41 | 4.86 | 11.76 | 8+/0- | -0.966 |

Results computed using the ProtParam™ online tool available from ExPASy™ Bioinformatics Resource Portal (http://web.expasy.org/protparam/)
MW: Molecular weight
pI: Isoelectric point
Charge: Total number of positively (+) and negatively (-) charged residues Example 2

Peptide shuttle agents facilitate escape of endosomally-trapped calcein 2.1 Endosome escape assays Microscopy-based and flow cytometry-based fluorescence assays were developed to study endosome leakage and to determine whether the addition of the shuttle agents facilitates endosome leakage of the polypeptide cargo. These methods are described in Example 2 of PCT/CA2016/050403.

2.1.1 Endosomal leakage visualization by microscopy

Calcein is a membrane-impermeable fluorescent molecule that is readily internalized by cells when administered to the extracellular medium. Its fluorescence is pH-dependent and calcein self-quenches at higher concentrations. Once internalized, calcein becomes sequestered at high concentrations in cell endosomes and can be visualized by fluorescence microscopy as a punctate pattern. Following endosomal leakage, calcein is released to the cell cytoplasm and this release can be visualized by fluorescence microscopy as a diffuse pattern.

One day before the calcein assay was performed, cells in exponential growth phase were harvested and plated in a 24-well plate (80,000 cells per well). The cells were allowed to attach by incubating overnight in appropriate growth media, as described in Example 1. The next day, the media was removed and replaced with 300 µL of fresh media without FBS containing 62.5 µg/mL (100 µM) of calcein, except for HEK293A (250 µg/mL, 400 µM). At the same time, the shuttle agent(s) to be tested was added at a predetermined concentration. The plate was incubated at 37° C. for 30 minutes. The cells were washed with 1× PBS (37° C.) and fresh media containing FBS was added. The plate was incubated at 37° C. for 2.5 hours. The cells were washed three times and were visualized by phase contrast and fluorescence microscopy (IX81™, Olympus).

Figure 1A:
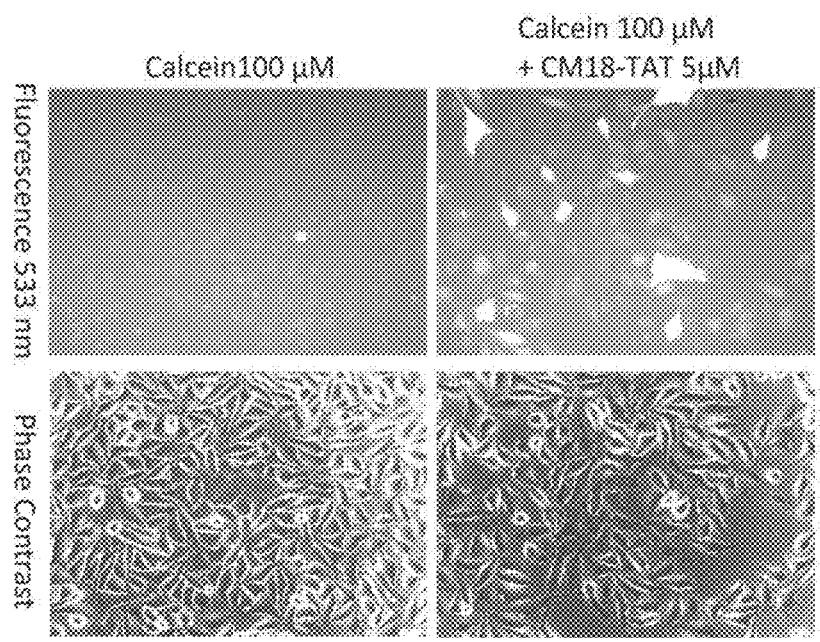
FIGS. 1A and 1B show a typical result of a calcein endosomal escape assay in which HEK293A cells were loaded with the fluorescent dye calcein ("100 μM calcein"), and were then treated (or not) with a shuttle agent that facilitates endosomal escape of the calcein ("100 μM calcein+CM18-TAT 5 μM").

A typical result is shown in FIG. 1A, in which untreated HEK293A cells loaded with calcein (100 µM calcein") show a low intensity, punctate fluorescent pattern when visualized by fluorescence microscopy (upper left panel). In contrast, HeLa cells treated with a shuttle agent that facilitates endosomal escape of calcein ("100 µM calcein+CM18-TAT 5 µM") show a higher intensity, more diffuse fluorescence pattern in a greater proportion of cells (upper right panel).

2.1.2 Endosomal Leakage Quantification by Flow Cytometry

In addition to microscopy, flow cytometry allows a more quantitative analysis of the endosomal leakage as the fluorescence intensity signal increases once the calcein is released in the cytoplasm. Calcein fluorescence is optimal at physiological pH (e.g., in the cytosol), as compared to the acidic environment of the endosome.

One day before the calcein assay was performed, cells in exponential growth phase were harvested and plated in a 96-well plate (20,000 cells per well). The cells were allowed to attach by incubating overnight in appropriate growth media, as described in Example 1. The next day, the media in wells was removed and replaced with 50 µL of fresh media without serum containing 62.5 µg/mL (100 µM) of calcein, except for HEK293A (250 µg/mL, 400 µM). At the same time, the shuttle agent(s) to be tested was added at a predetermined concentration. The plate was incubated at 37° C. for 30 minutes. The cells were washed with 1× PBS (37° C.) and fresh media containing 5-10% serum was added. The plate was incubated at 37° C. for 2.5 hours. The cells were washed with 1× PBS and detached using trypsinization. Trypsinization was stopped by addition of appropriate growth media, and calcein fluorescence was quantified using flow cytometry (Accuri C6, Becton, Dickinson and Company (BD)).

Untreated calcein-loaded cells were used as a control to distinguish cells having a baseline of fluorescence due to endosomally-trapped calcein from cells having increased fluorescence due to release of calcein from endosomes. Fluorescence signal means ("mean counts") were analyzed for endosomal escape quantification. In some cases, the "Mean Factor" was calculated, which corresponds to the fold-increase of the mean counts relative to control (untreated calcein-loaded cells). Also, the events scanned by flow cytometry corresponding to cells (size and granularity) were analyzed. The cellular mortality was monitored with the percentage of cells in the total events scanned. When it became lower than the control, it was considered that the number of cellular debris was increasing due to toxicity and the assay was discarded.

Figure 1B:
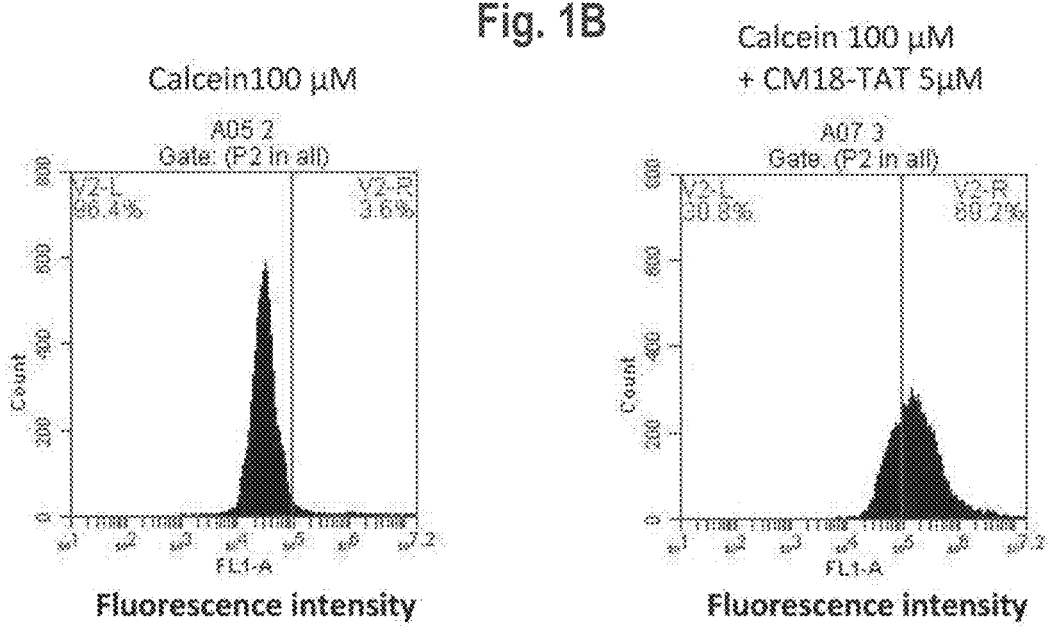

A typical result is shown in FIG. 1B, in which an increase in fluorescence intensity (right-shift) is observed for calcein-loaded HeLa cells treated with a shuttle agent that facilitates endosomal escape ("Calcein 100 µM+CM18-TAT 5 µM", right panel), as compared to untreated calcein-loaded HeLa cells ("Calcein 100 µM", left panel). The increase in calcein fluorescence is caused by the increase in pH associated with the release of calcein from the endosome (acidic) to the cytoplasm (physiological).

2.2 Results from Endosome Escape Assays
2.2.1 HeLa Cells

HeLa cells were cultured and tested in the endosomal escape assays as described in Example 2.1. The results of flow cytometry analyses are summarized below. In each case, the flow cytometry results were also confirmed by fluorescence microscopy (data not shown).

TABLE 2.1

CM18-Penetratin-Cys v. Controls in Hela cells

| Domains | Peptide | Cells | Concentration (µm) | Mean Counts (±St Dev.: n = 3) | Mean Factor |
|---|---|---|---|---|---|
| — | No peptide | HeLa | 0 | 55 359 ± 6844 | 1.0 |
| ELD | CM18 | HeLa | 5 | 46 564 ± 9618 | 0.8 |
| CPD | TAT-Cys | HeLa | 5 | 74 961 ± 9337 | 1.3 |
|  | Penetratin-Cys | HeLa | 5 | 59 551 ± 7119 | 1.1 |
| ELD + CPD | CM18 + TAT-Cys | HeLa | 5 + 5 | 64 333 ± 6198 | 1.2 |
|  | CM18 + Penetratin-Cys | HeLa | 5 + 5 | 40 976 ± 8167 | 0.7 |
| ELD – CPD | CM18 – Penetratin-Cys | HeLa | 5 | 262 066 ± 28 146 | 4.7 |

TABLE 2.2

CM18-TAT-Cys v. Control in HeLa cells

| Domains | Peptide | Cells | Concentration (µM) | Mean counts (n = 3) | Stand. dev. | Mean Factor |
|---|---|---|---|---|---|---|
| — | No peptide | HeLa | 0 | 53 369 | 4192 | 1.0 |
| ELD-CPD | CM18-TAT-Cys | HeLa | 5 | 306 572 | 46 564 | 5.7 |

The results in Tables 2.1 and 2.2 show that treating calcein-loaded HeLa cells with the shuttle agents CM18-Penetratin-Cys and CM18-TAT-Cys (having the domain structure ELD-CPD) results in increased mean cellular calcein fluorescence intensity, as compared to untreated control cells or cells treated with single-domain peptides used alone (CM 18, TAT-Cys, Penetratin-Cys) or together (CM18+TAT-Cys, CM18+Penetratin-Cys). These results suggest that CM18-Penetratin-Cys and CM18-TAT-Cys facilitate escape of endosomally-trapped calcein, but that single domain peptides (used alone or together) do not.

TABLE 2.3

Figure 2:
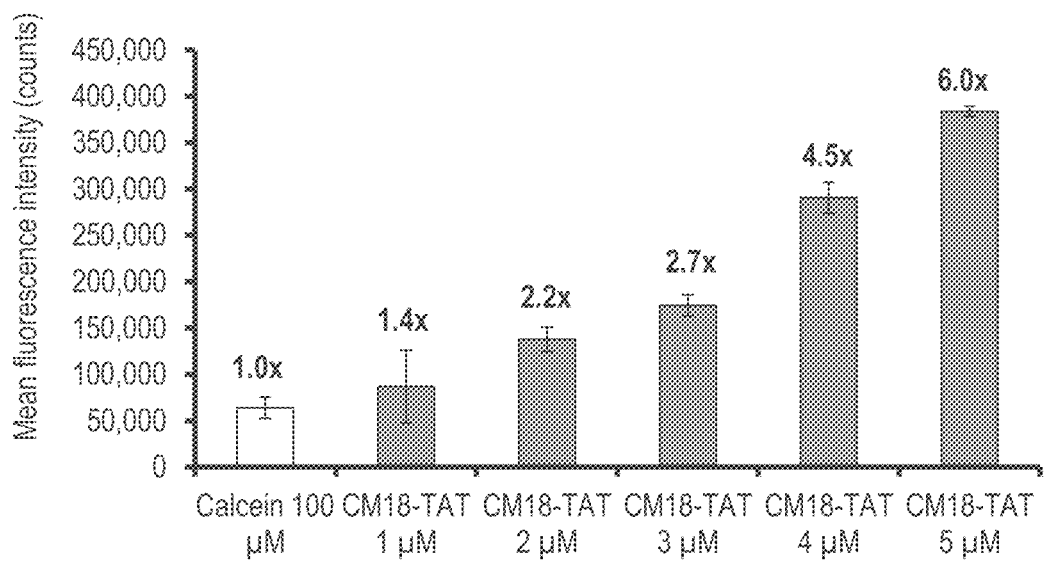
FIG. 2 shows the results of a calcein endosomal escape flow cytometry assay in which HeLa cells were loaded with calcein ("calcein 100 μM"), and were then treated with increasing concentrations of the shuttle agent CM18-TAT-Cys (labeled "CM18-TAT").

Dose response of CM18-TAT-Cys in HeLa cells, data from FIG. 2

| Domains | Peptide | Cells | Concentration (μM) | Mean counts (n = 3) | Stand. dev. | Mean Factor |
| --- | --- | --- | --- | --- | --- | --- |
| — | No peptide ("calcein 100 μM") | HeLa | 0 | 63 872 | 11 587 | 1.0 |
| ELD-CPD | CM18-TAT-Cys | HeLa | 1 | 86 919 | 39 165 | 1.4 |
|  | CM18-TAT-Cys | HeLa | 2 | 137 887 | 13 119 | 2.2 |
|  | CM18-TAT-Cys | HeLa | 3 | 174 327 | 11 519 | 2.7 |
|  | CMl8-TAT-Cys | HeLa | 4 | 290 548 | 16 593 | 4.5 |
|  | CMl8-TAT-Cys | HeLa | 5 | 383 685 | 5578 | 6.0 |

TABLE 2.4

Dose response of CM18-TAT-Cys in HeLa cells

| Domains | Peptide | Cells | Concentration (μM) | Mean counts (n = 3) | Stand. dev. | Mean Factor |
| --- | --- | --- | --- | --- | --- | --- |
| — | No peptide | HeLa | 0 | 81 013 | 14 213 | 1.0 |
| ELD-CPD | CM18-TAT-Cys | HeLa | 3 | 170 652 | 63 848 | 2.1 |
|  | CM18-TAT-Cys | HeLa | 4 | 251 799 | 33 880 | 3.1 |
|  | CM18-TAT-Cys | HeLa | 5 | 335 324 | 10 651 | 4.1 |

TABLE 2.5

Figure 3:
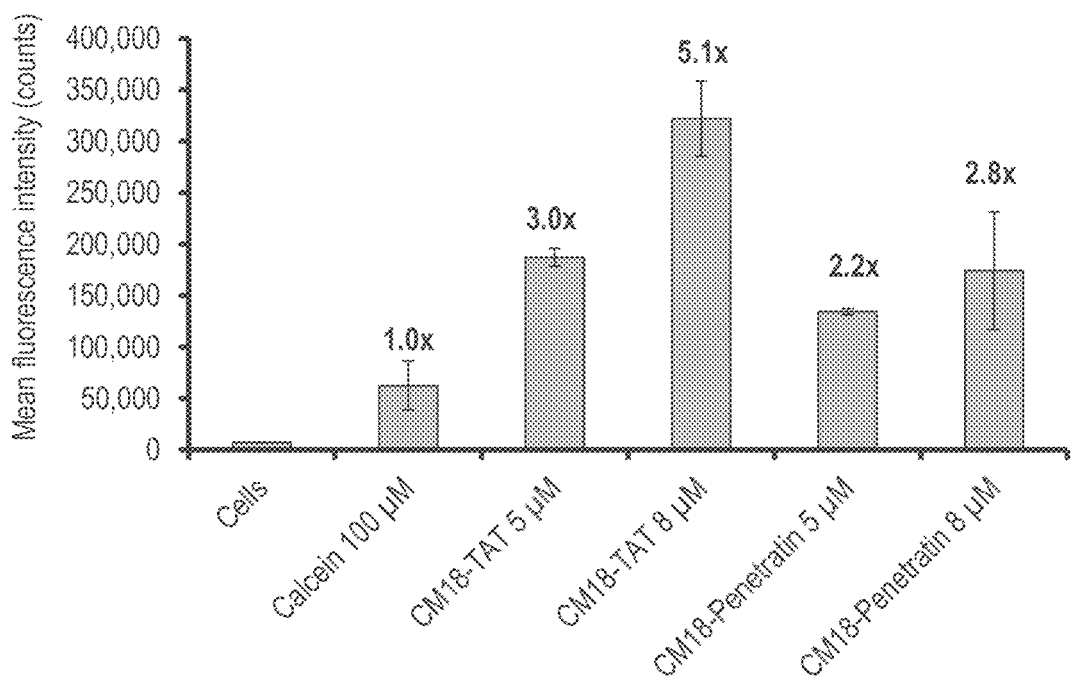
FIGS. 3 and 4 show the results of calcein endosomal escape flow cytometry assays in which HeLa cells (FIG. 3) or primary myoblasts (FIG. 4) were loaded with calcein ("calcein 100 μM"), and were then treated with 5 μM or 8 μM of the shuttle agents CM18-TAT-Cys or CM18-Penetratin-Cys (labeled "CM18-TAT" and "CM18-Penetratin", respectively).

Dose response of CM18-TAT-Cys and CM18-Penetratin-Cys in HeLa cells, data from FIG. 3

| Domains | Peptide | Cells | Concentration (μM) | Mean counts (n = 3) | Stand. dev. | Mean Factor |
| --- | --- | --- | --- | --- | --- | --- |
| — | No peptide | HeLa | 0 | 62 503 | 23 752 | 1.0 |
| ELD-CPD | CM18-TAT-Cys | HeLa | 5 | 187 180 | 8593 | 3.0 |
|  | CM18-TAT-Cys | HeLa | 8 | 321 873 | 36 512 | 5.1 |
|  | CM18-Penetratin-Cys | HeLa | 5 | 134 506 | 2992 | 2.2 |
|  | CM18-Penetratin-Cys | HeLa | 8 | 174 233 | 56 922 | 2.8 |

The results in Tables 2.3 (FIG. 2), 2.4, and 2.5 (FIG. 3) suggest that CM18-TAT-Cys and CM18-Penetratin-Cys facilitate escape of endosomally-trapped calcein in HeLa cells in a dose-dependent manner. In some cases, concentrations of CM18-TAT-Cys or CMl18-Penetratin-Cys above 10 μM were associated with an increase in cell toxicity in HeLa cells.

TABLE 2.6

Dimers v. monomers of CM18-TAT-Cys and CM18-Penetratin-Cys in HeLa cells

| Domains | Peptide | Cells | Concentration (µM) | Mean counts (n = 4) | Stand. dev. | Mean Factor |
|---|---|---|---|---|---|---|
| — | No peptide | HeLa | 0 | 60 239 | 9860 | 1.0 |
| ELD-CPD | CM18-TAT-Cys | HeLa | 4 | 128 461 | 25 742 | 2.1 |
|  | CM18-Penetratin-Cys | HeLa | 4 | 116 873 | 3543 | 1.9 |
| ELD-CPD dimer | dCM18-TAT-Cys | HeLa | 2 | 79 380 | 4297 | 1.3 |
|  | dCM18-Penetratin-Cys | HeLa | 2 | 128 363 | 8754 | 2.1 |

TABLE 2.7

Monomers v. dimers of CM18-TAT-Cys and CM18-Penetratin-Cys in HeLa cells

| Domains | Peptide | Cells | Concentraton (µM) | Mean counts (n = 3) | Stand. dev. | Mean Factor |
|---|---|---|---|---|---|---|
| — | No peptide | HeLa | 0 | 55 834 | 1336 | 1.0 |
| ELD-CPD | CM18-TAT-Cys | HeLa | 4 | 159 042 | 16 867 | 2.8 |
| ELD-CPD dimer | dCM18-TAT-Cys | HeLa | 2 | 174 274 | 9 553 | 3.1 |

The results in Table 2.6 and 2.7 suggest that shuttle peptide dimers (which are molecules comprising more than one ELD and CPD) are able to facilitate calcein endosomal escape levels that are comparable to the corresponding monomers.

2.2.3 HEK293A Cells

To examine the effects of the shuttle agents on a different cell line, HEK293A cells were cultured and tested in the endosomal escape assays as described in Example 2.1. The results of flow cytometry analyses are summarized below in Table 2.8 and in FIG. 1B.

TABLE 2.8

CM18-TAT-Cys in HEK293A cells

| Domains | Peptide | Cells | Concentration (µM) | Mean counts (n = 2) | Stand. dev. | Mean Factor |
|---|---|---|---|---|---|---|
| — | No peptide | HEK293A | 0 | 165 819 | 7693 | 1.0 |
| ELD-CPD | CM18-TAT-Cys | HEK293A | 0.5 | 196 182 | 17 224 | 1.2 |
|  | CM18-TAT-Cys | HEK293A | 5 | 629 783 | 1424 | 3.8 |

The results in Table 2.8 and in FIG. 1B show that treating calcein-loaded HEK293A cells with the shuttle agent CM18-TAT-Cys results in increased mean cellular calcein fluorescence intensity, as compared to untreated control cells.

2.2.2 Myoblasts

To examine the effects of the shuttle agents on primary cells, primary myoblast cells were cultured and tested in the endosomal escape assays as described in Example 2.1. The results of flow cytometry analyses are summarized below in Tables 2.9 and 2.10, and in FIG. 4. In each case, the flow cytometry results were also confirmed by fluorescence microscopy.

TABLE 2.9

Figure 4:
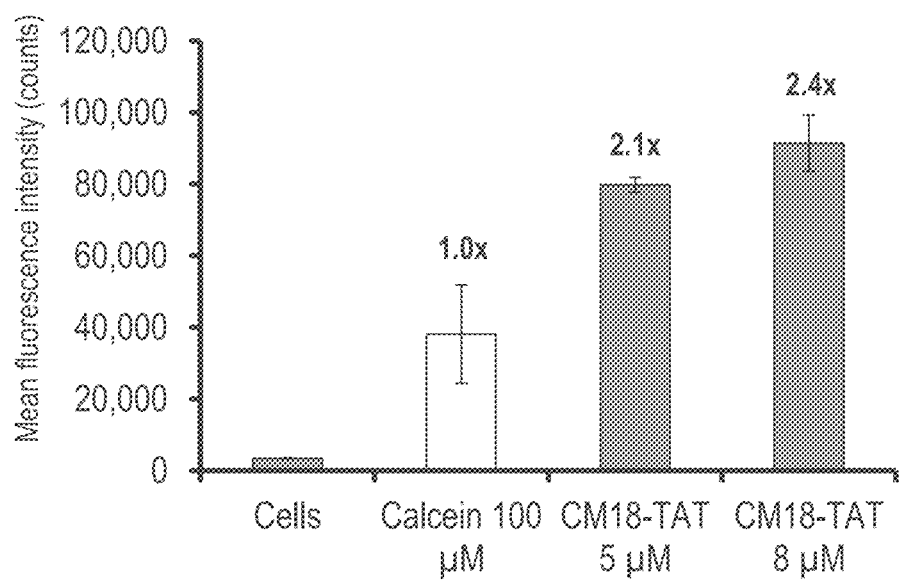

Dose response of CM18-TAT-Cys in primary myoblasts, data from FIG. 4

| Domains | Peptide | Cells | Peptide Conc. (µM) | Mean counts (n = 3) | Stand. dev. | Mean Factor |
|---|---|---|---|---|---|---|
| — | No peptide; no calcein ("Cells") | Myoblasts | 0 | 863 | 61 | n/a |
| — | No peptide ("Calcein 100 µM") | Myoblasts | 0 | 38 111 | 13 715 | 1.0 |
| ELD-CPD | CM18-TAT-Cys | Myoblasts | 5 | 79 826 | 12 050 | 2.1 |
|  | CM18-TAT-Cys | Myoblasts | 8 | 91 421 | 10 846 | 2.4 |

TABLE 2.10

Dose response of CM18-TAT-Cys in primary myoblasts

| Domains | Peptide | Cells | Peptide Conc. (µM) | Mean counts (n = 3) | Stand. dev. | Mean Factor |
|---|---|---|---|---|---|---|
| — | No peptide | Myoblasts | 0 | 31 071 | 21 075 | 1.0 |
| ELD-CPD | CM18-TAT-Cys | Myoblasts | 5 | 91 618 | 10 535 | 2.9 |
|  | CM18-TAT-Cys | Myoblasts | 7.5 | 95 289 | 11 266 | 3.1 |

The results in Table 2.9 (shown graphically in FIG. 4) and Table 2.10 suggest that CM18-TAT-Cys facilitates escape of endosomally-trapped calcein in a dose-dependent manner in primary myoblasts. Concentrations of CM18-TAT-Cys above 10 µM were associated with an increase in cell toxicity in myoblast cells, as for HeLa cells.

TABLE 2.11

Monomers v. dimers CM18-TAT-Cys and CM18-Penetratin-Cys in primary myoblasts

| Domains | Peptide | Cells | Concentration (µM) | Mean counts | Stand. dev. | Mean Factor |
|---|---|---|---|---|---|---|
| — | No peptide | Myoblasts | 0 | 30 175 | 4687 | 1.0 |
| ELD-CPD | CM18-TAT-Cys | Myoblasts | 5 | 88 686 | 19 481 | 2.9 |
| ELD-CPD dimer | dCM18-TAT-Cys | Myoblasts | 2.5 | 64 864 | 1264 | 2.1 |
| ELD-CPD | CM18-Penetratin-Cys | Myoblasts | 5 | 65 636 | 3288 | 2.2 |

TABLE 2.11-continued

Monomers v. dimers CM18-TAT-Cys and CM18-Penetratin-Cys in primary myoblasts

| Domains | Peptide | Cells | Concentration (µM) | Mean counts | Stand. dev. | Mean Factor |
|---|---|---|---|---|---|---|
| ELD-CPD dimer | dCM18-Penetratin-Cys | Myoblasts | 2.5 | 71 547 | 10 975 | 2.4 |

The results in Table 2.11 suggest that shuttle peptide dimers are able to facilitate calcein endosomal escape levels that are comparable to the corresponding monomers in primary myoblasts.

Example 3

Peptide Shuttle Agents Increase GFP Transduction Efficiency 3.1 Protein Transduction Assay One day before the transduction assay was performed, cells in exponential growth phase were harvested and plated in a 96-well plate (20,000 cells per well). The cells were incubated overnight in appropriate growth media containing FBS (see Example 1). The next day, in separate sterile 1.5 mL tubes, cargo protein at the indicated concentration was pre-mixed (pre-incubated) for 1 or 10 min (depending on the protocol) at 37° C. with the peptide(s) to be tested shuttle agents (0.5 to 5 µM) in 50 µL of fresh medium without serum (unless otherwise specified). The media in wells was removed and the cells were washed three times with freshly prepared phosphate buffered saline (PBS) previously warmed at 37° C. The cells were incubated with the cargo protein/shuttle agent mixture at 37° C. for the indicated time (e.g., 1, 5 or 60 min). After the incubation, the cells were quickly washed three times with freshly prepared PBS and/or heparin (0.5 mg/mL) previously warmed at 37° C. The washes with heparin were required for human THP-1 blood cells to avoid undesired cell membrane-bound protein background in subsequent analyses (microscopy and flow cytometry). The cells were finally incubated in 50 µL of fresh medium with serum at 37° C. before analysis.

3.1a Protocol A: Protein Transduction Assay for Adherent Cells

One day before the transduction assay was performed, cells in exponential growth phase were harvested and plated in a 96-well plate (20,000 cells per well). The cells were incubated overnight in appropriate growth media containing serum (see Example 1). The next day, in separate sterile 1.5-mL tubes, peptides were diluted in sterile distilled water at room temperature (if the cargo is or comprised a nucleic acid, nuclease-free water was used). Cargo protein(s) were then added to the peptides and, if necessary, sterile PBS or cell culture medium (serum-free) was added to obtain the desired concentrations of shuttle agent and cargo in a sufficient final volume to cover the cells (e.g., 10 to 100 µL per well for a 96-well plate). The peptides/cargo mixture was then immediately used for experiments. At least three controls were included for each experiment, including: (1) peptides alone (e.g., at highest concentration tested); (2) cargo alone; and (3) without any cargo or shuttle agent. The media in wells was removed, cells were washed once with PBS previously warmed at 37° C., and the cells were incubated with the cargo protein/peptide mixture at 37° C. for the desired length of time. The peptide/cargo mixture in wells was removed, the cells were washed once with PBS, and fresh complete medium was added. Before analysis, the cells were washed once with PBS one last time and fresh complete medium was added.

3.1b Protocol B: Protein Transduction Assay for Suspension Cells

One day before the transduction assay was performed, suspension cells in exponential growth phase were harvested and plated in a 96-well plate (20,000 cells per well). The cells were incubated overnight in appropriate growth media containing serum (see Example 1). The next day, in separate sterile 1.5-mL tubes, peptides were diluted in sterile distilled water at room temperature (if the cargo is or comprised a nucleic acid, nuclease-free water was used). Cargo protein(s) were then added to the peptides and, if necessary, sterile PBS or cell culture medium (serum-free) was added to obtain the desired concentrations of shuttle agent and cargo in a sufficient final volume to resuspend the cells (e.g., 10 to 100 µL per well in a 96-well plate). The shuttle agent/peptide was then immediately used for experiments. At least three controls were included for each experiment, including: (1) peptide alone (e.g., at highest concentration tested); (2) cargo alone; and (3) without any cargo or shuttle agent. The cells were centrifuged for 2 minutes at 400g, the medium was then removed and the cells were resuspended in PBS previously warmed at 37° C. The cells were centrifuged again 2 minutes at 400g, the PBS removed, and the cells were resuspended with the cargo protein/peptide mixture at 37° C. for the desired length of time. After that, 200 µL of complete medium was added directly on the cells. Cells were centrifuged for 2 minutes at 400g and the medium was removed. The pellet was resuspended and washed in 200 µL of PBS previously warmed at 37° C. After another centrifugation, the PBS was removed and the cells were resuspended in 50 µL of trypsin-EDTA solution for 2 min. 200 of complete medium was directly added and cells were centrifuged for 2 minutes at 400g. The medium was removed and the cells were resuspended in 200 µL of complete medium.

3.2 Fluorescence Microscopy Analysis

The delivery of fluorescent protein cargo in cytosolic and nuclear cell compartments was observed with an Olympus IX70™ microscope (Japan) equipped with a fluorescence lamp (Model U-LH100HGAPO) and different filters. The Olympus filter U-MF2™ (C54942-Exc495/Em510) was used to observe GFP and FITC-labeled antibody fluorescent signals. The Olympus filter HQ-TR™ (V-N41004-Exc555-60/Em645-75) was used to observe mCherry™ and GFP antibody fluorescent signals. The Olympus filter U-MWU2™ (Exc330/Em385) was used to observe DAPI or Blue Hoechst fluorescent signals. The cells incubated in 50 µL of fresh medium were directly observed by microscopy (Bright-field and fluorescence) at different power fields (4× to 40×). The cells were observed using a CoolSNAP-PRO™ camera (Series A02D874021) and images were acquired using the Image-Proplus™ software.

3.2a Cell Immuno-Labelling

Adherent cells were plated on a sterile glass strip at 1.5×10⁵ cells per well in a 24-plate well and incubated overnight at 37° C. For fixation, cells were incubated in 500 µL per well of formaldehyde (3.7% v/v) for 15 minutes at room temperature, and washed 3 times for 5 minutes with PBS. For permeabilization, cells were incubated in 500 µL per well of Triton™ X-100 (0.2%) for 10 minutes at room temperature, and washed 3 times for 5 minutes with PBS. For blocking, cells were incubated in 500 µL per well of PBS containing 1% BSA (PBS/BSA) for 60 minutes at room temperature. Primary mouse monoclonal antibody was diluted PBS/BSA (1%). Cells were incubated in 30 μL of primary antibody overnight at 4° C. Cells were washed 3 times for 5 minutes with PBS. Secondary antibody was diluted in PBS/BSA (1%) and cells were incubated in 250 μL of secondary antibody 30 minutes at room temperature in the dark. Cells were washed 3 times for 5 minutes with PBS. Glass strips containing the cells were mounted on microscope glass slides with 10 μL of the mounting medium Fluoroshield™ with DAPI.

3.3 Flow Cytometry Analysis:

The fluorescence of GFP was quantified using flow cytometry (Accuri C6, Becton, Dickinson and Company (BD)). Untreated cells were used to establish a baseline in order to quantify the increased fluorescence due to the internalization of the fluorescent protein in treated cells. The percentage of cells with a fluorescence signal above the maximum fluorescence of untreated cells, "mean %" or "Pos cells (%)", is used to identify positive fluorescent cells. "Relative fluorescence intensity (FL1–A)" corresponds to the mean of all fluorescence intensities from each cell with a fluorescent signal after fluorescent protein delivery with the shuttle agent. Also, the events scanned by flow cytometry corresponding to cells (size and granularity) were analyzed. The cellular toxicity (% cell viability) was monitored comparing the percentage of cells in the total events scanned of treated cells comparatively to untreated cells.

3.3a Viability Analysis

Where indicated, the viability of cells was assessed with a resazurin test. Resazurin is a sodium salt colorant that is converted from blue to pink by mitochondrial enzymes in metabolically active cells. This colorimetric conversion, which only occurs in viable cells, can be measured by spectroscopy analysis in order to quantify the percentage of viable cells. The stock solution of resazurin was prepared in water at 1 mg/100 mL and stored at 4° C. 25 μL of the stock solution was added to each well of a 96-well plate, and cells were incubated at 37° C. for one hour before spectrometry analysis. The incubation time used for the resazurin enzymatic reaction depended on the quantity of cells and the volume of medium used in the wells.

3.4 Construction and Amino Acid Sequence of GFP

The GFP-encoding gene was cloned in a T5 bacterial expression vector to express a GFP protein containing a 6× histidine tag and a serine/glycine rich linker in the N-terminal end, and a serine/glycine rich linker and a stop codon (–) at the C-terminal end. Recombinant GFP protein was purified as described in Example 1.4. The sequence of the GFP construct was:

[SEQ ID NO: 60]
MHHHHHHGGGGSGGGGSGGASTGTGIR<u>MVSKGEELFTGVVPILVELDGDVN

GHKFSVSGEGEGDATYGKLTLKFICTTGKLPVPWPTLVTTLTYGVQCFSRY

PDHMKQHDFFKSAMPEGYVQERTIFFKDDGNYKTRAEVKFEGDTLVNRIEL

KGIDFKEDGNILGHKLEYNYNSHNVYIMADKQKNGIKVNFKIRHNIEDGSV

QLADHYQQNTPIGDGPVLLPDNHYLSTQSALSKDPNEKRDHMVLLEFVTAA

Figure 5:
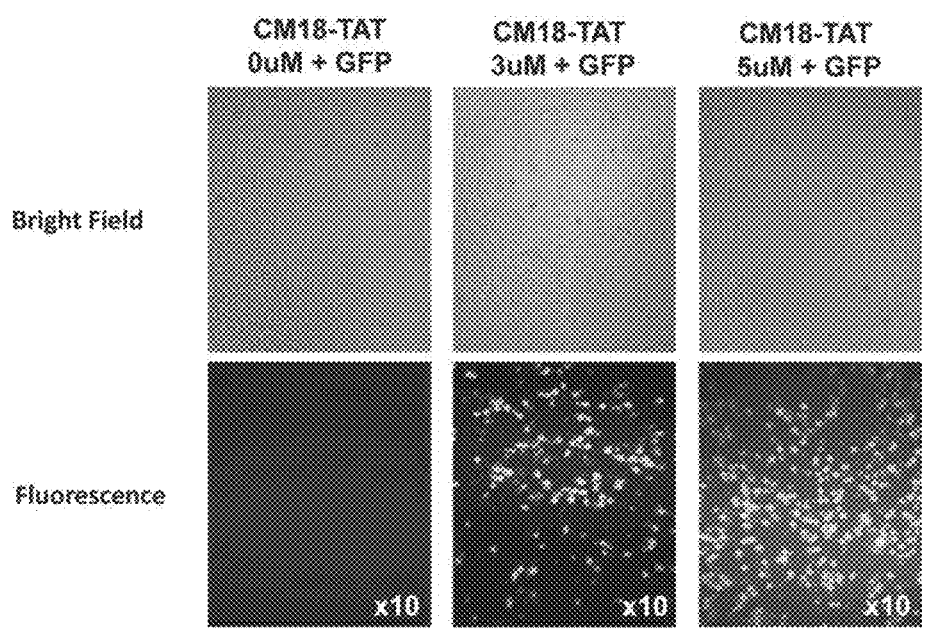
FIG. 5 shows the results of a GFP transduction experiment visualized by fluorescence microscopy in which a GFP cargo protein was co-incubated with 0, 3 or 5 μM of CM18-TAT-Cys (labeled "CM18-TAT"), and then exposed to HeLa cells. The cells were observed by bright field (upper panels) and fluorescence microscopy (lower panels).

GITLGMDELYK</u>GGSGGGSGGGSGWIRASSGGREIS-
(MW = 31.46 kDa; pI = 6.19)
Serine/glycine rich linkers are in bold
GFP sequence is underlined 3.5 GFP Transduction by CM18-TAT-Cys in HeLa Cells: Fluorescence Microscopy HeLa cells were cultured and tested in the protein transduction assay described in Example 3.1. Briefly, GFP recombinant protein was co-incubated with 0, 3 or 5 μM of CM18-TAT, and then exposed to HeLa cells for 1 hour. The cells were observed by bright field and fluorescence microscopy as described in Example 3.2. The results presented in FIG. 5 show that GFP was delivered intracellularly to HeLa cells in the presence of the shuttle agent CM18-TAT.

3.6 GFP Transduction by Shuttle Agents in HeLa Cells: Dose Responses (CM18-TAT-Cys, dCM18-TAT-Cys, GFP) and Cell Viability HeLa cells were cultured and tested in the protein transduction assay described in Examples 3.1-3.3. Briefly, GFP recombinant protein was co-incubated with different concentrations of CM18-TAT-Cys or dimerized CM18-TAT-Cys (dCM18-TAT-Cys), and then exposed to HeLa cells for 1 hour. The results are shown in Table 3.1 and FIGS. 6A-6B.

TABLE 3.1

Figure 6A:
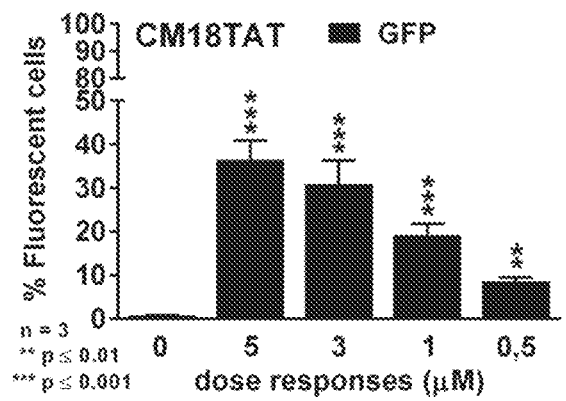
FIGS. 6A and 6B show the results of a GFP transduction efficiency experiment in which GFP cargo protein (10 μM) was co-incubated with different concentrations of CM18-TAT-Cys (labeled "CM18-TAT"), prior to being exposed to HeLa cells. Cells were evaluated by flow cytometry and the percentage of fluorescent (GFP-positive) cell is shown in FIG. 6A, and corresponding cell toxicity data is shown in FIG. 6B.
Figure 6B:
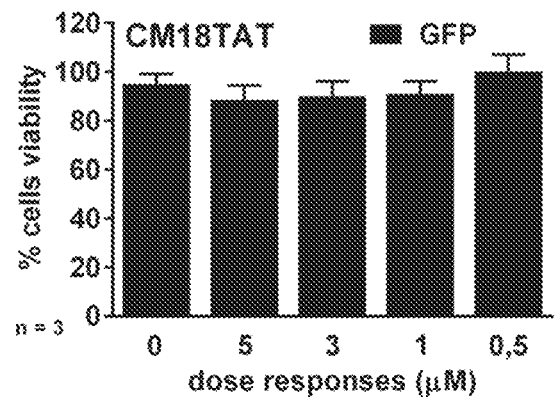

Dose response (CM18-TAT) and cell viability, data from FIGS. 6A and 6B

| | | | FIG. 6A | | FIG. 6B Cell viability |
|---|---|---|---|---|---|
| Shuttle | Cells | Concentration (μM) | Mean (%) (n = 3) | Standard deviation | (%) (±St. Dev.; n = 3) |
| CM18-TAT-Cys | HeLa | 0 | 0.69 | 0.12 | 95 ± 4 |
| | HeLa | 0.5 | 8.67 | 0.96 | 88.4 ± 6 |
| | HeLa | 1 | 20.03 | 2.55 | 90 ± 6 |
| | HeLa | 3 | 31.06 | 5.28 | 91 ± 5 |
| | HeLa | 5 | 36.91 | 4.33 | 90 ± 7 |

Table 3.1 and FIG. 6A show the results of flow cytometry analysis of the fluorescence intensity of HeLa cells transduced with GFP (5 μM) without or with 5, 3, 1, and 0.5 μM of CM18-TAT-Cys. Corresponding cellular toxicity data are presented in Table 3.1 and in FIG. 6B. These results suggest that the shuttle agent CM18-TAT-Cys increases the transduction efficiency of GFP in a dose-dependent manner.

TABLE 3.2

Figure 7A:
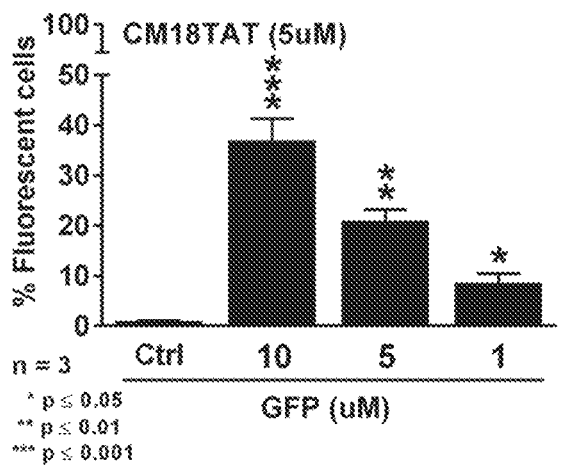
FIGS. 7A and 7B shows the results of a GFP transduction efficiency experiment in which different concentrations of GFP cargo protein (10, 5 or 1 μM) were co-incubated with either 5 μM of CM18-TAT-Cys (FIG. 7A, labeled "CM18TAT"), or 2.5 μM of dCM18-TAT-Cys (FIG. 7B, labeled "dCM18TAT"), prior to being exposed to HeLa cells. Cells were evaluated by flow cytometry and the percentages of fluorescent (GFP-positive) cells are shown.
Figure 7B:
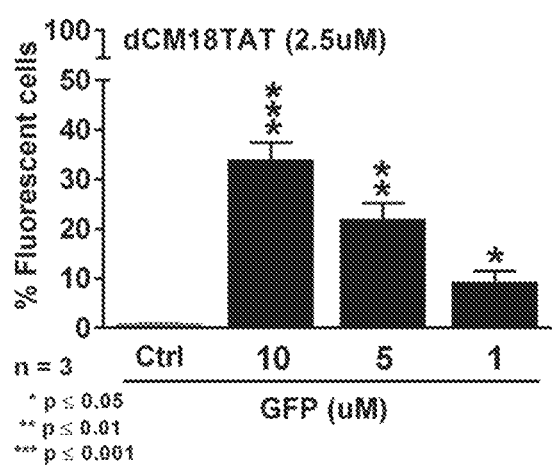

Dose response (GFP), data from FIGS. 7A and 7B

| Shuttle | Cells | Conc. of shuttle agent (μM) | Conc. of GFP (μM) | Mean (%) (n = 3) | Standard deviation |
|---|---|---|---|---|---|
| Control | HeLa | 0 | 10 | 0.93 | 0.08 |
| CM18-TAT-Cys | HeLa | 5 | 10 | 37.1 | 4.29 |
| | HeLa | 5 | 5 | 21.1 | 2.19 |
| | HeLa | 5 | 1 | 8.56 | 1.91 |
| Control | HeLa | 0 | 10 | 0.91 | 0.09 |
| dCM18-TAT-Cys | HeLa | 2.5 | 10 | 34.2 | 3.42 |
| | HeLa | 2.5 | 5 | 22.2 | 3.17 |
| | HeLa | 2.5 | 1 | 9.38 | 2.11 |

Table 3.2 and FIG. 7 show the results of flow cytometry analysis of the fluorescence intensity of HeLa cells transduced with different concentrations of GFP (1 to 10 μM) without or with 5 μM of CM18-TAT-Cys (FIG. 7A) or 2.5 μM dCM18-TAT-Cys (FIG. 7B).

3.7 GFPC Transduction in HeLa Cells: Dose Responses of CM18-TAT-Cys and CM-Penetratin-Cys, and Dimers Thereof HeLa cells were cultured and tested in the protein transduction assay described in Example 3.1. Briefly, GP recombinant protein (5 μM) was co-incubated with different concentrations and combinations of CM18-TAT-Cys, CM18-Penetratin-Cys, and dimers of each (dCM18-TAT-Cys, dCM18-Penetratin-Cys), and then exposed to HeLa cells for 1 hour. The cells were subjected to flow cytometry analysis as described in Example 3.3. The results are shown in Table 3.3 and FIG. 8, as well as in Table 3.4 and FIG. 9.

TABLE 3.3

Figure 8:
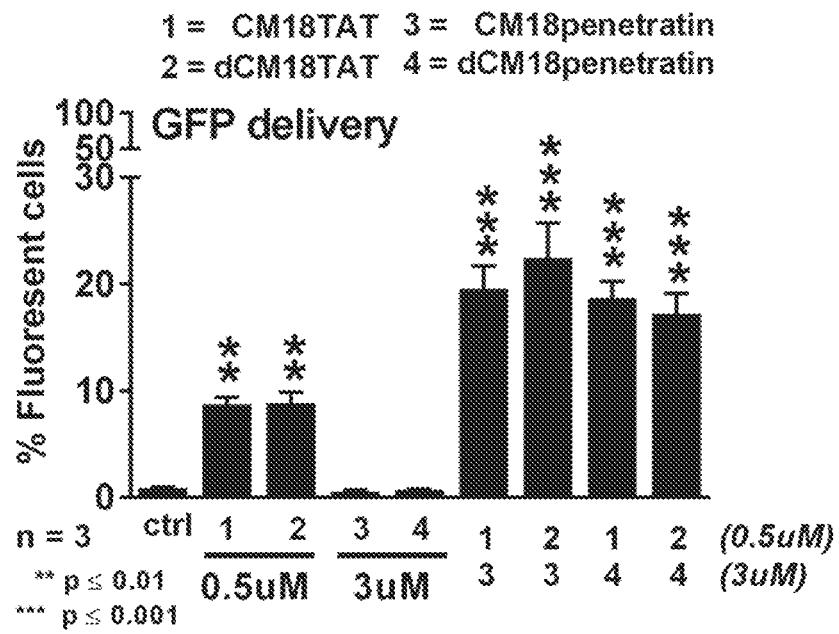
FIGS. 8 and 9 show the results of GFP transduction efficiency experiments in which GFP cargo protein (10 μM) was co-incubated with different concentrations and combinations of CM18-TAT-Cys (labeled "CM18TAT"), CM18-Penetratin-Cys (labeled "CM18penetratin"), and dimers of each (dCM18-TAT-Cys (labeled "dCM18TAT"), dCM18-Penetratin-Cys (labeled "dCM18penetratin"), prior to being exposed to HeLa cells. Cells were evaluated by flow cytometry and the percentages of fluorescent (GFP-positive) cells are shown.

Data in FIG. 8

| No. in FIG. 8 | Shuttle agent | Cells | Concentration (μM) | Mean (%) (n = 3) | Standard deviation |
|---|---|---|---|---|---|
| Control ("ctrl") | No shuttle | HeLa | 0 | 0.43 | 0.08 |
| 1 | CM18-TAT-Cys | HeLa | 0.5 | 8.75 | 0.63 |
| 2 | dCM18-TAT-Cys | HeLa | 0.5 | 8.86 | 1.03 |
| 3 | CM18-Penetratin-Cys | HeLa | 3 | 0.59 | 0.11 |
| 4 | dCM18-Penetratin-Cys | HeLa | 3 | 0.73 | 0.08 |
| 1 + 3 | CM18-TAT-Cys + CM18Penetratin-Cys | HeLa | 0.5 3 | 19.52 | 2.18 |
| 2 + 3 | dCM18-TAT-Cys + CM18-Penetratin-Cys | HeLa | 0.5 3 | 22.44 | 3.29 |
| 1 + 4 | CM18-TAT-Cys + dCM18-Penetratin-Cys | HeLa | 0.5 3 | 18.73 | 1.55 |
| 2 + 4 | dCM18-TAT-Cys + dCM18-Penetratin-Cys | HeLa | 0.5 3 | 17.19 | 1.93 |

The results in Table 3.3 and FIG. 8 show that the transduction efficiency of GFP is increased in HeLa cells using the shuttle agents CM18-TAT-Cys and dCM18-TAT-Cys (see bars "1" and "2" in FIG. 8). Although no GFP intracellular delivery was observed using CM18-Penetratin-Cys or dCM18-Penetratin-Cys alone (see bars "3" or "4" in FIG. 8), combination of CM18-TAT-Cys with CM18-Penetratin-Cys (monomer or dimer) improved GFP protein delivery (see four right-most bars in FIG. 8).

TABLE 3.4

Figure 9:
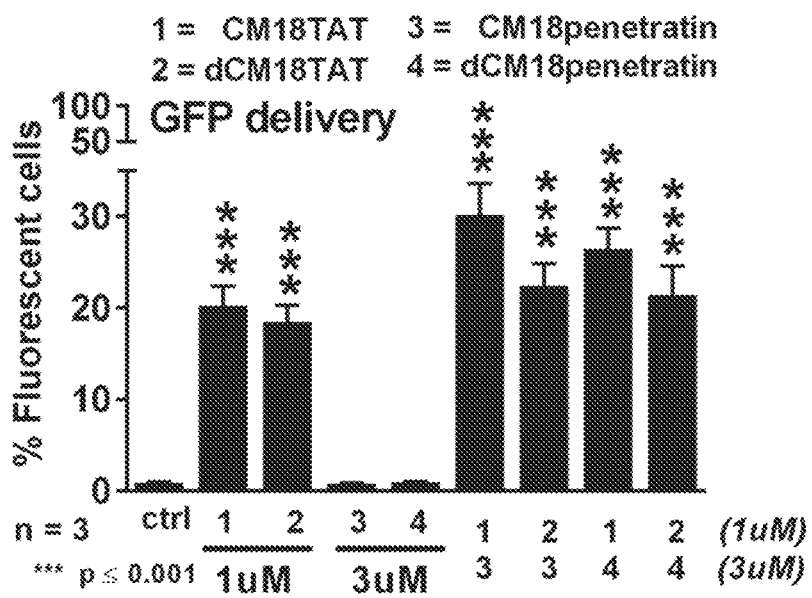

Data in FIG. 9

| No. in FIG. 9 | Shuttle | Cells | Concentration (μM) | Mean (%) (n = 3) | Standard deviation |
|---|---|---|---|---|---|
| Control ("ctrl") | No shuttle | HeLa | 0 | 0.51 | 0.07 |
| 1 | CM18-TAT-Cys | HeLa | 1 | 20.19 | 2.19 |
| 2 | dCM18-TAT-Cys | HeLa | 1 | 18.43 | 1.89 |
| 3 | CM18-Penetratin-Cys | HeLa | 3 | 0.81 | 0.07 |
| 4 | dCM18-Penetratin-Cys | HeLa | 3 | 0.92 | 0.08 |
| 1 + 3 | CM18-TAT-Cys + CM18-Penetratin-Cys | HeLa | 1 3 | 30.19 | 3.44 |
| 2 + 3 | dCM18-TAT-Cys + CM18-Penetratin-Cys | HeLa | 1 3 | 22.36 | 2.46 |
| 1 + 4 | CM18-TAT-Cys + dCM18-Penetratin-Cys | HeLa | 1 3 | 26.47 | 2.25 |
| 2 + 4 | dCM18-TAT-Cys + dCM18-Penetratin-Cys | HeLa | 1 3 | 21.44 | 3.11 |

The results in Table 3.4 and FIG. 9 show that the transduction efficiency of GFP is increased in HeLa cells using the shuttle agents CM18-TAT-Cys and dCM18-TAT-Cys (see bars "1" and "2" in FIG. 9). Although no GFP intracellular delivery was observed using CM18-Penetratin-Cys or dCM18-Penetratin-Cys alone (see bars "3" or "4" in FIG. 9), combination of CM18-TAT-Cys with CM18-Penetratin-Cys (monomer or dimer) improved GFP protein delivery (see four right-most bars in FIG. 9).

3.8 GFP Transduction by Shuttle Agents in HeLa Cells: Controls

HeLa cells were cultured and tested in the protein transduction assay described in Example 3.1. Briefly, GFP recombinant protein (5 µM) was co-incubated with 5 µM of each of the following peptide(s): TAT-Cys; CM18; Penetratin-Cys; TAT-Cys+CM18; Penetratin-Cys+CM18; and CM18-TAT-Cys, and then exposed to HeLa cells for 1 hour. GFP fluorescence was visualized by bright field and fluorescence microscopy. The microscopy results (data not shown) showed that GFP was successfully delivered intracellularly using CM18-TAT-Cys. However, GFP was not successfully delivered intracellularly using single-domain peptides used alone (CM18, TAT-Cys, Penetratin-Cys) or together (CM18+TAT-Cys, CM18+Penetratin-Cys). These results are consistent with those presented in Tables 2.1 and 2.2 with respect to the calcein endosome escape assays.

Example 4

Peptide Shuttle Agents Increase TAT-GFP Transduction Efficiency

The experiments in Example 3 showed the ability of shuttle agents to deliver GFP intracellularly. The experiments presented in this example show that the shuttle agents can also increase the intracellular delivery of a GFP cargo protein that is fused to a CPD (TAT-GFP).

4.1 Construction and Amino Acid Sequence of TAT-GFP

Construction was performed as described in Example 3.4, except that a TAT sequence was cloned between the 6× histidine tag and the GFP sequences. The 6× histidine tag, TAT, GFP and a stop codon (−) are separated by serine/glycine rich linkers. The recombinant TAT-GFP protein was purified as described in Example 1.4. The sequence of the TAT-GFP construct was:

```
                                           SEQ ID NO: 61]
MHHHHHHGGGGSGGGGSGGASTGTGRKKRRQRRRPPQGGGGSGGGGSGGGT

GIRMVSKGEELFTGVVPILVELDGDVNGHKFSVSGEGEGDATYGKLTLKFI

CTTGKLPVPWPTLVTTLTYGVQCFSRYPDHMKQHDFFKSAMPEGYVQERTI

FFKDDGNYKTRAEVKFEGDTLVNRIELKGIDFKEDGNILGHKLEYNYNSHN

VYIMADKQNGIKVNFKIRHNIEDGSVQLADHYQQNTPIGDGPVLLPDNHYL

STQSALSKDPNEKRDHMVLLEFVTAAGITLGMDELYKGGSGGGSGGGSGWI

RASSGGREIS-
(MW = 34.06 kDa; pI = 8.36)
TAT sequence is underlined
Serine/glycine rich linkers are in bold
```

Figure 10:
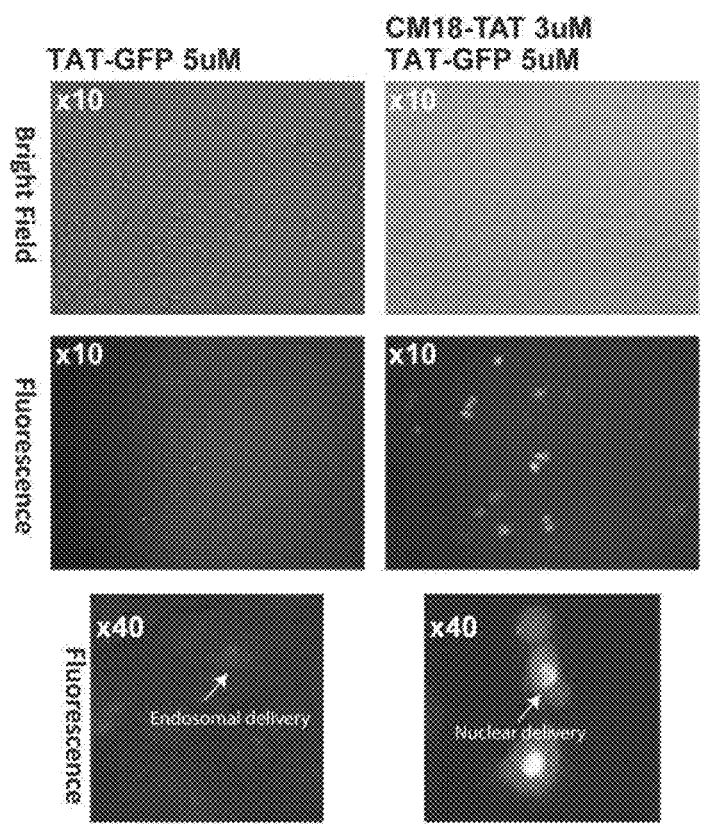
FIG. 10 shows typical results of a TAT-GFP transduction experiment in which TAT-GFP cargo protein (5 μM) was co-incubated with 3 μM of CM18-TAT-Cys (labeled "CM18-TAT"), prior to being exposed to HeLa cells. Cells and GFP fluorescence were visualized by bright field and fluorescence microscopy at 10× and 40× magnifications. Arrows indicate the endosome delivery of TAT-GFP in the absence of CM18-TAT-Cys, as well as its nuclear delivery in the presence of CM18-TAT-Cys.

4.2 TAT-GFP Transduction by CM18-TAT-Cys in HeLa Cells: Visualisation by Fluorescence Microscopy HeLa cells were cultured and tested in the protein transduction assay described in Example 3.1. Briefly, TAT-GFP recombinant protein (5 µM) was co-incubated with 3 µM of CM18-TAT-Cys and then exposed to HeLa cells for 1 hour. Cells and GFP fluorescence were visualized by bright field and fluorescence microscopy (as described in Example 3.2) at 10× and 40× magnifications, and sample results are shown in FIG. 10. The microscopy results revealed that in the absence of CM18-TAT-Cys, TAT-GFP shows a low intensity, endosomal distribution as reported in the literature. In contrast, TAT-GFP is delivered to the cytoplasm and to the nucleus in the presence of the shuttle agent CM18-TAT-Cys. Without being bound by theory, the TAT peptide itself may act as a nuclear localization signal (NLS), explaining the nuclear localization of TAT-GFP. These results show that CM18-TAT-Cys is able to increase TAT-GFP transduction efficiency and allow endosomally-trapped TAT-GFP to gain access to the cytoplasmic and nuclear compartments.

4.3 TAT-GFP Transduction by CM18-TAT-Cys in HeLa Cells: Dose Responses and Viability of Cells Transduced HeLa cells were cultured and tested in the protein transduction assay described in Example 3.1. Briefly, TAT-GFP recombinant protein (5 µM) was co-incubated with different concentrations of CM18-TAT-Cys (0, 0.5, 1, 3, or 5 µM) and then exposed to HeLa cells for 1 hour. The cells were subjected to flow cytometry analysis as described in Example 3.3. Results are shown in Table 4.3 and FIG. 11A. Corresponding cellular toxicity data are presented in FIG. 11B.

TABLE 4.3

Figure 11A:
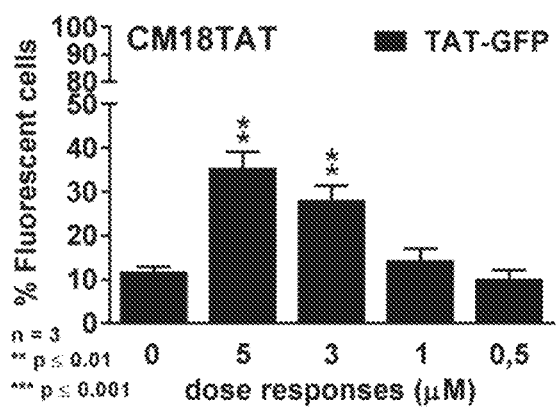
FIGS. 11A and 11B show the results of a TAT-GFP transduction efficiency experiment in which TAT-GFP cargo protein (5 μM) was co-incubated with different concentrations of CM18-TAT-Cys (labeled "CM18TAT"), prior to being exposed to HeLa cells. Cells were evaluated by flow cytometry and the percentage of fluorescent (GFP-positive) cell is shown in FIG. 11A, and corresponding cell toxicity data is shown in FIG. 11B.
Figure 11B:
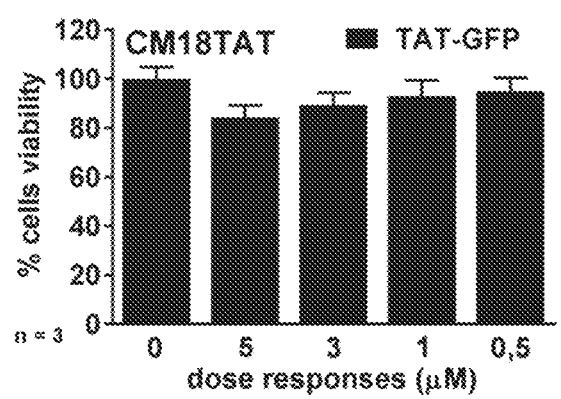

Data from FIG. 11A and 11B

| Shuttle agent | Cells | Concentration (µM) | FIG. 11A Mean (%) (n = 3) | Standard deviation | FIG. 11B Cell viability (%) (±St. Dev.; n = 3) |
|---|---|---|---|---|---|
| CM18-TAT-Cys | HeLa | 0 | 11.79[1] | 1.16 | 100 |
|  | HeLa | 0.5 | 10.19 | 1.94 | 84.36 ± 5 |
|  | HeLa | 1 | 14.46 | 2.59 | 89.26 ± 5.26 |
|  | HeLa | 3 | 28.12 | 3.27 | 93.18 ± 6.28 |
|  | HeLa | 5 | 35.5[2] | 3.59 | 95.14 ± 5.28 |

[1]The fluorescence was mostly endosomal, as confirmed by fluorescence microscopy.
[2]Fluorescence was more diffuse and also nuclear, as confirmed by fluorescence microscopy.

Example 5

Peptide Shuttle Agents Increase GFP-NLS Transduction Efficiency and Nuclear Localization The experiments in Examples 3 and 4 showed the ability of shuttle agents to deliver GFP and TAT-GFP intracellularly. The experiments presented in this example show that the shuttle agents can facilitate nuclear delivery of a GFP protein cargo fused to a nuclear localization signal (NLS).

5.1 Construction and Amino Acid Sequence of GFP-NLS

Construction was performed as described in Example 3.4, except that an optimized NLS sequence was cloned between the GFP sequence and the stop codon (−). The NLS sequence is separated from the GFP sequence and the stop codon by two serine/glycine rich linkers. The recombinant GFP-NLS protein was purified as described in Example 1.4. The sequence of the GFP-NLS construct was: IDC-49 DNA

[SEQ ID NO: 62]
MHHHHHHGGGGSGGGGSGGASTGIRMVSKGEELFTGVVPILVELDGDVNGH

KFSVSGEGEGDATYGKLTLKFICTTGKLPVPWPTLVTTLTYGVQCFSRYPD

HMKQHDFFKSAMPEGYVQERTIFFKDDGNYKTRAEVKFEGDTLVNRIELKG

IDFKEDGNILGHKLEYNYNSHNVYIMADKQKNGIKVNFKIRHNIEDGSVQL

ADHYQQNTPIGDGPVLLPDNHYLSTQSALSKDPNEKRDHMVLLEFVTAAGI

TLGMDELYKGGSGGGSGGGSGWIRASSGGRSSDDEATADSQHAAPPKKKRK

Figure 12:
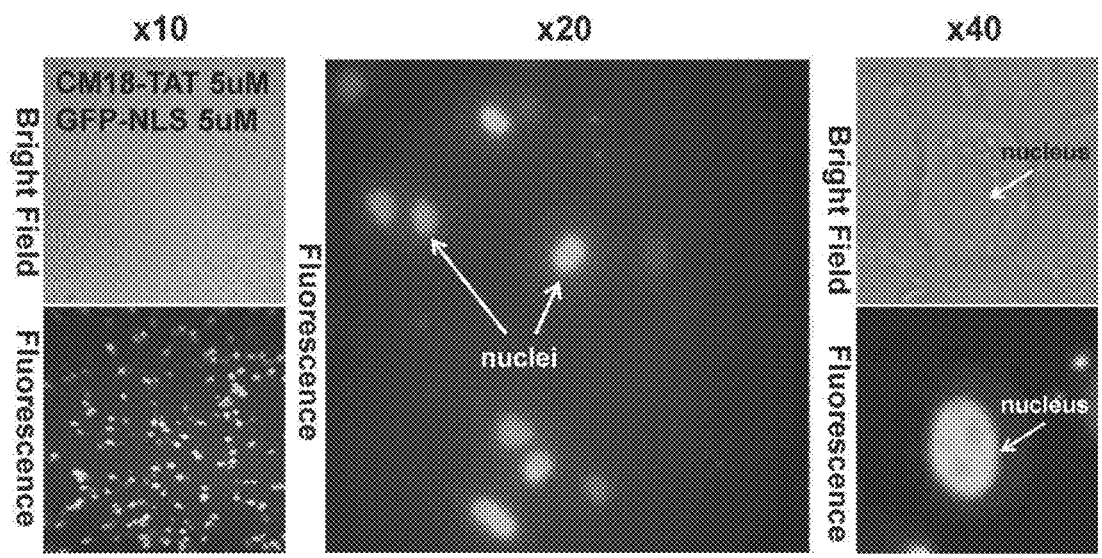
FIG. 12 shows typical results of a GFP-NLS transduction experiment in which GFP-NLS cargo protein (5 μM) was co-incubated with 5 μM of CM18-TAT-Cys (labeled "CM18-TAT"), prior to being exposed to HeLa cells for 5 minutes. Cells and GFP fluorescence were visualized by bright field and fluorescence microscopy at 10×, 20×, and 40× magnifications. Arrows indicate areas of nuclear delivery of GFP-NLS.

VGGSGGGSGGGSGGGRGTEIS-
(MW = 34.85 kDa; pI = 6.46)
NLS sequence is underlined
Serine/glycine rich linkers are in bold 5.2 Nuclear Delivery of GFP-NLS by CM18-TAT-Cys in HeLa Cells in 5 Minutes: Visualisation by Fluorescence Microscopy HeLa cells were cultured and tested in the protein transduction assay described in Example 3.1. Briefly, GFP-NLS recombinant protein (5 µM) was co-incubated with 5 µM of CM18-TAT-Cys, and then exposed to HeLa cells. GFP fluorescence was visualized by bright field and fluorescence microscopy after 5 minutes (as described in Example 3.2) at 10×, 20× and 40× magnifications, and sample results are shown in FIG. 12. The microscopy results revealed that GFP-NLS is efficiently delivered to the nucleus in the presence of the shuttle agent CM18-TAT-Cys, after only 5 minutes of incubation.

5.3 GFP-NLS Transduction by CM18-TAT-Cys in HeLa Cells: Dose Responses and Viability of Cells Transduced HeLa cells were cultured and tested in the protein transduction assay described in Example 3.1. GFP-NLS recombinant protein (5 µM) was co-incubated with 0, 0.5, 1, 3, or 5 µM of CM18-TAT-Cys, and then exposed to HeLa cells for 1 hour. The cells were subjected to flow cytometry analysis as described in Example 3.3. Results are shown in Table 5.1 and FIG. 13A. Corresponding cellular toxicity data are presented in FIG. 13B.

TABLE 5.1

Figure 13A:
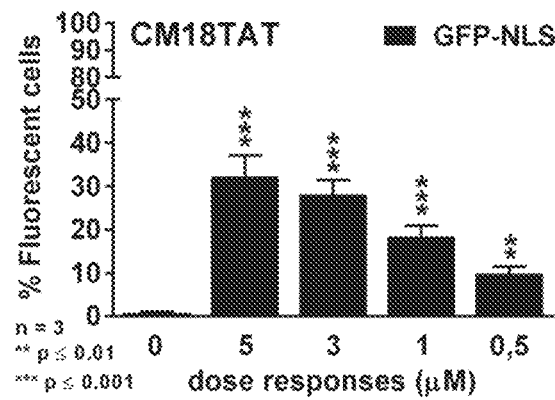
FIGS. 13A and 13B show the results of a GFP-NLS transduction efficiency experiment in which GFP-NLS cargo protein (5 μM) was co-incubated with different concentrations of CM18-TAT-Cys (labeled "CM18TAT"), prior to being exposed to HeLa cells. Cells were evaluated by flow cytometry and the percentage of fluorescent (GFP-positive) cell is shown in FIG. 13A, and corresponding cell toxicity data is shown in FIG. 13B.
Figure 13B:
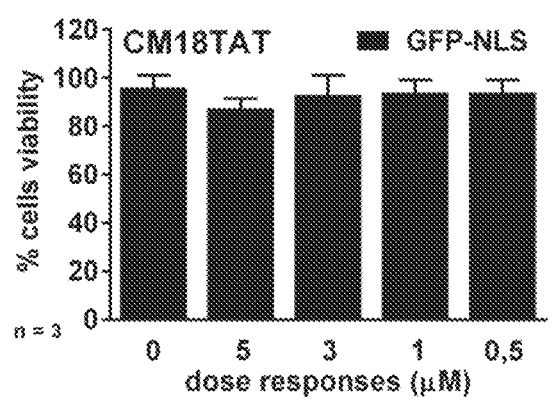

Data from FIGS. 13A and 13B

| | | | FIG. 13A | | FIG. 13B Cell viability |
|---|---|---|---|---|---|
| Shuttle agent | Cells | Concentration (µM) | Mean (%) (n = 3) | Standard deviation | (%) (±St Dev.; n = 3) |
| CM18-TAT-Cys | HeLa | 0 | 0.90 | 0.12 | 100 |
| | HeLa | 0.5 | 9.81 | 1.63 | 87.6 ± 4 |
| | HeLa | 1 | 18.42 | 2.47 | 93 ± 8 |
| | HeLa | 3 | 28.09 | 3.24 | 94 ± 5 |
| | HeLa | 5 | 32.26 | 4.79 | 93 ± 4 |

These results show that CM18-TAT-Cys is able to increase GFP-NLS transduction efficiency in HeLa cells in a dose-dependent manner.

5.4 GFP-NLS Transduction by CM18-TAT-Cys, CM18-Penetratin-Cys, and Dimers Thereof in HeLa Cells HeLa cells were cultured and tested in the protein transduction assay described in Example 3.1. GFP-NLS recombinant protein (5 µM) was co-incubated with different concentrations and combinations of CM18-TAT-Cys, CM18-Penetratin-Cys, and dimers of each (dCM18-TAT-Cys, dCM18-Penetratin-Cys), and then exposed to HeLa cells for 1 hour. The cells were subjected to flow cytometry analysis as described in Example 3.3. The results are shown in Tables 5.2 and 5.3, and in FIGS. 14 and 15.

TABLE 5.2

Figure 14:
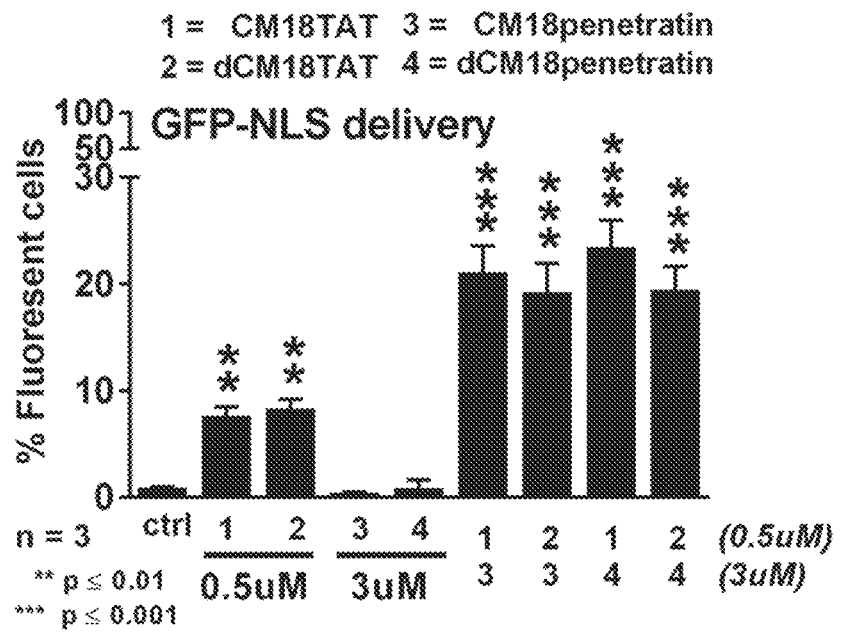
FIGS. 14 and 15 show the results of GFP-NLS transduction efficiency experiments in which GFP-NLS cargo protein (5 μM) was co-incubated with different concentrations and combinations of CM18-TAT (labeled "CM18TAT"), CM18-Penetratin (labeled "CM18penetratin"), and dimers of each (dCM18-TAT-Cys, dCM18-Penetratin-Cys; labeled "dCM18TAT" and "dCM18penetratin", respectively), prior to being exposed to HeLa cells. Cells were evaluated by flow cytometry and the percentages of fluorescent (GFP-positive) cells are shown.

Data in FIG. 14

| No. in FIG. 14 | Shuttle agent | Cells | Concentration (µM) | Mean (%) (n = 3) | Standard deviation |
|---|---|---|---|---|---|
| ctrl | No shuttle | HeLa | 0 | 0.41 | 0.10 |
| 1 | CM18-TAT-Cys | HeLa | 0.5 | 7.64 | 0.85 |
| 2 | dCM18-TAT-Cys | HeLa | 0.5 | 8.29 | 0.91 |
| 3 | CM18-Penetratin-Cys | HeLa | 3 | 0.43 | 0.08 |
| 4 | dCM18-Penetratin-Cys | HeLa | 3 | 0.85 | 0.07 |
| 1 + 3 | CM18-TAT-Cys + CM18-Penetratin-Cys | HeLa | 0.5 3 | 21.1 | 2.47 |
| 2 + 3 | dCM18-TAT-Cys + CM18-Penetratin-Cys | HeLa | 0.5 3 | 19.22 | 2.73 |
| 1 + 4 | CM18-TAT-Cys + dCM18-Penetratin-Cys | HeLa | 0.5 3 | 23.44 | 2.51 |
| 2 + 4 | dCM18-TAT-Cys + dCM18-Penetratin-Cys | HeLa | 0.5 3 | 19.47 | 2.16 |

TABLE 5.3

Figure 15:
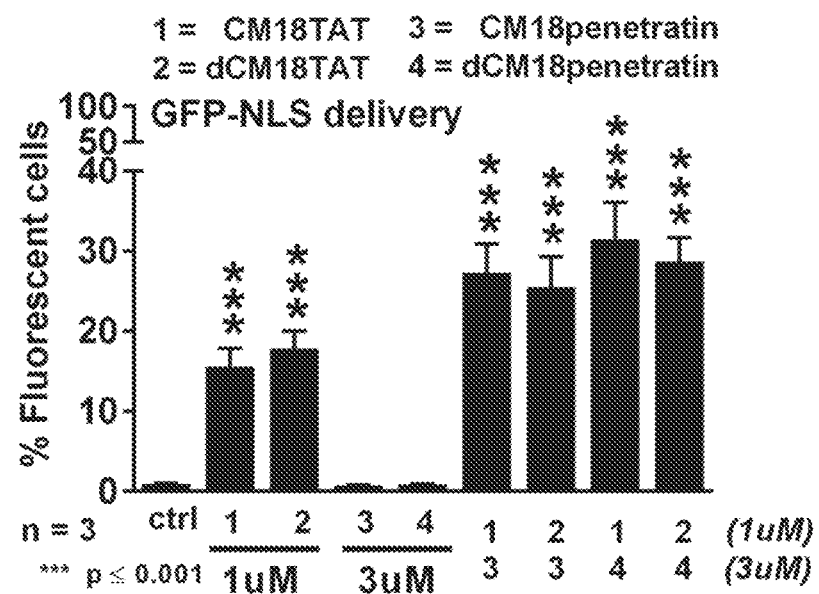

Data in FIG. 15

| No. in FIG. 15 | Shuttle agent | Cells | Concentration (µM) | Mean (%) (n = 3) | Standard deviation |
|---|---|---|---|---|---|
| ctrl | No shuttle | HeLa | 0 | 0.44 | 0.12 |
| 1 | CM18-TAT-Cys | HeLa | 1 | 15.56 | 2.24 |
| 2 | dCM18-TAT-Cys | HeLa | 1 | 17.83 | 2.13 |
| 3 | CM18-Penetratin-Cys | HeLa | 3 | 0.68 | 0.05 |
| 4 | dCM18-Penetratin-Cys | HeLa | 3 | 0.84 | 0.07 |
| 1 + 3 | CM18-TAT-Cys + CM18-Penetratin-Cys | HeLa | 1 3 | 27.26 | 3.61 |
| 2 + 3 | dCM18-TAT-Cys + CM18-Penetratin-Cys | HeLa | 1 3 | 25.47 | 3.77 |
| 1 + 4 | CM18-TAT-Cys + dCM18-Penetratin-Cys | HeLa | 1 3 | 31.47 | 4.59 |
| 2 + 4 | dCM18-TAT-Cys + dCM18-Penetratin-Cys | HeLa | 1 3 | 28.74 | 2.93 |

The results in Tables 5.2 and 5.3 and FIGS. 14 and 15 show that the transduction efficiency of GFP-NLS is increased in HeLa cells using the shuttle agents CM18-TAT-Cys and dCM18-TAT-Cys (see bars "1" and '2' in FIGS. 14 and 15). Although no GFP-NLS intracellular delivery was observed using CM18-Penetratin-Cys or dCM18-Penetratin-Cys alone (see bars "3" and "4" in FIGS. 14 and 15), combination of CM18-TAT-Cys with CM18-Penetratin-Cys (monomer or dimer) improved GFP-NLS intracellular delivery (see four right-most bars in FIGS. 14 and 15).

5.5 GFP-NLS Transduction by Shuttle Agents in HeLa Cells: 5 Min v. 1 h Incubation; with or without FBS HeLa cells were cultured and tested in the protein transduction assay described in Example 3.1. GFP-NLS recombinant protein (5 µM) was co-incubated with either CM18-

TAT-Cys (3.5 μM) alone or with dCM18-Penetratin-Cys (1 μM). Cells were incubated for 5 minutes or 1 hour in plain DMEM media ("DMEM") or DMEM media containing 10% FBS ("FBS"), before being subjected to flow cytometry analysis as described in Example 3.3. The results are shown in Table 5.4, and in FIG. 16. Cells that were not treated with shuttle agent or GFP-NLS ("ctrl"), and cells that were treated with GFP-NLS without shuttle agent ("GFP-NLS 5 μM") were used as controls.

TABLE 5.4

Figure 16:
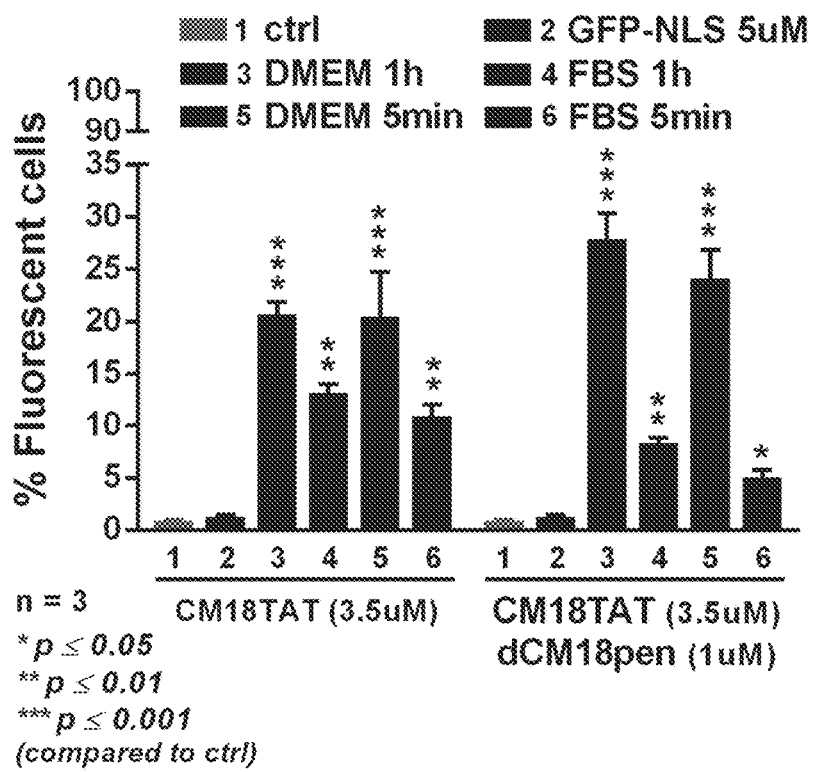
FIG. 16 shows the results of a GFP-NLS transduction efficiency experiment in which GFP-NLS cargo protein (5 μM) was co-incubated with either CM18-TAT-Cys (3.5 μM, labeled "CM18TAT") alone or with dCM18-Penetratin-Cys (1 μM, labeled "dCM18pen") for 5 minutes or 1 hour in plain DMEM media ("DMEM") or DMEM media containing 10% FBS ("FBS"), before being subjected to flow cytometry analysis. The percentages of fluorescent (GFP-positive) cells are shown. Cells that were not treated with shuttle agent or GFP-NLS ("ctrl"), and cells that were treated with GFP-NLS without shuttle agent ("GFP-NLS 5 μM") were used as controls.

Data in FIG. 16

| Shuttle | No. in FIG. 16 | Cells | Medium | Incubation time | Shuttle Conc. (μM) | Mean (%) (n = 3) | Standard deviation |
|---|---|---|---|---|---|---|---|
| No shuttle (Ctrl) | 1 | HeLa | DMEM | 1 h | 0 | 0.59 | 0.09 |
| GFP-NLS alone | 2 | HeLa | DMEM | 1 h | 0 | 1.19 | 0.31 |
| CM18-TAT-Cys | 3 | HeLa | DMEM | 1 h | 3.5 | 20.69 | 1.19 |
|  | 4 | HeLa | FBS | 1 h | 3.5 | 13.20 | 0.82 |
| CM18-TAT-Cys | 5 | HeLa | DMEM | 5 min | 3.5 | 20.45 | 4.26 |
|  | 6 | HeLa | FBS | 5 min | 3.5 | 10.83 | 1.25 |
| No shuttle (Ctrl) | 1 | HeLa | DMEM | 1 h | 0 | 0.53 | 0.11 |
| GFP-NLS alone | 2 | HeLa | DMEM | 1 h | 0 | 1.25 | 0.40 |
| CM18-TAT-Cys + dCM18-Penetratin-Cys | 3 | HeLa | DMEM | 1 h | 3.51 | 27.90 | 2.42 |
|  | 4 | HeLa | FBS | 1 h | 3.51 | 8.35 | 0.46 |
| CM18-TAT-Cys + dCM18-Penetratin-Cys | 5 | HeLa | DMEM | 5 min | 3.51 | 24.10 | 2.76 |
|  | 6 | HeLa | FBS | 5 min | 3.51 | 5.02 | 0.72 |

The results in Table 5.4 and FIG. 16 show that the addition of even a relatively low amount of the dimer dCM18-Penetratin-Cys (1 μM; "dCM18pen") to the CM18-TAT-Cys monomer improved GFP-NLS transduction efficiency. Interestingly, intracellular GFP-NLS delivery was achieved in as little as 5 minutes of incubation, and delivery was still achievable (although reduced) in the presence of FBS.

5.6 GFP-NLS Transduction by Shuttle Agents in THP-1 Suspension Cells

The ability of the shuttle agents to deliver GFP-NLS intracellularly was tested in THP-1 cells, which is an acute monocytic leukemia cell line that grows in suspension. THP-1 cells were cultured (see Example 1) and tested in the protein transduction assay described in Example 3.1. GFP-NLS recombinant protein (5 μM) was co-incubated with or without 1 μM CM18-TAT-Cys, and exposed to the THP-1 cells for 5 minutes, before being subjected to flow cytometry analysis as described in Example 3.3. The results are shown in Table 5.5 and in FIG. 17A. Corresponding cellular toxicity data are presented in FIG. 17B.

TABLE 5.5

Figure 17A:
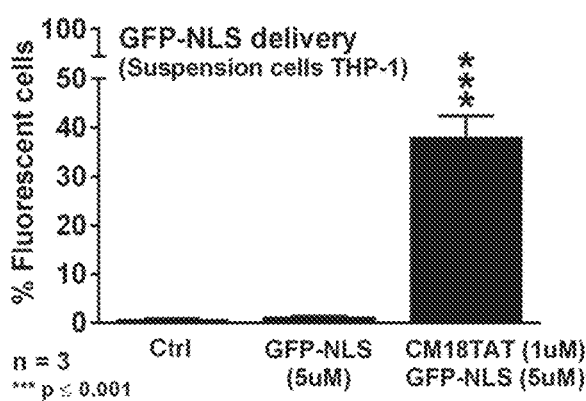
FIGS. 17A and 17B show the results of a GFP-NLS transduction efficiency experiment in which GFP-NLS cargo protein (5 μM) was co-incubated with or without 1 μM CM18-TAT-Cys (labeled "CM18TAT"), prior to being exposed to THP-1 cells. Cells were evaluated by flow cytometry and the percentage of fluorescent (GFP-positive) cells is shown in FIG. 17A, and corresponding cell toxicity data is shown in FIG. 17B.
Figure 17B:
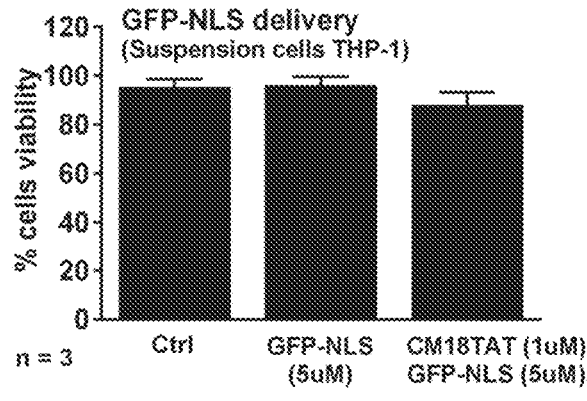

Data in FIGS. 17A and 17B

| | | | FIG. 17A | | FIG. 17B Cell viability |
|---|---|---|---|---|---|
| Shuttle | Cells | Shuttle Conc. (μM) | Mean (%) (n = 3) | Standard deviation | (%) (±St Dev.; n = 3) |
| No shuttle (Ctrl) | THP-1 | 0 | 1.23 | 0.16 | 95 ± 4 |
| GFP-NLS alone | | 0 | 2.49 | 0.37 | 96 ± 3 |
| CM18-TAT-Cys | | 1 | 38.1 | 4.16 | 85 ± 6 |

The results in Table 5.5 and FIG. 17 demonstrate the ability of the shuttle agents to deliver protein cargo intracellularly to a human monocytic cell line grown in suspension.

Example 6

Peptide Shuttle Agents Increase Transduction Efficiency of an FITC-Labeled Anti-Tubulin Antibody The experiments in Examples 3-5 showed the ability of shuttle agents to increase the transduction efficiency of GFP, TAT-GFP, and GFP-NLS. The experiments presented in this example show that the shuttle agents can also deliver a larger protein cargo: an FITC-labeled anti-tubulin antibody. The FITC-labeled anti-tubulin antibody was purchased from (Abcam, ab64503) and has an estimated molecular weight of 150 KDa. The delivery and microscopy protocols are described in Example 3.

Figure 18:
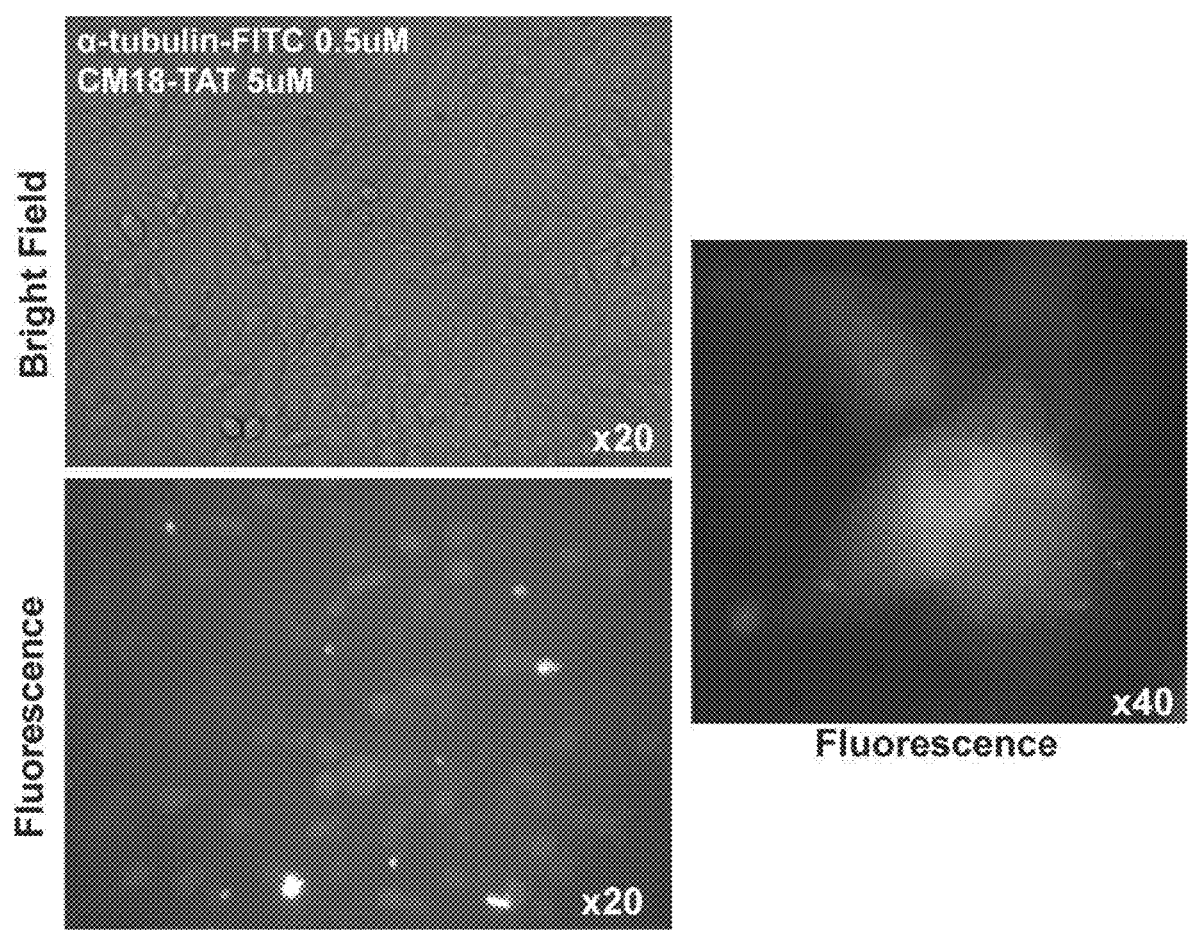
FIG. 18 shows the results of a transduction efficiency experiment in which the cargo protein, FITC-labeled anti-tubulin antibody (0.5 μM), was co-incubated with 5 μM of CM18-TAT-Cys (labeled "CM18-TAT"), prior to being exposed to HeLa cells. Functional antibody delivery was visualized by bright field (20×) and fluorescence microscopy (20× and 40×), in which fluorescent tubulin fibers in the cytoplasm were visualized.

6.1 Transduction of a Functional Antibody by CM18-TAT-Cys in HeLa Cells: Visualization by Microscopy FITC-labeled anti-tubulin antibody (0.5 μM) was co-incubated with 5 μM of CM18-TAT-Cys and exposed to HeLa cells for 1 hour. Antibody delivery was visualized by bright field (20×) and fluorescence microscopy (20× and 40×). As shown in FIG. 18, fluorescent tubulin fibers in the cytoplasm were visualized, demonstrating the functionality of the antibody inside the cell.

6.2 Transduction of a Functional Antibody by CM18-TAT-Cys, CM18-Penetratin-Cys, and Dimers in HeLa Cells: Flow Cytometry HeLa cells were cultured and tested in the protein transduction assay described in Example 3.1. FITC-labeled anti-tubulin antibody (0.5 μM) was co-incubated with 3.5 μM of CM18-TAT-Cys, CM18-Penetratin-Cys or dCM18-Penetratin-Cys, or a combination of 3.5 μM of CM18-TAT-Cys and 0.5 μM of dCM18-Penetratin-Cys, and exposed to HeLa cells for 1 hour. The cells were subjected to flow cytometry analysis as described in Example 3.3. Results are shown in Table 6.1 and FIG. 19A. Corresponding cellular toxicity data are presented in FIG. 19B.

TABLE 6.1

Figure 19A:
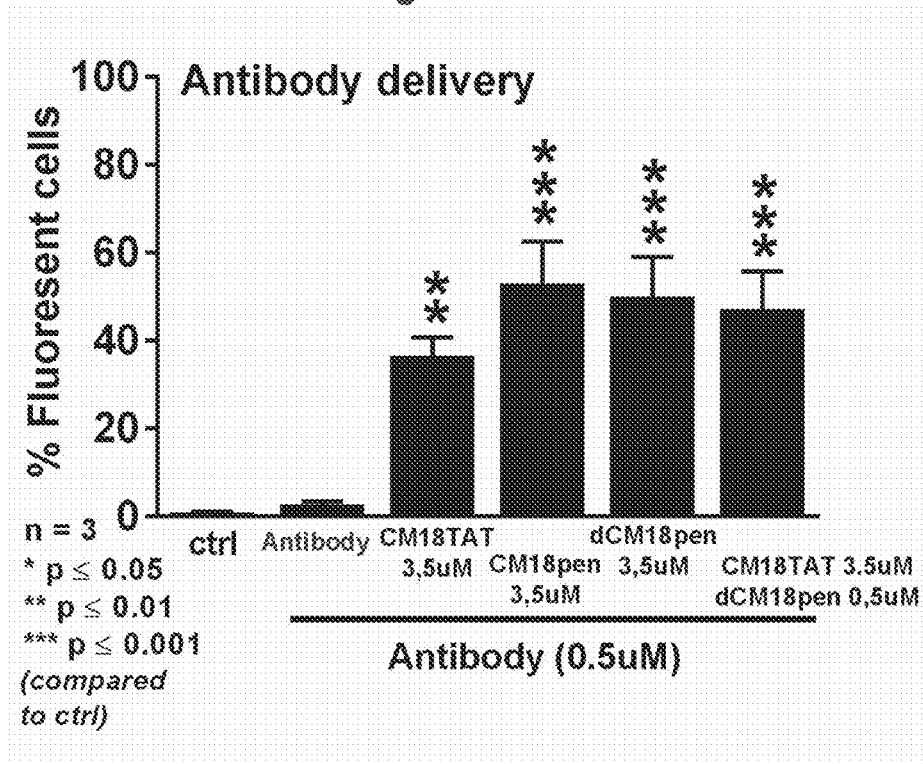
FIGS. 19A and 19B shows the results of an FITC-labeled anti-tubulin antibody transduction efficiency experiment in which the antibody cargo protein (0.5 μM) was co-incubated with 3.5 μM of CM18-TAT-Cys (labeled "CM18TAT"), CM18-Penetratin-Cys (labeled "CM18pen") or dCM18-Penetratin-Cys (labeled "dCM18pen"), or a combination of 3.5 μM of CM18-TAT-Cys and 0.5 μM of dCM18-Penetratin-Cys, prior to being exposed to HeLa cells. Cells were evaluated by flow cytometry and the percentage of fluorescent (FITC-positive) cell is shown in FIG. 19A, and corresponding cell toxicity data is shown in FIG. 19B.
Figure 19B:
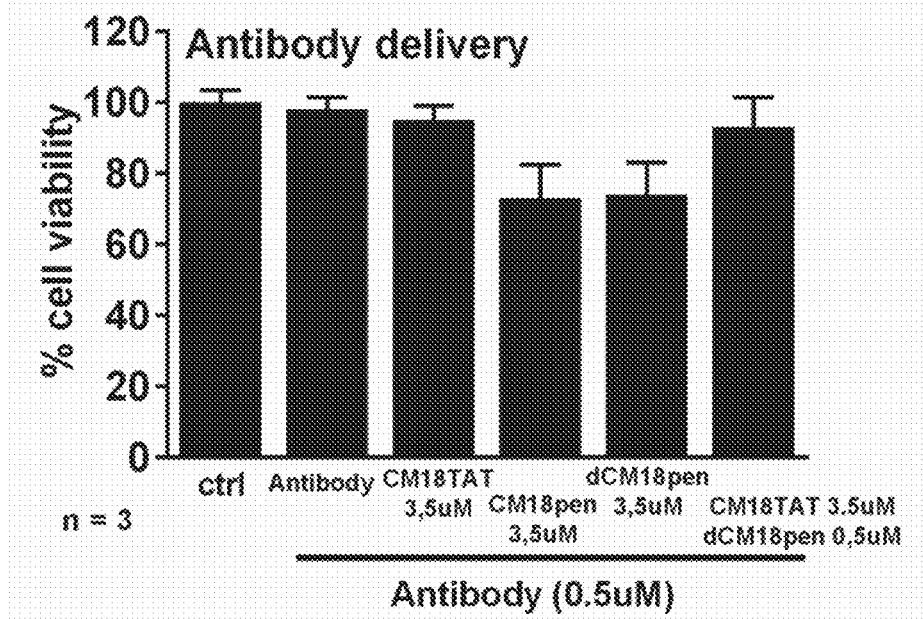

Data from FIG. 19A and 19B

| Domains | Shuttle agent | Cells | Shuttle Conc. (μM) | FIG. 19A Mean (%) (n = 3) | Standard deviation | FIG. 19B Cell viability (%) (± St. Dev.; n = 3) |
|---|---|---|---|---|---|---|
| — | No shuttle ("Ctrl") | HeLa | 0 | 0.9 | 0.06 | 98 ± 1.0 |
| — | Antibody alone ("antibody") | HeLa | 0 | 2.66 | 0.61 | 96 ± 3.4 |
| ELD-CPD | CM18-TAT-Cys | HeLa | 3.5 | 36.56 | 4.06 | 95 ± 4.06 |
| | CM18-Penetratin-Cys | HeLa | 3.5 | 53.05 | 9.5 | 73 ± 9.5 |
| ELD-CPD dimer | dCM18-Penetratin-Cys | HeLa | 3.5 | 50.23 | 9.12 | 74 ± 9.0 |
| ELD-CPD + ELD-CPD dimer | CM18-TAT-Cys + dCM18-Penetratin-Cys | HeLa | 3.5 0.5 | 47.19 | 8.5 | 93 ± 8.5 |

The results in Table 6.1 and FIGS. 18 and 19 show that both CM18-TAT-Cys and CM18-Penetratin-Cys facilitate intracellular delivery of an FITC-labeled anti-tubulin antibody. In contrast to the results with GFP, TAT-GFP, and GFP-NLS in Examples 3-5, CM18-Penetratin-Cys was able to deliver the antibody cargo intracellularly when used alone (without CM18-TAT-Cys). However, combination of CM18-TAT-Cys and dCM18-Penetratin-Cys allowed for higher intracellular delivery as compared with CM18-TAT-Cys alone, and with less cell toxicity as compared to CM18-Penetratin-Cys and dCM18-Penetratin-Cys (see FIGS. 19A and 19B).

Example 7

CM18-TAT-Cys Enables Intracellular Plasmid DNA Delivery but Poor Plasmid Expression The ability of the CM18-TAT-Cys shuttle agent to deliver plasmid DNA intracellularly was tested in this example on HEK293A cells using a plasmid encoding GFP.

7.1 Transfection Assay in HEK293A Cells

One day before the transfection assay was performed, mammalian cells (HEK293A) in exponential growth phase were harvested and plated in a 24-well plate (50,000 cells per well). The cells were incubated overnight in appropriate growth media containing FBS. The next day, in separate sterile 1.5 mL tubes, pEGFP labeled with a Cy5™ fluorochrome was mixed for 10 min at 37° C. with CM18-TAT-Cys (0.05, 0.5, or 5 p M) in fresh PBS at a final 100 μL volume. The media in wells was removed and the cells were quickly washed three times with PBS and 500 μL of warm media without FBS was added. The pEGFP and CM18-TAT-Cys solution was added to the cells and incubated at 37° C. for 4 hours. After the incubation, cells were washed with PBS and fresh media containing FBS was added. Cells were incubated at 37° C. before being subjected to flow cytometry analysis as described in Example 3.

7.2 Plasmid DNA Delivery with CM18-TAT-Cys

Plasmid DNA (pEGFP) was labeled with a Cy5™ dye following the manufacturer's instructions (Mirus Bio LLC). Cy5™ Moiety did not influence transfection efficiency when compared to unlabelled plasmid using standard transfection protocol (data not shown). Flow cytometry analysis allowed quantification of Cy5™ emission, corresponding to DNA intracellular delivery, and GFP emission, corresponding to successful nuclear delivery, DNA transcription and protein expression. The results are shown in Table 7.1 and in FIG. 20.

TABLE 7.1

Data from FIG. 20

| Sample | DNA (ng) | Cy5™ fluorescence Mean Cy5™ signal (n = 3) | Standard deviation | GFP expression Mean (% of cells with GFP signal; n = 3) | Standard deviation |
|---|---|---|---|---|---|
| pEGFP-Cy5 alone | 500 | 914 | 0 | 0.0% | n/a |
| CM18-TAT-Cys, 0.05 μM | 500 | 1450 | 120 | 0.0% | n/a |
| CM18-TAT-Cys, 0.5 μM | 500 | 8362 | 294 | 0.0% | n/a |
| CM18-TAT-Cys, 5 μM | 500 | 140 497 | 3977 | 0.1% | n/a |

The results shown in Table 7.1 and in FIG. 20 show that CM18-TAT-Cys was able to increase the intracellular delivery the plasmid DNA when used at 0.05, 0.5 and 5 μM concentrations, as compared to cell incubated with DNA alone ("pEGFP-Cy5"). However, no expression of GFP was detected in the cells, which suggests that very little of the plasmid DNA gained access to the cytoplasmic compartment, allowing nuclear localization. Without being bound by theory, it is possible that the plasmid DNA was massively sequestered in endosomes, preventing escape to the cytoplasmic compartment. Salomone et al., 2013 reported the use of a CM18-TAT11 hybrid peptide to deliver plasmid DNA intracellularly. They used the luciferase enzyme reporter assay to assess transfection efficiency, which may not be ideal for quantifying the efficiency of cytoplasmic/nuclear delivery, as the proportion of plasmid DNA that is successfully released from endosomes and delivered to the nucleus may be overestimated due to the potent activity of the luciferase enzyme. In this regard, the authors of Salomone et al., 2013 even noted that the expression of luciferase occurs together with a massive entrapment of (naked) DNA molecules into vesicles, which is consistent with the results shown in Table 7.1 and in FIG. 20.

7.3 Plasmid DNA Delivery by Peptides in HeLa Cells

Following the poor transfection efficiency of the peptide CM18-TAT-Cys (0.1%, see Table 7.1) observed in HEK293A cells, the experiment was repeated with CM18-TAT-Cys in another cell line (HeLa), along with other peptides listed in Table 1.3, Table B1, and Table C1.

One day before the transfection assay was performed, HeLa cells in exponential growth phase were harvested and plated in a 96-well plate (10,000 cells per well). The cells were incubated overnight in appropriate growth media containing FBS. The next day, in separate sterile 1.5 mL tubes, the peptide to be tested and the polynucleotide cargo (pEGFP-C1) were mixed for 10 min at 37° C. in serum-free medium at a final volume of 50 µL. The media in wells was removed and the cells were quickly washed one time with PBS at 37° C. The mix containing the peptide to be tested and the polynucleotide cargo was added to the cells and incubated at 37° C. for the indicated period of time (e.g., 1 min, 1 h or 4 h). After the incubation, cells were washed one time with PBS at 37° C. and fresh media containing FBS was added. Cells were incubated at 37° C. before being subjected to flow cytometry analysis as described in Example 3.2, to qualify transfection efficiency (i.e., cells expression EGFP) and viability. Results are shown in Table 7.2. Table 7.2. DNA transfection in HeLa cells using peptides Peptide Mean % cells with GFP signal Cell viability (%)

TABLE 7.2

DNA transfection in HeLa cells using peptides

| Peptide | Mean % cells with GFP signal (±St. Dev.; n = 3) | Cell viability (%) (±St. Dev.; n = 3) |
|---|---|---|
| No peptide (neg. control) | 0.0 ± 0.0 | 100 |
| PTD4-KALA | 0.85 ± 0.04 | 53.64 ± 3.91 |
| FSD9 | 0.81 ± 0.09 | 36.1 ± 3.41 |
| KALA | 0.79 ± 0.06 | 90.62 ± 4.16 |
| His-CM18-Transportan | 0.55 ± 0.01 | 11.89 ± 1.07 |
| FSD12 | 0.37 ± 0.14 | 58.6 ± 2.07 |
| dCM18-Pen-Cys | 0.35 ± 0.02 | 3.36 ± 0.26 |
| His-CM18-PTD4-His | 0.34 ± 0.03 | 29.4 ± 2.38 |
| FSD2 | 0.34 ± 0.00 | 55.77 ± 4.19 |
| Pep1-KALA | 0.31 ± 0.03 | 92.47 ± 3.42 |
| F5D25 | 0.31 ± 0.02 | 98.19 ± 1.19 |
| FSD7 | 0.29 ± 0.07 | 60.9 ± 7.59 |
| CM18-PTD4-His | 0.26 ± 0.01 | 29.5 ± 0.21 |
| FSD19 | 0.24 ± 0.01 | 97.41 ± 2.07 |
| FSD10 | 0.21 ± 0.01 | 72.36 ± 8.61 |
| FSD24 | 0.20 ± 0.00 | 96.45 ± 3.02 |
| FSD15 | 0.18 ± 0.02 | 98.3 ± 1.07 |
| 12His-CM18-PTD4 | 0.18 ± 0.01 | 97.55 ± 1.57 |
| CM18-L1-PTD4 | 0.16 ± 0.01 | 84.3 ± 5.64 |
| FSD33 | 0.15 ± 0.01 | 75.3 ± 4.19 |
| TAT-LAH4 | 0.15 ± 0.00 | 96.17 ± 2.70 |
| CM18-L2-PTD4 | 0.14 ± 0.01 | 93.7 ± 3.07 |
| M-His-CM18-TAT-Cys | 0.13 ± 0.01 | 33.1 ± 0.4 |
| FSD42 | 0.12 ± 0.02 | 96.67 ± 1.96 |
| FSD11 | 0.11 ± 0.01 | 46.2 ± 1.35 |
| Xentry-KALA | 0.1 ± 0.02 | 75.3 ± 4.29 |
| FSD5 | 0.1 ± 0.01 | 93.24 ± 8.63 |
| 3HA-CM18-PTD4 | 0.09 ± 0.01 | 51.48 ± 4.83 |
| FSD32 | 0.08 ± 0.02 | 98.36 ± 0.15 |
| CM18-TAT-Cys | 0.08 ± 0.01 | 96.28 ± 1.86 |
| FSD8 | 0.06 ± 0.84 | 42.3 ± 6.42 |
| CM18-L3-PTD4 | 0.06 ± 0.01 | 98.4 ± 0.83 |
| 3His-CM18-PTD4 | 0.06 ± 0.01 | 82.05 ± 6.81 |
| CM18-PTD4 | 0.06 ± 0.01 | 49.64 ± 5.06 |
| TAT-CM18 | 0.06 ± 0.01 | 44.79 ± 4.17 |
| HA-CM18-PTD4 | 0.06 ± 0.0 | 53.21 ± 4.62 |
| His-CM18-TAT | 0.05 ± 0.01 | 13.6 ± 0.18 |
| VSVG-PTD4 | 0.05 ± 0.01 | 96.21 ± 2.57 |
| 9His-CM18-PTD4 | 0.04 ± 0.01 | 98.72 ± 0.93 |
| JST-PTD4 | 0.04 ± 0.01 | 70.2 ± 5.39 |
| His-CM18-PTD4 | 0.04 ± 0.01 | 63.2 ± 4.07 |
| FSD23 | 0.04 ± 0.00 | 98.18 ± 1.03 |
| FSD20 | 0.04 ± 0.00 | 20.49 ± 3.53 |

TABLE 7.2-continued

DNA transfection in HeLa cells using peptides

| Peptide | Mean % cells with GFP signal (±St. Dev.; n = 3) | Cell viability (%) (±St. Dev.; n = 3) |
|---|---|---|
| FSD38 | 0.02 ± 0.00 | 95 ± 2.78 |
| FSD16 | 0.02 ± 0.00 | 99.07 ± 0.73 |
| FSD26 | 0.02 ± 0.00 | 97.2 ± 1.53 |
| FSD27 | 0.02 ± 0.00 | 98 ± 0.63 |
| FSD35 | 0.02 ± 0.00 | 96.14 ± 1.67 |
| CM18 | 0.02 ± 0.00 | 99.4 ± 0.14 |
| FSD30 | 0.02 ± 0.00 | 97.41 ± 2.06 |
| His-CM18-9Arg | 0.02 ± 00.0 | 31.63 ± 0.11 |
| FSD21 | 0.01 ± 0.00 | 96.17 ± 1.69 |
| 6His-PTD4 | 0.01 ± 0.00 | 97.25 ± 1.34 |
| FSD31 | 0.01 ± 0.00 | 98.43 ± 0.43 |
| FSD34 | 0.01 ± 0.00 | 96.43 ± 2.41 |
| FSD36 | 0.01 ± 0.00 | 97.05 ± 1.99 |
| FSD40 | 0.01 ± 0.00 | 98.63 ± 1.08 |
| FSD41 | 0.01 ± 0.00 | 94.38 ± 2.81 |
| FSD28 | 0.01 ± 0.00 | 97 ± 1.11 |
| CM18-Pen-Cys | 0.01 ± 0.0 | 16.1 ± 0.12 |
| PTD4 | 0.00 ± 0.01 | 98.2 ± 0.69 |
| FSD39 | 0.00 ± 0.00 | 99.2 ± 0.61 |
| His-CMH18-PTD4 | 0.00 ± 0.00 | 95.15 ± 2.33 |
| Penetratin | 0.00 ± 0.00 | 97.42 ± 1.03 |
| C(LLKK)3 | 0.00 ± 0.00 | 81.74 ± 2.34 |

All the peptides tested in Table 7.2 showed transfection efficiencies lower than 1%. Furthermore, the low transfection efficiency of CM18-TAT-Cys was confirmed in HeLa cells (0.08%). These results show that peptides which are suitable for delivering polypeptide cargos may not necessarily be suitable for delivering plasmid DNA. For example, the shuttle agent His-CM18-PTD4-His is shown herein to effectively transduce polypeptide cargos (e.g., see Example 10), yet this peptide displayed only a DNA plasmid transfection efficiency of 0.34% (Table 7.2).

Example 8

Addition of a Histidine-Rich Domain to Shuttle Agents Further Improves GFP-NLS Transduction Efficiency 8.1 GFP-NLS Transduction by his-CM18-TAT-Cys in HeLa Cells: Visualization by Microscopy GFP-NLS (5 µM; see Example 5) was co-incubated with 5 µM of CM18-TAT-Cys or His-CM18-TAT and exposed to HeLa cells for 1 hour. Nuclear fluorescence of intracellularly delivered GFP-NLS was confirmed by fluorescence microscopy (data not shown), indicating successful delivery of GFP-NLS to the nucleus.

8.2 GFP-NLS Transduction by his-CM18-TAT in HeLa Cells: Flow Cytometry

HeLa cells were cultured and tested in the protein transduction assay described in Example 3.1. GFP-NLS (5 µM) was co-incubated with 0, 1, 3, or 5 µM of CM18-TAT-Cys or His-CM18-TAT, and exposed to HeLa cells for 1 hour. The cells were subjected to flow cytometry analysis as described in Example 3.3. Results are shown in Table 8.1 and FIG. 21A. Corresponding cellular toxicity data are presented in FIG. 21B.

TABLE 8.1

Data from FIGS. 21A and 21B

| | | | FIG. 21A | | FIG. 21B |
|---|---|---|---|---|---|
| Shuttle agent | Cells | Shuttle Conc. (μM) | Mean (%) cell with GFP signal (n = 3) | Standard deviation | Cell viability (%) (±St. Dev.; n = 3) |
| Ctrl (no shuttle, no GFP-NLS) | HeLa | 0 | 0.63 | 0.10 | 96 ± 3.17 |
| GFP-NLS alone | | 0 | 0.93 | 0.26 | 97 ± 2.05 |
| CM18-TAT-Cys | | 5 | 20.54 | 3.51 | 81 ± 6.34 |
| | | 3 | 15.66 | 2.18 | 89 ± 5.37 |
| | | 1 | 8.64 | 1.11 | 94 ± 4.28 |
| Ctrl (no shuttle, no GFP-NLS) | HeLa | 0 | 0.51 | 0.28 | 95 ± 4.19 |
| GFP-NLS alone | | 0 | 1.07 | 0.42 | 96 ± 3.16 |
| His-CM18-TAT | | 5 | 41.38 | 4.59 | 86 ± 4.59 |
| | | 3 | 29.58 | 3.61 | 91 ± 5.18 |
| | | 1 | 8.45 | 1.83 | 95 ± 3.05 |

Strikingly, the results in Table 8.1 and in FIG. 21 show that His-CM18-TAT was able to increase GFP-NLS protein transduction efficiency by about 2-fold at 3 μM and 5 μM concentrations, as compared to CM18-TAT-Cys. These results suggest that adding a histidine-rich domain to a shuttle agent comprising an ELD and CPD, may significantly increase its polypeptide cargo transduction efficiency. Alternatively or in parallel, combining the shuttle agents with a further independent synthetic peptide containing a histidine-rich domain fused to a CPD (but lacking an ELD) may provide a similar advantage for protein transduction, with the added advantage of allowing the concentration of the histidine-rich domain to be varied or controlled independently from the concentration of the shuttle agent. Without being bound by theory, the histidine-rich domain may act as a proton sponge in the endosome, providing another mechanism of endosomal membrane destabilization.

Example 9

His-CM18-PTD4 Increases Transduction Efficiency and Nuclear Delivery of GFP-NLS, mCherry™-NLS and FITC-Labeled Anti-Tubulin Antibody 9.1 Protein Transduction Protocols
Protocol A: Protein Transduction Assay for Delivery in Cell Culture Medium One day before the transduction assay was performed, cells in exponential growth phase were harvested and plated in a 96-well plate (20,000 cells per well). The cells were incubated overnight in appropriate growth media containing FBS (see Example 1). The next day, in separate sterile 1.5-mL tubes, cargo protein at the desired concentration was pre-mixed (pre-incubated) for 10 min at 37° C. with the desired concentration of shuttle agents in 50 μL of fresh serum-free medium (unless otherwise specified). The media in wells was removed and the cells were washed one to three times (depending on the type of cells used) with PBS previously warmed at 37° C. The cells were incubated with the cargo protein/shuttle agent mixture at 37° C. for the desired length of time. After the incubation, the cells were washed three times with PBS and/or heparin (0.5 mg/mL) previously warmed at 37° C. The washes with heparin were used for human THP-1 blood cells to avoid undesired cell membrane-bound protein background in subsequent analyses (microscopy and flow cytometry). The cells were finally incubated in 50 μL of fresh medium with serum at 37° C. before analysis.

Protocol B: Protein Transduction Assay for Adherent Cells in PBS

One day before the transduction assay was performed, cells in exponential growth phase were harvested and plated in a 96-well plate (20,000 cells per well). The cells were incubated overnight in appropriate growth media containing serum (see Example 1). The next day, in separate sterile 1.5-mL tubes, shuttle agents were diluted in sterile distilled water at room temperature (if the cargo is or comprised a nucleic acid, nuclease-free water was used). Cargo protein(s) were then added to the shuttle agents and, if necessary, sterile PBS was added to obtain the desired concentrations of shuttle agent and cargo in a sufficient final volume to cover the cells (e.g., 10 to 100 μL per well for a 96-well plate). The shuttle agent/cargo mixture was then immediately used for experiments. At least three controls were included for each experiment, including: (1) shuttle agent alone (e.g., at highest concentration tested); (2) cargo alone; and (3) without any cargo or shuttle agent. The media in wells was removed, cells were washed once with PBS previously warmed at 37° C., and the shuttle agent/cargo mixture was then added to cover all cells for the desired length of time. The shuttle agent/cargo mixture in wells was removed, the cells were washed once with PBS, and fresh complete medium was added. Before analysis, the cells were washed once with PBS and fresh complete medium was added.

Protocol C: Protein Transduction Assay for Suspension Cells in PBS

One day before the transduction assay was performed, suspension cells in exponential growth phase were harvested and plated in a 96-well plate (20,000 cells per well). The cells were incubated overnight in appropriate growth media containing serum (see Example 1). The next day, in separate sterile 1.5-mL tubes, shuttle agents were diluted in sterile distilled water at room temperature (if the cargo is or comprised a nucleic acid, nuclease-free water was used). Cargo protein(s) were then added to the shuttle agents and, if necessary, sterile PBS or cell culture medium (serum-free) was added to obtain the desired concentrations of shuttle agent and cargo in a sufficient final volume to resuspend the cells (e.g., 10 to 100 μL per well in a 96-well plate). The shuttle agent/cargo mixture was then immediately used for experiments. At least three controls were included for each experiment, including: (1) shuttle agent alone (e.g., at highest concentration tested); (2) cargo alone; and (3) without any cargo or shuttle agent. The cells were centrifuged for 2 minutes at 400g, the medium was then removed and the cells were resuspended in PBS previously warmed at 37° C. The cells were centrifuged again 2 minutes at 400g, the PBS removed, and the cells were resuspended in the shuttle agent/cargo mixture. After the desired incubation time, 100 μL of complete medium was added directly on the cells. Cells were centrifuged for 2 minutes at 400g and the medium was removed. The pellet was resuspended and washed in 200 μL of PBS previously warmed at 37° C. After another centrifugation, the PBS was removed and the cells were resuspended in 100 μL of complete medium. The last two steps were repeated one time before analysis.

Figure 22A:
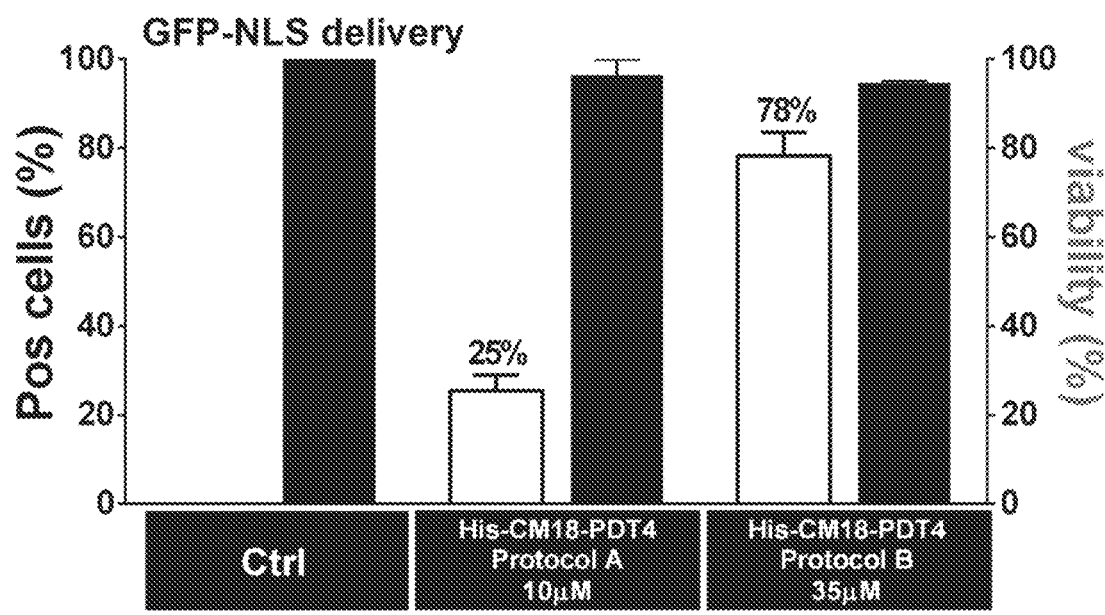
FIGS. 22A and 22B show the results of a transduction efficiency experiment in which GFP-NLS cargo protein was intracellularly delivered using the shuttle His-CM18-PTD4 in HeLa cells. GFP-NLS transduction efficiency was evaluated by flow cytometry and the percentage of GFP fluorescent cells ("Pos cells (%)"), as well as corresponding cell viability data ("viability (%)") are shown.

9.2 GFP-NLS Transduction by his-CM18-PTD4 in HeLa Cells Using Protocol A or B: Flow Cytometry To compare the effects of different protocols on shuttle agent transduction efficiency, HeLa cells were cultured and tested in the protein transduction assays using Protocol A or B as described in Example 9.1. Briefly, GFP-NLS recombinant protein (5 µM; see Example 5.1) was co-incubated with 10 µM of His-CM18-PTD4 and exposed to HeLa cells for 1 hour using Protocol A, or was co-incubated with 35 µM of His-CM18-PTD4 and exposed to HeLa cells for 10 seconds using Protocol B. The cells were subjected to flow cytometry analysis as described in Example 3.3. Results are shown in Table 9.1 and FIG. 22A. ("Pos cells (%)" is the percentage of cells emanating a GFP signal).

TABLE 9.1

Comparison of Protein Transduction Protocols A and B: Data from FIG. 22A

| Protocol | Shuttle | Cells | Conc. of shuttle (µM) | Conc. of GFP-NLS (µM) | Mean % cells with GFP signal (± St. Dev.; n = 3) | Cell viability (%) (± St. Dev.; n = 3) |
|---|---|---|---|---|---|---|
| B | None ("Ctrl") | HeLa | 0 | 5 | 0.53 ± 0.07 | 100 |
| A | His-CM18-PTD4 | HeLa | 10 | 5 | 25.4 ± 3.6 | 96.4 ± 2.7 |
| B | His-CM18-PTD4 | HeLa | 35 | 5 | 78.3 ± 5.3 | 94.6 ± 0.4 |

The above results show that higher protein transduction efficiency for the cargo GFP-NLS using the shuttle agent His-CM18-PTD4 was obtained using Protocol B, as compared to Protocol A.

Figure 22B:
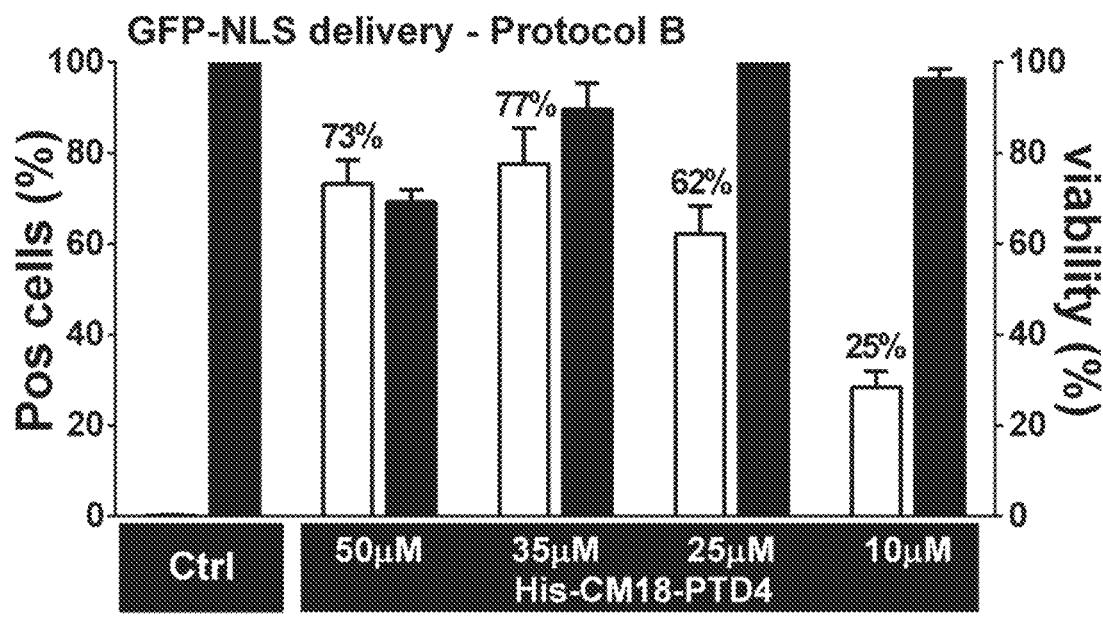

9.3 GFP-NLS Transduction by his-CM18-PTD4 in HeLa Cells Using Protocol B: Flow Cytometry A dose response experiment was performed to evaluate the effect of His-CM18-PTD4 concentration on protein transduction efficiency. HeLa cells were cultured and tested in the protein transduction assay described in Protocol B of Example 9.1. Briefly, GFP-NLS recombinant protein (5 µM; see Example 5.1) was co-incubated with 0, 50, 35, 25, or 10 µM of His-CM18-PTD4, and then exposed to HeLa cells for 10 seconds. The cells were subjected to flow cytometry analysis as described in Example 3.3. Results are shown in Table 9.2 and FIG. 22B.

TABLE 9.2

Dose response of shuttle agent using Protocol B: Data from FIG. 22B

| Protocol | Shuttle | Cells | Conc. of shuttle (µM) | Conc. of GFP-NLS (µM) | Mean % cells with GFP signal (± St. Dev.; n = 3) | Cell viability (%) (± St. Dev.; n = 3) |
|---|---|---|---|---|---|---|
| B | None ("Ctrl") | HeLa | 0 | 5 | 0.13 ± 0.1 | 100 ± 0 |
|  | His-CM18-PTD4 |  | 50 | 5 | 73.2 ± 5.2 | 69.2 ± 2.7 |
|  |  |  | 35 | 5 | 77.7 ± 7.8 | 79.6 ± 5.9 |
|  |  |  | 25 | 5 | 62.1 ± 6.1 | 95.3 ± 3.7 |
|  |  |  | 10 | 5 | 25.3 ± 3.6 | 96.3 ± 2.3 |

The above results show that His-CM18-PTD4 is able to increase GFP-NLS transduction efficiency in HeLa cells in a dose-dependent manner.

9.4 GFP-NLS Transduction by his-CM18-PTD4 in HeLa Cells Using Protocol B: Visualization by Microscopy GFP-NLS recombinant protein (5 µM; see Example 5.1) was co-incubated with 35 µM of His-CM18-PTD4, and then exposed to HeLa cells for 10 seconds using Protocol B as described in Example 9.1. The cells were then subjected to fluorescence microscopy analysis as described in Examples 3.2 and 3.2a.

For the sample results shown in FIGS. 23 and 24, GFP fluorescence of the HeLa cells was immediately visualized by bright field and fluorescence microscopy at 4×, 20× and 40× magnifications after the final washing step.

In FIG. 23, the upper panels in FIGS. 23A, 23B and 23C show nuclei labelling (DAPI) at 4×, 20× and 40× magnifications, respectively, while the lower panels show corresponding GFP-NLS fluorescence. In FIG. 23C, white triangle windows indicate examples of areas of co-labelling between nuclei (DAPI) and GFP-NLS signals. In FIG. 23D, the upper and bottom panels show sample bright field images of the HeLa cells, and the middle panel shows the results of a corresponding FACS analysis (performed as described in Example 3.3), which indicates the percentage of cells in a 96-plate with a GFP signal. No significant GFP fluorescence was observed in negative control samples (i.e., cells exposed to GFP-NLS without any shuttle agent; data not shown).

FIG. 24 shows bright field (FIG. 24A) and fluorescent images (FIG. 24B). The inset in FIG. 24B shows the results of a corresponding FACS analysis (performed as described in Example 3.3), which indicates the percentage of cells in a 96-plate well with a GFP signal. No significant GFP fluorescence was observed in negative control samples (i.e., cells exposed to GFP-NLS without any shuttle agent; data not shown).

For the sample results shown in FIG. 25, the HeLa cells were fixed, permeabilized and subjected to immuno-labelling as described in Example 3.2a before visualization by fluorescence microscopy as described in Example 3.2. GFP-NLS was labelled using a primary mouse monoclonal anti-GFP antibody (Feldan, #A017) and a secondary goat anti-mouse Alexa™-594 antibody (Abcam #150116). The upper panels in FIGS. 25A and 25B show nuclei labelling (DAPI), and the lower panels show corresponding labelling for GFP-NLS. FIGS. 25A and 25B show sample images at 20× and 40× magnifications, respectively. White triangle windows indicate examples of areas of co-labelling between nuclei and GFP-NLS. No significant GFP-NLS labelling was observed in negative control samples (i.e., cells exposed to GFP-NLS without any shuttle agent; data not shown).

FIG. 26 shows sample images captured with confocal microscopy at 63× magnification of living cells. FIG. 26A shows a bright field image, while FIG. 26B shows the corresponding fluorescent GFP-NLS. FIG. 26C is an overlay between the images in FIG. 26A and FIG. 26B. No significant GFP-NLS fluorescence was observed in negative control samples (i.e., cells exposed to GFP-NLS without any shuttle agent; data not shown).

Figure 24C:
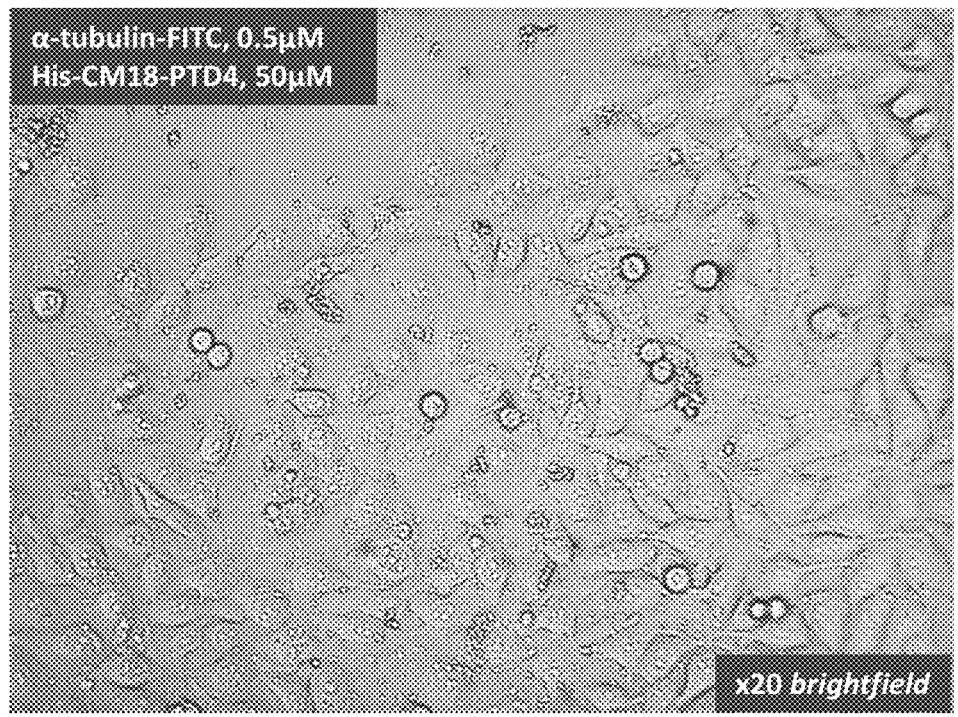
Figure 24D:
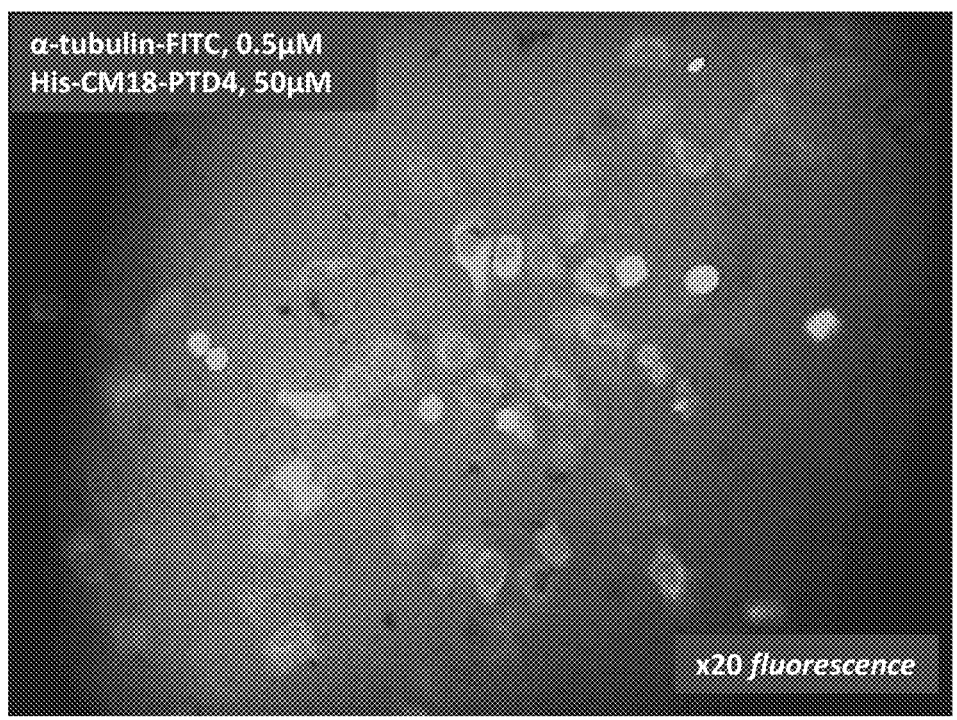

9.4a FTIC-Labeled Anti-Tubulin Antibody Transduction by his-CM18-PTD4 in HeLa Cells Using Protocol B: Visualization by Microscopy FITC-labeled anti-tubulin antibody (0.5 µM; Abcam, ab64503) was co-incubated with 50 µM of His-CM18-PTD4, and then exposed to HeLa cells for 10 seconds using Protocol B as described in Example 9.1. The cells were then subjected to fluorescence microscopy analysis as described in Examples 3.2 and 3.2a, wherein the FITC fluorescence of the anti-tubulin antibody in the HeLa cells was immediately visualized by bright field and fluorescence microscopy at 20× magnification after the final washing step. Sample results are shown in FIGS. 24C and 24D. No significant FTIC fluorescence was observed in negative control samples (i.e., cells exposed to the FITC-labeled anti-tubulin antibody without any shuttle agent; data not shown).

Overall, the results in Examples 9.4 and 9.4a show that GFP-NLS and FITC-labeled anti-tubulin antibody cargos are successfully transduced and delivered to the nucleus and/or the cytosol of HeLa cells in the presence of the shuttle agent His-CM18-PTD4.

9.5 GFP-NLS Kinetic Transduction by his-CM18-PTD4 in HeLa Cells: Visualization by Microscopy GFP-NLS recombinant protein (5 µM; see Example 5.1) was co-incubated with 50 µM of His-CM18-PTD4, and then exposed to HeLa cells for 10 seconds using Protocol B as described in Example 9.1. After a washing step, the GFP fluorescence of the HeLa cells was immediately visualized by fluorescence microscopy (Example 3.2) at 20× magnification after different intervals of time. Typical results are shown in FIG. 27, in which fluorescence microscopy images were captured after 45, 75, 100, and 120 seconds (see FIGS. 27A, 27B, 27C and 27D, respectively).

Figure 27A:
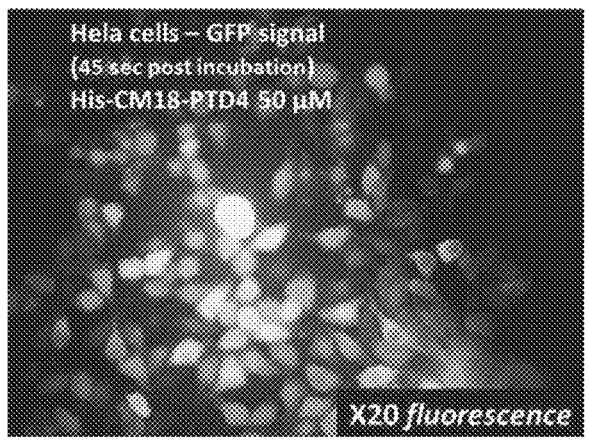
FIGS. 27A-27D show microscopy images of a kinetic (time-course) transduction experiment in HeLa cells, where the fluorescence of GFP-NLS cargo protein was tracked after 45 (FIG. 27A), 75 (FIG. 27B), 100 (FIG. 27C), and 120 (FIG. 27D) seconds following intracellular delivery with the shuttle His-CM18-PTD4. The diffuse cytoplasmic fluorescence pattern observed after 45 seconds (FIG. 27A) gradually becomes a more concentrated nuclear pattern at 120 seconds (FIG. 27D).
Figure 27B:
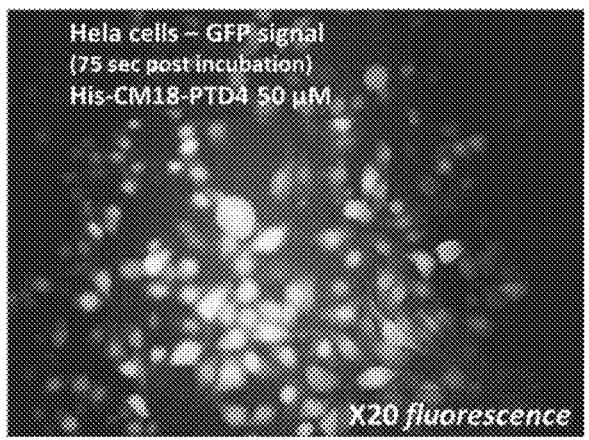
Figure 27C:
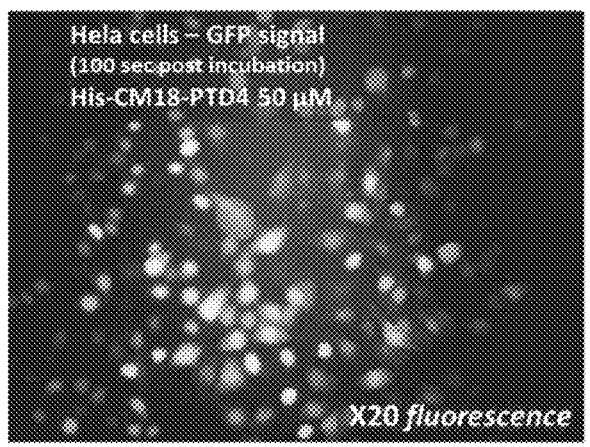
Figure 27D:
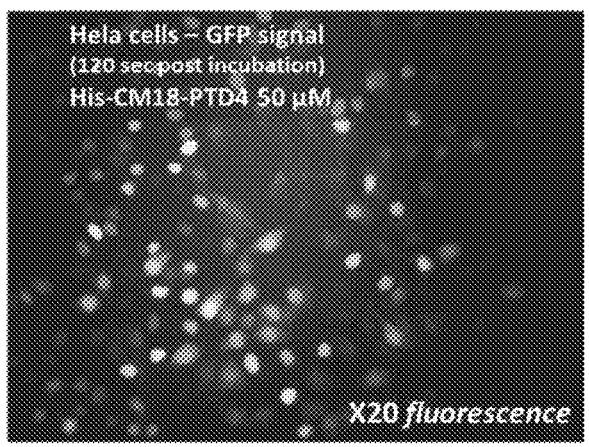
Figure 28A:
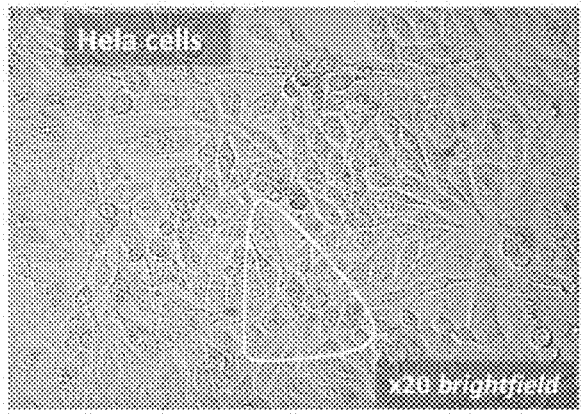
FIGS. 28A-28D show microscopy images of co-delivery transduction experiment in which two cargo proteins (GFP-NLS and mCherry™-NLS) are simultaneously delivered intracellularly by the shuttle His-CM18-PTD4 in HeLa cells. Cells and fluorescent signals were visualized by (FIG. 28A) bright field and (FIG. 28B.28D) fluorescence microscopy. White triangle windows indicate examples of areas of co-labelling between nuclei (DAPI) and GFP-NLS or mCherry™.
Figure 28B:
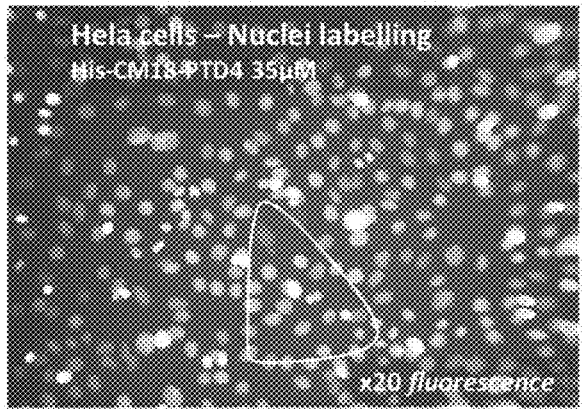
Figure 28C:
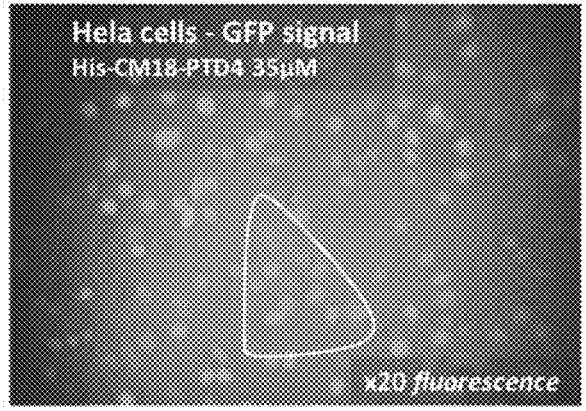
Figure 28D:
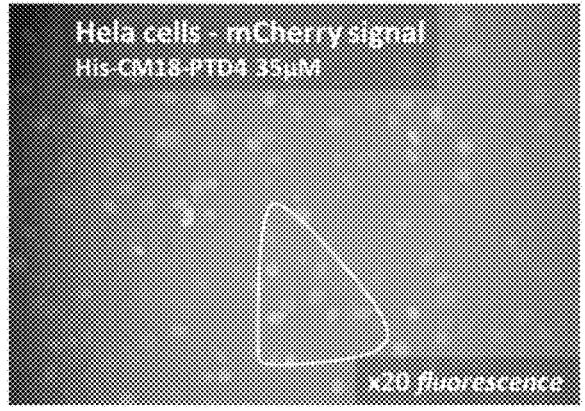

As shown in FIG. 27A, diffuse cellular GFP fluorescence was generally observed after 45 seconds, with areas of lower GFP fluorescence in the nucleus in many cells. These results suggest predominantly cytoplasmic and low nuclear distribution of the GPF-NLS delivered intracellularly via the shuttle agent after 45 seconds. FIGS. 27B-27D show the gradual redistribution of GFP fluorescence to the cell nuclei at 75 seconds (FIG. 27B), 100 seconds (FIG. 27C), and 120 seconds (FIG. 27D) following exposure to the His-CM18-PTD4 shuttle agent and GFP-NLS cargo. No significant cellular GFP fluorescence was observed in negative control samples (i.e., cells exposed to GFP-NLS without any shuttle agent; data not shown).

The results in Example 9.5 show that GFP-NLS is successfully delivered to the nucleus of HeLa cells in the presence of the shuttle agent His-CM18-PTD4 by 2 minutes.

9.6 GFP-NLS and mCherry™-NLS Co-Transduction by his-CM18-PTD4 in HeLa Cells: Visualization by Microscopy mCherry™-NLS recombinant protein was constructed, expressed and purified from a bacterial expression system as described in Example 1.4. The sequence of the mCherry™-NLS recombinant protein was:

[SEQ ID NO: 73]
MHHHHHHGGGGSGGGGSGGASTGIRHVSKCEEDNMAIIKEFMRFKVHMEGS

VNGHEFEIEGEGEGRPYEGTQTAKLKVTKGGPLPFAWDILSPQFMYGSKAY

VKHPADIPDYLKLSFPEGFKWERVMNFEDGGVVTVTQDSSLQDGEFIYKVK

LRGTNFPSDGQVMQKKTMGWEASSERMYPEDGALKGEIKQRLKLKDGGHYD

AEVKTTYKAKKPVQLPGAYNVNIKLDITSHNEDYTIVEQYERAEGRHSTGG

MDELYKGGSGGGSGGGSGWIRASSGGR<u>SSDDEATADSQHAAPPKKKRKV</u>GG

SGGGSGGGSGGGRGTEIS
(MW = 34.71 kDa; pI = 6.68)
NLS sequence is underlined
Serine/glycine rich linkers are in bold GFP-NLS recombinant protein (5 µM; see Example 5.1) and mCherry™-NLS recombinant protein (5 µM) were co-incubated together with 35 µM of His-CM18-PTD4, and then exposed to HeLa cells for 10 seconds using Protocol B as described in Example 9.1. After washing steps, the cells were immediately visualized by bright field and fluorescence microscopy at 20× magnifications as described in Example 3.2. Sample results are shown in FIG. 28, in which corresponding images showing bright field (FIG. 28A), DAPI fluorescence (FIG. 28B), GFP-NLS fluorescence (FIG. 28C), and mCherry™-NLS fluorescence (FIG. 28D) are shown. White triangle windows indicate examples of areas of co-labelling between GFP-NLS and mCherry™ fluorescence signals in cell nuclei. No significant cellular GFP or mCherry™ fluorescence was observed in negative control samples (i.e., cells exposed to GFP-NLS or mCherry™ without any shuttle agent; data not shown).

These results show that GFP-NLS and mCherry™-NLS are successfully delivered together to the nucleus in HeLa cells in the presence of the shuttle agent His-CM18-PTD4.

9.7 GFP-NLS Transduction by his-CM18-PTD4 in THP-1 Suspension Cells: Flow Cytometry The ability of the His-CM18-PTD4 to deliver GFP-NLS in the nuclei of suspension cells was tested using THP-1 cells. THP-1 cells were cultured and tested in the protein transduction assays using Protocols A and C as described in Example 9.1. GFP-NLS (5 µM; see Example 5.1) was co-incubated with 1 µM of His-CM18-PTD4 and exposed to THP-1 cells for 1 hour (Protocol A), or was co-incubated with 5 µM of His-CM18-PTD4 and exposed to THP-1 cells for 15 seconds (Protocol C). The cells were subjected to flow cytometry analysis as described in Example 3.3. Results are shown in Table 9.3 and in FIG. 31.

TABLE 9.3

Figure 31:
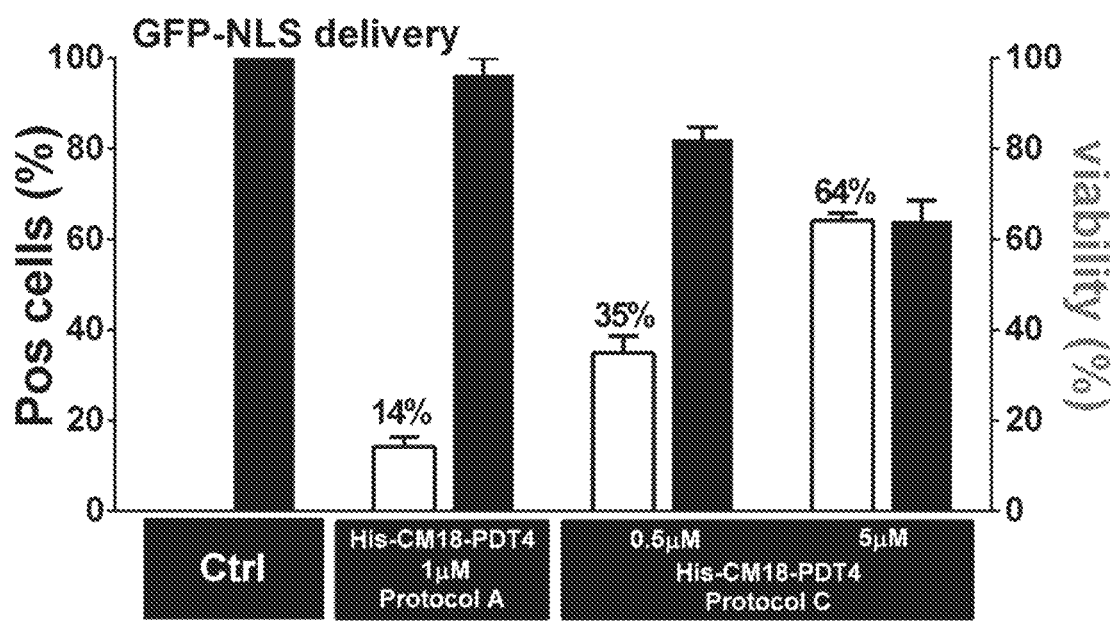
FIG. 31 shows the results of a transduction efficiency experiment in which GFP-NLS cargo protein was intracellularly delivered using the shuttle His-CM18-PTD4 in THP-1 cells using different Protocols (Protocol A vs C). GFP-NLS transduction efficiency was evaluated by flow cytometry and the percentage of GFP fluorescent cells ("Pos cells (%)"), as well as corresponding cell viability data ("viability (%)") are shown. "Ctrl" corresponds to THP-1 cells exposed to GFP-NLS cargo protein in the absence of a shuttle agent.

Data from FIG. 31

| Protocol | Shuttle | Cells | Conc. of shuttle (µM) | Conc. of GFP-NLS (µM) | Mean % cells with GFP signal (± St. Dev.; n = 3) | Cell viability (%) (± St. Dev.; n = 3) |
|---|---|---|---|---|---|---|
| C | No shuttle ("Ctrl") | THP-1 | 0 | 5 | 0.2 ± 0.03 | 99.1 ± 0.7 |
| A | His-CM18-PTD4 | | 1 | 5 | 14.2 ± 2.2 | 96.9 ± 3.6 |
| C | His-CM18-PTD4 | | 0.5 | 5 | 34.9 ± 3.8 | 82.1 ± 2.7 |
| | | | 5 | 5 | 64.1 ± 1.6 | 64.0 ± 4.1 |

9.8 GFP-NLS Transduction by his-CM18-PTD4 in THP-1 Cells: Visualization by Microscopy GFP-NLS recombinant protein (5 µM; see Example 5.1) was co-incubated with 5 µM of His-CM18-PTD4, and then exposed to THP-1 cells for 15 seconds using Protocol C as described in Example 9.1. The cells were subjected to microscopy visualization as described in Example 3.2.

For the sample results shown in FIG. 32, GFP fluorescence of the HeLa cells was immediately visualized by bright field (upper panels) and fluorescence (lower panels) microscopy at 4×, 10× and 40× magnifications (FIG. 32A-32C, respectively) after the final washing step. White triangle windows in FIG. 32C indicate examples of areas of co-labelling between bright field and fluorescence images. FIG. 32D shows typical results of a corresponding FACS analysis (performed as described in Example 3.3), which indicates the percentage of cells in a 96-plate well with a GFP signal. Additional results are shown in FIG. 33, in which FIGS. 33A and 33B show bright field images, and FIGS. 33C and 33D show corresponding fluorescence images. White triangle windows indicate examples of areas of co-labelling between FIGS. 33A and 33C, as well as FIGS. 33B and 33D. The right-most panel shows typical results of a corresponding FACS analysis (performed as described in Example 3.3), which indicates the percentage of cells in a 96-plate well with a GFP signal.

No significant cellular GFP fluorescence was observed in negative control samples (i.e., cells exposed to GFP-NLS without any shuttle agent; data not shown).

The results in this example show that GFP-NLS is successfully delivered intracellularly in THP-1 cells in the presence of the shuttle agent His-CM18-PTD4.

Example 10

Different Multi-Domain Shuttle Agents, but not Single-Domain Peptides, Successfully Transduce GFP-NLS in HeLa and THP-1 Cells 10.1 GFP-NLS Transduction by Different Shuttle Agents in HeLa Cells: Flow Cytometry HeLa cells were cultured and tested in the protein transduction assays using Protocol B as described in Example 9.1. Briefly, GFP-NLS recombinant protein (5 µM; see Example 5.1) was co-incubated with 50 µM of different shuttle agents and exposed to the HeLa cells for 10 seconds. The cells were subjected to flow cytometry analysis as described in Example 3.3. Results are shown in Table 10.1 and FIG. 29A. "Pos cells (%)" is the mean percentages of all cells that emanate a GFP signal. The negative control ("Ctrl") corresponds to cells that were incubated with GFP-NLS recombinant protein (5 µM) without any shuttle agent.

TABLE 10.1

Figure 29A:
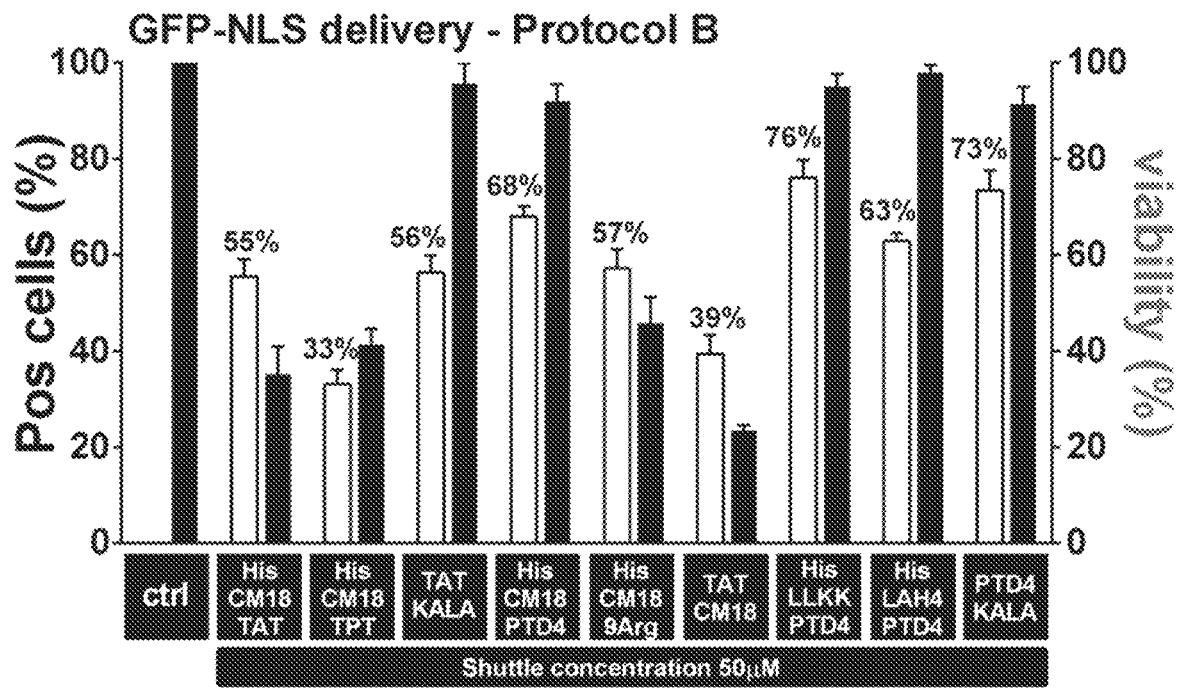
FIGS. 29A-29I show the results of GFP-NLS transduction efficiency experiments in HeLa cells using different shuttle agents or single-domain/control peptides. GFP-NLS transduction efficiency was evaluated by flow cytometry and the percentage of GFP fluorescent cells ("Pos cells (%)"), as well as corresponding cell viability data ("viability (%)") are shown in FIGS. 29A, 29B, 29D-29G and 29I.

| | Data from FIG. 29A | | | | | |
|---|---|---|---|---|---|---|
| Protocol | Shuttle agent | Cells | Conc. of shuttle (µM) | Conc. of GFP-NLS (µM) | Mean % cells with GFP signal (± St. Dev.; n = 3) | Cell viability (%) (± St. Dev.; n = 3) |
| B | No shuttle ("ctrl") | HeLa | 0 | 5 | 0 | 100 |
| | His-CM18-TAT | HeLa | 50 | | 55.5 ± 3.6 | 35.2 ± 5.7 |
| | His-CM18-Transportan (TPT) | HeLa | | | 33.2 ± 2.8 | 41.3 ± 3.3 |
| | TAT-KALA | HeLa | | | 56.3 ± 3.6 | 95.6 ± 4.3 |
| | His-CM18-PTD4 | HeLa | | | 68 ± 2.2 | 92 ± 3.6 |
| | His-CM18-9Arg | HeLa | | | 57.2 ± 3.9 | 45.8 ± 5.4 |
| | TAT-CM18 | HeLa | | | 39.4 ± 3.9 | 23.5 ± 1.1 |
| | His-C(LLKK)3C-PTD4 | HeLa | | | 76 ± 3.8 | 95 ± 2.7 |
| | His-LAH4-PTD4 | HeLa | | | 63 ± 1.64 | 98 ± 1.5 |
| | PTD4-KALA | HeLa | | | 73.4 ± 4.12 | 91.4 ± 3.67 |

* His-LAH4-PTD4: the intracellular GFP fluorescence pattern was observed by fluorescence microscopy as being punctate, suggesting that the GFP cargo remained trapped in endosomes.

10.2 GFP-NLS Transduction by Different Shuttle Agents with Varying Incubation Times in HeLa Cells: Flow Cytometry HeLa cells were cultured and tested in the protein transduction assays using Protocol B as described in Example 9.1. Briefly, GFP-NLS recombinant protein (5 µM; see Example 5.1) was co-incubated with 10 µM of TAT-KALA, His-CM18-PTD4, or His-C(LLKK)3C-PTD4 for 1, 2, or 5 minutes. After the final washing step, the cells were subjected to flow cytometry analysis as described in Example 3.3. Results are shown in Table 10.2 and FIG. 29B. "Pos cells (%)" is the mean percentages of all cells that emanate a GFP signal. The negative control ("Ctrl") corresponds to cells that were incubated with GFP-NLS recombinant protein (5 µM) without any shuttle agent.

TABLE 10.2

Figure 29B:
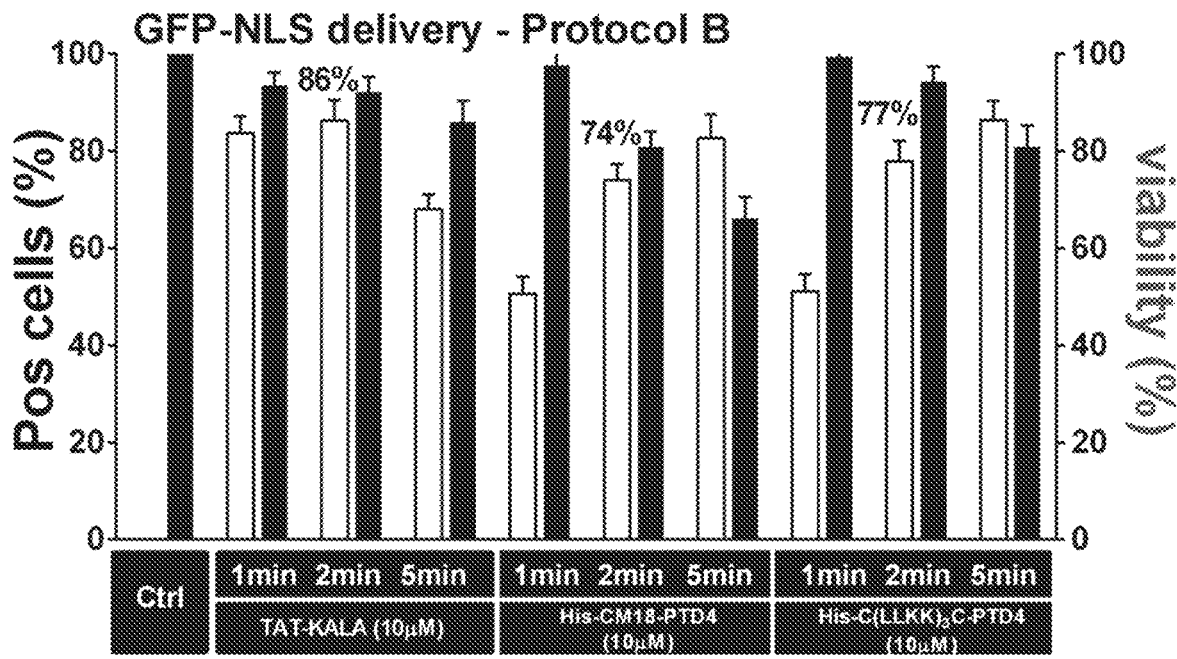

Data from FIG. 29B

| Protocol | Shuttle agent | Cells | Conc. of shuttle (μM) | Incubation time | Mean % cells with GFP signal (± St. Dev.; n = 3) | Cell viability (%) (± St Dev.; n = 3) |
|---|---|---|---|---|---|---|
| — | No shuttle ("Ctrl") | HeLa | 0 | 5 min. | 0 ± n/a | 97.5 ± 1.7 |
| B | TAT-KALA | HeLa | 10 | 1 min. | 83.7 ± 3.5 | 93.5 ± 2.7 |
|  |  |  |  | 2 min. | 86.2 ± 4.3 | 92.1 ± 3.1 |
|  |  |  |  | 5 min. | 68.1 ± 3.0 | 86 ± 4.4 |
|  | His-CM18-PTD4 | HeLa | 10 | 1 min. | 50.6 ± 3.5 | 97.6 ± 2.7 |
|  |  |  |  | 2 min. | 74 ± 3.3 | 80.9 ± 3.2 |
|  |  |  |  | 5 min. | 82.7 ± 5.0 | 66.2 ± 4.4 |
|  | His-C(LLKK)$_3$C-PTD4 | HeLa | 10 | 1 min. | 51.1 ± 3.5 | 99.5 ± 2.7 |
|  |  |  |  | 2 min. | 77.8 ± 4.3 | 94.3 ± 3.2 |
|  |  |  |  | 5 min. | 86.4 ± 4.0 | 80.8 ± 4.4 |

10.3 GFP-NLS Transduction by TAT-KALA, his-CM18-PTD4 and his-C(LLKK)$_3$C-PTD4 with Varying Incubation Times in HeLa Cells: Flow Cytometry HeLa cells were cultured and tested in the protein transduction assays using Protocol C as described in Example 9.1. Briefly, GFP-NLS recombinant protein (5 μM; see Example 5.1) was co-incubated with 5 μM of TAT-KALA, His-CM18-PTD4, or His-C(LLKK)$_3$C-PTD4 for 1, 2, or 5 minutes. After the final washing step, the cells were subjected to flowcytometry analysis as described in Example 3.3. Results are shown in Table 10.3 and FIG. 29C. The negative control ("Ctrl") corresponds to cells that were incubated with GFP-NLS recombinant protein (5 μM) without any shuttle agent.

TABLE 10.3

Figure 29C:
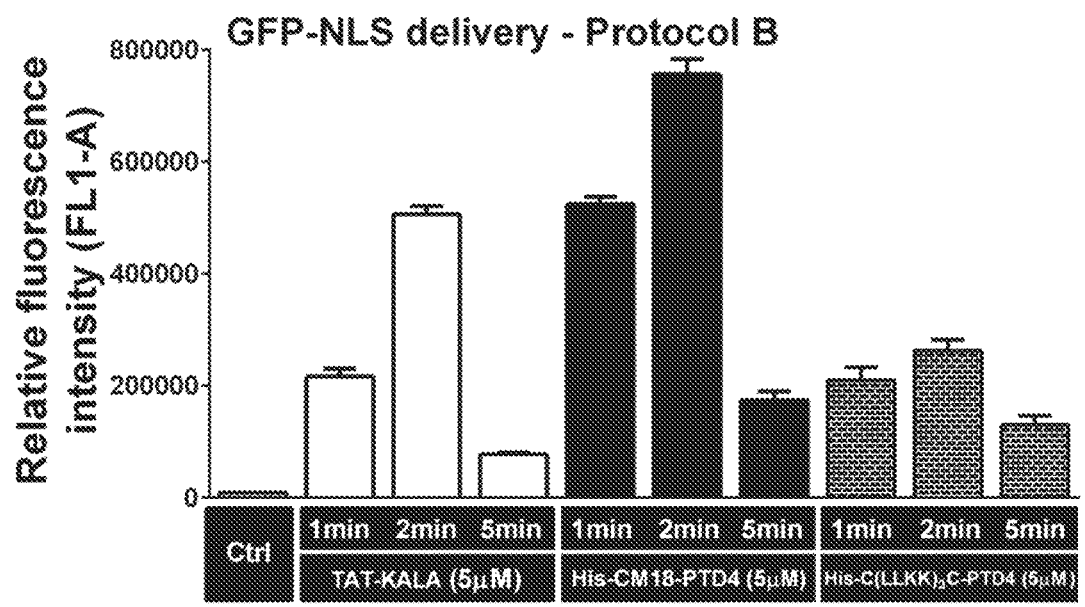

Data from FIG. 29C

| Protocol | Shuttle agent | Cells | Conc. of shuttle (μM) | Incubation time | Relative fluorescence intensity (FL1-A) (n = 3) | St. Dev. |
|---|---|---|---|---|---|---|
|  | No shuttle ("Ctrl") |  | 0 | 5 min. | 8903 | 501 |
| C | TAT-KALA | HeLa | 10 | 1 min. | 216 367 | 13 863.48 |
|  |  |  |  | 2 min. | 506 158 | 14 536.28 |
|  |  |  |  | 5 min. | 78 010 | 2 463.96 |
|  | His-CM18-PTD4 | HeLa | 10 | 1 min. | 524 151 | 12 366.48 |
|  |  |  |  | 2 min. | 755 624 | 26 933.16 |
|  |  |  |  | 5 min. | 173 930 | 15 567.33 |
|  | His-C(LLKK)$_3$C-PTD4 | HeLa | 10 | 1 min. | 208 968 | 23 669.19 |
|  |  |  |  | 2 min. | 262 411.5 | 19 836.84 |
|  |  |  |  | 5 min. | 129 890 | 16 693.29 |

10.4 GFP-NLS Transduction by Different Shuttle Agents in HeLa Cells: Flow Cytometry HeLa cells were cultured and tested in the protein transduction assays using Protocol B as described in Example 9.1. Briefly, GFP-NLS recombinant protein (5 MM; see Example 5.1) was co-incubated with 50 μM of different shuttle agents (see Table 1.3 for amino acid sequences and properties) and exposed to the HeLa cells for 10 seconds. The cells were subjected to flow cytometry analysis as described in Example 3.3. Results are shown in Tables 10.3a & 10.3b and FIGS. 29E & 29F. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.3a

Figure 29D:
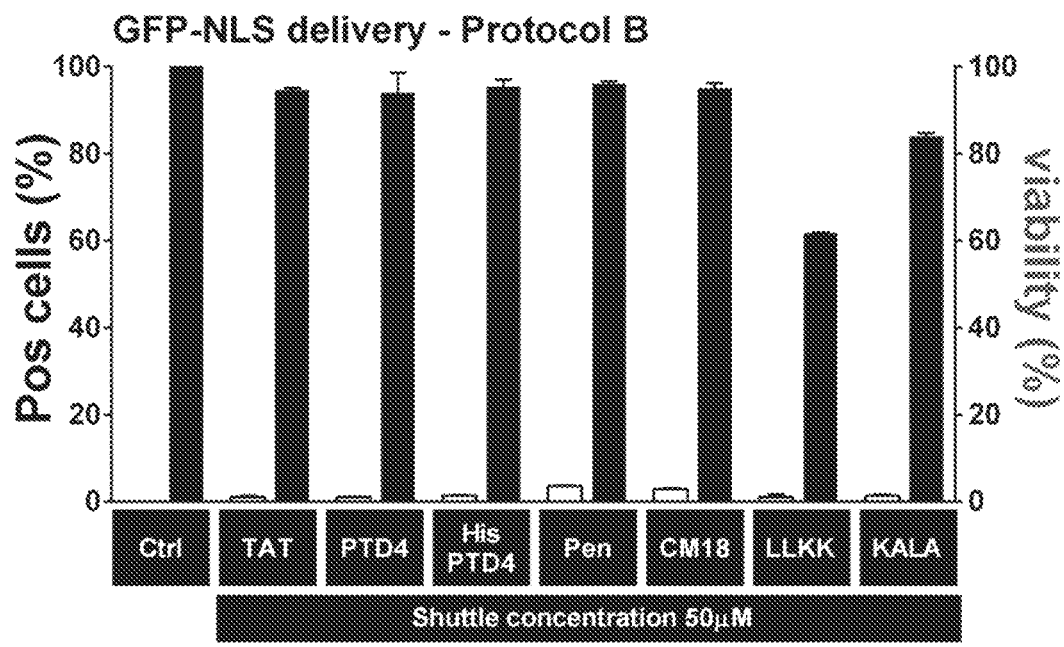
Figure 29E:
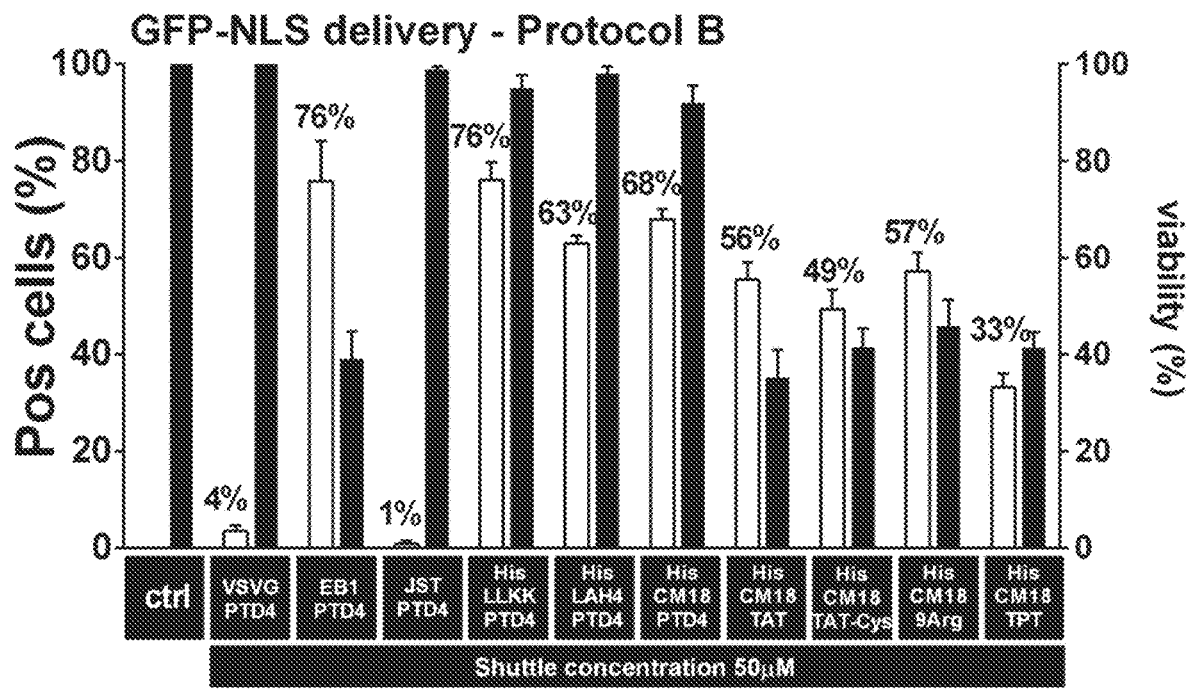

Data from FIG. 29E

| Domain structure | Shuttle agent | Conc. of shuttle (μM) | Conc. of GFP-NLS (μM) | Mean % cells with GFP signal (±St. Dev.; n = 3) | Cell viability (%) (±St. Dev., n = 3) |
|---|---|---|---|---|---|
| — | No shuttle ("Ctrl") | 0 | 5 | 0 | 100 |
| ELD-CPD | VSVG-PTD4 | 50 | 5 | 3.5 ± 1.1 | 100 |
|  | EB1-PTD4 |  |  | 75.8 ± 8.26 | 39 ± 5.6 |
|  | JST-PTD4 |  |  | 0.84 ± 0.69 | 98.9 ± 0.57 |
| His-ELD-CPD | His-C(LLKK)₃C-PTD4 | 50 | 5 | 76 ± 3.8 | 95 ± 2.7 |
|  | His-LAH4-PTD4* |  |  | 63 ± 1.64 | 98 ± 1.5 |
|  | His-CM18-PTD4 |  |  | 68 ± 2.2 | 92 ± 3.6 |
|  | His-CM18-TAT |  |  | 55.5 ± 3.6 | 35.2 ± 5.7 |
|  | His-CM18-TAT-Cys** |  |  | 49.3 ± 4.1 | 41.4 ± 3.91 |
|  | His-CM18-9Arg |  |  | 57.2 ± 3.93 | 45.8 ± 3.53 |
|  | His-CM18-Transportan (TPT) |  |  | 33.2 ± 2.82 | 41.3 ± 3.29 |

*His-LAH4-PTD4: the intracellular GFP fluorescence pattern was observed by fluorescence microscopy as being punctate, suggesting that the GFP cargo remained trapped in endosomes.
**Not shown in FIG. 29E.

TABLE 10.3b

Figure 29F:
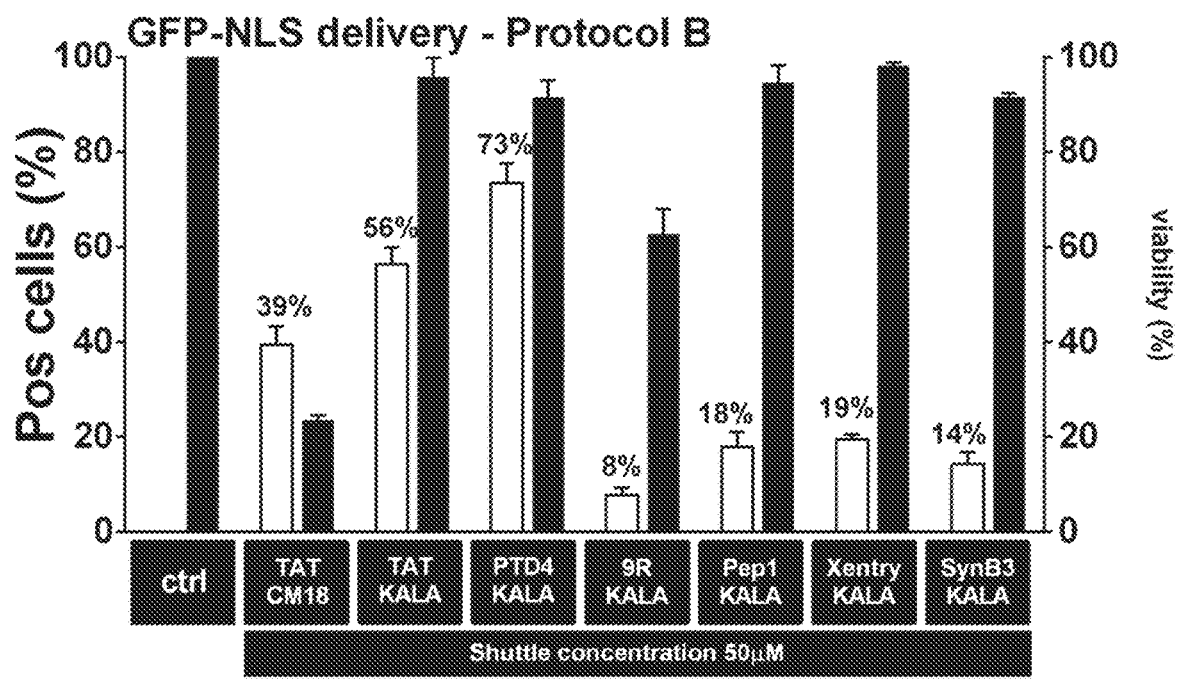

Data from FIG. 29F

| Domain structure | Shuttle agent | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|
| — | No shuttle ("Ctrl") | 0 | 5 | 0 | 100 |
| CPD-ELD | TAT-CM18 | 50 | 5 | 39.4 ± 3.9 | 23.5 ± 1.1 |
|  | TAT-KALA |  |  | 56.3 ± 3.6 | 95.6 ± 4.3 |
|  | PTD4-KALA |  |  | 73.4 ± 4.12 | 91.4 ± 3.67 |
|  | 9Arg-KALA |  |  | 7.8 ± 1.53 | 62.8 ± 5.11 |
|  | Pep1-KALA |  |  | 17.2 ± 3.07 | 94.7 ± 3.77 |
|  | Xentry-KALA |  |  | 19.4 ± 1.01 | 98.3 ± 0.64 |
|  | SynB3-KALA |  |  | 14.3 ± 2.37 | 91.1 ± 0.82 |

HeLa cells were cultured and tested in the protein transduction assays using Protocol B as described in Example 9.1. Briefly, GFP-NLS recombinant protein (5 μM; see Example 5.1) was co-incubated with 10 μM of TAT-KALA, His-CM18-PTD4, or His-C(LLKK)₃C-PTD4 for 1, 2, or 5 minutes. After the final washing step, the cells were subjected to flow cytometry analysis as described in Example 3.3. Results are shown in Tables 10.3c & 10.3b and FIGS. 29G and 29H. "Pos cells (%)" is the mean percentages of all cells that emanate a GFP signal. The negative control ("Ctrl") corresponds to cells that were incubated with GFP-NLS recombinant protein (5 μM) without any shuttle agent.

TABLE 10.3c

Figure 29G:
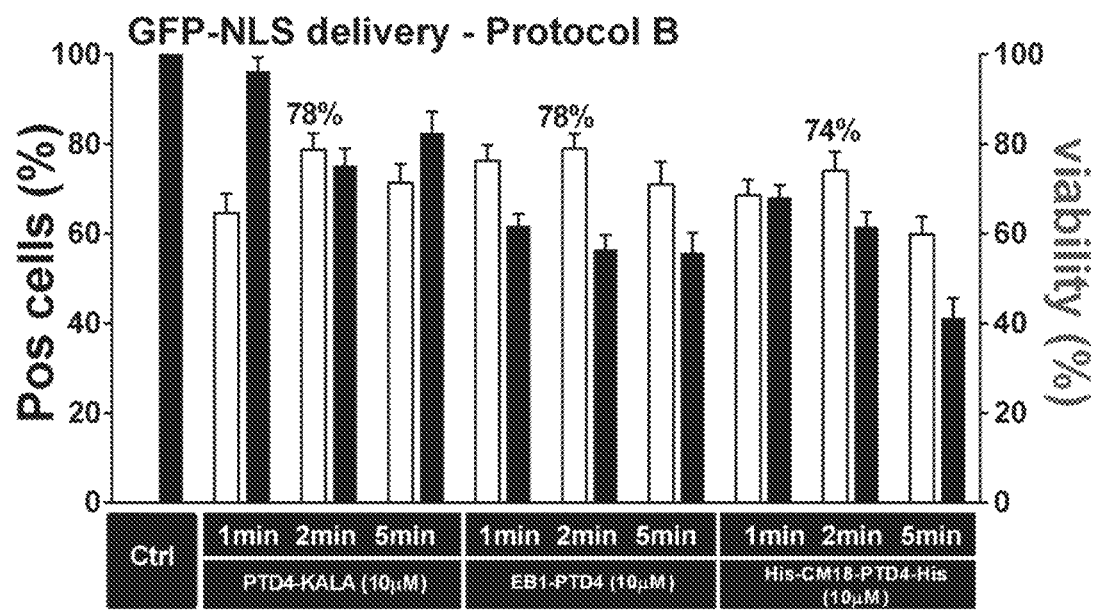

Data from FIG. 29G

| Domain structure | Shuttle agent | Conc. of shuttle (μM) | Conc. of GFP-NLS (μM) | Incubation time (min) | Mean % cells with GFP signal (± St. Dev.; n = 3) | Cell viability (%) (± St. Dev.; n = 3) |
|---|---|---|---|---|---|---|
| — | No shuttle ("Ctrl") | 0 | 5 | 5 | 0 ± n/a | 98.3 ± 0.9 |
| CPD-ELD | PTD4-KALA | 10 | 5 | 1 | 64.6 ± 4.3 | 96.2 ± 3.0 |
|  |  |  |  | 2 | 78.8 ± 3.6 | 75.3 ± 3.8 |
|  |  |  |  | 5 | 71.4 ± 4.2 | 82.4 ± 4.7 |
| ELD-CPD | EB1-PTD4 | 10 | 5 | 1 | 76.3 ± 3.5 | 61.7 ± 2.7 |
|  |  |  |  | 2 | 79.0 ± 3.3 | 56.6 ± 3.2 |
|  |  |  |  | 5 | 71.1 ± 5.0 | 55.8 ± 4.4 |
| His-ELD-CPD-His | His-CM18-PTD4-His | 10 | 5 | 1 | 68.6 ± 3.5 | 68.1 ± 2.7 |
|  |  |  |  | 2 | 74.1 ± 4.3 | 61.6 ± 3.2 |
|  |  |  |  | 5 | 59.8 ± 4.0 | 41.2 ± 4.4 |

TABLE 10.3d

Figure 29H:
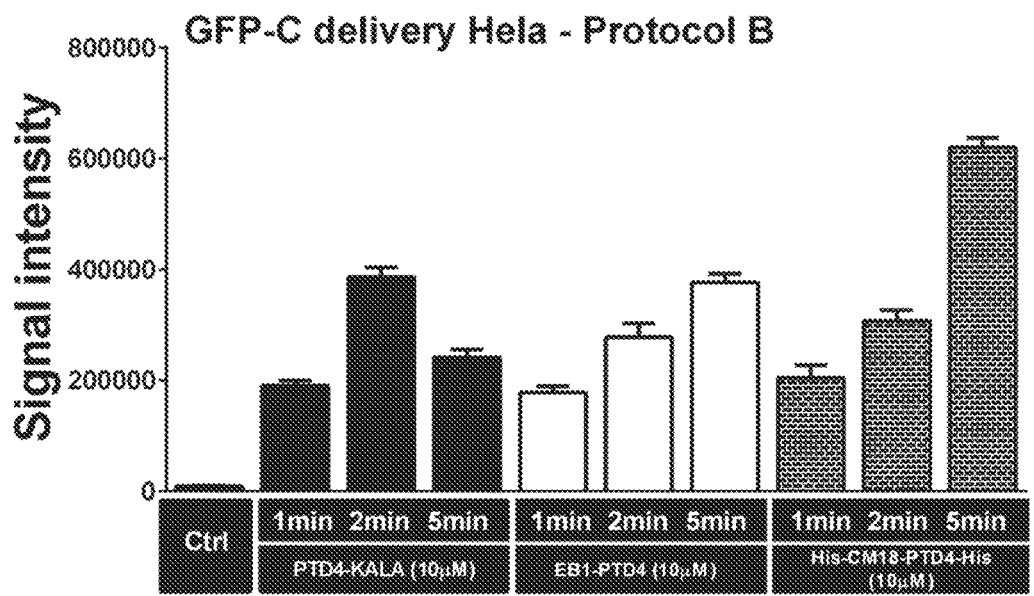

Data from FIG. 29H

| Domain structure | Shuttle agent | Conc. of shuttle (µM) | Conc. of GFP-NLS (µM) | Incubation time (min) | Relative Fluorescence Intensity (FL1-A) (±St. Dev.; n = 3) |
|---|---|---|---|---|---|
| — | No shuttle ("Ctrl") | 0 | 5 | 5 | 8903 ± 501.37 |
| CPD-ELD | PTD4-KALA | 10 | 5 | 1 | 190 287 ± 9445 |
|  |  |  |  | 2 | 386 480 ± 17 229 |
|  |  |  |  | 5 | 241 230 ± 14 229 |
| ELD-CPD | EB1-PTD4 | 10 | 5 | 1 | 178 000 ± 11 934 |
|  |  |  |  | 2 | 277 476 ± 25 319 |
|  |  |  |  | 5 | 376 555 ± 16 075 |
| His-ELD-CPD-His | His-CM18-PTD4-His | 10 | 5 | 1 | 204 338 ± 22 673 |
|  |  |  |  | 2 | 307 329 ± 19 618 |
|  |  |  |  | 5 | 619 964 ± 17 411 |

The shuttle agent CM18-PTD4 was used as a model to demonstrate the modular nature of the individual protein domains, as well as their ability to be modified. More particularly, the presence or absence of: an N-terminal cysteine residue ("Cys"); different flexible linkers between the ELD and CPD domains ("L1": GGS; "L2": GGSGGGS (SEQ ID NO: 10 243); and "L3": GGSGGGSGGGS (SEQ ID NO: 10 244)) and different lengths, positions, and variants to histidine-rich domains; were studied.

HeLa cells were cultured and tested in the protein transduction assays using Protocol B as described in Example 9.1. Briefly, GFP-NLS recombinant protein (5 µM; see Example 5.1) was co-incubated with 20 µM of different shuttle peptide variants (see Table 1.3 for amino acid sequences and properties) of the shuttle agent His-CM18-PTD4 for 1 minute. After the final washing step, the cells were subjected to flow cytometry analysis as described in Example 3.3. Results are shown in Table 10.3e and FIG. 29I. "Pos cells (%)" is the mean percentages of all cells that emanate a GFP signal. The negative control ("Ctrl") corresponds to cells that were incubated with GFP-NLS recombinant protein (5 µM) without any shuttle agent.

TABLE 10.3e

Figure 29I:
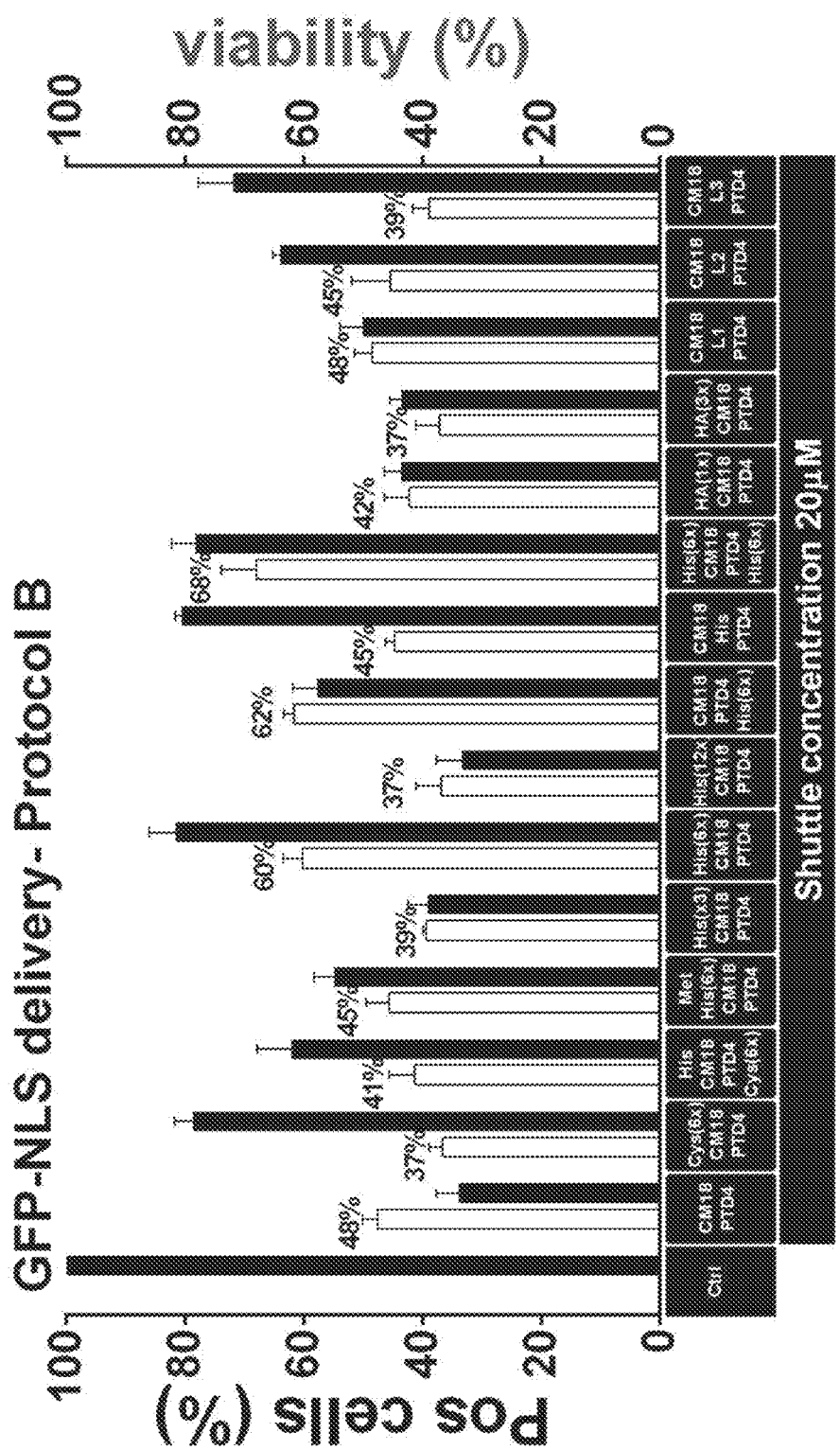
Figure 30A:
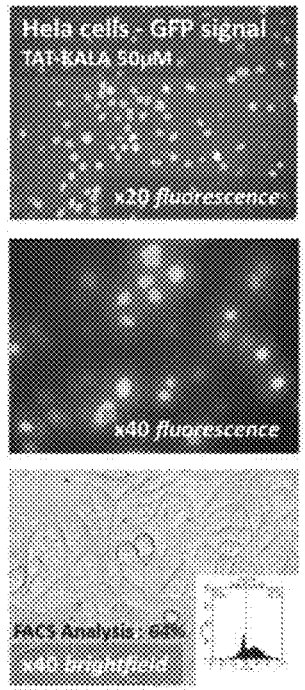
FIGS. 30A-30F show microscopy images of HeLa cells transduced with GFP-NLS using the shuttle agent
Figure 30B:
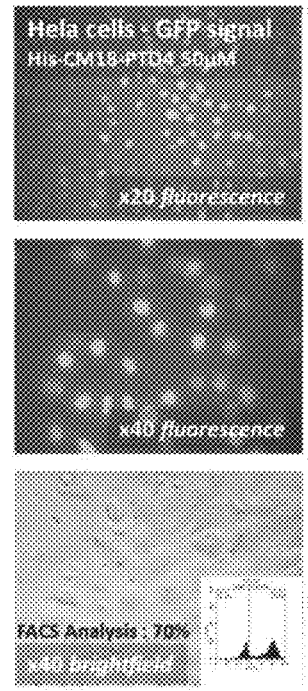
Figure 30C:
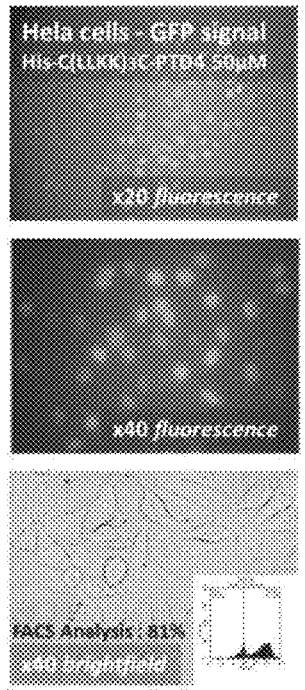
Figure 30D:
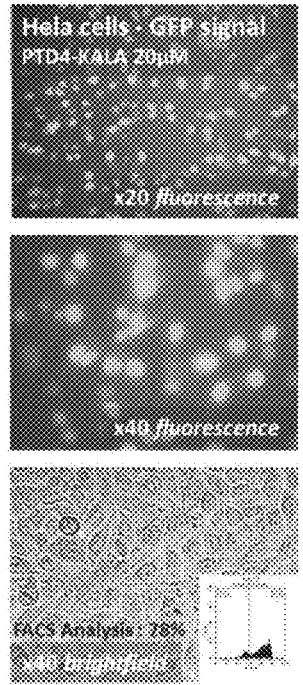
Figure 30E:
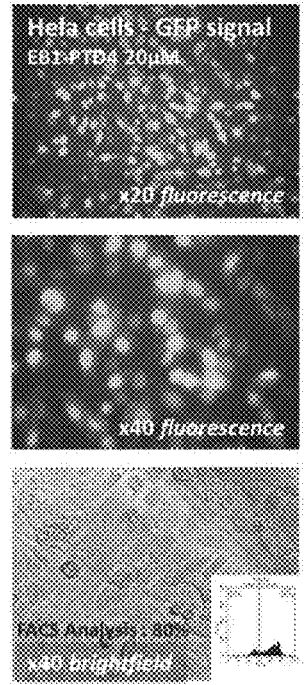
Figure 30F:
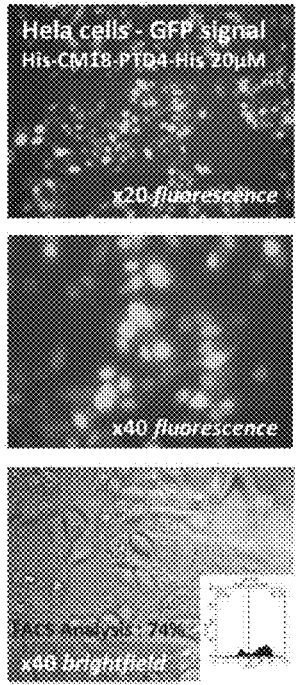

Data from FIG. 29I

| Domain structure | Shuttle agent | Conc. of shuttle (µM) | Conc. of GFP-NLS (µM) | Mean % cells with GFP signal (±St Dev.; n = 3) | Cell viability (%) (±St. Dev.; n = 3) |
|---|---|---|---|---|---|
| — | No shuttle ("Ctrl") | 0 | 5 | 0 | 99.6 ± 0.12 |
| ELD-CPD | CM18-PTD4 |  |  | 47.6 ± 2.6 | 33.9 ± 3.7 |
|  | Cys-CM18-PTD4 |  |  | 36.6 ± 2.3 | 78.7 ± 3.1 |
|  | CM18-L1-PTD4 | 20 | 5 | 48.5 ± 3.0 | 50.1 ± 3.8 |
|  | CM18-L2-PTD4 |  |  | 45.5 ± 6.5 | 64.0 ± 1.3 |
|  | CM18-L3-PTD4 |  |  | 39.0 ± 2.7 | 71.9 ± 6.0 |
| His-ELD-CPD | His-CM18-PTD4 | 20 | 5 | 60.3 ± 3.2 | 81.6 ± 4.5 |
|  | His-CM18-PTD4-6Cys |  |  | 41.3 ± 4.28 | 62 ± 5.76 |
|  | Met-His-CM18-PTD4-Cys |  |  | 45.6 ± 3.88 | 54.9 ± 3.45 |

TABLE 10.3e-continued

Data from FIG. 29I

| Domain structure | Shuttle agent | Conc. of shuttle (µM) | Conc. of GFP-NLS (µM) | Mean % cells with GFP signal (±St Dev.; n = 3) | Cell viability (%) (±St. Dev.; n = 3) |
|---|---|---|---|---|---|
|  | 3His-CM18-PTD4 |  |  | 39.4 ± 0.5 | 39.2 ± 3.3 |
|  | 12His-CM18-PTD4 |  |  | 36.9 ± 4.3 | 33.4 ± 4.3 |
|  | HA-CM18-PTD4 |  |  | 42.3 ± 4.2 | 68.3 ± 4.1 |
|  | 3HA-CM18-PTD4 |  |  | 37.2 ± 3.9 | 43.6 ± 2.8 |
| ELD-His-CPD | CM18-His-PTD4 | 20 | 5 | 61.7 ± 1.8 | 57.7 ± 4.2 |
| His-ELD-CPD-His | His-CM18-PTD4-His | 20 | 5 | 68.0 ± 6.0 | 78.6 ± 1.1 |

These results show that variations in a given shuttle (e.g., CM18-PTD4) may be used to modulate the degree of transduction efficiency and cell viability of the given shuttle. More particularly, the addition of an N-terminal cysteine residue to CM18-PTD4 (see Cys-CM18-PTD4), decreased GFP-NLS transduction efficiency by 11% (from 47.6% to 36.6%), but increased cell viability from 33.9% to 78.7%. Introduction of flexible linker domains (L1, L2, and L3) of different lengths between the CM18 and PTD4 domains did not result in a dramatic loss of transduction efficiency, but increased cell viability (see CM18-L1-PTD4, CM18-L2-PTD4, and CM18-L3-PTD4). Finally, variations to the amino acid sequences and/or positions of the histidine-rich domain(s) did not result in a complete loss of transduction efficiency and cell viability of His-CM18-PTD4 (see 3His-CM18-PTD4, 12His-CM18-PTD4, HA-CM18-PTD4, 3HA-CM18-PTD4, CM18-His-PTD4, and His-CM18-PTD4-His). Of note, adding a second histidine-rich domain at the C terminus of His-CM18-PTD4 (i.e., His-CM18-PTD4-His) increased transduction efficiency from 60% to 68% with similar cell viability.

10.5 Lack of GFP-NLS Transduction by Single-Domain Peptides or a his-CPD Peptide in HeLa Cells: Flow Cytometry HeLa cells were cultured and tested in the protein transduction assays using Protocol B as described in Example 9.1. Briefly, GFP-NLS recombinant protein (5 µM; see Example 5.1) was co-incubated with 50 µM of different single-domain peptides (TAT; PTD4; Penetratin; CM18; C(LLKK)₃C; KALA) or the two-domain peptide His-PTD4 (lacking an ELD), and exposed to the HeLa cells for 10 seconds. After the final washing step, the cells were subjected to flow cytometry analysis as described in Example 3.3. Results are shown in Table 10.4 and FIG. 29D. "Pos cells (%)" is the mean percentages of all cells that emanate a GFP signal. The negative control ("Ctrl") corresponds to cells that were incubated with GFP-NLS recombinant protein (5 µM) without any single-domain peptide or shuttle agent.

TABLE 10.4

Data from FIG. 29D

| Protocol | Domain | Single-domain peptide | Cells | Conc. of shuttle (μM) | Conc. of GFP-NLS (μM) | Mean % cells with GFP signal (±St. Dev.; n = 3) | Cell viability (%) (±St. Dev.; n = 3) |
|---|---|---|---|---|---|---|---|
| B | — | No peptide ("Ctrl") | HeLa | 0 | 5 | 0.1 ± 0.02 | 98.3 ± 0.59 |
| | CPD | TAT | HeLa | 50 | 5 | 1.1 ± 0.27 | 94.6 ± 0.44 |
| | | PTD4 | | | | 1.1 ± 0.06 | 94 ± 4.5 |
| | | Penetratin (Pen) | | | | 3.6 ± 0.1 | 96 ± 0.6 |
| | ELD | CM18 | HeLa | 50 | 5 | 2.9 ± 0.2 | 95 ± 1.2 |
| | | C(LLKK)$_3$C | | | | 1.1 ± 0.57 | 61.8 ± 0.1 |
| | | KALA | | | | 1.4 ± 0.13 | 84 ± 0.7 |
| | His-CPD | His-PTD4 | HeLa | 50 | 5 | 1.04 ± 0.12 | 96.5 ± 0.28 |

These results show that the single-domain peptides TAT, PTD4, Penetratin, CM18, C(LLKK)$_3$C, KALA, or the two-domain peptide His-PTD4 (lacking an ELD), are not able to successfully transduce GFP-NLS in HeLa cells.

10.6 GFP-NLS Transduction by TAT-KALA, his-CM18-PTD4, his-C(LLKK)$_3$C-PTD4, PTD4-KALA, EB1-Ptd4, and his-CM18-PTD4-his in HeLa Cells: Visualization by Microscopy GFP-NLS recombinant protein (5 μM; see Example 5.1) was co-incubated with 50 μM of shuttle agent, and then exposed to HeLa cells for 10 seconds using Protocol B as described in Example 9.1. The cells were visualized by microscopy as described in Example 3.2, after an incubation time of 2 minutes.

For the sample results shown in FIG. 30, GFP fluorescence of the HeLa cells was immediately visualized by bright field (bottom row panels) and fluorescence (upper and middle row panels) microscopy at 20× or 40× magnifications after the final washing step. The results with the shuttle agents TAT-KALA, His-CM18-PTD4, and His-C(LLKK)$_3$C-PTD4 are shown in FIGS. 30A, 30B and 30C, respectively. The results with the shuttle agents PTD4-KALA, EB1-PTD4, and His-CM18-PTD4-His are shown in FIGS. 30D, 30E and 30F, respectively. The insets in the bottom row panels show the results of corresponding FACS analyses (performed as described in Example 3.3), which indicates the percentage of cells in a 96-plate well with a GFP signal. No significant cellular GFP fluorescence was observed in negative control samples (i.e., cells exposed to GFP-NLS without any shuttle agent; data not shown).

10.7 GFP-NLS Transduction by TAT-KALA, his-CM18-PTD4 and his-C(LLKK)$_3$C-PTD4 with Varying Incubation Times in THP-1 Cells: Flow Cytometry THP-1 cells were cultured and tested in the protein transduction assays using Protocol C as described in Example 9.1. Briefly, GFP-NLS recombinant protein (5 μM; see Example 5.1) was co-incubated with 1 μM of TAT-KALA, His-CM18-PTD4, or His-C(LLKK)$_3$C-PTD4 for 15, 30, 60, or 120 seconds. After the final washing step, the cells were subjected to flow cytometry analysis as described in Example 3.3. The mean percentages of cells emanating a GFP signal ("Pos cells (%)") are shown in Table 10.4a and in FIG. 34A. The mean fluorescence intensity is shown in Table 10.5 and FIG. 34B. The negative control ("Ctrl") corresponds to cells that were incubated with GFP-NLS recombinant protein (5 (M) without any shuttle agent.

TABLE 10.4a

Figure 34A:
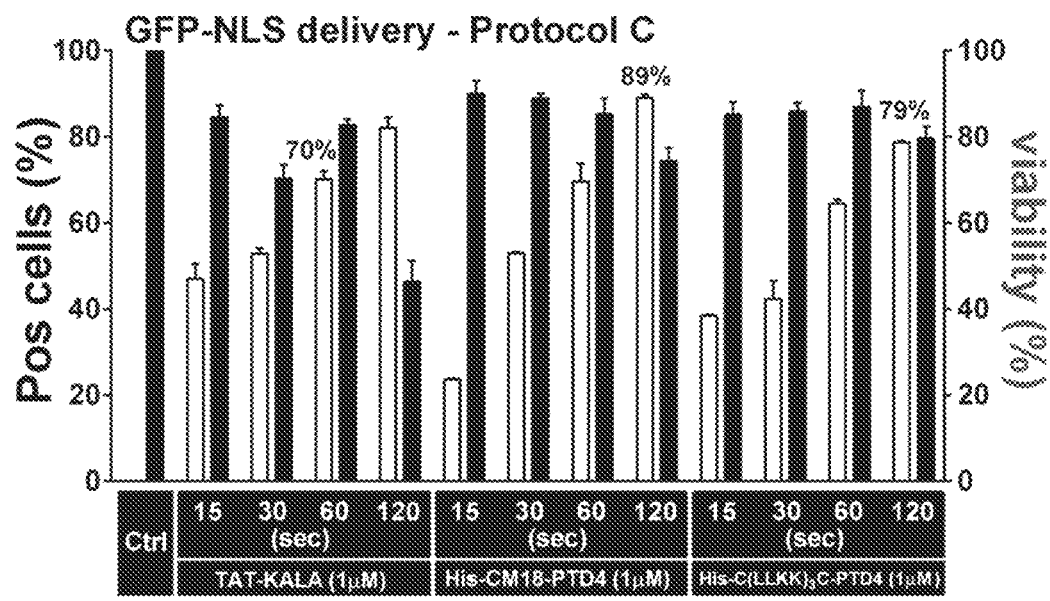
FIGS. 34A-34B show the results of GFP-NLS transduction efficiency experiments in THP-1 cells using the shuttle TAT-KALA, His-CM18-PTD4, or His-C(LLKK)$_3$C-PTD4. The cargo protein/shuttle agents were exposed to the THP-1 cells for 15, 30, 60 or 120 seconds. GFP-NLS transduction efficiency was evaluated by flow cytometry and the percentage of GFP fluorescent cells ("Pos cells (%)"), as well as corresponding cell viability data ("viability (%)") are shown in FIG. 34A.

Data from FIG. 34A

| Protocol | Shuttle agent | Cells | Conc. of shuttle (μM) | Conc. of GFP-NLS (μM) | Incubation time (sec.) | Mean % cells with GFP signal (±St. Dev.; n = 3) | Cell viability (%) (±St. Dev.; n = 3) |
|---|---|---|---|---|---|---|---|
| C | No shuttle ("Ctrl") | THP-1 | 0 | 5 | 120 | 1.12 ± 0.27 | 97.3 ± 1.55 |
| | TAT-KALA | THP-1 | 1 | 5 | 15 | 47 ± 3.5 | 84.6 ± 2.7 |
| | | | | | 30 | 52.9 ± 1.3 | 70.3 ± 3.2 |
| | | | | | 60 | 70.1 ± 2.0 | 82.7 ± 1.4 |
| | | | | | 120 | 82.1 ± 2.5 | 46.3 ± 4.9 |
| | His-CM18-PTD4 | THP-1 | 1 | 5 | 15 | 23.7 ± 0.2 | 90 ± 3.0 |
| | | | | | 30 | 53 ± 0.3 | 89 ± 1.1 |
| | | | | | 60 | 69.6 ± 4.2 | 85.3 ± 3.6 |
| | | | | | 120 | 89 ± 0.8 | 74.3 ± 3.2 |
| | His-C(LLKK)$_3$C-PTD4 | THP-1 | 1 | 5 | 15 | 38.4 ± 0.3 | 85.2 ± 2.8 |
| | | | | | 30 | 42.3 ± 4.2 | 86 ± 2.0 |
| | | | | | 60 | 64.5 ± 1.0 | 86.9 ± 3.8 |
| | | | | | 120 | 78.7 ± 0.3 | 79.6 ± 2.8 |

TABLE 10.5

Figure 34B:
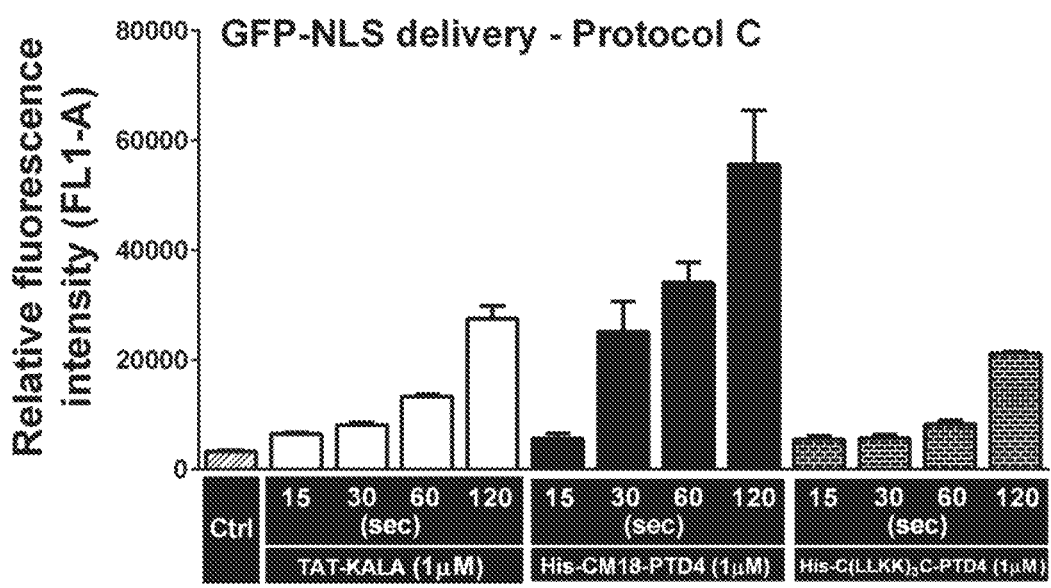

Data from FIG. 34B

| Protocol | Shuttle agent | Cells | Conc. of shuttle (µM) | Incubation time (sec.) | Relative fluorescence intensity (FL1-A) (n = 3) | Standard Deviation |
|---|---|---|---|---|---|---|
| C | No shuttle ("Ctrl") | THP-1 | 0 | 120 | 217 | 23.09 |
|   | TAT-KALA | THP-1 | 1 | 15 | 6 455.12 | 333.48 |
|   |   |   |   | 30 | 8 106.81 | 436.28 |
|   |   |   |   | 60 | 13 286.2 | 463.96 |
|   |   |   |   | 120 | 27 464.92 | 2 366.48 |
|   | His-CM18-PTD4 | THP-1 | 1 | 15 | 5 605.45 | 933.16 |
|   |   |   |   | 30 | 25 076.41 | 5 567.33 |
|   |   |   |   | 60 | 34 046.94 | 3 669.19 |
|   |   |   |   | 120 | 55 613.48 | 9 836.84 |
|   | His-C(LLKK)$_3$C-PTD4 | THP-1 | 1 | 15 | 5 475.12 | 693.29 |
|   |   |   |   | 30 | 5 755.8 | 635.18 |
|   |   |   |   | 60 | 8 267.38 | 733.29 |
|   |   |   |   | 120 | 21 165.06 | 209.37 |

Example 11

Repeated Daily Treatments with Low Concentrations of Shuttle Agent in the Presence of Serum Results in GFP-NLS Transduction in THP-1 Cells 11.1 GFP-NLS Transduction with his-CM18-PTD4 or his-C(LLKK)3C-PTD4 in THP-1 Cells: Flow Cytometry THP-1 cells were cultured and tested in the protein transduction assay using Protocol A as described in Example 9.1, but with the following modifications. GFP-NLS recombinant protein (5, 2.5, or 1 µM; see Example 5.1) was co-incubated with 0.5 or 0.8 µM of His-CM18-PTD4, or with 0.8 µM of His-C(LLKK)$_3$C-PTD4, and then exposed to THP-1 cells each day for 150 min in the presence of cell culture medium containing serum. Cells were washed and subjected to flow cytometry analysis as described in Example 3.3 after 1 or 3 days of repeated exposure to the shuttle agent/cargo. The results are shown in Table 11.1 and in FIGS. 35A, 35B, 35C and 35F. The negative control ("Ctrl") corresponds to cells that were incubated with GFP-NLS recombinant protein (5 µM) without any shuttle agent.

TABLE 11.1

Data from FIG. 35A, 35B, 35C and 35F

| FIG. | Shuttle agent | Cells | Conc. of shuttle (µM) | Conc. of GFP-NLS (µM) | Exposure to shuttle/cargo (days) | Mean % cells with GFP signal (±St. Dev.; n = 3) | Cell viability (%) (±St. Dev.; n = 3) |
|---|---|---|---|---|---|---|---|
| 35A | No shuttle (Ctrl) | THP-1 | 0 | 5 | 0 | 0.15 ± 0.04 | 98.7 ± 0.1 |
|   | His-CM18-PTD4 |   | 0.5 | 5 | 1 | 12.1 ± 1.5 | 98.2 ± 2.4 |
|   |   |   |   |   | 3 | 73.4 ± 1.1 | 84.3 ± 3.8 |
| 35B | No shuttle (Ctrl) | THP-1 | 0 | 5 | 0 | 0.36 ± 0.09 | 97.1 ± 1.2 |
|   | His-CM18-PTD4 |   | 0.8 | 2.5 | 1 | 12.2 ± 0.9 | 92.3 ± 1.9 |
|   |   |   |   |   | 3 | 62.4 ± 3.5 | 68.5 ± 2.2 |
| 35C | No shuttle (Ctrl) | THP-1 | 0 | 5 | 0 | 0.28 ± 0.05 | 96.4 ± 2.0 |
|   | His-CM18-PTD4 |   | 0.8 | 1 | 1 | 1.6 ± 0.2 | 98.4 ± 6.4 |
|   |   |   |   |   | 3 | 6.5 ± 0.9 | 80.6 ± 4.6 |
| 35F | No shuttle (Ctrl) | THP-1 | 0 | 5 | 0 | 0.62 ± 0.11 | 96.3 ± 1.4 |
|   | His-C(LLKK)$_3$C-PTD4 |   | 0.8 | 1 | 1 | 1.8 ± 0.2 | 97.2 ± 2.2 |
|   |   |   |   |   | 3 | 6.6 ± 0.8 | 76.6 ± 3.4 |

The viability of THP-1 cells repeatedly exposed to His-CM18-PTD4 and GFP-NLS was determined as described in Example 3.3a. The results are shown in Tables 11.2 and 11.3 and in FIGS. 35D and 35E. The results in Table 11.2 and FIG. 35D show the metabolic activity index of the THP-1 cells after 1, 2, 4, and 24 h, and the results in Table 11.3 and FIG. 35E show the metabolic activity index of the THP-1 cells after 1 to 4 days.

TABLE 11.2

Data from FIG. 35D

| Shuttle agent | Cells | Conc. of shuttle (µM) | Conc. of GFP-NLS (µM) | Mean metabolic activity index (±St. Dev.; n = 3) (Exposure to shuttle/cargo) | | | |
|---|---|---|---|---|---|---|---|
|   |   |   |   | 1 h | 2 h | 4 h | 24 h |
| No shuttle (Ctrl) | THP-1 | 0 | 5 | 40810 ± 757.39 | 38223 ± 238.66 | 44058 ± 320.23 | 42362 ± 333.80 |
| His-CM18-PTD4 | THP-1 | 0.5 | 5 | 9974 ± 1749.85 | 9707 ± 1259.82 | 3619 ± 2247.54 | 2559 ± 528.50 |
|   |   | 1 | 5 | 42915 ± 259.67 | 41386 ± 670.66 | 44806 ± 824.71 | 43112 ± 634.56 |

TABLE 11.3

Data from FIG. 35E

| Shuttle agent | Cells | Conc. of shuttle (μM) | Conc. of GFF-NLS (μM) | Mean metabolic activity index (±St. Dev.; n = 3) (Exposure to shuttle/cargo) | | | |
|---|---|---|---|---|---|---|---|
| | | | | 1 day | 2 days | 3 days | 4 days |
| No shuttle (Ctrl) | THP-1 | 0 | 5 | 44684 ± 283.27 | 43389 ± 642.47 | 45312 ± 963.40 | 43697 ± 1233 |
| | | 0.5 | 5 | 44665 ± 310.3 | 42664 ± 398.46 | 43927 ± 3511.54 | 43919 ± 4452.25 |
| His-CM184FTD4 | THP-1 | 0.8 | 5 | 44531 ± 176.66 | 43667 ± 421.66 | 44586 ± 383.68 | 44122 ± 239.98 |
| | | 1 | 5 | 41386 ± 670.66 | 36422 ± 495.01 | 27965 ± 165.33 | 22564 ± 931.28 |

The results in Example 11 show that repeated daily (or chronic) treatments with relatively low concentrations of His-CM18-PTD4 or His-C(LLKK)$_3$C-PTD4 in the presence of serum result in intracellular delivery of GFP-NLS in THP-1 cells. The results also suggest that the dosages of the shuttle agents and the cargo can be independently adjusted to improve cargo transduction efficiency and/or cell viability.

Example 12

His-CM18-PTD4 Increases Transduction Efficiency and Nuclear Delivery of GFP-NLS in a Plurality of Cell Lines 12.1 GFP-NLS Transduction with his-CM18-PTD4 in Different Adherent & Suspension Cells: Flow Cytometry The ability of the shuttle agent His-CM18-PTD4 to deliver GFP-NLS to the nuclei of different adherent and suspension cells using Protocols B (adherent cells) or C (suspension cells) as described in Example 9.1 was examined. The cell lines tested included: HeLa, Balb3T3, HEK 293T, CHO, NIH3T3, Myoblasts, Jurkat, THP-1, CA46, and HT2 cells, which were cultured as described in Example 1. GFP-NLS (5 μM; see Example 5.1) was co-incubated with 35 μM of His-CM18-PTD4 and exposed to adherent cells for 10 seconds (Protocol B), or was co-incubated with 5 μM of His-CM18-PTD4 and exposed to suspension cells for 15 seconds (Protocol C). Cells were washed and subjected to flow cytometry analysis as described in Example 3.3. Results are shown in Table 12.1 and FIG. 36. "Pos cells (%)" is the mean percentages of all cells that emanate a GFP signal.

TABLE 12.1

Figure 36:
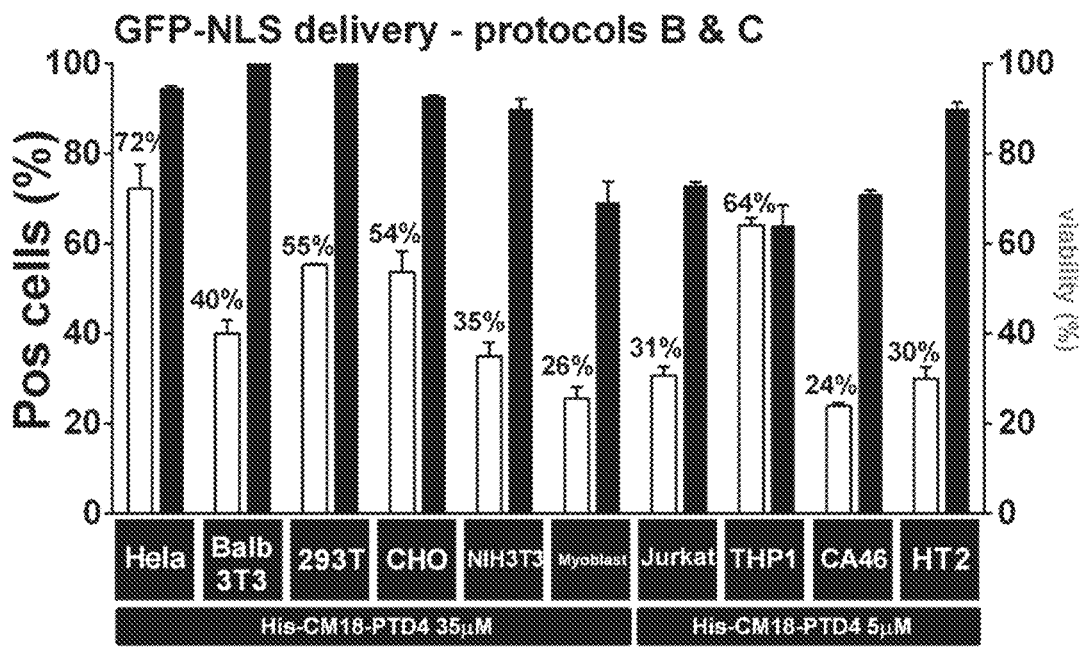
FIG. 36 shows a comparison of the GFP-NLS transduction efficiencies in a plurality of different types of cells (e.g., adherent and suspension, as well as cell lines and primary cells) using the shuttle His-CM18-PTD4, as measured by flow cytometry. The results are expressed as the percentage of GFP fluorescent cells ("Pos cells (%)"), as well as corresponding cell viability data ("viability (%)").

Data from FIG. 36

| Shuttle agent | Protocol | Conc. of shuttle (μM) | Conc. of GFP-NLS (μM) | Cells | Mean % cells with GFP signal (±St. Dev.; n = 3) | Cell viability (%) (±St. Dev.; n = 3) |
|---|---|---|---|---|---|---|
| His-CM18-PTD4 | B | 35 | 5 | HeLa | 72.3 ± 5.3 | 94.6 ± 0.4 |
| | | | | Balb3T3 | 40.2 ± 3.1 | 98.4 ± 0.6 |
| | | | | HEK 293T | 55.3 ± 0.2 | 95.3 ± 1.2 |
| | | | | CHO | 53.7 ± 4.6 | 92.8 ± 0.1 |
| | | | | NIH3T3 | 35.4 ± 3.9 | 3.3 ± 5.4 |
| | | | | Myoblasts | 25.6 ± 2.6 | 23.5 ± 1.1 |
| | C | 5 | 5 | Jurkat | 30.7 ± 2.2 | 73.6 ± 0.7 |
| | | | | THP-1 | 64.1 ± 1.6 | 64.1 ± 4.5 |
| | | | | CA46 | 24.4 ± 0.6 | 71.6 ± 1.0 |
| | | | | HT2 | 30.5 ± 2.5 | 90.6 ± 1.5 |

TABLE 12.1

Data from FIG. 36

| Shuttle agent | Protocol | Conc. of shuttle (μM) | Conc. of GFP-NLS (μM) | Cells | Mean % cells with GFP signal (±St. Dev.; n = 3) | Cell viability (%) (±St. Dev.; n = 3) |
|---|---|---|---|---|---|---|
| His-CM18-PTD4 | B | 35 | 5 | HeLa | 72.3 ± 5.3 | 94.6 ± 0.4 |
| | | | | Balb3T3 | 40.2 ± 3.1 | 98.4 ± 0.6 |
| | | | | HEK 293T | 55.3 ± 0.2 | 95.3 ± 1.2 |
| | | | | CHO | 53.7 ± 4.6 | 92.8 ± 0.1 |
| | | | | NIH3T3 | 35.4 ± 3.9 | 3.3 ± 5.4 |
| | | | | Myoblasts | 25.6 ± 2.6 | 23.5 ± 1.1 |
| | C | 5 | 5 | Jurkat | 30.7 ± 2.2 | 73.6 ± 0.7 |
| | | | | THP-1 | 64.1 ± 1.6 | 64.1 ± 4.5 |
| | | | | CA46 | 24.4 ± 0.6 | 71.6 ± 1.0 |
| | | | | HT2 | 30.5 ± 2.5 | 90.6 ± 1.5 |

Figure 37A:
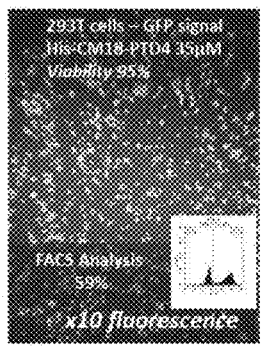
FIGS. 37A-37H show fluorescence microscopy images of different types of cells transduced with GFP-NLS cargo using the shuttle His-CM18-PTD4. GFP fluorescence was visualized by fluorescence microscopy at a 10× magnification. The results of parallel flow cytometry experiments are also provided in the insets (viability and percentage of GFP-fluorescing cells).
Figure 37B:
Figure 37C:
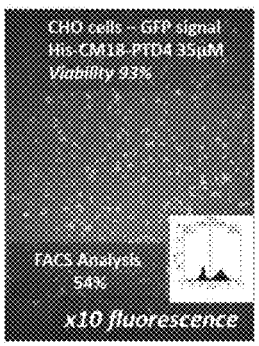
Figure 37D:
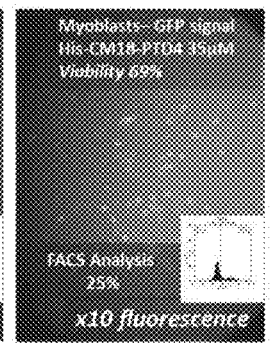
Figure 37E:
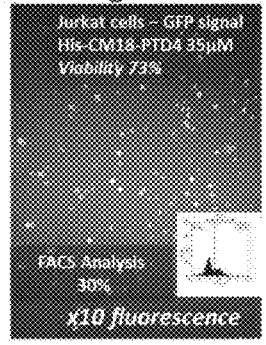
Figure 37F:
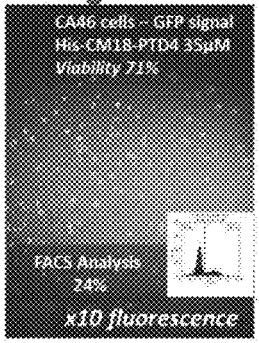
Figure 37G:
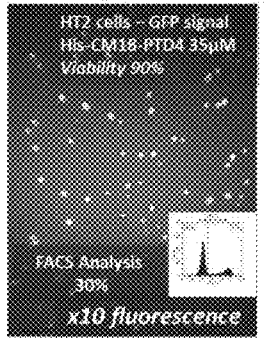
Figure 37H:
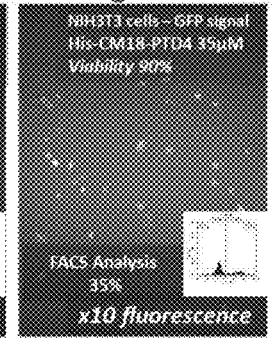

12.2 GFP-NLS Transduction with his-CM18-PTD4 in Several Adherent and Suspension Cells: Visualization by Microscopy GFP-NLS recombinant protein (5 μM; see Example 5.1) was co-incubated with 35 μM of His-CM18-PTD4 and exposed to adherent cells for 10 seconds using Protocol A, or was co-incubated with 5 μM of His-CM18-PTD4 and exposed to suspension cells for 15 seconds using Protocol B, as described in Example 9.1. After washing the cells, GFP fluorescence was visualized by bright field and fluorescence microscopy. Sample images captured at 10× magnifications showing GFP fluorescence are shown for 293T (FIG. 37A), Balb3T3 (FIG. 37B), CHO (FIG. 37C), Myoblasts (FIG. 37D), Jurkat (FIG. 37E), CA46 (FIG. 37F), HT2 (FIG. 37G), and NIH3T3 (FIG. 37H) cells. The insets show corresponding flow cytometry results performed as described in Example 3.3, indicating the percentage of GFP-NLS-positive cells. No significant cellular GFP fluorescence was observed in negative control samples (i.e., cells exposed to GFP-NLS without any shuttle agent; data not shown).

Figure 38A:
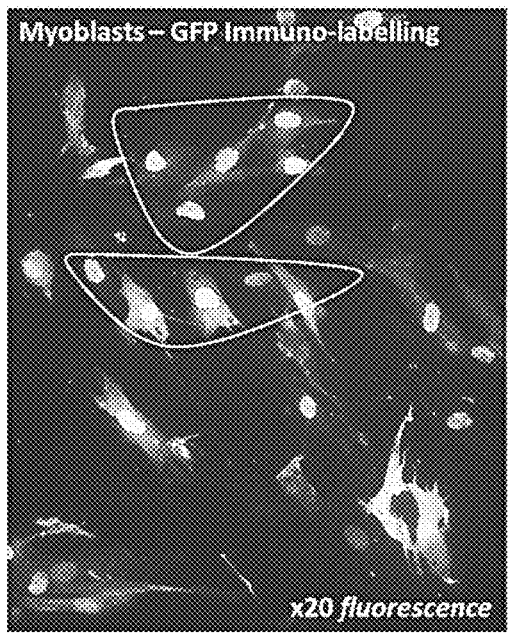
FIGS. 38A-38B show fluorescence microscopy images of primary human myoblasts transduced with GFP-NLS using the shuttle His-CM18-PTD4. Cells were fixed and permeabilized prior to immuno-labelling GFP-NLS with an anti-GFP antibody and a fluorescent secondary antibody. Immuno-labelled GFP is shown in FIG. 38A, and this image is overlaid with nuclei (DAPI) labelling in FIG. 38B.
Figure 38B:
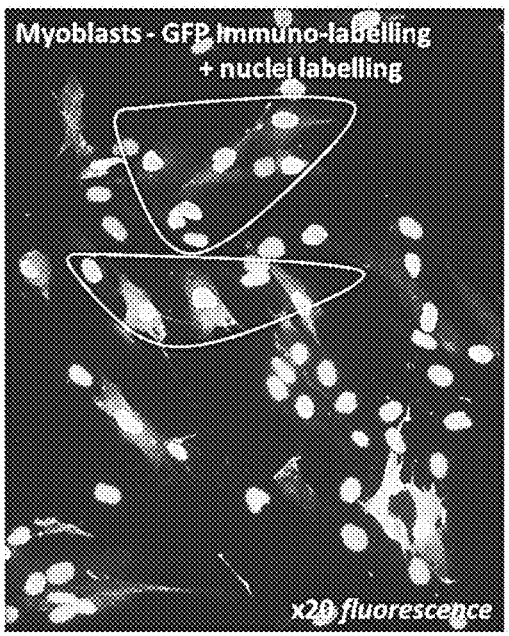

Nuclear localization of the GFP-NLS was further confirmed in fixed and permeabilized myoblasts using cell immuno-labelling as described in Example 3.2a. GFP-NLS was labeled using a primary mouse monoclonal anti-GFP antibody (Feldan, #A017) and a secondary goat anti-mouse Alexa™-594 antibody (Abcam #150116). Nuclei were labelled with DAPI. Sample results for primary human myoblast cells are shown in FIG. 38, in which GFP immuno-labelling is shown in FIG. 38A, and an overlay of the GFP immuno-labelling and DAPI labelling is shown in FIG. 38B. No significant cellular GFP labelling was observed in negative control samples (i.e., cells exposed to GFP-NLS without any shuttle agent; data not shown).

The microscopy results revealed that GFP-NLS is successfully delivered to the nucleus of all the tested cells using the shuttle agent His-CM18-PTD4.

Example 13

His-CM18-PTD4 Enables Transduction of a CRISPRICas9-NLS System and Genome Editing in Hela Cells 13.1 Cas9-NLS Recombinant Protein Cas9-NLS recombinant protein was constructed, expressed and purified from a bacterial expression system as described in Example 1.4. The sequence of the Cas9-NLS recombinant protein produced was:

[SEQ ID NO: 74]
MDKKYSIGLDIGTNSVGWAVITDEYKVPSKKFKVLGNTDRHSIKKNLIGAL
LFDSGETAEATRLKRTARRRYTRRKNRICYLQEIFSNEMAKVDDSFFHRLE
ESFLVEEDKKHERHPIFGNIVDEVAYHEKYPTIYHLRKKLVDSTDKADLRL
IYLALAHMIKFRGHFLIEGDLNPDNSDVDKLFIQLVQTYNQLFEENPINAS
GVDAKAILSARLSKSRRLENLIAQLPGEKKNGLFGNLIALSLGLTPNFKSN
FDLAEDAKLQLSKDTYDDDLDNLLAQIGDQYADLFLAAKNLSDAILLSDIL
RVNTEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGN
SRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTV
KQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVS
GQGDSLHEHIANLAGSPAIKKGILQTVKVVDELVKVMGRHKPENIVIEMAR
ENQTTQKGQKNSRERMKRIEEGIKELGSQILKEHPVENTQLQNEKLYLYYL
QNGRDMYVDQELDINRLSDYDVDHIVPQSFLKDDSIDNKVLTRSDKNRGKS
DNVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRKD
FQFYKVREINNYHHAHDAYLNAVVGTALIKKYPKLESEFVYGDYKVYDVRK
MIAKSEQEIGKATAKYFFYSNIMNFFKTEITLANGEIRKRPLIETNGETGE
IVWDKGRDFATVRKVLSMPQVNIVKKTEVQTGGFSKESILPKRNSDKLIAR
KKDWDPKKYGGFDSPTVAYSVLVVAKVEKGKSKKLKSVKELLGITIMERSS
FEKNPIDFLEAKGYKEVKKDLIIKLPKYSLFELENGRKRMLASAGELQKGN

```
ELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKY

FDTTIDRKRYTSTKEVLDATLIHQSITGLYETRIDLSQLGGDGGRSSDDEA

TADSQHAAPPKKKRKVGGSGGGSGGGSGGGRHHHHHH
(MW = 162.9 kDa; pI = 9.05)
NLS sequence is underlined
Serine/glycine rich linkers are in bold
```

13.2 Transfection Plasmid Surrogate Assay

Figure 39A:
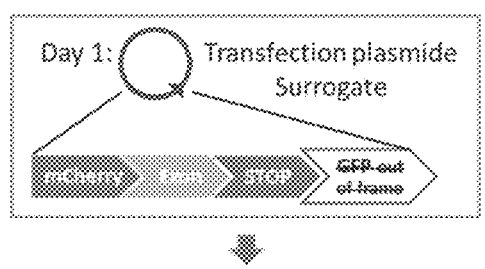
FIGS. 39A-39E show a schematic layout (FIGS. 39A, 39B and 39C) and sample fluorescence images (FIGS. 39D and 39E) of a transfection plasmid surrogate assay used to evaluate the activity of intracellularly delivered CRISPR/Cas9-NLS complex. At Day 1 (FIG. 39A), cells are transfected with an expression plasmid encoding the fluorescent proteins mCherry™ and GFP, with a STOP codon separating their two open reading frames. Transfection of the cells with the expression plasmid results in only mCherry™ expression (FIG. 39D). A CRISPR/Cas9-NLS complex, which has been designed/programmed to cleave the plasmid DNA at the STOP codon, is then delivered intracellularly to the transfected cells expressing mCherry™, resulting double-stranded cleavage of the plasmid DNA at the STOP codon (FIG. 39B). In a fraction of the cells, random non-homologous DNA repair of the cleaved plasmid occurs and results in removal of the STOP codon (FIG. 39C), and thus GFP expression and fluorescence (FIG. 39E). White triangle windows indicate examples of areas of co-labelling of mCherry™ and GFP fluorescence.
Figure 39B:
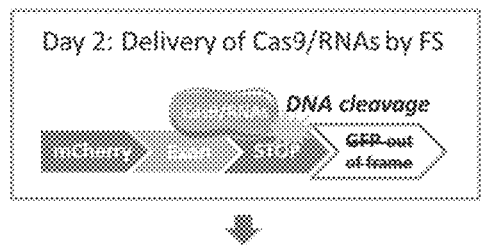
Figure 39C:
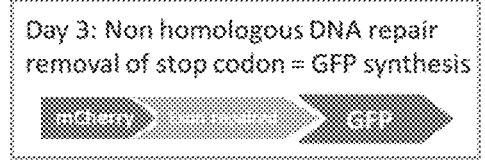
Figure 39D:
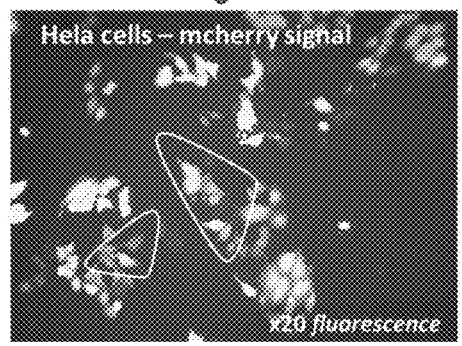
Figure 39E:
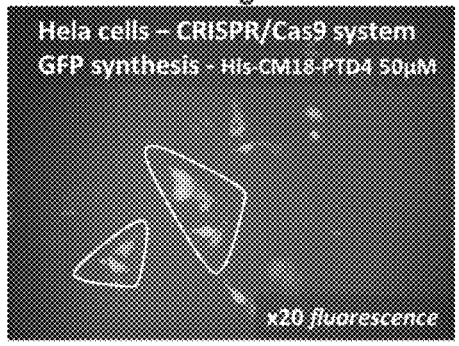

This assay enables one to visually identify cells that have been successfully delivered an active CRISPRICas9 complex. As shown in FIG. 39A, the assay involves transfecting cells with an expression plasmid DNA encoding the fluorescent proteins mCherry™ and GFP, with a STOP codon separating their two open reading frames. Transfection of the cells with the expression plasmid results in mCherry™ expression, but no GFP expression (FIG. 39B). A CRISPR/Cas9 complex, which has been designed/programmed to cleave the plasmid DNA at the STOP codon, is then delivered intracellularly to the transfected cells expressing mCherry™ (FIG. 39D). Successful transduction of an active CRISPR/Cas9 complex results in the CRISPR/Cas9 complex cleaving the plasmid DNA at the STOP codon (FIG. 39C). In a fraction of the cells, random non-homologous DNA repair of the cleaved plasmid occurs and results in removal of the STOP codon, and thus GFP expression and fluorescence (FIG. 39E).

On Day 1 of the transfection plasmid surrogate assay, DNA plasmids for different experimental conditions (250 ng) are diluted in DMEM (50 µL) in separate sterile 1.5-mL tubes, vortexed and briefly centrifuged. In separate sterile 1.5-mL tubes, Fastfect™ transfection reagent was diluted in DMEM (50 µL) with no serum and no antibiotics at a ratio of 3:1 (3 µL of Fastfect™ transfection reagent for 1 µg of DNA) and then quickly vortexed and briefly centrifuged. The Fastfect™/DMEM mixture was then added to the DNA mix and quickly vortexed and briefly centrifuged. The Fastfect™/DMEM/DNA mixture is then incubated for 15-20 min at room temperature, before being added to the cells (100 µL per well). The cells are then incubated at 37° C. and 5% $CO_2$ for 5 h. The media is then changed for complete medium (with serum) and further incubated at 37° C. and 5% $CO_2$ for 24-48 h. The cells are then visualized under fluorescent microscopy to view the mCherry™ signal.

13.3 his-CM18-PTD4-Mediated CRISPR/Cas9-NLS System Delivery and Cleavage of Plasmid DNA RNAs (crRNA & tracrRNA) were designed to target a nucleotide sequence of the EMX1 gene, containing a STOP codon between the mCherry™ and GFP coding sequences in the plasmid of Example 13.2. The sequences of the crRNA and tracrRNA used were as follows:

```
crRNA [SEQ ID NO: 75]:
5'-GAGUCCGAGCAGAAGAAGAAGUUUUAGAGCUAUGCUGUUUUG-3' tracrRNA [SEQ ID NO: 76]:
5'-AAACAGCAUAGCAAGUUAAAAUAAGGCUAGUCCGUUAUCAACUUGAAA
AAGUGGCACCGAGUCGGUGCU-3'
```

HeLa cells were cultured and subjected to the transfection plasmid surrogate assay as described in Example 13.2). On Day 1, the HeLa cells were transfected with a plasmid surrogate encoding the mCherry™ protein as shown in FIG. 39A. On Day 2, a mix of Cas9-NLS recombinant protein (2 µM; see Example 13.1) and RNAs (crRNA & tracrRNA; 2 µM; see above) were co-incubated with 50 µM of His-CM18-PTD4, and the mixture (CRISPR/Cas9 complex) was exposed to HeLa cells for 10 seconds using Protocol B as described in Example 9.1. Double-stranded plasmid DNA cleavage by the CRISPR/Cas9 complex at the STOP codon between the mCherry™ and GFP coding sequences (FIG. 39B), and subsequent non-homologous repair by the cell in some cases results in removal of the STOP codon (FIG. 39C), thereby allowing expression of both the mCherry™ and GFP fluorescent proteins in the same cell on Day 3 (FIG. 39D-39E). White triangle windows in FIGS. 39D and 39E indicate examples of areas of co-labelling between mCherry™ and GFP.

As a positive control for the CRISPR/Cas9-NLS system, HeLa cells were cultured and co-transfected with three plasmids: the plasmid surrogate (as described in Example 13.2) and other expression plasmids encoding the Cas9-NLS protein (Example 13.1) and the crRNAltracrRNAs (Example 13.3). Typical fluorescence microscopy results are shown in FIGS. 40A-D. Panels A and B show cells 24 hours post-transfection, while panels C and D show cells 72 hours post-transfection.

FIG. 40E-40H shows the results of a parallel transfection plasmid surrogate assay performed using 35 µM of the shuttle His-CM18-PTD4, as described for FIG. 39. FIGS. 40E and 40F show cells 24 hours post-transduction, while panels G and H show cells 48 hours post-transduction. FIGS. 40E and 40G show mCherry™ fluorescence, and FIGS. 40F and 40H show GFP fluorescence, the latter resulting from removal of the STOP codon by the transduced CRISPR/Cas9-NLS complex and subsequent non-homologous repair by the cell. No significant cellular GFP fluorescence was observed in negative control samples (i.e., cells exposed to CRISPR/Cas9-NLS complex without any shuttle agent; data not shown).

13.4 T7E1 Assay

The T7 endonuclease I (T7E1) can be used to detect on-target CRISPR/Cas genome editing events in cultured cells. As an overview, genomic DNA from target cells is amplified by PCR. The PCR products are then denatured and reannealed to allow heteroduplex formation between wild-type DNA and CRISPR/Cas-mutated DNA. T7E1, which recognizes and cleaves mismatched DNA, is used to digest the heteroduplexes. The resulting cleaved and full-length PCR products are visualized by gel electrophoresis.

The T7E1 assay was performed with the Edit-R™ Synthetic crRNA Positive Controls (Dharmacon #U-007000-05) and the T7 Endonuclease I (NEB, Cat #M0302S). After the delivery of the CRISPR/Cas complex, cells were lysed in 100 µL of Phusion™ High-Fidelity DNA polymerase (NEB #M0530S) laboratory with additives. The cells were incubated for 15-30 minutes at 56° C., followed by deactivation for 5 minutes at 96° C. The plate was briefly centrifuged to collect the liquid at bottom of the wells. 50-µL PCR samples were set up for each sample to be analyzed. The PCR samples were heated to 95° C. for 10 minutes and then slowly (>15 minutes) cooled to room temperature. PCR product (-5 µL) was then separated on an agarose gel (2%) to confirm amplification. 15 µL of each reaction was incubated with T7E1 nuclease for 25 minutes at 37° C. Immediately, the entire reaction volume was run with the appropriate gel loading buffer on an agarose gel (2%).

13.5 his-CM18-PTD4 and his-C(LLKK)₃C-PTD4-Mediated CRISPR/Cas9-NLS System Delivery and Cleavage of Genomic PPIB Sequence A mix composed of a Cas9-NLS recombinant protein (25 nM; Example 13.1) and crRNA/tracrRNA (50 nM; see below) targeting a nucleotide sequence of the PPIB gene were co-incubated with 10 µM of His-CM18-PTD4 or His-C(LLKK)₃C-PTD4, and incubated with HeLa cells for 16 h in medium without serum using Protocol A as described in

Example 9.1

The sequences of the crRNA and tracrRNAs constructed and their targets were:

```
- Feldan tracrRNA [SEQ ID NO: 77]:
5'- AAACAGCAUAGCAAGUUAAAAUAAGGCUAGUCCGUUAUCAACUUG

AAAAAGUGGCACCGAGUCGGUGCU-3'

- PPIB crRNA [SEQ ID NO: 78]:
5'-GUGUAUUUUGACCUACGAAUGUUUUAGAGCUAUGCUGUUUUG-3'

- Dharmacon tracrRNA [SEQ ID NO: 79]:
5'-AACAGCAUAGCAAGUUAAAAUAAGGCUAGUCCGUUAUCAACUUGAA

AAAGUGGCACCGAGUCGGUGCUUUUUUU-3'
```

After 16 h, HeLa cells were washed with PBS and incubated in medium with serum for 48 h. HeLa cells were harvested to proceed with the T7E1 protocol assay as described in Example 13.4.

FIG. 41A shows an agarose gel with the PPIB DNA sequences after PCR amplification. Lane A shows the amplified PPIB DNA sequence in HeLa cells without any treatment (i.e., no shuttle or Cas9/RNAs complex). Lanes B: The two bands framed in white box #1 are the cleavage product of the PPIB DNA sequence by the CRIPR/Cas9 complex after the delivery of the complex with the shuttle His-C(LLKK)₃C-PTD4. Lane C: These bands show the amplified PPIB DNA sequence after incubation of the HeLa cells with the Cas9/RNAs complex without shuttle (negative control). Lane D: The bands framed in white box #2 show the amplified PPIB DNA sequence after incubation of the HeLa cells with the Cas9/RNAs complex in presence of a lipidic transfection agent (DharmaFect™ transfection reagent #T-20XX-01) (positive control). Similar results were obtained using the shuttle His-CM18-PTD4 (data not shown).

Figure 41B:
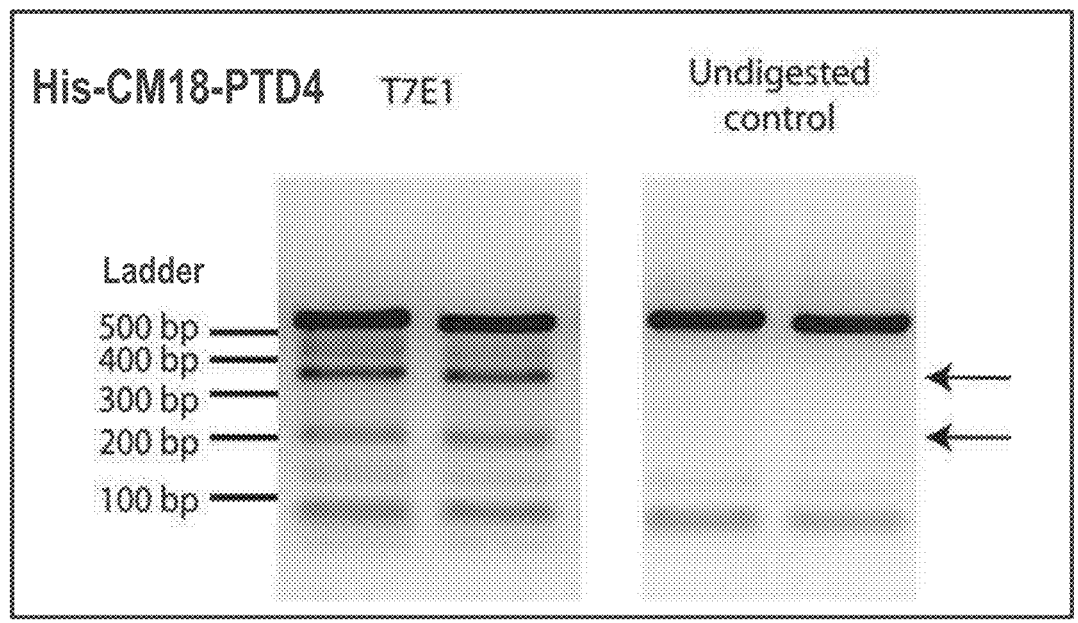
FIG. 41B shows the products of a DNA cleavage assay (T7E1 assay) separated by agarose gel electrophoresis, which is used to measure CRISPR/Cas9-mediated cleavage of cellular genomic DNA (PPIB DNA sequences). The left panel shows the cleavage product of the amplified PPIB DNA sequence by the CRIPR/Cas9 complex after the delivery of the complex with the shuttle agent His-CM18-PTD4 in HeLa cells. The right panel shows amplified DNA sequence before the T7E1 digestion procedure as a negative control.

FIG. 41B shows an agarose gel with the PPIB DNA sequences after PCR amplification. The left panel shows the cleavage product of the amplified PPIB DNA sequence by the CRIPR/Cas9 complex after the delivery of the complex with the shuttle agent His-CM18-PTD4 in HeLa cells. The right panel shows amplified DNA sequence before the T7E1 digestion procedure as a negative control.

Figure 41C:
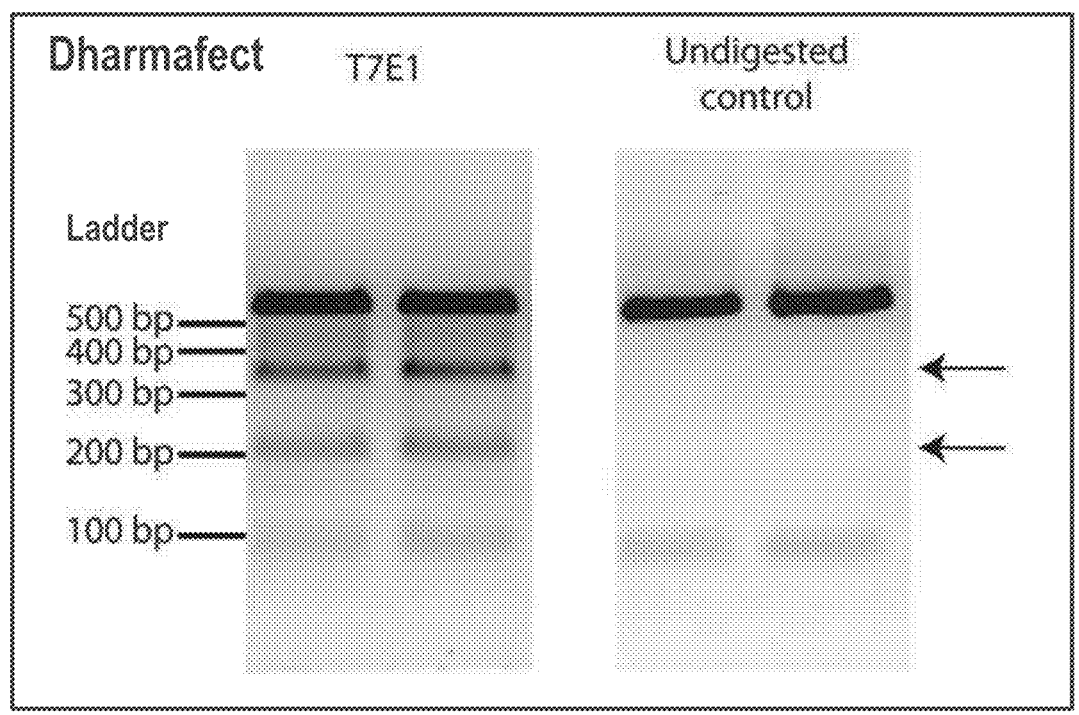
FIG. 41C shows the products of a DNA cleavage assay (T7E1 assay) separated by agarose gel electrophoresis, which is used to measure CRISPR/Cas9-mediated cleavage of cellular genomic DNA (PPIB DNA sequences). The left panel shows the amplified PPIB DNA sequence after incubation of the HeLa cells with the Cas9/RNAs complex in presence of a lipidic transfection agent (DharmaFect™ transfection reagent #T-20XX-01) (positive control). The right panel shows amplified DNA sequence before the T7E1 digestion procedure as a negative control.

FIG. 41C shows an agarose gel with the PPIB DNA sequences after PCR amplification. The left panel shows the amplified PPIB DNA sequence after incubation of the HeLa cells with the Cas9/RNAs complex in presence of a lipidic transfection agent (DharmaFect™ transfection reagent #T-20XX-01) (positive control). The right panel shows amplified DNA sequence before the T7E1 digestion procedure as a negative control.

These results show that the shuttle agents His-CM18-PTD4 and His-C(LLKK)₃C-PTD4 successfully deliver a functional CRISPR/Cas9 complex to the nucleus of HeLa cells, and that this delivery results in CRISPR/Cas9-mediated cleavage of genomic DNA.

13.6 CRISPR/Cas9-NLS System Delivery by Different Shuttle Agents, and Cleavage of Genomic HPTR Sequence in HeLa and Jurkat Cells A mix composed of a Cas9-NLS recombinant protein (2.5 µM; Example 13.1) and crRNA/tracrRNA (2 µM; see below) targeting a nucleotide sequence of the HPTR gene were co-incubated with 35 µM of His-CM18-PTD4, His-CM18-PTD4-His, His-C(LLKK)3C-PTD4, or EB1-PTD4, and incubated with HeLa or Jurkat cells for 2 minutes in PBS using Protocol B as described in Example 9.1.

The sequences of the crRNA and tracrRNAs constructed and their targets were:

```
- Feldan tracrRNA [SEQ ID NO: 77]:
5'-AAACAGCAUAGCAAGUUAAAAUAAGGCUAGUCCGUUAUCAACUUG

AAAAAGUGGCACCGAGUCGGUGCU-3'

- HPRT crRNA [SEQ ID NO: 103]:
5'- AAUUAUGGGGAUUACUAGGAGUUUUAGAGCUAUGCU-3'
```

Figure 46A:
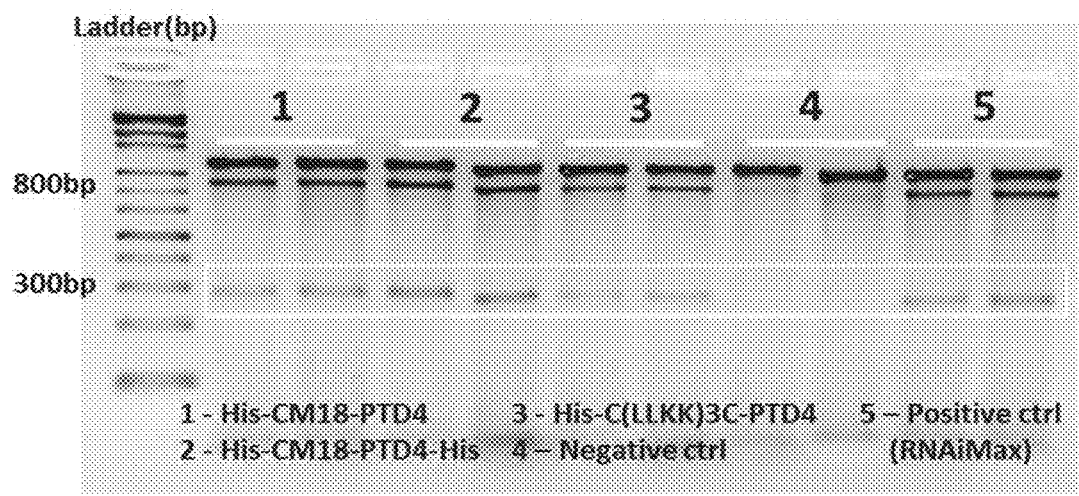
FIGS. 46A and 46B show the products of a DNA cleavage assay separated by agarose gel electrophoresis, which is used to measure CRISPR/Cas9-mediated cleavage of cellular genomic DNA (HPTR sequence) after intracellular delivery of the complex with different shuttle agents.
Figure 46B:
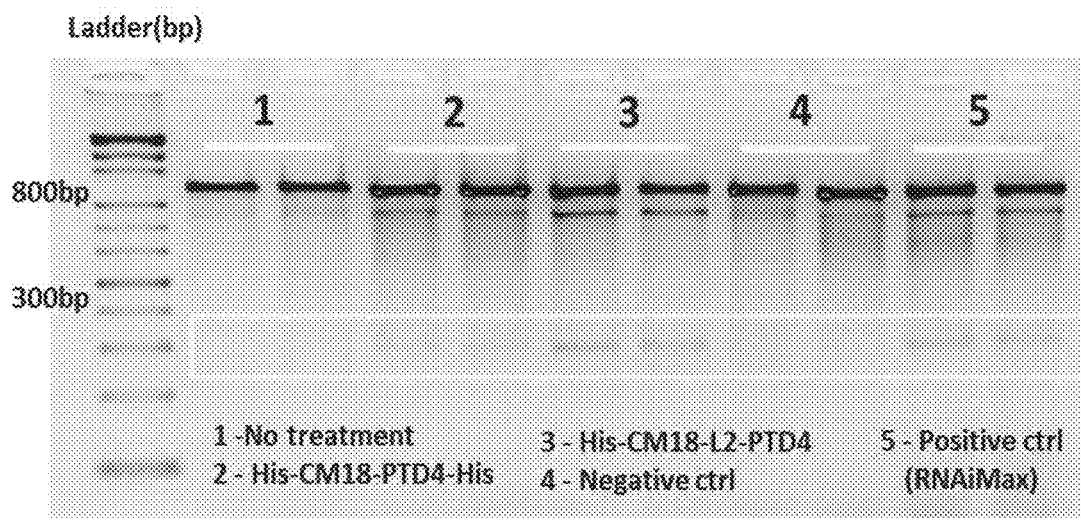

After 2 minutes, cells were washed with PBS and incubated in medium with serum for 48 h. Cells were harvested to proceed with the T7E1 protocol assay as described in Example 13.4. FIG. 46 shows an agarose gel with the HPTR DNA sequences after PCR amplification and the cleavage product of the amplified HPTR DNA sequence by the CRISPR/Cas9 complex after the delivery of the complex with the different shuttle agents. FIG. 46A shows the results with the shuttle agents: His-CM18-PTD4, His-CM18-PTD4-His, and His-C(LLKK)3C-PTD4 in HeLa cells. FIG. 46B shows the results with His-CM18-PTD4 and His-CM18-L2-PTD4 in Jurkat cells. Negative controls (lanes 4) show amplified HPTR DNA sequence after incubation of the cells with the CRISPR/Cas9 complex without the presence of the shuttle agent. Positive controls (lane 5 in FIGS. 46A and 46B) show the amplified HPTR DNA sequence after incubation of the cells with the Cas9/RNAs complex in presence of a lipidic transfection agent (Lipofectamine® RNAiMAX™ Transfection Reagent ThermoFisher Product No. 13778100).

These results show that different polypeptide shuttle agents of the present description may successfully deliver a functional CRISPR/Cas9 complex to the nucleus of HeLa and Jurkat cells, and that this delivery results in CRISPR/Cas9-mediated cleavage of genomic DNA.

Example 14

His-CM18-PTD4 Enables Transduction of the Transcription Factor HOXB4 in THP-1 Cells

14.1 HOXB4-WT Recombinant Protein

Human HOXB4 recombinant protein was constructed, expressed and purified from a bacterial expression system as described in Example 1.4. The sequence of the HOXB4-WT recombinant protein produced was:

```
                                        [SEQ ID NO: 80]
MHHHHHHMAMSSFLINSNYVDPKFPPCEEYSQSDYLPSDHSPGYYAGGQR

RESSFQPEAGFGRRAACTVQRYPPPPPPPPPPGLSPRAPAPPPAGALLPE

PGQRCEAVSSSPPPPPCAQNPLHPSPSHSACKEPVVYPWMRKVHVSTVNP
```

-continued
NYAGGEPKRSRTAYTRQQVLELEKEFHYNRYLTRRRRVEIAHALCLSERQ

IKIWFQNRRMKWKKDHKLPNTKIRSGGAAGSAGGPPGRPNGGPRAL
(MW = 28.54 kDa; pI = 9.89)
The initiator methionine and the 6x Histidine tag are shown in bold.

14.2 Real-Time Polymerase Chain Reaction (rt-PCR)

Control and treated cells are transferred to separate sterile 1.5-mL tubes and centrifuged for 5 minutes at 300g. The cell pellets are resuspended in appropriate buffer to lyse the cells. RNAase-free 70% ethanol is then added followed by mixing by pipetting. The lysates are transferred to an RNeasy™ Mini spin column and centrifuged 30 seconds at 13000 RPM. After several washes with appropriate buffers and centrifugation steps, the eluates are collected in sterile 1.5-mL tubes on ice, and the RNA quantity in each tube is then quantified with a spectrophotometer. For DNase treatment, 2 µg of RNA is diluted in 15 µL of RNase-free water. 1.75 µL of 10X DNase buffer and 0.75 µL of DNase is then added, followed by incubation at 37° C. for 15 minutes. For reverse transcriptase treatment, 0.88 µL of EDTA (50 nM) is added, followed by incubation at 75° C. for 5 minutes. In a PCR tube, 0.5 pg of DNase-treated RNA is mixed with 4 µL of iScript™ Reverse transcription Supermix (5X) and 20 µL of nuclease-free water. The mix is incubated in a PCR machine with the following program: 5 min at 25° C., 30 min at 42° C. and 5 min at 85° C. Newly synthesized cDNA is transferred in sterile 1.5-mL tubes and diluted in 2 µL of nuclease-free water. 18 µL per well of a qPCR machine (CFX-96™) mix is then added in a PCR plate for analysis.

14.3 HOXB4-WT Transduction by his-CM18-PTD4 in THP-1 Cells: Dose Responses and Viability THP-1 cells were cultured and tested in the protein transduction assay using Protocol A as described in Example 9.1. Briefly, THP-1 cells were plated at 30 000 cells/well one day before transduction. HOXB4-WT recombinant protein (0.3, 0.9, or 1.5 M; Example 14.1) was co-incubated with different concentrations of His-CM18-PTD4 (0, 0.5, 7.5, 0.8 or 1 M) and then exposed to THP-1 cells for 2.5 hours in the presence of serum. The cells were subjected to real time-PCR analysis as described in Example 14.2 to measure the mRNA levels of a target gene as a marker for HOXB4 activity, which was then normalized to the target gene mRNA levels detected in the negative control cells (no treatment), to obtain a "Fold over control" value. Total RNA levels (ng/µL) were also measured as a marker for cell viability. Results are shown in Table 14.1 and FIG. 42.

TABLE 14.1

Figure 42:
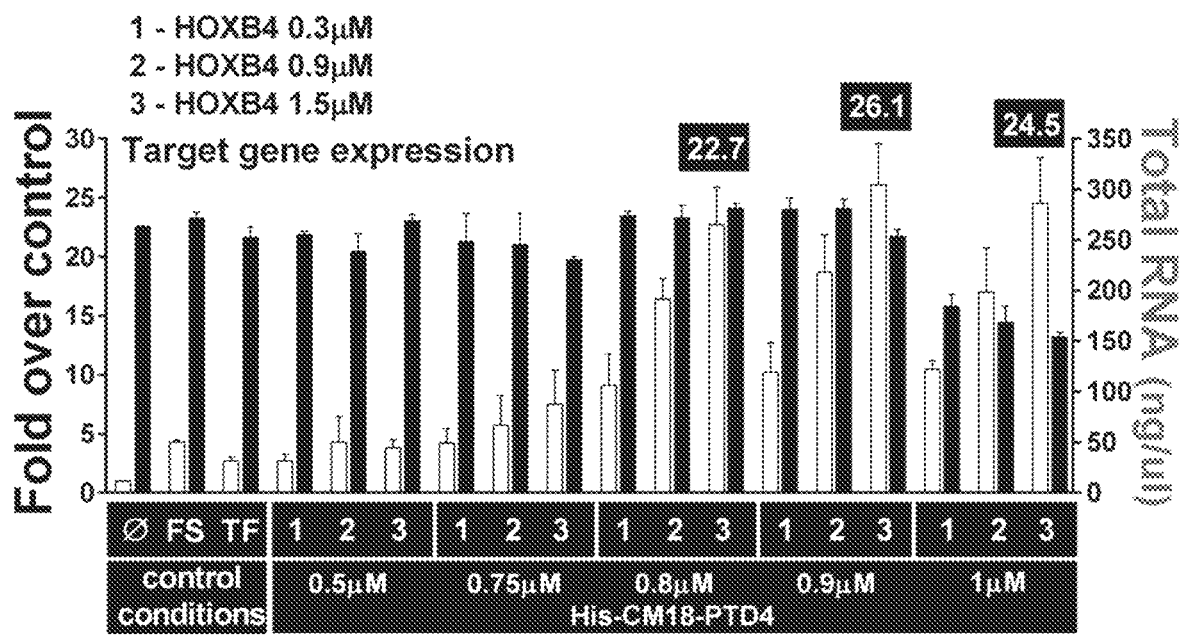

Data from FIG. 42

| Cargo/ shuttle agent (FIG. 41) | Cells | Conc. of shuttle (µM) | Conc. of HOXB4-WT (µM) | Fold over control (mean ± St. Dev) | Total RNA in ng/µL (mean ± St. Dev) |
|---|---|---|---|---|---|
| No treatment ("Ø") | THP-1 | 0 | 0 | 1 ± 0.1 | 263 ± 0.4 |
| HOXB4-WT alone ("TF") | THP-1 | 0 | 1.5 | 4.3 ± 0.1 | 271 ± 6.0 |
| His-CM18-PTD4 alone ("FS") | THP-1 | 1 | 0 | 2.7 ± 0.3 | 252 ± 10.7 |
| His-CM18-PTD4 + HOXB4-WT | THP-1 | 0.5 | 0.3 | 2.7 ± 0.6 | 255 ± 3.9 |
|  |  |  | 0.9 | 4.3 ± 2.1 | 239 ± 17.5 |
|  |  |  | 1.5 | 3.8 ± 0.7 | 269 ± 6.4 |
| His-CM18-PTD4 + HOXB4-WT | THP-1 | 0.75 | 0.3 | 4.2 ± 1.2 | 248 ± 28 |
|  |  |  | 0.9 | 5.7 ± 2.5 | 245 ± 31 |
|  |  |  | 1.5 | 7.5 ± 2.8 | 230 ± 3.3 |
| His-CM18-PTD4 + HOXB4-WT | THP-1 | 0.8 | 0.3 | 9.1 ± 2.7 | 274 ± 4.4 |
|  |  |  | 0.9 | 16.4 ± 1.7 | 272 ± 12.5 |
|  |  |  | 1.5 | 22.7 ± 3.2 | 282 ± 4.7 |
| His-CM18-PTD4 + HOXB4-WT | THP-1 | 0.9 | 0.3 | 10.2 ± 2.5 | 280 ± 11.3 |
|  |  |  | 0.9 | 18.7 ± 3.1 | 281 ± 9.2 |
|  |  |  | 1.5 | 26.1 ± 3.5 | 253 ± 7.1 |
| His-CM18-PTD4 + HOXB4-WT | THP-1 | 1 | 0.3 | 10.5 ± 0.7 | 184 ± 12.3 |
|  |  |  | 0.9 | 17 ± 3.7 | 168 ± 16.2 |
|  |  |  | 1.5 | 24.5 ± 3.9 | 154 ± 4.7 |

These results show that exposing THP-1 cells to a mixture of the shuttle agent His-CM18-PTD4 and the transcription factor HOXB4-WT for 2.5 hours in the presence of serum results in a dose-dependent increase in mRNA transcription of the target gene. These results suggest that HOXB4-WT is successfully delivered in an active form to the nucleus of THP-1 cells, where it can mediate transcriptional activation.

14.4 HOXB4-WT Transduction by his-CM18-PTD4 in THP-1 Cells: Time Course and Viability (0 to 48 Hours)

THP-1 cells were cultured and tested in the protein transduction assay using Protocol A as described in Example 9.1. Briefly, THP-1 cells were plated at 30 000 cells/well one day before the first time course experiment. HOXB4-WT recombinant protein (1.5 µM; Example 14.1) was co-incubated with His-CM18-PTD4 (0.8 µM) and then exposed to THP-1 cells for 0, 2.5, 4, 24 or 48 hours in presence of serum. The cells were subjected to real time-PCR analysis as described in Example 14.2 to measure mRNA levels of a target gene as a marker for HOXB4 activity, which was then normalized to the target gene mRNA levels detected in the negative control cells (no treatment), to obtain a "Fold over control" value. Total RNA levels (ng/µL) were also measured as a marker for cell viability. Results are shown in Table 14.2 and FIG. 43.

TABLE 14.2

Figure 43:
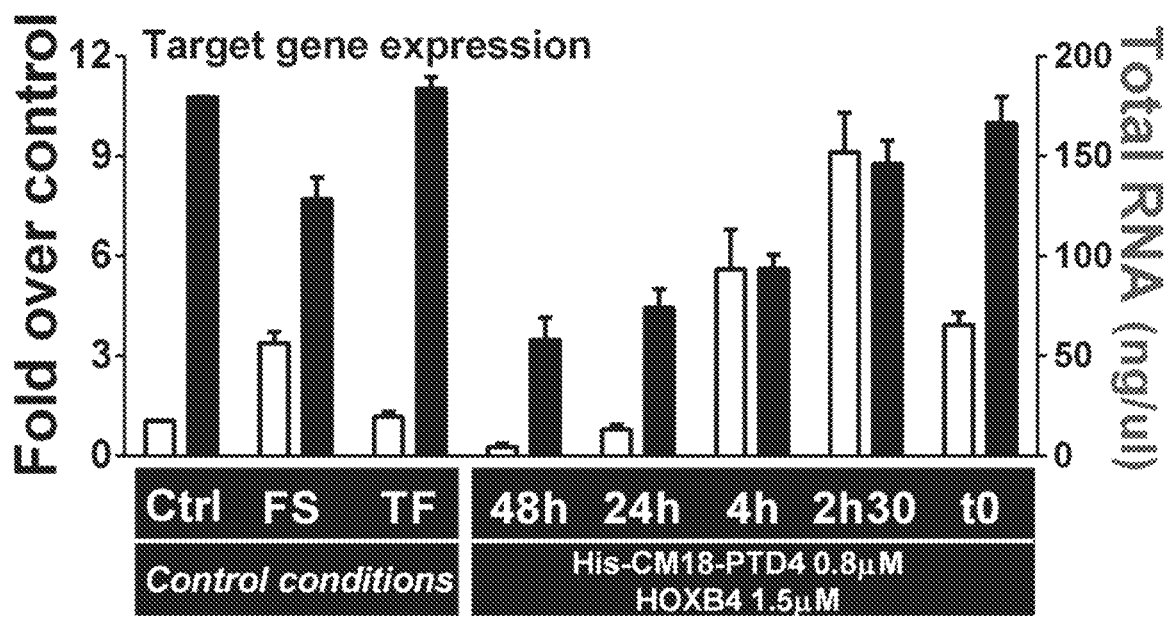

Data from FIG. 43

| Cargo/shuttle agent (FIG. 43) | Cells | Conc. of shuttle (µM) | Conc. of HOXB4-WT (µM) | Exposure time (hours) | Fold over control (mean ± St. Dev) | Total RNA in ng/µL (mean ± St. Dev) |
|---|---|---|---|---|---|---|
| No treatment ("Ctrl") | THP-1 | 0 | 0 | — | 1 ± 0.1 | 180 ± 0.4 |
| HOXB4-WT alone ("TF") | THP-1 | 0 | 1.5 | 2.5 h | 3.4 ± 0.3 | 129 ± 10.7 |
| His-CM18-PTD4 alone ("FS") | THP-1 | 0.8 | 0 | 2.5 h | 1.2 ± 0.14 | 184 ± 6.0 |

TABLE 14.2-continued

Data from FIG. 43

| Cargo/shuttle agent (FIG. 43) | Cells | Conc. of shuttle ($\mu$M) | Conc. of HOXB4-WT ($\mu$M) | Exposure time (hours) | Fold over control (mean ± St. Dev) | Total RNA in ng/$\mu$L (mean ± St. Dev) |
|---|---|---|---|---|---|---|
| His-CM18-PTD4 + HOXBA-WT | THP-1 | 0.8 | 1.5 | 48 h | 0.27 ± 0.1 | 58 ± 11.2 |
|  |  |  |  | 24 h | 0.8 ± 0.14 | 74 ± 9.2 |
|  |  |  |  | 4 h | 5.6 ± 1.2 | 94 ± 7.1 |
|  |  |  |  | 2.5 h | 9.1 ± 1.2 | 146 ± 11.6 |
|  |  |  |  | 0 | 3.9 ± 0.4 | 167 ± 13 |

14.5 HOXB4-WT Transduction by his-CM18-PTD4 in THP-1 Cells: Time Course and Viability (0 to 4 Hours)

THP-1 cells were cultured and tested in the protein transduction assay using Protocol A as described in Example 9.1. Briefly, THP-1 cells were plated at 30 000 cells/well one day before the first time course experiment. HOXB4-WT recombinant protein (0.3 $\mu$M; Example 14.1) was co-incubated with His-CM18-PTD4 (0.8 $\mu$M) and then exposed to THP-1 cells for 0, 0.5, 1, 2, 2.5, 3 or 4 hours in presence of serum. The cells were subjected to real time-PCR analysis as described in Example 14.2 to measure mRNA levels of a target gene as a marker for HOXB4 activity, which was then normalized to target gene mRNA levels detected in the negative control cells (no treatment), to obtain a "Fold over control" value. Total RNA levels (ng/$\mu$L) were also measured as a marker for cell viability. Results are shown in Table 14.3 and FIG. 44.

TABLE 14.3

Data from FIG. 44

| Cargo/shuttle agent (FIG. 42) | Cells | Conc. of shuttle ($\mu$M) | Conc. of HOXB4-WT ($\mu$M) | Exposure time (hours) | Fold over control (mean ± St. Dev) | Total RNA in ng/$\mu$L (mean ± St. Dev) |
|---|---|---|---|---|---|---|
| No treatment ("Ctrl") | THP-1 | 0 | 0 | — | 1 ± 0.1 | 289 ± 9.2 |
| His-CM18-PTD4 alone ("FS") | THP-1 | 0 | 0.3 | 2.5 h | 2.5 ± 0.2 | 260 ± 7.1 |
| HOXB4-WT alone ("TF") | THP-1 | 0.8 | 0 | 2.5 h | 1 ± 0.14 | 264 ± 12.3 |
| His-CM18-PTD4 + HOXBA-WT | THP-1 | 0.8 | 0.3 | 4 h | 1.2 ± 0.1 | 198 ± 6.0 |
|  |  |  |  | 3 h | 1.3 ± 0.21 | 268 ± 12.5 |
|  |  |  |  | 2.5 h | 2 ± 0.3 | 275 ± 4.7 |
|  |  |  |  | 2 h | 2.2 ± 0.2 | 269 ± 12.5 |
|  |  |  |  | 1 | 9.7 ± 2.6 | 268 ± 3.9 |
|  |  |  |  | 0.5 | 23.1 ± 2.0 | 266 ± 17.5 |
|  |  |  |  | 0 | 4 ± 0.5 | 217 ± 6.4 |

14.6 HOXB4-WT Transduction by his-CM18-PTD4 in HeLa Cells: Immuno-Labelling and Visualization by Microscopy Recombinant HOXB4-WT transcription factor (25 $\mu$M; Example 14.1) was co-incubated with 35 $\mu$M of His-CM18-PTD4 and exposed to HeLa cells for 10 seconds using Protocol B as described in Example 9.1. After a 30-minute incubation to allow transduced HOXB4-WT to accumulate in the nucleus, the cells were fixed, permeabilized and immuno-labelled as described in Example 3.2a. HOXB4-WT was labelled using a primary mouse anti-HOXB4 monoclonal antibody (Novus Bio #NBP2-37257) diluted 1/500, and a secondary anti-mouse antibody Alexa™-594 (Abcam #150116) diluted 1/1000. Nuclei were labelled with DAPI. The cells were visualized by bright field and fluorescence microscopy at 20× and 40× magnifications as described in Example 3.2, and sample results are shown in FIG. 45. Co-localization was observed between nuclei labelling (FIGS. 45A and 45C) and HOXB4-WT labelling (FIGS. 45B and 45D), indicating that HOXB4-WT was successfully delivered to the nucleus after 30 min in the presence of the shuttle agent His-CM18-PTD4. White triangle windows show examples of areas of co-localization between the nuclei (DAPI) and HOXB4-WT immuno-labels.

14.7 HOXB4-WT Transduction by Different Shuttle Agents in THP-1 Cells: Dose Responses and Viability THP-1 cells were cultured and tested in the protein transduction assay using Protocol A as described in Example 9.1. Briefly, THP-1 cells were plated at 30 000 cells/well one day before the first time course experiment. HOXB4-WT recombinant protein (1.5 $\mu$M; Example 14.1) co-incubated with the shuttle agents His-CM18-PTD4, TAT-KALA, EB1-PTD4, His-C(LLKK)3C-PTD4 and His-CM18-PTD4-His at 0.8 $\mu$M, and then exposed to THP-1 cells for 2.5 hours in presence of serum. The cells were subjected to real time-PCR analysis as described in Example 14.2 to measure mRNA levels of a target gene as a marker for HOXB4 activity, which was then normalized to target gene mRNA levels detected in the negative control cells (no treatment), to obtain a "Fold over control" value. Total RNA levels (ng/$\mu$L) were also measured as a marker for cell viability. Results are shown in Table 14.4 and FIG. 47.

TABLE 14.4

Figure 47:
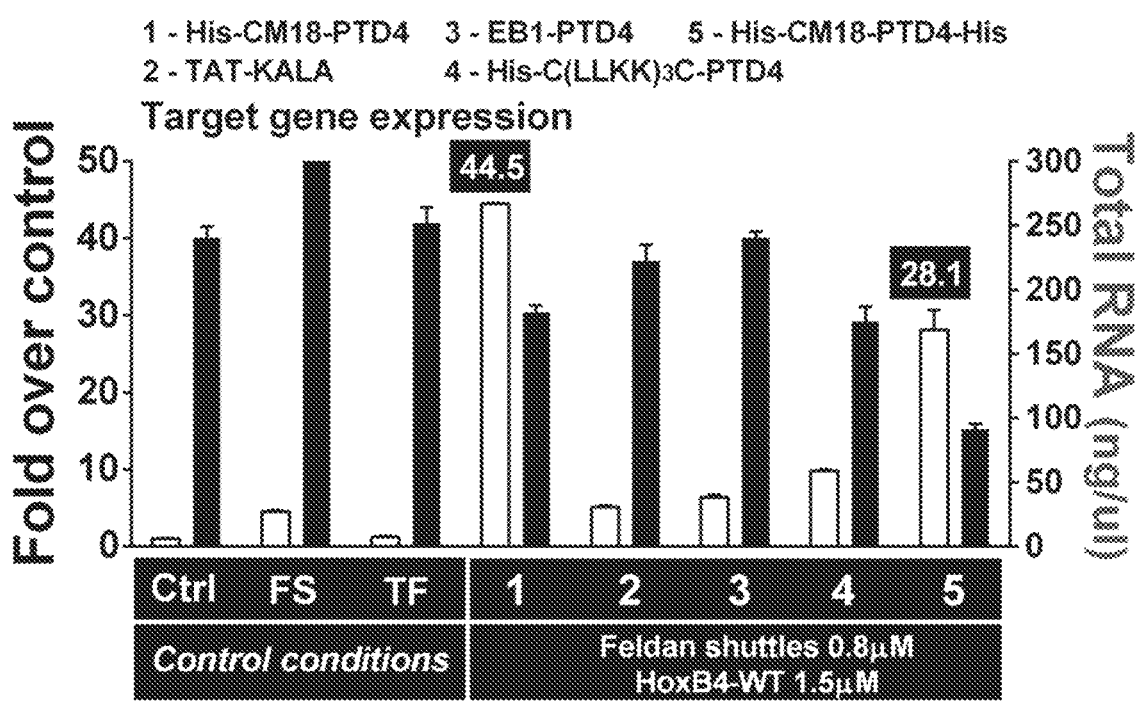
FIG. 47 shows the transcriptional activity of THP-1 cells that have been transduced with the transcription factor HOXB4 using the shuttle agents His-CM18-PTD4, TAT-KALA, EB1-PTD4, His-C(LLKK)3C-PTD4 and His-CM18-PTD4-His. Successful intra-nuclear delivery of HOXB4 was determined by monitoring mRNA levels of a target gene by real-time PCR, and the results were normalized against those in the negative control (HOXB4 without shuttle agent) and expressed as "Fold over control" (left bars). Total cellular RNA (ng/µL) was quantified and used a marker for cell viability (right bars). "0" or "Ctrl" means "no treatment"; "TF" means "Transcription Factor alone"; "FS" means "shuttle alone".

Data from FIG. 47

| Cargo/ shuttle agent | Shuttle conc. (μM) | HOXB4-WT Conc. (μM) | Exposure time | Fold over control (mean ± St. Dev) | Total RNA in ng/μL (mean ± St. Dev) |
|---|---|---|---|---|---|
| No treatment ("Ctrl") | 0 | 0 | — | 1 ± 0.09 | 240.3 ± 8.9 |
| His-CM18-PTD4 alone ("FS") | 0 | 1.5 | 2.5 h | 2.5 ± 0.3 | 303.9 ± 7.6 |
| HOXB4-WT alone ("TF") | 0.8 | 0 | 2.5 h | 1 ± 0.11 | 251.9 ± 11.9 |
| His-CM18-PTD4 + HOXB4-WT | 0.8 | 1.5 | 2.5 h | 44.5 ± 0.09 | 182 ± 5.97 |
| TAT-KALA + HOXB4-WT | | | | 5.1 ± 0.21 | 222.4 ± 12.5 |
| EB1-PTD4 + HOXB4-WT | | | | 6.4 ± 0.3 | 240.4 ± 4.71 |
| His-C(LLKK)3C-PTD4 + HOXB4-WT | | | | 9.8 ± 0.19 | 175.3 ± 11.25 |
| His-CM18-PTD4-His + HOXB4-WT | | | | 28.1 ± 2.61 | 91.4 ± 3.92 |

Example 15

In Vivo GFP-NLS Delivery in Rat Parietal Cortex by his-CM18-PTD4

The ability of the shuttle agent His-CM18-PTD4 to deliver GFP-NLS in vivo in the nuclei of rat brain cells was tested.

In separate sterile 1.5-mL tubes, shuttle agent His-CM18-PTD4 was diluted in sterile distilled water at room temperature. GFP-NLS, used as cargo protein, was then added to the shuttle agent and, if necessary, sterile PBS was added to obtain the desired concentrations of shuttle agent and cargo in a sufficient final volume for injection in rat brain (e.g., 5 μL per each injection brain site). The shuttle agent/cargo mixture was then immediately used for experiments. One negative control was included for the experiment, which corresponds to the injection of the GFP-NLS alone.

Bilateral injections were performed in the parietal cortex of three rats. In the left parietal cortex (ipsilateral), a mix composed of the shuttle agent (20 μM) and the GFP-NLS (20 μM) was injected, and in the right parietal cortex (contralateral), only the GFP-NLS (20 μM) was injected as a negative control. For surgical procedures, mice were anesthetized with isoflurane. Then the animal was placed in a stereotaxic frame, and the skull surface was exposed. Two holes were drilled at the appropriate sites to allow bilateral infusion of the shuttle/cargo mix or GFP-NLS alone (20 μM) with 5-μL Hamilton syringe. Antero-posterior (AP), lateral (L), and dorso-ventral (DV) coordinates were taken relative to the bregma: (a) AP+0.48 mm, L±3 mm, V-5 mm; (b) AP-b 2 mm, L±1.3 mm, V-1.5 mm; (c) AP-2.6 mm, L 1.5 mm, V-1.5 mm. The infused volume of the shuttle/cargo mix or cargo alone was 5 μL per injection site and the injection was performed for 10 minutes. After that, experimenter waited 1 min before removing the needle from the brain. All measures were taken before, during, and after surgery to minimize animal pain and discomfort. Animals were sacrificed by perfusion with paraformaldehyde (4%) 2 h after surgery, and brain were collected and prepared for microscopy analysis. Experimental procedures were approved by the Animal Care Committee in line with guidelines from the Canadian Council on Animal Care.

Figure 48A:
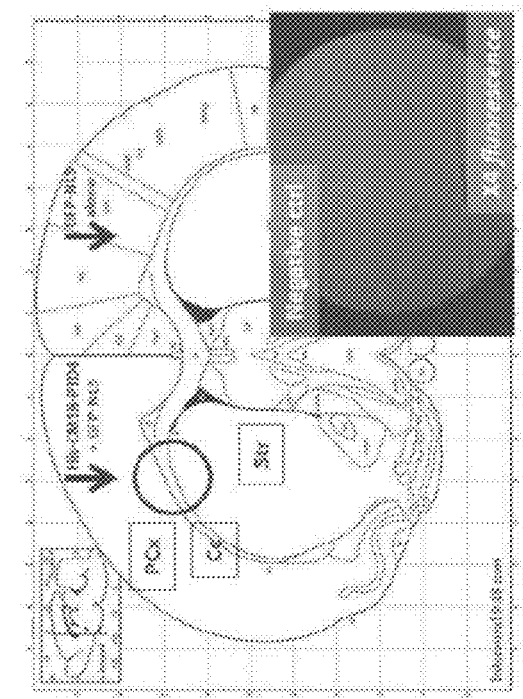
FIGS. 48A-48D show in vivo GFP-NLS delivery in rat parietal cortex by His-CM18-PTD4. Briefly, GFP-NLS (20 µM) was injected in the parietal cortex of rat in presence of the shuttle agent His-CM18-PTD4 (20 µM) for 10 min. Dorso-ventral rat brain slices were collected and analyzed by fluorescence microscopy at 4× (FIG. 48A), 10× (FIG. 48C) and 20× magnifications (FIG. 48D). The injection site is located in the deepest layers of the parietal cortex (PCx). In presence of the His-CM18-PTD4 shuttle agent, the GFP-NLS diffused in cell nuclei of the PCx, of the Corpus Callus (Cc) and of the striatum (Str) (white curves mark limitations between brains structures).
Figure 48B:
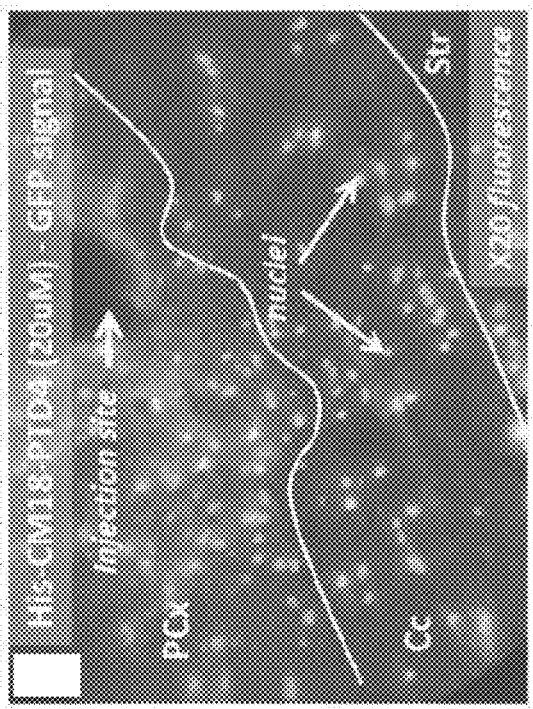
Figure 48C:
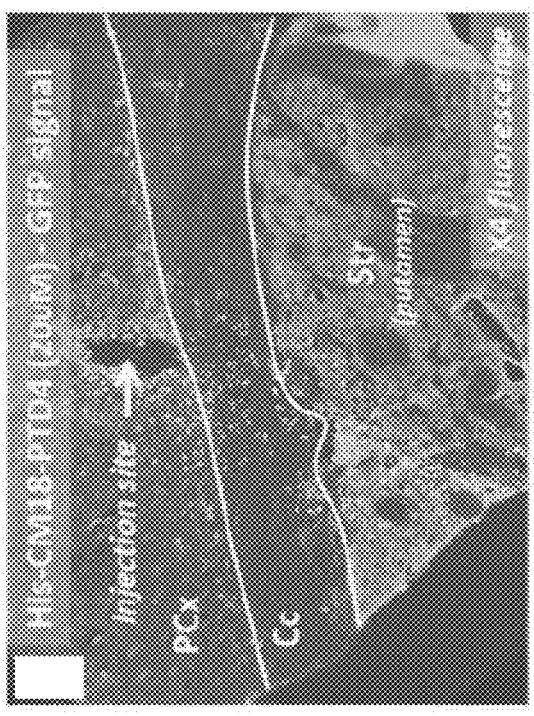
Figure 48D:
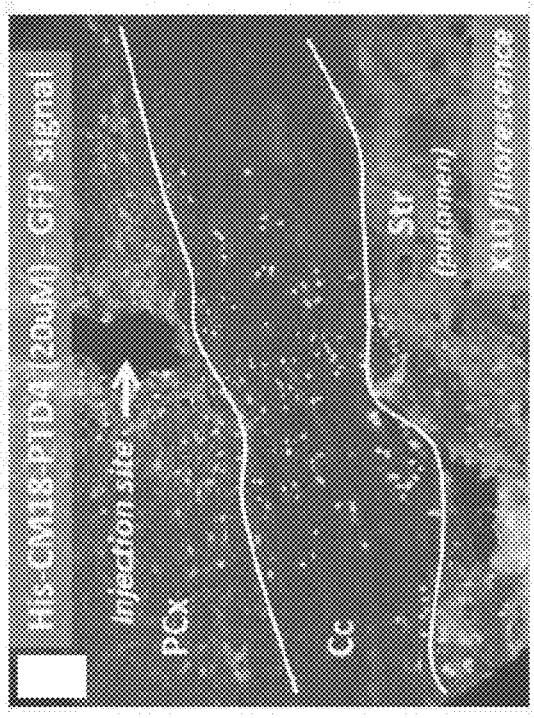

Dorso-ventral rat brain slices were collected and analysed by fluorescence microscopy and results are shown in at 4× (FIG. 48A), 10× (FIG. 48C) and 20× (FIG. 48D) magnifications. The injection site is located in the deepest layers of the parietal cortex (PCx). In the presence of the His-CM18-PTD4 shuttle, the GFP-NLS diffused in cell nuclei of the PCx, of the Corpus Callus (Cc) and of the striatum (Str) (White curves mean limitations between brains structures). FIG. 48B shows the stereotaxic coordinates of the injection site (black arrows) from the rat brain atlas of Franklin and Paxinos. The injection of GFP-NLS in presence of His-CM18-PTD4 was performed on the left part of the brain, and the negative control (an injection of GFP-NLS alone), was done on the contralateral site. The black circle and connected black lines in FIG. 48B show the areas observed in the fluorescent pictures (FIGS. 48A, 48C and 48D).

This experiment demonstrated the cell delivery of the cargo GFP-NLS after its stereotaxic injection in the rat parietal cortex in the presence of the shuttle agent His-CM18-PTD4. Results show the delivery of the GFP-NLS in the nucleus of cells from the deeper layers of the parietal cortex (injection site) to the corpus callus and the dorsal level of the striatum (putamen). In contrast, the negative control in which GFP-NLS is only detectable locally around the injection site. This experiment shows that shuttle agent induced nuclear delivery of the cargo in the injection site (parietal cortex) and its diffusion through both neighboring brain areas (corpus callus and striatum rat brain).

Example A

Physiochemical Properties of Domain-Based Peptide Shuttle Agents

A plurality of different peptides was initially screened with the goal of identifying polypeptide-based shuttle agents that can deliver independent polypeptide cargos intracellularly to the cytosol/nucleus of eukaryotic cells. On one hand, these large-scale screening efforts led to the discovery that domain-based peptide shuttle agents (see Examples 1-15), comprising an endosome leakage domain (ELD) operably linked to a cell penetrating domain (CPD), and optionally one or more histidine-rich domains, can increase the transduction efficiency of an independent polypeptide cargo in eukaryotic cells, such that the cargo gains access to the cytosol/nuclear compartment. Conversely, these screening efforts revealed some peptides having no or low polypeptide cargo transduction power, excessive toxicity, and/or other undesirable properties (e.g., poor solubility and/or stability).

Based on these empirical data, the physiochemical properties of successful, less successful, and failed peptides were compared in order to better understand properties common to the more successful shuttle agents. This approach involved manually stratifying the different peptides according to transduction performance with due consideration to, for example: (1) their solubility/stability/ease of synthesis; (2) their ability to facilitate endosomal escape of calcein (e.g., see Example 2); (3) their ability to deliver one or more types of independent polypeptide cargo intracellularly, as evaluated by flow cytometry (e.g., see Examples 3-6 and 8-15) in different types of cells and cell lines (e.g., primary, immortalized, adherent, suspension, etc.) as well as under different transduction protocols; and (4) their ability to deliver polypeptide cargos to the cytosol and/or nucleus, as evaluated by fluorescence microscopy (e.g., for fluorescently labelled cargos), increased transcriptional activity (e.g., for transcription factor cargos), or genome editing capabilities (e.g., for nuclease cargos such as CRISPR/Cas9 or CRISPR/Cpf1) (e.g., see Examples 3-6 and 8-15), and toxicity towards different types of cells and cell lines (e.g., primary, immortalized, adherent, suspension, etc.), under different transduction protocols.

In parallel to the above-mentioned manual curation, the transduction power and cellular toxicity of each peptide for a given fluorescently-labelled cargo (GFP, GFP-NLS, or fluorescently-labelled antibodies) and cell line were combined into a single "transduction score" as a further screening tool, which was calculated as follows: [(Highest percentage transduction efficiency observed by flow cytometry for a given peptide in a cell type) x (Percentage viability for the peptide in the tested cell line)]/1000, giving an overall transduction score between 0 and 10 for a given cell type and polypeptide cargo. These analyses identified domain-based peptides having transduction scores ranging from about 8 (e.g., for successful domain-based peptide shuttle agents) to as low as 0.067 (e.g., for single-domain negative control peptides).

The above-mentioned manual curation and "transduction score"-based analyses revealed a number of parameters that are common to many successful domain-based shuttle agents. Some of these parameters are listed in the Table A1. An example of a "transduction score"-based analyses in HeLa cells using GFP as a polypeptide cargo is shown in Table A2. Other transduction score-based analyses using cell lines other than HeLa and polypeptides cargos other than GFP, were also performed but are not shown here for brevity.

No successful shuttle agents were found having less than 20 amino acid residues in length (see parameter 1 in Tables A1 and A2). The four amino acids alanine, leucine, lysine and arginine, were the principal and most recurrent residues in most of the successful shuttle agents (35-85% of residues of the peptide; see parameter 10). These residues dictate the alpha-helical structure and amphiphilic nature of these peptide sequences (parameters 2-5). There was often a balance between the percentages of A/L residues (15-45%) and K/R residues (20-45%) in the shuttle agents (parameters 11,12 and 14), and the percentages of negatively charged residues was often found to be not greater than 10% (parameter 14). Conversely, the sixteen other amino acid residues (other than A, L, K, and R) represented generally between 10-45% of the shuttle agents (parameter 15). Successful shuttle agents generally had a predicted isoelectric point (µI) of between 8-13 (parameter 7), and a predicted net charge greater than or equal to +4 (parameter 6), with dCM18-TAT-Cys having a predicted net charge of as high as +26. Hydrophobic residues (A, C, G, I, L, M, F, P, W, Y, V) composed generally between 35-65% of the shuttle agents, and neutral hydrophilic residues (N, Q, S, T) represented generally from 0-30% (parameters 8 and 9).

As shown in Table A2, the most successful shuttle agents (e.g., transduction scores above 5.0) generally had few parameters outside the ranges set forth in Table A1. However, significant increases in transduction efficiency were also observed for shuttle agents in which several parameters were not satisfied, depending for example on the extent to which the unsatisfied parameters fall outside the recommended range, and/or on whether other parameters fall closer to the middle of a recommended range. Thus, shuttle agents having several parameters which fall within "optimal" ranges may compensate for other parameters falling outside of the recommended ranges. As mentioned above, peptides shorter than 20 amino acids did not show any significant transduction ability (e.g. transduction scores less than 0.4), regardless of how many other parameters were satisfied. Among the peptides greater than 20 amino acids in length and having transduction scores lower than 0.4, VSVG-PTD4 (score of 0.35) failed to satisfy six parameters, while JST-PTD4 (score of 0.083) failed to satisfy ten parameters. KALA (score of 0.12) failed to satisfy four parameters, with parameters 11 and 14 far exceeding the recommended ranges, reflecting an overabundance of A/L residues and a large imbalance between the percentages of A/L and L/R residues. It is to be understood that the transduction score ranges appearing the Table A2 are arbitrarily selected, and that other ranges can be selected and are within the scope of the present description.

TABLE A1

General physicochemical properties of successful domain-based peptide shuttle agents

| | Parameter | Description | Result |
|---|---|---|---|
| 1 | Minimum length | The minimum length of peptide shuttle agent. | 20 amino acids |
| 2 | Amphipathic alpha-helix | Peptide shuttle agent comprises a predicted amphipathic alpha-helix conformation, (Based on 3D modeling using PEP-FOLD, an online resource for de novo peptide structure prediction: http://bioserv.rpbs.univ-paris-diderot.fr/services/PEP-FOLD/). | Yes |
| 3 | Positively-charged surface | Predicted amphipathic alpha-helix conformation comprises a positively-charged hydrophilic face rich in R and/or K residues, (Based on observation of at least 3 K/R residues clustered to one side of a helical wheel modeling, using the online helical wheel projection tool available at: http://rzlab.ucr.edu/scripts/wheel/wheel.cgi). | Yes |
| 4 | % Highly hydrophobic core | Predicted amphipathic alpha-helix conformation comprises a highly hydrophobic core composed of spatially adjacent L, I, F, V, W, and/or M residues representing a percentage of the overall peptide sequence (calculated excluding histidine-rich domains). This parameter was calculated by first arranging the amino acids of the peptide in an opened cylindrical representation, then delineating an | 12-50% |

TABLE A1-continued

General physicochemical properties of successful domain-based peptide shuttle agents

| | Parameter | Description | Result |
|---|---|---|---|
| | | area of contiguous highly hydrophobic residues (L, I, F, V, W, M), as shown in FIG. 49A, right panel. The number of highly hydrophobic residues comprised in this delineated highly hydrophobic core was then divided by the total amino acid length of the peptide, excluding N- and/or C-terminal histidine-rich domains. For example, for the peptide shown in FIG. 49A, there are 8 residues in the delineated highly hydrophobic core, and 25 total residues in the peptide (excluding the terminal 12 histidines). Thus, the highly hydrophobic core is 32% (8/25). | |
| 5 | Hydrophobic moment | Calculated hydrophobic moment (μ; calculated while excluding histidine-rich domains), using the online helical wheel projection program available from: http://rzlab.ucr.edu/scripts/wheel/wheel.cgi. | 3.5-11 |
| 6 | Net charge | Predicted net charge at physiological pH (calculated from the side chains of K, R, D, and E residues). | ≥+4 |
| 7 | pI | Predicted isoelectric point (pI). (Calculated with the Prot Param software available at: http://web.expasy.org/protparam/). | 8-13 |
| 8 | % hydrophobic residues | Overall percentage of hydrophobic residues (A, C, G, I, L, M, F, P, W, Y, V) in the peptide shuttle agent. | 35-65% |
| 9 | % neutral hydrophilic residues | Overall percentage of neutral hydrophilic residues (N, Q, S, T) in the peptide shuttle agent. | 0-30% |
| 10 | % A, L, K, R | Overall percentage of residues in the peptide shuttle agent which are A, L, K, or R. | 35-85% |
| 11 | % A or L | Overall percentage of residues in the peptide shuttle agent which are A or L. (Number of A + L residues)/(Total number of residues), with there being at least 5% of L in the peptide. | 15-45% |
| 12 | % Positive residues | Overall percentage of residues in the peptide shuttle agent which are K or R. (Number of K + R residues)/(Total number of residues). | 20-45% |
| 13 | % Negative residues | Overall percentage of residues in the peptide shuttle agent which are D or E. (Number of D + E residues)/(Total number of residues). | 0-10% |
| 14 | Difference between % of A/L and K/R | Overall difference (absolute value) between the percentage of A or L (parameter 11) and the percentage of K or R (parameter 12) in the peptide shuttle agent. (Parameter 11) – (Parameter 12). | ≤10% |
| 15 | % infrequent amino acid residues | Overall percentage of residues which are Q, Y, W, P, I, S, G, V, F, E, D, C, M, N, T or H (i.e., not A, L, K, or R). (Number of Q + Y + W + P + I + S + G + V + F + E + D + C + M + N + T + H residues)/(Total number of residues). | 10-45% |

TABLE A2

Physiochemical properties of domain-based peptides stratified by transduction score (in Hela cells using GFP or GFP-NLS as cargo)

| Peptide name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| *Transduction scores between 3.1-8.0* | | | | | | | | | | | | | | | |
| TAT-KALA | 42 | Y | Y | 12.1 | 3.6 | 13 | 11.5 | 54.5 | 7.5 | 81 | 43.9 | 36.5 | 4.9 | 7.3 | 11.9 |
| His-CM18-PTD4-His | 41 | Y | Y | 24.1 | 6.7 | 8 | 11.8 | 51.6 | 8.1 | 52 | 22.6 | 23 | 0 | −5.7 | 26.8 |
| His-CM18-PTD4 | 35 | Y | Y | 26 | 6.7 | 8 | 11.8 | 51.6 | 8.1 | 52 | 22.6 | 23 | 0 | −5.7 | 31.4 |
| His-C(LLKK)3C-PTD4 | 31 | Y | Y | 24 | 3.6 | 9 | 11.2 | 45.8 | 2.7 | 43 | 20 | 22.9 | 2.9 | −2.9 | 35.5 |
| CM18-L2-PTD4 | 36 | Y | Y | 22.2 | 6.9 | 8 | 11.8 | 63.9 | 14 | 50 | 27.7 | 22.2 | 0 | 5.5 | 50 |
| CM18-His-PTD4 | 35 | Y | Y | 22.8 | 6.7 | 8 | 11.8 | 51.6 | 8.1 | 52 | 22.6 | 23 | 0 | −5.7 | 31.4 |
| CM18-PTD4-His | 35 | Y | Y | 22.8 | 6.7 | 8 | 11.8 | 51.6 | 8.1 | 52 | 22.6 | 23 | 0 | −5.7 | 31.4 |
| His-CM18-TAT | 35 | Y | Y | 24. | 6 | 13 | 12.3 | 37.4 | 8.6 | 49 | 11.5 | 37.1 | 0 | −25 | 34.4 |
| EB1-PTD4 | 34 | Y | Y | 26.5 | 6.3 | 10 | 12.3 | 52.8 | 14.6 | 59 | 29.4 | 29 | 0 | 0 | 35.3 |
| *Transduction scores between 0.5-3.0* | | | | | | | | | | | | | | | |
| HA-CM18-PTD4 | 36 | Y | Y | 26.6 | 6.7 | 8 | 11.8 | 52.4 | 8.9 | 53 | 30.5 | 22.2 | 0 | 8.3 | 30.6 |
| 6Cys-CM18-PTD4 | 35 | Y | Y | 22.6 | 6.5 | 8 | 9.7 | 68.7 | 8.6 | 52 | 28.6 | 22.9 | 0 | 3.7 | 48.8 |
| CM18-L3-PTD4 | 41 | Y | Y | 19.5 | 3.9 | 8 | 11.8 | 64 | 16.3 | 44 | 24.4 | 19.5 | 0 | 4.9 | 51.3 |
| His-CM18-PTD4-6Cys | 41 | Y | Y | 32 | 6.8 | 8 | 9.7 | 58.4 | 2.4 | 44 | 24.4 | 19.5 | 0 | 4.9 | 41.5 |
| Met-His-CM18-TAT-Cys | 37 | Y | Y | 20 | 6.2 | 13 | 12 | 54 | 8.1 | 49 | 10.8 | 21.6 | 0 | 5.4 | 35.2 |
| CM18-L1-PTD4 | 32 | Y | Y | 25.8 | 6.1 | 8 | 11.8 | 59.1 | 14.9 | 56 | 31.3 | 25 | 0 | −11 | 43.8 |
| Xentry-KALA | 37 | Y | Y | 25 | 5.2 | 6 | 9.9 | 67.3 | 0.7 | 76 | b | 21.6 | 5.4 | 32 | 16.2 |
| CM18-TAT-Cys | 30 | N | N | 10.8 | 6.2 | 13 | 12 | 46.3 | 10 | 57 | 13.3 | 43.3 | 0 | −30 | 43.5 |
| Pep1-KALA | 51 | Y | Y | 26.6 | 9.1 | 8 | 10 | 51.1 | 58.9 | 61 | 35.3 | 25.5 | 9.8 | 9.8 | 27.5 |
| 3HA-CM18-PTD4 | 38 | Y | Y | 15.9 | 6.7 | 8 | 11.8 | 57.9 | 7.9 | 55 | 34.2 | 21.1 | 0 | 13.1 | 29 |
| CM18-PTD4 | 29 | Y | Y | 24.2 | 6.7 | 8 | 11.8 | 60.8 | 10.3 | 62 | 34.4 | 27.5 | 0 | 6.9 | 38 |
| 3His-CM18-PTD4 | 32 | Y | Y | 27.6 | 6.7 | 8 | 11.8 | 56.1 | 9.3 | 56 | 29.4 | 25 | 0 | 0 | 34.5 |
| His-CM18-Transportan | 50 | Y | Y | 25 | 2.6 | 9 | 10.6 | 58 | 14 | 51 | 32 | 18 | 0 | 13 | 38 |
| SynB3-KALA | 40 | Y | Y | 22.8 | 3.7 | 10 | 11. | 57.5 | 5 | 78 | 47.5 | 30 | 5 | 17.5 | 15 |

TABLE A2-continued

Physiochemical properties of domain-based peptides stratified by transduction score
(in Hela cells using GFP or GFP-NLS as cargo)

| Peptide name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 12His-CM18-PTD4 | 41 | Y | Y | 15 | 6.7 | 8 | 11.8 | 46.4 | 8.8 | 44 | 24.4 | 21.2 | 0 | 4.9 | 26.9 |
| TAT-CM18 | 30 | Y | Y | 27.6 | 4 | 13 | 12 | 46.6 | 10 | 57 | 13.3 | 43.3 | 0 | −30 | 43.5 |
| 9Arg-KALA | 39 | Y | Y | 23.5 | 4.5 | 14 | 12.1 | 51.4 | 0 | 87 | 46.2 | 41 | 5.1 | 5.2 | 5.1 |
| Transduction scores between 0.07–0.4 ||||||||||||||||
| VSVG-PTD4 | 36 | N | N | 11.1 | 4.1 | 6 | 10.3 | 47.4 | 14 | 33 | 16.7 | 16.6 | 0 | 0.1 | 61.3 |
| Penetratin-cys | 17 | N | N | 23.5 | 5.5 | 7 | 11.8 | 41.3 | 17.7 | 41 | 0 | 41.1 | 0 | −41 | 58.8 |
| CM18 | 18 | N | N | 47 | 4.3 | 5 | 10.6 | 61.3 | 11.1 | 50 | 22.3 | 27.8 | 0 | −5.5 | 50 |
| KALA | 30 | Y | Y | 20 | 4.5 | 5 | 9.9 | 66.6 | 0 | 83 | 60 | 23.3 | 6.7 | 36.7 | 6.7 |
| TAT-cys | 12 | N | N | 0 | 1.9 | 8 | 12 | 24.9 | 8.3 | 57 | 0 | 67 | 0 | −67 | 33.3 |
| PTD4 | 11 | Y | Y | 0 | 2.4 | 3 | 11.7 | 64.6 | 9.1 | 82 | 54.5 | 27.3 | 0 | 27.2 | 18.2 |
| His-PTD4 | 17 | Y | Y | 0 | 2.4 | 3 | 11.7 | 41.2 | 5.9 | 53 | 35.3 | 17.6 | 0 | 17.7 | 11.8 |
| JST-PTD4 | 31 | N | N | 35.6 | 13.8 | 2 | 4.7 | 67.6 | 9.6 | 65 | 54.8 | 9.7 | 16.1 | 45.1 | 19.4 |
| C(LLKK)3C | 14 | Y | Y | 42.9 | 5 | 6 | 10.1 | 57.2 | 0 | 86 | 42.9 | 42.9 | 0 | 0 | 14.3 |

Y = Yes;
N = No;
Regular font = value falls within parameter range set forth in Table A1;
Bolded font = value falls outside parameter range set forth in Table A1. His-LAH4-PTD4 yielded a transduction score of above 5.0, but was excluded from this analysis because the intracellular GFP fluorescence pattern was observed by fluorescence microscopy as being punctate, suggesting that the GFP cargo remained trapped in endosomes. Nevertheless, it is worth noting that His-LAH4-PTD4 had several parameters falling outside the ranges set forth in Table A1 with respect to parameters 2, 3, 11, 12, 14 and 15.

Example B

Rational Design of Synthetic Peptide Shuttle Agents

The parameters set forth in Table A1, and empirical knowledge gained (e.g., from Examples 1-15), were used to manually design the peptides listed in Table B1 in order to evaluate whether the parameters can be used for designing successful peptide shuttle agents.

The peptides listed in Table B1 were tested for their ability to transduce GFP-NLS cargo (see Example 3.4) in HeLa cells, using the protein transduction assay as generally described in Example 3.1a. GFP-NLS recombinant protein (10 µM) was co-incubated with 10 µM of the peptides and then exposed to HeLa cells for 1 min. The cells were subjected to flow cytometry analysis as described in Example 3.3. Results are shown in Tables B2 and B3. A "transduction score"-based analysis was also performed as discussed is Example A, and the results are shown in Table B4. Successful nuclear delivery of the transduced GFP-NLS (generally after only 1 minute of exposure to the peptide) was confirmed by fluorescence microscopy as described in Example 3.2 (data not shown).

Peptides FSD1-FSD5 were initially designed based on the successful domain-based shuttle agent His-CM18-PTD4-His, with peptides FSD1-FSD4 being designed to intentionally unrespect one or more parameters set forth in Table A1, and FSD5 being designed to respect all fifteen parameters. As can be seen from Table B2, peptides FSD1-FSD4 displayed transduction efficiencies ranging from 2.45% to 37.6%. In contrast, the peptide FSD5 displayed high transduction efficiency (70.5%) and low toxicity (cell viability of 86%).

3-dimensional modeling using PEP-FOLD, an online resource for de novo peptide structure prediction, predicted an alpha-helical conformation for FSD5 (see FIG. 49C; http://bioserv.rpbs.univ-paris-diderot.fr/services/PEP-FOLD/). In contrast, the peptide VSVG-PTD4, which showed only 3.5% transduction efficiency (see Table 10.3a), was predicted to adopt a different structure which included a shorter alpha helix, short beta-sheets (white arrows), and random coils (white shapeless lines).

Figure 49B:
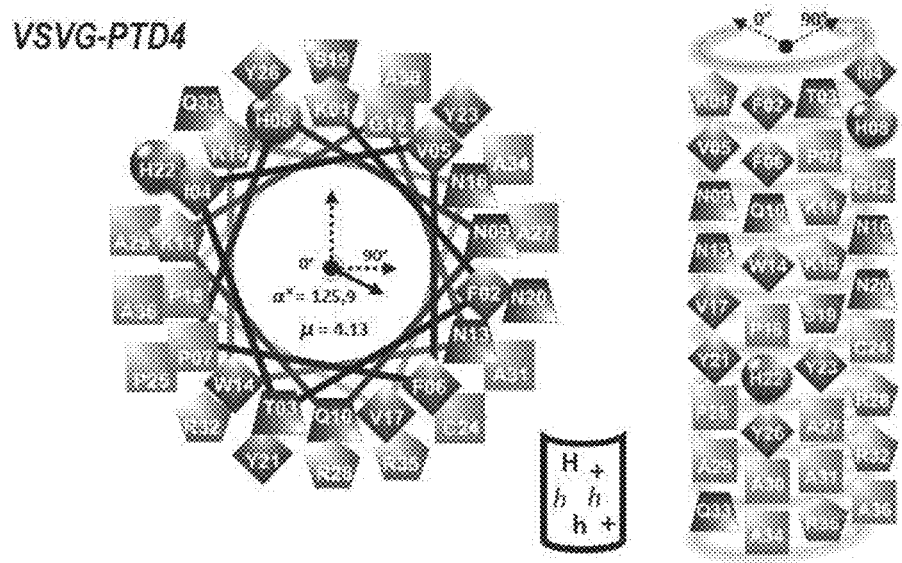

Helical wheel projections and side opened cylindrical representations of FSD5 and VSVG-PTD4 shown in FIGS. 49A and 49B (adapted from: http://rzlab.ucr.edu/scripts/wheel/wheel.cgi) illustrate the amphipathic nature of FSD5, as compared to VSVG-PTD4. The geometrical shape of each amino acid residue corresponds to its biochemical property based on the side chain of the residue (i.e., hydrophobicity, charge, or hydrophilicity). One of the main differences between the two opened cylindrical representations of FSD5 and VSVG-PTD4 is the presence of a highly hydrophobic core in FSD5 (outlined in FIG. 49A, left and right panels), which is not present in VSVG-PTD4. The cylinder in the lower middle panels of FIGS. 49A and 49B represent simplified versions of the opened cylindrical representations in the right panels, in which: "H" represents the high hydrophobic surface area; "h" represents low hydrophobic surface area; "+" represents positively charged residues; and "h" represent hydrophilic residues.

In light of the high transduction efficiency of FSD5, we used this shuttle agent as model to design peptides FSD6-FSD26. As shown in Table B2, a relatively high degree of amino acid substitutions was possible without completely losing transduction power, provided that most of the design parameters set forth in Table A1 were respected. The only peptide that displayed nearly a complete loss transduction efficiency among FSD6-FSD26 was FSD6, which is not predicted to adopt an amphipathic alpha-helix structure. Interestingly, peptide FSD18 showed high toxicity in HeLa cells when used at 10 µM, but showed high transduction efficiency and relatively low toxicity when used in other types of cells (see Examples E and G), suggesting that peptide toxicity may vary depending on the type of cells. 3-dimensional modeling using PEP-FOLD predicted two separate alpha-helices for FSD18 (see FIG. 49D).

Peptides FSN1-FSN8 were designed to explore the effects on transduction efficiency when one or more of the design parameters set forth in Table A1 are not respected.

TABLE B1

Manually-designed synthetic peptides and shuttle agents

| Peptide | SEQ ID NO: | Amino acid sequence | Length (a.a.) | MW (kDa) | pI | Charge |
|---|---|---|---|---|---|---|
| FSD1 | 104 | HHHHHHKWKLLRRAAKKAARRYLKLLLKQLKLHHHHHH | 38 | 4.85 | 12.03 | 11+/0- |
| FSD2 | 105 | HHHHHHWLKLLRRAAKKAARLYRKLLRKARKLHHHHHH | 38 | 4.86 | 12.31 | 12+/0- |
| FSD3 | 106 | HHHHHHKRKKKRRAKKKRAWLYLALLLWALALHHHHHH | 38 | 4.87 | 12.03 | 11+/0- |
| FSD4 | 107 | HHHHHHKRQLKRKLRKWKRLLRLLRLLARLWLHHHHHH | 38 | 5.1 | 12.78 | 12+/0- |
| FSD5 | 108 | HHHHHHLLKLWSRLLKLWTQGRRLKAKRAKAHHHHHH | 37 | 4.68 | 12.49 | 9+/0- |
| FSD6 | 109 | HHHHHHWYLALLALYWQRAKAKTRQRRRHHHHHH | 34 | 4.49 | 11.84 | 7+/0- |
| FSD7 | 110 | HHHHHHWARLARAFARAIKKLYARALRRQARTG | 33 | 3.99 | 12.4 | 9+/0- |
| FSD8 | 111 | HHHHHHKWKLARAFARAIKKLYARALRRQARTG | 33 | 4.02 | 12.31 | 10+/0- |
| FSD9 | 112 | HHHHHHKWKLARAFARAIKKLYARALRRQARTGHHHHHH | 39 | 4.85 | 12.31 | 10+/0- |
| FSD10 | 113 | KWKLARAFARAIKKLGGSGGGSYARALRRQARTG | 34 | 3.66 | 12.31 | 10+/0- |
| FSD11 | 114 | HHHHHHKWKLARAFARALRAIKKLYARALRRQARTG | 36 | 4.36 | 12.4 | 11+/0- |
| FSD12 | 115 | KWKLARAFARAIKKLYARALRRQARTG | 27 | 3.2 | 12.31 | 10+/0- |
| FSD13 | 116 | HHHHHHKWAKLLRAFAKAIKKLYARLARRQARTGHHHHHH | 40 | 4.93 | 12.19 | 10+/0- |
| FSD14 | 117 | HHHHHHLALARWARYFRILAKLKRTKRGQAKAHHHHHH | 38 | 4.73 | 12.19 | 9+/0- |
| FSD15 | 118 | HHHHHHKWKIARAFARSLKKLYARLLARQAKTGHHHHHH | 39 | 4.79 | 12.02 | 9+/0- |
| FSD16 | 119 | HHHHHHLLKLWSRLLKLWTQGRRLKAKRAKA | 31 | 3.86 | 12.49 | 9+/0- |
| FSD17 | 120 | HHHHHHLAKLFKWLRALIRQGAKRKTKRASAHHHHHH | 37 | 4.56 | 12.49 | 9+/0- |
| FSD18 | 121 | LLKLWSRLLKLWTQGGSGGGSGRRLKAKRAKA | 32 | 3.49 | 12.49 | 9+/0- |
| FSD19 | 122 | HHHHHHLLKLWSRLLKTWTQGRRLKAKSAQASTRQAHHHHHH | 36 | 4.32 | 12.48 | 8+/0- |
| FSD20 | 123 | HHHHAAVLKLWKRLLKLFRKGRRLKAKRAKAKR | 33 | 4.12 | 12.71 | 14+/0- |
| FSD21 | 124 | HHHHHHFLKIWSRLIKIWTQGRRKGAQAAFR | 31 | 3.85 | 12.48 | 7+/0- |
| FSD22 | 125 | HHHHHHVLKLWSRILKAFTQGRRMAAKRAKCNHHHHHH | 32 | 3.87 | 12.02 | 8+/0- |
| FSD23 | 126 | HHHHHHLLKLWSRLLKEWTQGRRLEAKRAEAHHHHHH | 31 | 3.88 | 10.93 | 7+/3- |
| FSD24 | 127 | HHHHHHLLCLWSRLLKLWTQGERLKAKCAKACER | 34 | 4.14 | 9.75 | 7+/2- |
| FSD25 | 128 | HHHHHHVWKLFWTLLAAIYGRGKARQKRAKRQARG | 35 | 4.25 | 12.19 | 9+/0- |
| FSD26 | 129 | ALLGLFIKWVKKVGTLFRKAKAGAQNRRAKAQKGK | 35 | 3.88 | 12.33 | 11+/0- |
| FSN1 | 130 | HHHHHHKRKRRSKKRKLWTQGWLLLALLALAHHHHHH | 31 | 3.86 | 12.49 | 9+/0- |
| FSN2 | 131 | HHHHHHKLKLRSRLKWGRTQLWRALAKKALLHHHHHH | 31 | 3.86 | 12.49 | 9+/0- |
| FSN3 | 132 | HHHHHHQFLCFWLNKMGKHNTVWHGRHLKCHKRGKG | 31 | 3.82 | 11.75 | 7+/0- |
| FSN4 | 133 | HHHHHHLLYLWRRLLKFWCAGRRVYAKCAKAYGCF | 35 | 4.23 | 10.06 | 7+/0- |
| FSN5 | 134 | HHHHHHLLKLWRRLLKLFRKALRALAKRAKSALKRAQAA | 39 | 4.68 | 12.71 | 12+/0- |
| FSN6 | 135 | HHHHHHLLKLWSRLLKLWTQALRALAKRAKALAHHHHHH | 33 | 3.96 | 12.31 | 7+/0- |
| FSN7 | 136 | LIKLWSRFIKFWTQGRRIKAKLARAGQSWFG | 31 | 3.75 | 12.48 | 8+/0- |

TABLE B1-continued

Manually-designed synthetic peptides and shuttle agents

| Peptide | SEQ ID NO: | Amino acid sequence | Length (a.a.) | MW (kDa) | pI | Charge |
|---|---|---|---|---|---|---|
| FSN8 | 137 | HHHHHHFRKLWLAIVRAKK | 19 | 2.4 | 12.02 | 5+/0− |
| FSD43 to FSD116 | 169 to 242 | [Refer to Sequence Listing] | — | — | — | — |

Results computed using ProtParam ™ online tool available from ExPASy ™ Bioinformatics Resource Portal (http:/web.expasy.org/protparam/);
pI: Isoelectric point;
Charge: Total number of positively (+) and negatively (−) charged residues

TABLE B2

Transduction of GFP-NLS in HeLa cells

| Cells | Peptide | Mean % cells with GFP signal (±St. Dev.; n = 3) | Cell viability (%) (±St Dev.; n = 3) | Design comments |
|---|---|---|---|---|
| HeLa | No peptide | 0.41 ± 0.015 | 100 | n/a |
| | FSD1 | 37.6 ± 3.44 | 60.3 ± 6.18 | Low % of infrequent amino acids (Q, Y, W, P, I, S, G, V, F, E, D, C, M, N, T, H) |
| | FSD2 | 11.9 ± 1.69 | 76.3 ± 5.99 | High hydrophobic moment |
| | FSD3 | 2.45 ± 0.32 | 91.1 ± 6.37 | No predicted amphipathic alpha helix |
| | FSD4 | 6.60 ± 0.84 | 86.1 ± 8.15 | Low % of hydrophobic amino acids; Low % of infrequent amino acids (Q, Y, W, P, I, S, G, V, F, E, D, C, M, N, T, H) |
| | FSD5 | 70.5 ± 6.44 | 86 ± 7.45 | — |
| | FSD6 | 1 ± 0.12 | 88.1 ± 7.66 | No predicted amphipathic alpha helix |
| | FSD7 | 78.30 ± 5.11 | 38.5 ± 3.48 | — |
| | FSD8 | 62.30 ± 5.61 | 64.8 ± 7.59 | — |
| | FSD9 | 68.21 ± 6.35 | 67.3 ± 5.19 | — |
| | FSD10 | 73.23 ± 4.94 | 79.8 ± 4.73 | — |
| | FSD11 | 68.29 ± 3.11 | 60.9 ± 7.59 | — |
| | FSD12 | 61.58 ± 5.33 | 67.8 ± 4.83 | — |
| | FSD13 | 75.94 ± 7.48 | 49.5 ± 5.13 | High hydrophobic moment |
| | FSD14 | 43.25 ± 5.35 | 92.8 ± 7.42 | — |
| | FSD15 | 54.97 ± 4.28 | 96.1 ± 2.61 | — |
| | FSD16 | 57.34 ± 4.11 | 88.2 ± 2.66 | — |
| | FSD17 | 52.83 ± 6.69 | 99.1 ± 2.09 | — |
| | FSD18 | 77.11 ± 3.25 | 82.4 +/− 4.71 | — |
| | FSD19 | 55.17 ± 4.62 | 80.6 ± 5.36 | — |
| | FSD20 | 75.23 ± 5.91 | 65.4 ± 6.18 | — |
| | FSD21 | 46.74 ± 4.03 | 75.6 ± 5.99 | — |
| | FSD22 | 45.09 ± 3.95 | 80.2 ± 7.21 | — |
| | FSD23 | 50.34 ± 4.29 | 65.3 ± 5.44 | — |
| | FSD24 | 37.48 ± 4.08 | 75.3 ± 3.93 | — |

TABLE B2-continued

Transduction of GFP-NLS in HeLa cells

| Cells | Peptide | Mean % cells with GFP signal (±St. Dev.; n = 3) | Cell viability (%) (±St Dev.; n = 3) | Design comments |
|---|---|---|---|---|
| | FSD25 | 32.67 ± 3.17 | 71.7 ± 5.08 | — |
| | FSD26 | 47.63 ± 4.19 | 59.26 ± 1.27 | — |

"—" = No parameters outside the limits set forth in Table A1.

TABLE B3

Transduction of GFP-NLS in HeLa cells

| Cells | Peptide | Mean % cells with GFP signal (±St Dev.; n = 3) | Cell viability (%) (±St. Dev.; n = 3) | Design comments |
|---|---|---|---|---|
| HeLa | No peptide | 0.38 ± 0.02 | 100 | |
| | FSN1 | 9.14 ± 0.93 | 94.3 ± 3.07 | Low hydrophobic moment; weak amphiphilic structure |
| | FSN2 | 12.13 ± 2.06 | 91.3 ± 4.66 | Weak hydrophobic surface |
| | FSN3 | 1.86 ± 97.15 | 97.2 ± 2.03 | No predicted alpha-helical stricture |
| | FSN4 | 5.84 ± 0.49 | 90.5 ± 4.18 | >65% hydrophobic amino acids |
| | FSN5 | 13.29 ± 1.24 | 85.36 ± 6.16 | Alanine + Leucine > 40% |
| | FSN6 | 15.74 ± 1.63 | 32.63 ± 4.26 | High hydrophobic moment; difference between A/L and K/R residues is > 20% |
| | FSN7 | 3.56 ± 0.36 | 93.45 ± 3.61 | No predicted alpha-helical structure; high hydrophobic moment; 55% of infrequent residues (other than A, L, K, R) |
| | FSN8 | 3.52 ± 0.41 | 94.53 ± 3.72 | Peptide length is less than 20 |

TABLE B4

Physiochemical properties of peptides stratified by transduction score
(in Hela cells using GFP-NLS as cargo)

| Peptide name | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| *Transduction scores above 4.0* | | | | | | | | | | | | | | | |
| FSD5 | 37 | Y | Y | 32 | 8.3 | 9 | 12.5 | 42 | 9.6 | 51 | 27 | 29 | 0 | 2.7 | 16.2 |
| FSD10 | 34 | Y | Y | 14.7 | 7 | 10 | 12.3 | 58.6 | 11.7 | 59 | 29.4 | 29.4 | 0 | 0 | 41.3 |
| FSD15 | 39 | Y | Y | 22.2 | 6.7 | 9 | 12 | 45.3 | 9 | 58 | 30.3 | 27.3 | 0 | 8 | 20.5 |
| FSD17 | 37 | Y | Y | 29.2 | 5.5 | 9 | 12.5 | 41.8 | 9.6 | 58 | 29 | 29 | 0 | 0 | 18.9 |
| FSD16 | 31 | Y | Y | 32 | 8.3 | 9 | 12.5 | 42 | 9.6 | 61 | 27 | 29 | 0 | 2.7 | 19.4 |
| FSD20 | 33 | Y | Y | 27.2 | 7.2 | 14 | 12.7 | 45.4 | 0 | 76 | 33.4 | 42,4 | 0 | −9 | 12 |
| FSD9 | 39 | Y | Y | 18.5 | 6.3 | 10 | 12.3 | 38.6 | 5.2 | 51 | 25.6 | 25.7 | 0 | −0.1 | 17.9 |
| FSD19 | 36 | Y | Y | 19.1 | 8.7 | 8 | 12.5 | 36.2 | 24.9 | 43 | 23.8 | 22.2 | 0 | 4.8 | 28.5 |
| FSD12 | 27 | Y | Y | 18.5 | 6.3 | 10 | 12.3 | 44.4 | 7.4 | 74 | 37 | 37 | 0 | 0 | 25.9 |
| FSD11 | 36 | Y | Y | 17.6 | 7.3 | 11 | 12.4 | 47.3 | 5.6 | 64 | 33.4 | 30.5 | 0 | 2.9 | 19.4 |
| FSD8 | 33 | Y | Y | 18.5 | 6.3 | 10 | 12.3 | 45.3 | 6 | 61 | 33.3 | 30.3 | 0 | 3 | 21.2 |
| FSD14 | 38 | Y | Y | 26.9 | 5.2 | 9 | 12,2 | 46.8 | 6,2 | 59 | 31.3 | 28.1 | 0 | 3.2 | 18.5 |
| *Transduction scores between 1.0-4.0* | | | | | | | | | | | | | | | |
| FSD13 | 40 | Y | Y | 25 | 10.3 | 10 | 12.2 | 35.1 | 8.1 | 46 | 21.6 | 24.3 | 0 | −2.7 | 20 |
| FSD22 | 32 | Y | Y | 20.9 | 7.1 | 8 | 12 | 43.6 | 9.3 | 39 | 18.4 | 25 | 0 | −2.6 | 28.6 |
| FSD21 | 31 | Y | Y | 35.7 | 9.5 | 7 | 12.5 | 45.3 | 12.9 | 39 | 16.2 | 22.6 | 0 | −6.4 | 42.1 |
| FSD23 | 31 | Y | Y | 21.6 | 8.2 | 4 | 10.9 | 38.8 | 9.6 | 43 | 24.3 | 22.6 | 0 | 5.4 | 24.3 |
| FSD7 | 33 | Y | Y | 17.2 | 8.3 | 9 | 12.4 | 48.3 | 5 | 61 | 33.3 | 27.3 | 0 | 10 | 21.2 |
| FSD24 | 34 | Y | Y | 26.5 | 8 | 5 | 9.75 | 47 | 8.7 | 50 | 29.4 | 20.6 | 5.9 | 8.8 | 32.3 |
| FSD26 | 35 | Y | Y | 28.6 | 7 | 11 | 12.3 | 60 | 11.5 | 60 | 28.5 | 31.5 | 0 | −3 | 40.1 |
| FSD25 | 35 | Y | Y | 14.3 | 7.1 | 8 | 12.2 | 48.8 | 8.6 | 63 | 37.1 | 25.7 | 2.9 | 9.7 | 20.1 |
| FSD1 | 38 | Y | Y | 23 | 7.9 | 11 | 12 | 36.8 | 2.6 | 61 | 31.6 | 28.9 | 0 | 2.7 | 7.9 |
| FSD18 | 32 | Y | Y | 25 | 8 | 9 | 12.5 | 59 | 12.6 | 52 | 28.6 | 21.9 | 0 | 5.7 | 43.8 |
| FSN5 | 39 | Y | Y | 28.3 | 12.3 | 12 | 12.7 | 48.8 | 5.2 | 74 | 43.6 | 30.8 | 0 | 12.8 | 10.4 |
| FSN2 | 31 | Y | Y | 24.3 | 1.4 | 9 | 12.5 | 35.1 | 9.6 | 51 | 27 | 29 | 0 | 2.7 | 16.2 |
| *Transduction scores between 0.5-1.0* | | | | | | | | | | | | | | | |
| FSD2 | 38 | Y | Y | 15.4 | 10.9 | 12 | 12.3 | 43.7 | 0 | 63 | 31.6 | 28.9 | 0 | 0 | 19 |
| FSN1 | 31 | N | N | 24.3 | 2.4 | 9 | 12.5 | 35.1 | 9.6 | 51 | 27 | 29 | 0 | 2.7 | 16.2 |
| FSD4 | 38 | Y | Y | 30.8 | 8.8 | 12 | 12.8 | 33.2 | 2.6 | 61 | 28.9 | 31.6 | 0 | −2.7 | 7.9 |
| FSN4 | 35 | Y | Y | 28.6 | 9.9 | 7 | 10.1 | 68.7 | 0 | 46 | 25.7 | 20 | 0 | 5.7 | 37.2 |
| FSN6 | 33 | Y | Y | 28.2 | 11.3 | 7 | 12.3 | 51.6 | 9 | 57 | 38.5 | 21.2 | 0 | 20.5 | 12.9 |
| *Transduction scores below 0.5* | | | | | | | | | | | | | | | |
| FSN7 | 31 | Y | Y | 11.1 | 11 | 8 | 12.5 | 58.2 | 16.2 | 45 | 19.4 | 25.8 | 0 | −6.4 | 55 |
| FSN8 | 19 | Y | Y | 38.8 | 4.2 | 5 | 12 | 36.9 | 0 | 47 | 21 | 26.3 | 0 | −5.3 | 26.5 |
| FSD3 | 38 | N | N | 31.7 | 1.9 | 11 | 12 | 39.5 | 0 | 61 | 31.6 | 28.9 | 0 | 2.7 | 7.8 |
| FSN3 | 31 | N | Y | 29.6 | 5.4 | 7 | 11.8 | 35.5 | 19.3 | 28 | 8.3 | 22.6 | 0 | −11.2 | 44.7 |
| FSD6 | 34 | N | N | 25.1 | 3.5 | 7 | 11.8 | 42.8 | 10.7 | 44 | 23.6 | 25 | 0 | 3 | 17.7 |

Y = Yes;
N = No;
Regular font = value falls within parameter range set forth in Table A1;
Bolded font = value falls outside parameter range set forth in Table A1.

The primary amino acid sequences of peptides FSD5, FSD16, FSD18, FSD19, FSD20, FSD22, and FSD23 are related, as shown in the alignment below.

```
FSD23   --LLKLWSRLLKLWTQG------RRLEAKRAKA-----

FSD19   --LLKLWSRLLKEWTQG------RRLEAKRAEA-----

FSD5    --LLKLWSRLLKLWTQG------RRLKAKRAKA-----

FSD18   AAVLKLWKRLLKLFRKG------RRLKAKRAKAKR---

FSD16   --LLKLWSRLLKTWTQG------RRLKAKSAQASTRQA

FSD20   --LLKLWSRLLKLWTQGGSGGGSGRRLKAKRAKA-----

FSD22   --VLKLWSRILKAFTQG------RRMAAKRAKCN----
```

LKLW-R-LK----G    RR--AK-A (SEQ ID NO: 158)    (SEQ ID NO: 159)

Example C

Computer-Assisted Design of Synthetic Peptide Shuttle Agents

C.1 Machine-Learning-Assisted Design Approach

The peptides listed in Table C1 were designed using an algorithm described in an article by Sebastien Gigubre et al. entitled "Machine Learning Assisted Design of Highly Active Peptides for Drug Discovery" (Gigubre et al., 2014). This computational prediction method is founded on the use of algorithms based on the Kernel and machine learning methods (Shawe-Taylor J. and Cristianini N., 2004). These algorithms aim to sort peptides with maximal bioactivity depending on a biological effect of interest. Here, we considered all the peptides that we tested to date in protein transduction assays, and separated them into three distinct groups. The composition of the groups was based on a "transduction score" calculated as described in Example A. Group 1 was composed of peptides demonstrating efficient cell delivery with low toxicity; Group 2 was composed of peptides demonstrating efficient cell delivery but with elevated toxicity; and Group 3 was composed of peptides that did not demonstrate any significant polypeptide cargo transduction ability.

The scores of the peptides in each group were used as starting data points for the generation of further peptide variants. The algorithm was programmed to use the peptide sequences and the scores of the peptides of Group 1 as the positive references for the prediction of peptide variants with efficient transduction ability. The sequences and the scores of Groups 2 and 3 were included as negative controls in the algorithm to delineate the search field. The peptide variants generated by the algorithm were limited to those having a length of 35 amino acids. After running, the prediction method generated sixteen sequences (FSD27 to FSD42). After analyzing the sequences of these sixteen sequences with respect to the design parameters set forth in Table A1, only peptides FSD27, FSD34 and FSD40 satisfied all of the design parameters (see Table C2). The other peptide variants had one or more parameters outside those set forth in Table A1.

TABLE C1

Machine-designed synthetic peptides and shuttle agents tested

| Peptide | SEQ ID NO: | Amino acid sequence | Length (a.a.) | MW (kDa) | pI | Charge |
|---|---|---|---|---|---|---|
| FSD27 | 138 | HHHHHHKWKLFWEAKLAKYARAAARQARAARQARA | 35 | 4.21 | 11.85 | 9+/1- |
| FSD28 | 139 | HHHHHHHMAHLWESNARKFWKKAFAQHAAAHIAEA | 35 | 4.18 | 9.7 | 4+/2- |
| FSD29 | 140 | LHHHSHHLIHIWLLFKLKLKKKKAARRARRARRHH | 35 | 4.43 | 12.71 | 12+/0- |
| FSD30 | 141 | HHHHHHCLLKKWEAKLAKKIGGGGRQARAKALAKA | 35 | 3.88 | 10.74 | 9+/1- |
| FSD31 | 142 | YHHHHHKWKKRWEAKLAKALRAAGRQARAKALAKA | 35 | 4.12 | 11.62 | 11+/1- |
| FSD32 | 143 | IVRHEHCMIHLWYKNLAKYCSTSHARRLARRRAHH | 35 | 4.35 | 10.92 | 8+/1- |
| FSD33 | 144 | HHHHHHHHRQRRRWEARGGFLGGGGYARAARQARA | 35 | 4.12 | 12.22 | 8+/1- |
| FSD34 | 145 | HHHHHHKLIHIWEAKLFKKIRAAARQARARRAAKA | 35 | 4.19 | 12.19 | 10+/1- |
| FSD35 | 146 | HHHHHHKLLKRWEAKLAKALAKALAKHLAKALAKA | 35 | 3.97 | 10.82 | 9+/1- |
| FSD36 | 147 | HHHHHHCLIHIWEAKLAKKCGGGGYARAAARQARA | 35 | 3.89 | 10.06 | 6+/1- |
| FSD37 | 148 | RLHHSHHLIHIWLLFKLKLKKKKRAARRARRHHHL | 35 | 4.47 | 12.71 | 12+/0- |
| FSD38 | 149 | GHHHHHHHLIHIWEAKLAKLAKALARAAARQARAK | 35 | 3.99 | 11.74 | 7+/1- |
| FSD39 | 150 | HHHHHHHHRQRRRWEARGFLGGGGYARAARQARAA | 35 | 4.14 | 12.22 | 8+/1- |
| FSD40 | 151 | YGRKKRYMLRLWYQNLRMYCKKAYAQHRARQHAKL | 35 | 4.53 | 10.81 | 11+/0- |
| FSD41 | 152 | LHHHHHKLIHIWEAKLAKALAKALARRAAARQARA | 35 | 3.99 | 12.02 | 8+/1- |
| FSD42 | 153 | HHHHHHCMKWWEIVLAKYKGGGGRARAASRRARA | 35 | 3.98 | 11.47 | 8+/1- |

Results computed using ProtParam™ online tool available from ExPASy™ Bioinformatics Resource Portal (http:/web.expasy.org/protparam/);
pI: Isoelectric point;
Charge: Total number of positively (+) and negatively (-) charged residues

TABLE C2

FSD27 to FSD42 sequences and properties

| Peptide | Comments concerning out of limit parameter(s) with respect to Table A1 |
|---|---|
| FSD27 | No out of limit parameters. |
| FSD28 | No predicted amphiphilic alpha-helical structure<br>Highly hydrophobic core <12% of the total surface<br>Net charge below +4 (+2)<br>Low percentage K/R residues (11.5%)<br>Difference between % A/L and % K/R greater than 10% (17.1%) |
| FSD29 | No predicted amphiphilic alpha-helical structure<br>Highly hydrophobic core <12% of the total surface<br>Low hydrophobic moment (3.3) |
| FSD30 | Highly hydrophobic core <12% of the total surface<br>Low hydrophobic moment (2.6) |
| FSD31 | Highly hydrophobic Core <12% of the total surface |
| FSD32 | No predicted amphiphilic alpha-helical structure<br>Highly hydrophobic core <12% of the total surface |
| FSD33 | Highly hydrophobic core <12% of the total surface<br>Low hydrophobic moment (2.1)<br>Less than 5% leucines (2.9%)<br>Difference between % A/L and % K/R greater than 10% (22.9%) |
| FSD34 | No out of limit parameters. |
| FSD35 | Highly hydrophobic core <12% of the total surface<br>Low hydrophobic moment (2.8)<br>High % of A/L (48.6%)<br>Difference between % A/L and % K/R greater than 10% (22.8%)<br>Low % of total non-A/L/K/R residues (2.85%) |
| FSD36 | No predicted amphiphilic alpha-helical structure<br>Low hydrophobic moment (3.3)<br>Highly hydrophobic Core <12% of the total surface<br>Difference between % A/L and % K/R greater than 10% (11.4%) |
| FSD37 | No predicted amphiphilic alpha-helical structure |
| FSD38 | Difference between % A/L and % K/R greater than 10% (20%) |
| FSD39 | Highly hydrophobic core <12% of the total surface |
| FSD40 | No out of limit parameters. |
| FSD41 | High % of A/L (46%)<br>Difference between % A/L and % K/R greater than 10% (23%) |
| FSD42 | Less than 5% leucines (2.9%) |

HeLa cells were cultured and tested in the protein transduction assay described in Example 3.1a. GFP-NLS recombinant protein (10 µM) was co-incubated with 10 µM of the peptide and then exposed to HeLa cells for 1 min. The cells were subjected to flow cytometry analysis as described in Example 3.3. Results are shown in Table C3.

TABLE C3

Transduction of GFP-NLS in HeLa cells by machine-designed synthetic peptides

| Cells | Peptide | Mean % cells with GFP signal (±St. Dev.; n = 3) | Cell viability (%) (±St. Dev.; n = 3) |
|---|---|---|---|
| HeLa | No peptide | 0.22 ± 0.03 | 100 |
| | FSD27* | 25.49 ± 6.52 | 96.6 ± 4.94 |
| | FSD28 | 0.83 ± 0.29 | 99.4 ± 4.04 |
| | FSD29 | 6.43 ± 2.6 | 89.8 ± 8.48 |
| | FSD30 | 1.75 ± 1.14 | 99.1 ± 0.52 |
| | FSD31 | 6.90 ± 1.27 | 97.8 ± 4.22 |
| | FSD32 | 3.12 ± 1.03 | 99.2 ± 3.37 |
| | FSD33 | 0.68 ± 0.45 | 98.1 ± 1.73 |
| | FSD34* | 32.89 ± 8.9 | 97.9 ± 8.18 |
| | FSD35 | 2.08 ± 0.92 | 81.7 ± 3.45 |
| | FSD36 | 0.35 ± 0.2 | 98.9 ± 0.38 |
| | FSD37* | 11.57 ± 2.99 | 73.9 ± 2.62 |
| | FSD38 | 4.61 ± 1.33 | 98.1 ± 7.35 |
| | FSD39 | 0.23 ± 0.09 | 97.3 ± 2.07 |
| | FSD40* | 32.66 ± 0.77 | 83.9 ± 4.16 |
| | FSD41* | 36.99 ± 0.88 | 79.5 ± 0.33 |
| | FSD42 | 1.59 ± 0.39 | 97.3 ± 1.07 |

*Peptides demonstrating transduction efficiencies above 10% appear in bold.

Interestingly, the three peptides generated using the algorithm that respected all of the design parameters set forth in Table A1 (i.e., FSD27, FSD34 and FSD40) each demonstrated 25-33% transduction efficiency, with cell viabilities ranging from 83.9%-98%. The other peptides generally demonstrated transduction efficiencies below 12%, except for FSD41, which demonstrated a transduction efficiency of 37% (albeit with higher toxicity than FSD27, FSD34, and FSD40). Although only a single parameter (i.e., efficiency score) was used to program the algorithm, the results with FSD27, FSD34 and FSD40 validate the usefulness of the design parameters set forth in Table A1.

C.2 Computer-Assisted Generation of Peptide Variants

A computer-assisted design approach was employed to demonstrate the feasibility of designing and generating peptide variants that respect most or all of the design parameters set forth in Table A1. First, this approach involved manually considering and comparing the primary amino acid sequences of structurally different yet successful peptide shuttle agents to identify general consensus sequences that lead to structural parameters (2), (3) and (4) being respected (i.e., amphipathic alpha-helix formation, a positively-charged face, and a highly hydrophobic core of 12%-50%). Second, the approach involved computer-assisted random peptide sequence generation followed by descriptors filtering, implementing the consensus sequences, and one or more of the design parameters (1) and (5)-(15), in order to generate a list of peptide variants that respect nearly all of the design parameters. This is discussed in more detail below.

Figure 49G:
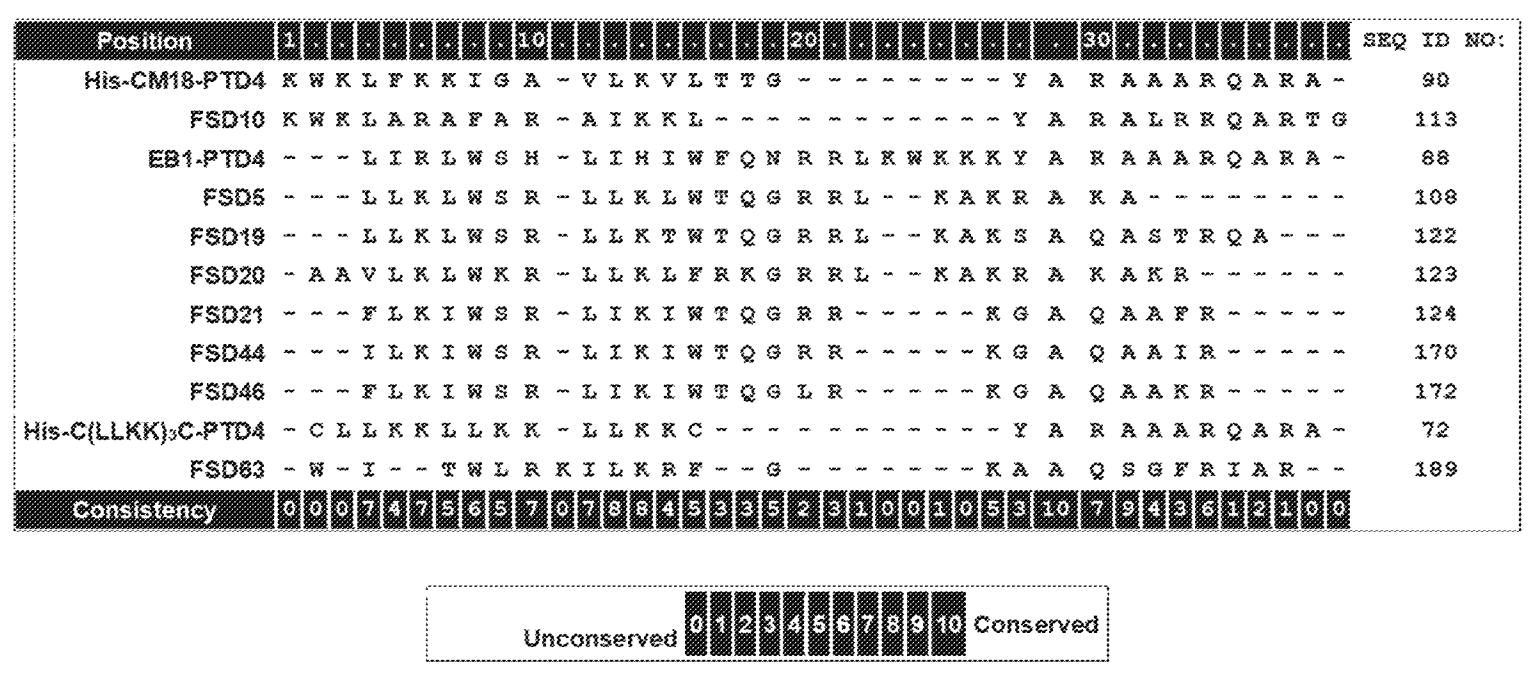

First, the primary amino acid sequences of peptides shown herein to have relatively high transduction efficiency scores were compared using online multiple sequence alignment tools, including CLUSTALW 2.1 (http://www.genome.jp/tools-bin/clustalw); MUltiple Sequence Comparison by Log-Expectation (MUSCLE) (https://www.ebi.ac.uk/Tools/msa/muscle/); and PRALINE (http://www.ibi.vu.nl/programs/pralinewww/). The peptides selected for comparison included the following eleven peptides: His-CM18-PTD4; EB1-PTD4; His-C(LLKK)$_3$C-PTD4; FSD5; FSD10; FSD19; FSD20; FSD21; FSD44; FSD46; and FSD63, but the analyses were not limited to only these eleven peptides. FIG. 49G shows an alignment of the eleven exemplary peptides using PRALINE, wherein the "Consistency" scores at the bottom of each aligned residue position represents the degree of conservation at that residue position (zero being the least conserved, and ten being the most conserved). For example, the alanine (A) at relative position 29 was conserved in all eleven peptides shown in FIG. 49G, and this was assigned a "Consistency" score of 10. Such multiple sequence analyses of the library of described peptides herein (and others) revealed the following general structures:

(a)[X1]–[X2]–[linker]–[X3]–[X4]         (Formula 1);

(b)[X1]–[X2]–[linker]–[X4]–[X3]         (Formula 2);

(c)[X2]–[X1]–[linker]–[X3]–[X4] (Formula 3);
(d)[X2]–[X1]–[linker]–[X4]–[X3] (Formula 4);
(e)[X3]–[X4]–[linker]–[X1]–[X2] (Formula 5);
(f)[X3]–[X4]–[linker]–[X2]–[X1] (Formula 6);
(g)[X4]–[X3]–[linker]–[X1]–[X2] (Formula 7); or
(h)[X4]–[X3]–[linker]–[X2]–[X1] (Formula 8), where [X1], [X2], [X3], [X4], and [linker] are as defined in the table below:

TABLE C4

| | |
|---|---|
| [X1] | <u>2[φ]-1[+]-2[φ]-1[ζ]-1[+]-</u> |
| | or 2[φ]-1[+]-2[φ]-2[+]- |
| | or 1[+]-1[φ]-1[+]-2[φ]-1[ζ]-1[+]- |
| | or 1[+]-1[φ]-1[+]-2[φ]-2[+]- |
| [X2] | <u>-2[φ]-1[+]-2[φ]-2[ζ]-</u> |
| | or -2[φ]-1[+]-2[φ]-2[+]- |
| | or -2[φ]-1[+]-2[φ]-1[+]-1[ζ]- |
| | or -2[φ]-1[+]-2[φ]-1[ζ]-1[+]- |
| | or -2[φ]-2[+]-1[φ]-2[+]- |
| | or -2[φ]-2[+]-1[φ]-2[ζ]- |
| | or -2[φ]-2[+]-1[φ]-1[+]-1[ζ]- |
| | or -2[φ]-2[+]-1[φ]-1[ζ]-1[+]- |
| [linker] | -Gn- |
| | or -Sn- |
| | or -(GnSn)n- |
| | or -(GnSn)nGn- |
| | or -(GnSn)nSn- |
| | or -(GnSn)nGn(GnSn)n- |
| | or -(GnSn)nSn(GnSn)n- |
| [X3] | -4[+]-A- |
| | or -3[+]-G-A- | or -3[+]-A-A- | |
| | or -2[+]-1[φ]-1 [+]-A- | or <u>-2[+]-1[φ]-G-A-</u> | or -2[+]-1[φ]-A-A- |
| | or -2[+]-A-1[+]-A | or -2[+]-A-G-A | or -2[+]-A-A-A- |
| | or -1[φ]-3[+]-A- | or -1[φ]-2[+]-G-A- | or -1[φ]-2[+]-A-A- |
| | or -1[φ]-1[+]-1[φ]-1[+]-A | or -1[φ]-1[+]-1[φ]-G-A | or -1[φ]-1[+]-1[φ]-A-A |
| | or -1[φ]-1[+]-A-1[+]-A | or -1[φ]-1[+]-A-G-A | or -1[φ]-1[+]-A-A-A |
| | or -A-1[+]-A-1[+]-A | or -A-1[+]-A-G-A | or -A-1[+]-A-A-A |
| [X4] | -1[ζ]-2A-1[+]-A | or -1[ζ]-2A-2[+] | or <u>-1[+]-2A-1[+]-A</u> |
| | or -1[ζ]-2A-1[+]-1[ζ]-A-1[+] | or -[ζ]-A-1[ζ]-A-1[+] | |
| | or -2[+]-A-2[+] | or -2[+]-A-1[+]-A | |
| | or -2[+]-A-1[+]-1[ζ]-A-1[+] | or -2[+]-1[ζ]-A-1[+] | |
| | or -1[+]-1[ζ]-A-1[+]-A | or -1[+]-1[ζ]-A-2[+] | |
| | or -1[+]-1[ζ]-A-1[+]-1[ζ]-A-1[+] | or -1[+]-2[ζ]-A-1[+] | |
| | or -1[+]-S[ζ]-2[+] | or -1[+]-2[ζ]-1[+]-A | |
| | or -1[+]-2[ζ]-1[+]-1[ζ]-A-1[+] | or -1[+]-2[ζ]-1[ζ]-A-1[+] | |
| | or -3[ζ]-2[+] | or -3[ζ]-1[+]-A | or -3[ζ]-1[+]-1[ζ]-A-1[+] |
| | or -1[ζ]-2A-1[+]-A | or -1[ζ]-2A-2[+] | or -1[ζ]-2A-1[+]-1[ζ]-A-1[+] |
| | or -2[+]-A-[+]-A | or -2[+]-1[ζ]-1[+]-A | |
| | or -1[+]-1[ζ]-A-1[+]-A | or -1[+]-2A-1[+]-1[ζ]-A-1[+] | |
| | or -1[ζ]-A-1[ζ]-A-1[+] | | |

Wherein:

[φ] = Leu, Phe, Trp, Ile, Met, Tyr, or Val

[+] = Lys or Arg

[ζ] = Gln, Asn, Thr, or Ser

A = Ala

G = Gly

S = Ser n = an integer from 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 1 to 4, or 1 to 3

The number preceding the square brackets indicate the number of contiguous residues (e.g., 3[φ] = [φ]-[φ]-[φ])

Underlined sequences indicate the most commonly occurring consensus sequences, based on the alignment shown in FIG. 49G.

Second, a script was designed and built in the programming language, Python, to randomly generate and filter sequences respecting all parameters (except for predicted isoelectric point (pI, parameter 7), because the source code to calculate this parameter was not available at the time of preparing the present example). Structural parameters 2, 3, 4 (amphipathic alpha-helix, positively-charged surface, and highly hydrophobic core) described in Table A1 were respected by entering the consensus sequences set forth in Formulas 1 to 8 and in Table C4 (appropriate alternance of Hydrophobic, Cationic, hydrophilic, Ala and Gly amino acids in the sequence) into the code, and biochemical parameters (1), (5), (6), and (8)-(15) described in Table A1 were all individually included into the code to generate 10 000 variant peptide sequences. These variant peptide sequences correspond to SEQ ID NOs: 243-10 242.

Example D

Rationally-Designed Peptides Facilitate Escape of Endosomally-Trapped Calcein

Calcein endosomal escape assays were performed as generally described in Example 2 and characterized fluorescence microscopy (data not shown) and by flow cytometry (results for FSD5 are shown below). FSD18 displayed similar results to FSD5 (data not shown).

TABLE D1

Calcein endosome escape assays

| Cells | Peptide | Peptide exposure time (min) | Peptide conc. (μM) | Mean Counts (±St. Dev.; n = 3) | Mean Factor |
|---|---|---|---|---|---|
| HeLa | No peptide | 0 | 0 | 4.94 ± 0.39 | 1.0 |
|  | FSD5 | 1 | 10 | 76.31 ± 5.18 | 15.4 |
|  |  |  | 7.5 | 56.41 ± 5.33 | 11.3 |
|  |  |  | 5 | 16.27 ± 1.27 | 3.0 |
|  |  |  | 2.5 | 12.41 ± 0.92 | 1.5 |

The result from fluorescence microscopy and flow cytometry experiments showed that rationally-designed peptide shuttle agents facilitate the escape of endosomally-trapped calcein in a dose-dependent fashion, similar to the domain-based peptide shuttle agents.

Example E

Rationally-Designed Peptides Increase Transduction Efficiency in Different Cell Types Protein transduction assays in different cell types were conducted as generally described in Example 3.1a (adherent cells) or Example 3.1b (suspension cells), using rationally-designed peptides at the indicated concentrations, 10 μM GFP-NLS as cargo, and at the indicated times, before being characterized by flow cytometry (Example 3.3) and fluorescence microscopy (Example 3.2). The results from the flow cytometry are shown in the tables below. Successful delivery of GFP-NLS to the nucleus of cells was verified by fluorescence microscopy (data not shown).

TABLE E1

GFP-NLS transduction in HeLa cells

| Cells | Peptide | Peptide conc. (μM) | Conc. of GFP-NLS (μM) | Incubation time (min) | Mean % cells with GFP signal (±St. Dev.; n = 3) | Cell viability (%) (±St. Dev.; n = 3) |
|---|---|---|---|---|---|---|
| HeLa | No peptide | 0 | 10 | 2 | 0.38 ± 0.05 | 100 |
|  | FSD5 | 10 |  | 1 | 70.5 ± 6.44 | 76 ± 7.45 |
|  |  | 8 |  | 1 | 68.5 ± 5.27 | 85 ± 6.27 |
|  |  | 5 |  | 2 | 63.1 ± 4.19 | 35.5 ± 4.82 |
|  | FSD9 | 10 |  | 1 | 73.5 ± 5.51 | 79.5 ± 6.33 |
|  |  | 8 |  | 1 | 70.2 ± 6.83 | 82.3 ± 7.16 |
|  |  | 5 |  | 2 | 58.4 ± 4.93 | 45.6 ± 3.64 |
|  | FSD10 | 10 |  | 1 | 73.1 ± 5.24 | 79.75 ± 6.37 |
|  |  | 8 |  | 1 | 55.9 ± 5.22 | 83.42 ± 6.38 |
|  |  | 5 |  | 2 | 45.8 ± 4.16 | 55.61 ± 4.28 |

TABLE E2

GFR-NLS transduction in HCC-78 cells (human non-small cell lung carcinoma)

| Cells | Peptide | Peptide conc. (μM) | Conc. of GFP-NLS (μM) | Incubation time (min) | Mean % cells with GFP signal (±St. Dev.; n = 3) | Cell viability (%) n = 3 |
|---|---|---|---|---|---|---|
| HCC-78 | No peptide | 0 | 10 | 2 | 0.21 ± 0.03 | 100 |
|  | FSD5 | 10 |  | 1 | 41.9 ± 3.61 | 15.9 ± 0.83 |
|  |  | 8 |  | 1 | 69.3 ± 5.27 | 87.7 ± 6.52 |
|  |  | 5 |  | 2 | 34.1 ± 3.57 | 75.3 ± 6.18 |
|  | FSD10 | 10 |  | 1 | 45.0 ± 4.23 | 63.1 ± 5.27 |
|  |  | 8 |  | 1 | 15.7 ± 2.67 | 76.1 ± 6.19 |
|  |  | 5 |  | 2 | 22.8 ± 3.06 | 83.1 ± 5.99 |
|  | FSD12 | 10 |  | 1 | 35.9 ± 3.18 | 46.5 ± 4.18 |
|  |  | 8 |  | 1 | 39.7 ± 4.08 | 66.3 ± 6.03 |
|  |  | 5 |  | 2 | 21.4 ± 2.53 | 75.1 ± 6.31 |

TABLE E3

GFP-NLS transduction in NCI-H196 cells (human small cell lung cancer)

| Cells | Peptide | Peptide conc. (μM) | Conc. of GFP-NLS (μM) | Incubation time (min) | Mean % cells with GFP signal (±St. Dev.; n = 3) | Cell viability (%) n = 3 |
|---|---|---|---|---|---|---|
| NCI-H196 | No peptide | 0 | 10 | 2 | 0.1 ± 0.02 | 100 |
|  | FSD5 | 10 |  | 1 | 16 ± 1.27 | 47.19 ± 3.54 |
|  |  | 8 |  | 1 | 9.1 ± 0.99 | 69.94 ± 6.38 |
|  |  | 5 |  | 2 | 7.3 ± 0.82 | 77.19 ± 6.17 |
|  | FSD10 | 10 |  | 1 | 8.3 ± 0.76 | 85.44 ± 7.66 |
|  |  | 8 |  | 1 | 7.4 ± 0.83 | 80.97 ± 8.02 |
|  |  | 5 |  | 2 | 6.4 ± 0.71 | 83.22 ± 7.51 |

TABLE E3-continued

GFP-NLS transduction in NCI-H196 cells (human small cell lung cancer)

| Cells | Peptide | Peptide conc. (μM) | Conc. of GFP-NLS (μM) | Incubation time (min) | Mean % cells with GFP signal (±St. Dev.; n = 3) | Cell viability (%) n = 3 |
|---|---|---|---|---|---|---|
|  | FSD12 | 10 |  | 1 | 6.3 ± 0.68 | 72.52 ± 6.29 |
|  |  | 8 |  | 1 | 4.5 ± 0.38 | 71.86 ± 6.44 |
|  |  | 5 |  | 2 | 5.1 ± 0.42 | 76.51 ± 6.37 |

TABLE E4

GFP-NLS transduction in THP-1 cells

| Cells | Peptide | Peptide conc. (μM) | Conc. of GFP-NLS (μM) | Incubation time (min) | Mean % cells with GFP signal (±St. Dev.; n = 3) | Cell viability (%) (±St. Dev.; n = 3) |
|---|---|---|---|---|---|---|
| THP-1 | No peptide | 0 | 10 | 1.5 | 0.27 ± 0.01 | 100 |
|  | FSD10 | 1 |  | 1 | 42.6 ± 4.29 | 93.5 ± 5.64 |
|  |  | 1 |  | 1.5 | 59.4 ± 3.61 | 78.4 ± 6.15 |
|  |  | 2 |  | 0.5 | 60.5 ± 5.27 | 96.3 ± 2.16 |
|  |  | 2 |  | 1 | 71.9 ± 5.63 | 85.6 ± 5.22 |
|  | FSD18 | 1 |  | 1 | 43.6 ± 3.55 | 95.3 ± 3.11 |
|  |  | 1 |  | 1.5 | 41.7 ± 2.82 | 86.5 ± 6.27 |
|  |  | 2 |  | 0.5 | 53.4 ± 4.29 | 97.9 ± 1.73 |
|  |  | 2 |  | 1 | 78.3 ± 5.48 | 98.6 ± 0.37 |
|  | FSD19 | 2 |  | 0.5 | 55.4 ± 4.63 | 68.7 ± 4.29 |
|  |  | 5 |  | 0.25 | 61.5 ± 6.07 | 60.5 ± 5.71 |
|  | FSD21 | 2 |  | 0.5 | 47.1 ± 3.83 | 75.6 ± 6.38 |
|  |  | 5 |  | 0.25 | 57.3 ± 4.52 | 62.5 ± 5.16 |
|  | FSD25 | 2 |  | 0.5 | 51.9 ± 6.39 | 79.7 ± 6.52 |
|  |  | 5 |  | 0.25 | 51.5 ± 4.17 | 66.9 ± 5.17 |

TABLE E5

GFP-NLS transduction in various suspension cells

| Peptide | Cells | Peptide conc. (μM) | Conc. of GFP-NLS (μM) | Incubation time (min) | Mean % cells with GFP signal (±St. Dev.; n = 3) | Cell viability (%) (±St. Dev.; n = 3) |
|---|---|---|---|---|---|---|
| No peptide | [All] | 0 | 10 | 90 | 0.36 ± 0.03* | 100* |
| FSD18 | DOHH2 | 1 |  | 90 | 2.4 ± 0.42 | 62.5 ± 6.17 |
|  |  | 2 |  | 30 | 26.8 ± 2.19 | 79.8 ± 6.18 |
|  |  | 10 |  |  | 27.2 ± 2.46 | 25.0 ± 2.66 |
|  | HT2 | 1 |  | 90 | 12.3 ± 0.96 | 88.3 ± 7.91 |
|  |  | 2 |  | 30 | 31.0 ± 2.55 | 80.7 ± 7.10 |
|  |  | 10 |  |  | 82.5 ± 4.07 | 63.9 ± 5.35 |
|  | Jurkat | 1 |  | 90 | 10.1 ± 1.11 | 98.6 ± 0.39 |
|  |  | 2 |  | 30 | 11.0 ± 1.29 | 97.4 ± 1.09 |
|  |  | 10 |  |  | 9.9 ± 1.06 | 96.6 ± 2.46 |
|  | KMS-12BM | 1 |  | 90 | 13.6 ± 2.17 | 97.6 ± 1.05 |
|  |  | 2 |  | 30 | 26.2 ± 3.93 | 95.1 ± 3.56 |
|  |  | 10 |  |  | 21.0 ± 1.76 | 92.7 ± 4.11 |
|  | REC-1 | 1 |  | 90 | 1.80 ± 0.88 | 96.2 ± 2.53 |
|  |  | 2 |  | 30 | 10.9 ± 1.34 | 99.0 ± 0.39 |
|  |  | 10 |  |  | 25.0 ± 1.89 | 25.0 ± 3.17 |
|  | NK | 1 |  | 90 | 2.80 ± 0.33 | 99.1 ± 0.08 |
|  |  | 2 |  | 30 | 6.41 ± 1.12 | 98.3 ± 1.00 |
|  |  | 5 |  | 15 | 65.7 ± 5.27 | 94.9 ± 1.63 |

*Quantification of the negative control ("no peptide") was similar for all cell lines tested. Thus, the data (*) represents an average from the "no peptide" controls for at cell lines tested.

Example F

Rationally-Designed Peptide Shuttle Agents Enable Transduction of Antibodies F.1 Transduction of Fluorescently Labeled Antibodies by FSD5 in HeLa Cells Protein transduction assays were conducted as generally described in Example 3.1, using the peptide FSD5 and an antibody as cargo after 1 min incubation time, before being characterized by fluorescence microscopy (Example 3.2). FIG. 50 shows the results of the cytoplasmic transduction of Goat Anti-Mouse IgG H&L (Alexa Fluor®488) and Goat Anti-Rabbit IgG H&L (Alexa Fluor® 594) antibodies delivered in HeLa cells by the peptide FSD5 (8 µM) for 1 min and visualized by fluorescence microscopy at 20× magnification for the Alexa Fluor 594 Ab (FIG. 50A); and at 10× and 20× magnification for the Alexa Fluor 488 Ab (FIGS. 50B and 50C, respectively). The bright field and fluorescence images of living cells are shown in upper and lower panels, respectively.

The following experiments show that other FSD peptides can also deliver functional antibodies: an anti-NUP98 antibody which labels the nuclear membrane, and two anti-Active Caspase3 antibodies that bind and inactivate the pro-apoptotic Caspase 3 protein. The delivery, microscopy and cell immune-labelling protocols are described in Example 3.

F.2 Transduction of Anti-NUP98 Antibody by FSD19 in HeLa Cells

Figure 50D:
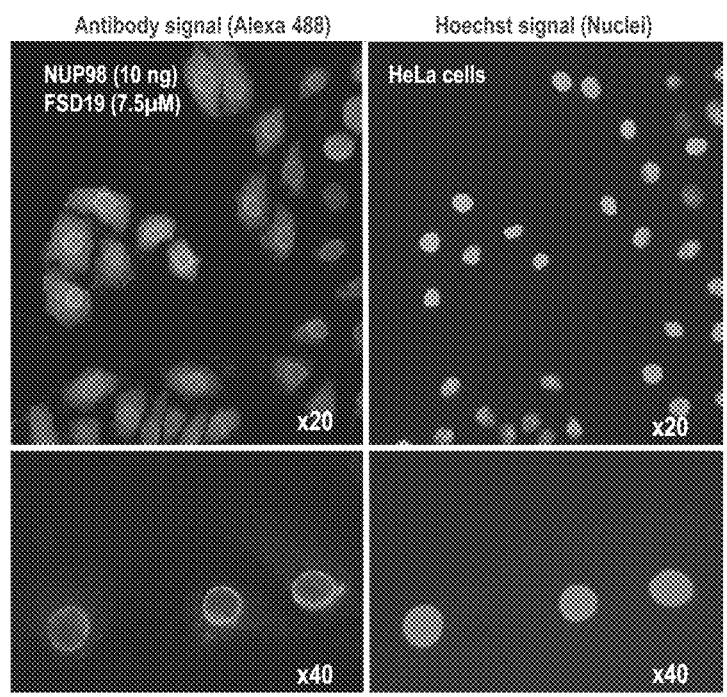
FIG. 50D shows the results of a transduction experiment in which an anti-NUP98 antibody, which recognizes an antigen in the perinuclear membrane, was transduced into HeLa cells using the shuttle agent FSD19. Following transduction, HeLa cells were fixed, permeabilized and labelled with a fluorescent (Alexa™ 488) secondary antibody recognizing the anti-NUP98 antibody (left panels) and Hoechst nuclear staining (right panels). Upper and lower panels indicate images taken under 20× and 40× magnification, respectively.

Anti-NUP98 antibody (10 pg) was co-incubated with 7.5 µM of FSD19 and exposed to HeLa cells for 4 hours. Cells are washed, fixed with paraformaldehyde 4%, permeabilized with 0.1% Triton™ and labeled with a fluorescently labeled (Alexa™ Fluor 488) goat anti-rat antibody. Antibody bound to the perinuclear membrane and cell nuclei were visualized by fluorescence microscopy at 20× (upper panels) and 40× (lower panels). As shown in FIG. 50D, green fluorescent signal emanated from the nuclear membrane (left panels) and overlapped with Hoechst staining (right panels), demonstrating that the anti-NUP98 antibody retained its functionality inside the cell following its transduction.

F.3 Transduction of Two Functional Anti-Active Caspase 3 Antibodies by FSD23 in THP-1 and Jurkat Cells: Quantification by ELISA Cleaved PARP Assay A monoclonal (mAb) and a polyclonal (pAb) anti-Active Caspase 3 antibodies (2 pg) were independently co-incubated with THP-1 and Jurkat cells for 5 min in the presence of FSD23 at 7.5 µM. The anti-apoptotic effect of each antibody was assessed via the level of Caspase 3-activated apoptosis with an ELISA cleaved PARP assay and quantified by spectrometry as described below.

The day of the experiment, cells in exponential growth phase were harvested, centrifuged (400g for 3 min) and resuspended in serum-free RPMI in a 96-well plate (500,000 cells in 150 µL per well). Cells were centrifuged and incubated for 5 min with a mix composed by the peptide to be tested (7.5 µM) and 2 µg of the antibody to be transduced. Cells were centrifuged and resuspended in RPMI with serum in a 24-well plate for 1 h at 37° C. Actinomycin D (2 µg/mL), a cytotoxic inducer of apoptosis, was incubated with the cells for 4 h. Cells were washed with cold PBS and tested using the PARP (Cleaved) [214/215]Human ELISA Kit (ThermoFisher) according to the manufacturer's instructions followed by spectroscopy analysis. Results are shown in Table F1. IDC-1 13,T1

TABLE F1

Cleaved PARP ELISA assay after transduction of anti-TNF or anti-Active Caspase 3 antibody by FSD23 in THP-1 and Jurkat cells

| Cell type | Antibody | Actinomycin D | Optical Density (O.D.) PARP cleavage assay |
|---|---|---|---|
| THP-1 | anti-TNF | − | 0.334 |
|  | (control) | + | 1.162 |
|  | anti-Active | − | 0.207 |
|  | Caspase 3 mAb | + | 0.856 |
|  | anti-Active | − | 0.192 |
|  | Caspase 3 pAb | + | 0.653 |
| Jurkat | anti-TNF | − | 0.281 |
|  | (control) | + | 0.486 |
|  | anti-Active | − | 0.174 |
|  | Caspase 3 mAb | + | 0.301 |
|  | anti-Active | − | 0.149 |
|  | Caspase 3 pAb | + | 0.333 |

Results in THP-1 and in Jurkat cells show that FSD23 successfully transduced functional anti-Active Caspase 3 antibodies. Anti-TNF antibody was used as a non-specific negative control and actinomycin D as a cytotoxic inducer of apoptosis. In the absence of actinomycin D ("−"), the delivery of each anti-Active Caspase 3 mAb and pAb resulted in the reduction of the basal level of apoptosis compared to the "anti-TNF" control, in which the delivery of the anti-TNF antibody had no discernable impact on cell viability. In presence of actinomycin D ("+"), the resulting apoptosis was reduced after the delivery of both anti-Active Caspase 3 antibodies with FSD23 compared to the "anti-TNF" control.

Example G

Rationally-Designed Peptide Shuttle Agents Enable Transduction of CRISPR-Based Genome Editing Complexes We tested the ability of rationally-designed peptide shuttle agents to deliver functional CRISPR-based genome editing complexes to the nucleus of eukaryotic cells using standard DNA cleavage assays. These assays were used to measure CRISPR/Cas9 and CRISPR/Cpf1-mediated cleavage of cellular genomic DNA sequences HPRT (Hypoxanthine Phosphoribosyltransferase 1) and DNMT1 (DNA (Cytosine-5-)-Methyltransferase 1), respectively. Homologous-directed recombination (HDR) of short (72 bp) and long (1631 bp) DNA templates were performed at the HPRT genomic cut site, and measured after intracellular delivery of the genome editing complexes with different shuttle agents.

G.1 CRISPR/Cas9-NLS Complex Transduction by Rationally-Designed Peptide Shuttle Agents, Cleavage of Genomic Target Sequence, and Homologous-Directed Recombination in Different Cell Lines G.1.1 Transduction of Functional CRISPR/Cas9-NLS Complexes Cas9-NLS recombinant protein was prepared as described in Example 13.1. A mix composed of a Cas9-NLS recombinant protein and crRNA/tracrRNA (see below) targeting a nucleotide sequence of the HPTR genes were co-incubated with different concentrations of FSD5, FSD8, FSD10 or FSD18 and incubated with HeLa, HCC-78, NIC-H196 or REC-1 cells for 2 min in PBS, or 48 h in medium with serum, using the transduction protocols as generally described in Example 3.1a. Cells were then washed with PBS and harvested to proceed with the T7E1 protocol assay as described in Example 13.4.

The sequences of the crRNA and tracrRNAs constructed and their targets were:

```
- Feldan tracrRNA [SEQ ID NO: 77]:
5'- AAACAGCAUAGCAAGUUAAAAUAAGGCUAGUCCGUUAUCAACUUG

AAAAAGUGGCACCGAGUCGGUGCU-3'

- HPRT crRNA [SEQ ID NO: 103]:
5'- AAUUAUGGGGAUUACUAGGAGUUUUAGAGCUAUGCU-3'
```

Figure 51A:
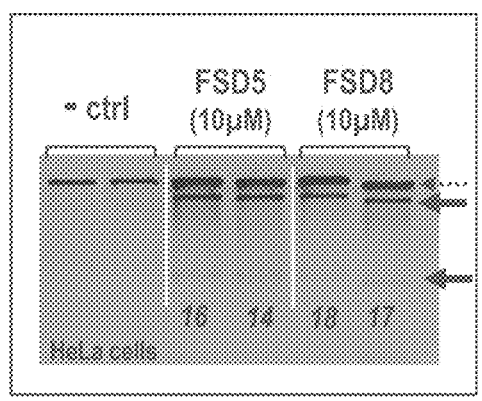
FIGS. 51A-51F show the results of genome editing experiments in which CRISPR/Cas9-NLS genome editing complexes were transduced into different cell types (HeLa (FIG. 51A and FIG. 51B), NK cells (FIG. 51C), NIC-H196 cells (FIG. 51D), HCC-78 cells (FIG. 51E), and REC-1 cells (FIG. 51F) using different shuttle agent peptides (FSD5, FSD8, FSD10, FSD18), and successful genome editing was verified by genomic DNA cleavage assays. The CRISPR/Cas9-NLS complexes consisted of recombinant Cas9-NLS complexed with a crRNA/tracrRNA designed to cleave the HPRT genomic DNA sequence. Successful genome editing was observed by the detection of genomic DNA cleavage products (thick solid arrows), as compared to the uncleaved genomic target gene (thin dashed arrows). The negative control ("ctrl") were from transduction experiments performed in the absence of any shuttle agent peptide. An imaging software was used to quantify the relative signal intensities of the cleavage product bands directly on gels. The sum of all the bands in a given lane corresponds to 100% of the signal, and the numerical value in italics at the bottom of each lane is the sum of the relative signals (%) of only the two cleavage product bands (thick solid arrows).
Figure 51B:
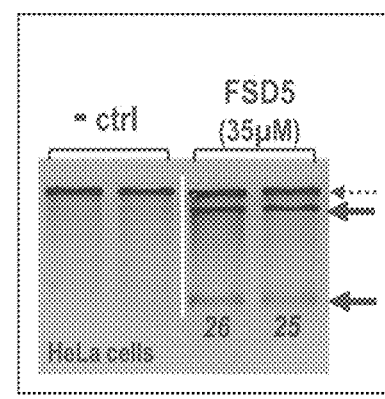
Figure 51C:
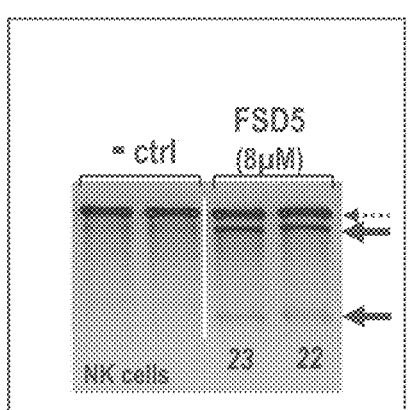
Figure 51D:
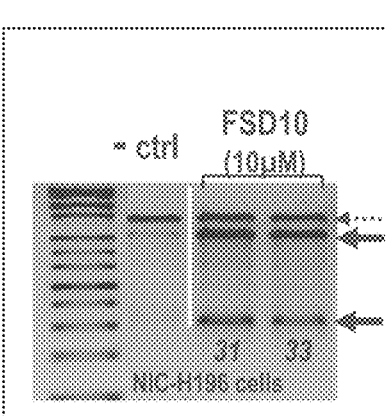
Figure 51E:
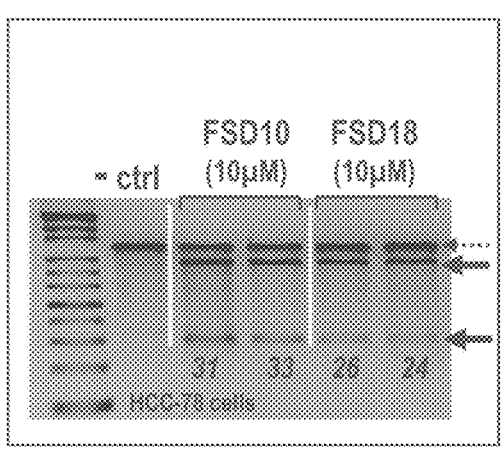
Figure 51F:
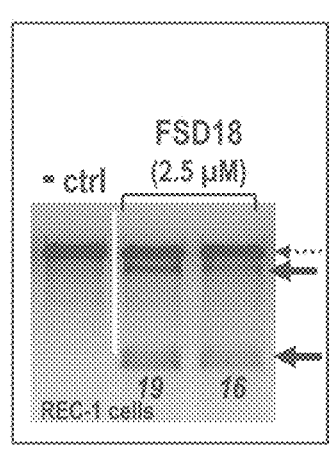

FIGS. 51A-51F show the results of the cleavage of the targeted genomic HPRT DNA sequence with the CRISPR/Cas9 (2.5 µM) and the crRNAltracrRNA (2 µM) in the absence ("-ctrl") or presence of the shuttle agents FSD5, FSD8, FSD10 or FSD18 used at different concentrations, exposure times, and in different types of cells: HeLa (FIGS. 51A and 51B); NK (FIG. 51C); NIC-196H (FIG. 51D); HCC-78 (FIG. 51E) and REC-1 cells (FIG. 51F), after separation by agarose gel electrophoresis. In some cases, gel lanes were loaded in duplicate. Thin dashed arrows indicate the bands corresponding to the target gene, and thicker solid arrows indicate the bands corresponding to the cleavage products of this target gene, which indicate the successful transduction of functional CRISPR/Cas9-NLS genome editing complexes. We used a Bio-Rad ImageLab™ software (Version 5.2.1, Bio-Rad, http://www.bio-rad.com/en-ca/product/image-lab-software?tab=Download) to quantify the relative signal intensities of each of the different bands directly on gels. The sum of all the bands in a given lane corresponds to 100% of the signal, and the numerical value in italics at the bottom of each lane is the sum of the relative signals (%) of only the two cleavage product bands (thicker solid arrows). No cleave product bands were found in the negative controls ("-ctrl", i.e., to cells that were exposed to CRISPR/Cas9-NLS complex in the absence of shuttle agent). These results indicate the successful delivery of the CRISPR genome-editing complexes to the nucleus, resulting in cleave of the target gene.

G.1.2 Transduction of CRISPR/Cas9-NLS Complexes with Short Linear DNA Template, Resulting in Homologous-Directed Recombination A mix was prepared containing: a Cas9-NLS recombinant protein (2.5 µM) (see Example 13.1); the crRNAltracrRNA (2 µM) targeting a nucleotide sequence of the HPTR genes (see above); the peptide shuttle agent FSD5 (15 µM); and either 0 ng or 500 ng of a short linear template DNA (72 bp; see below).

```
Short DNA template [SEQ ID NO: 154]:
5'-TGAAATGGAGAGCTAAATTATGGGGATTACAAGCTTGATAGCGAAG

GGGCAGCAATGAGTTGACACTACAGA-3'
```

This mixture was exposed to HeLa cells for 48 h in culture media containing serum. Cells were then washed and subjected to the T7E1 assay as described in Example 13.4.

Figure 51G:
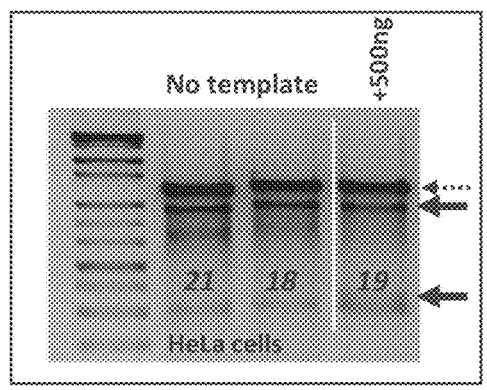
FIG. 51G shows the cleavage of the targeted HPRT genomic sequence by the CRISPR/Cas9-NLS complex transduced by FSD5, in the absence ("No template") or presence ("+500 ng") of a short DNA template (72 bp). Thin dashed arrows indicate the bands corresponding to the target gene, and thick solid arrows indicate the bands corresponding to the CRISPR/Cas9-NLS-mediated cleavage products of this target gene, which indicate the successful transduction of fully functional genome editing complexes in the presence and absence of the DNA template. The numerical value in italics at the bottom of each lane is the sum of the relative signals (%) of only the two cleavage product bands (thick solid arrows).

FIG. 51G shows the cleavage of the targeted HPRT genomic sequence by the CRISPR/Cas9 complex transduced by FSD5 (15 µM), in the absence ("No template") or presence (+500 ng) of the short DNA template. Thin dashed arrows indicate the bands corresponding to the target gene, and thicker solid arrows indicate the bands corresponding to the cleavage products of this target gene, which indicate the successful transduction of fully functional genome editing complexes. The numerical value in italics at the bottom of each lane is the sum of the relative signals (%) of only the two cleavage product bands (thicker solid arrows). These results show that FSD5 can transduce a functional CRISPR/Cas9 complex in the presence or absence of template DNA.

Figure 51H:
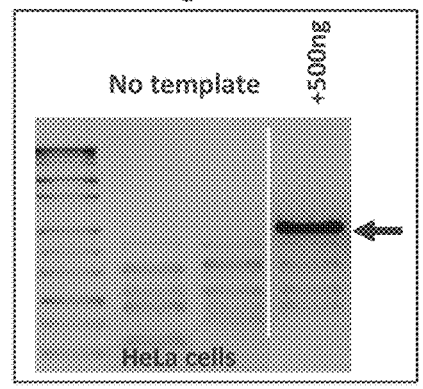
FIG. 51H shows the results of a PCR-amplification of the samples of FIG. 51G, using primers specific for the short DNA template, indicating genomic insertion of the DNA template sequence (see arrow in FIG. 51H).

To verify whether homologous-directed recombination occurred, we used the genomic DNA extracted from FSD5/CRISPR/short DNA template-treated cells to amplify the short DNA template sequence with specifically designed oligonucleotide primers targeting this sequence. The amplification of the short DNA template sequence confirmed the insertion of this template in the genome after the cutting of the HPRT gene by the CRISPR/Cas9-NLS genome editing complex. The PCR products were resolved by agarose gel electrophoresis and the results are shown in FIG. 51H. No amplification was detected in the "no template" sample, in which the genomic DNA was cut but no DNA template was provided (FIG. 51H). In contrast, an amplicon of appropriate size (FIG. 51H, thick solid line) was detected for the "+500 ng" sample, in which the genomic DNA was cut and a DNA template was provided. Detection of the amplicon indicates successful insertion of the short DNA template sequence into the genome. These results show that FSD5 can transduce CRISPR/Cas9 complex in the presence of a short DNA template, resulting in homologous-directed recombination.

G.1.3 Transduction of CRISPR/Cas9-NLS Complexes with Long Linear DNA Template, Resulting in Homologous-Directed Recombination A mix was prepared containing: a Cas9-NLS recombinant protein (2.5 µM) (see Example 13.1); the crRNAltracrRNA (2 µM) targeting a nucleotide sequence of the HPTR genes (see above); the peptide shuttle agent FSD5 (15 µM); and either 0 ng or 500 ng of a long linear template DNA encoding GFP (1631 bp; see below).

```
- GFP coding DNA template [SEQ ID NO: 156]:
5'AAGTAATCAATTACGGGGTCATTAGTTCATAGCCCATATATGGAGTT

CCGCGTTACATAACTTACGGTAAATGGCCCGCCTGGCTGACCGCCCAACG

ACCCCCGCCCATTGACGTCAATAATGACGTATGTTCCCATAGTAACGCCA

ATAGGGACTTTCCATTGACGTCAATGGGTGGAGTATTTACGGTAAACTGC

CCACTTGGCAGTACATCAAGTGTATCATATGCCAAGTACGCCCCCTATTG

ACGTCAATGACGGTAAATGGCCCGCCTGGCATTATGCCCAGTACATGACC

TTATGGGACTTTCCTACTTGGCAGTACATCTACGTATTAGTCATCGCTAT

TACCATGGTGATGCGGTTTTGGCAGTACATCAATGGGCGTGGATAGCGGT

TTGACTCACGGGGATTTCCAAGTCTCCACCCCATTGACGTCAATGGGAGT

TTGTTTTGGCACCAAAATCAACGGGACTTTCCAAAATGTCGTAACAACTC

CGCCCCATTGACGCAAATGGGCGGTAGGCGTGTACGGTGGGAGGTCTATA

TAAGCAGAGCTGGTTTAGTGAACCGTCAGATCCGCTAGCGCTACCGGTCG

CCACCATGGTGAGCAAGGGCGAGGAGCTGTTCACCGGGGTGGTGCCCATC

CTGGTCGAGCTGGACGGCGACGTAAACGGCCACAAGTTCAGCGTGTCCGG

CGAGGGCGAGGGCGATGCCACCTACGGCAAGCTGACCCTGAAGTTCATCT

GCACCACCGGCAAGCTGCCCGTGCCCTGGCCCACCCTCGTGACCACCCTG

ACCTACGGCGTGCAGTGCTTCAGCCGCTACCCCGACCACATGAAGCAGCA

CGACTTCTTCAAGTCCGCCATGCCCGAAGGCTACGTCCAGGAGCGCACCA

TCTTCTTCAAGGACGACGGCAACTACAAGACCCGCGCCGAGGTGAAGTTC
```

-continued

```
GAGGGCGACACCCTGGTGAACCGCATCGAGCTGAAGGGCATCGACTTCAA

GGAGGACGGCAACATCCTGGGGCACAAGCTGGAGTACAACTACAACAGCC

ACAACGTCTATATCATGGCCGACAAGCAGAAGAACGGCATCAAGGTGAAC

TTCAAGATCCGCCACAACATCGAGGACGGCAGCGTGCAGCTCGCCGACCA

CTACCAGCAGAACACCCCCATCGGCGACGGCCCCGTGCTGCTGCCCGACA

ACCACTACCTGAGCACCCAGTCCGCCCTGAGCAAAGACCCCAACGAGAAG

CGCGATCACATGGTCCTGCTGGAGTTCGTGACCGCCGCGGGATCACTCT

CGGCATGGACGAGCTGTACAAGTCCGGACTCAGATCTCGAGCTCAAGCTT

CGAATTCTGCAGTCGACGGTACCGCGGGCCCGGGATCCACCGGATCTAGA

TAACTGATCATAATCAGCCATACCACATTTGTAGAGGTTTTACTTGCTTT

AAAAAACCTCCCACACCTCCCCCTGAACCTGAAACATAAAATGAATGCAA

TTGTTGTTGTTAACTTGTTTATTGCAGCTTATAATGGTTACAAATAAAGC

AATAGCATCACAAATTTCACAAATAAAGCATTTTTTTCACTGCATTCTA

GTTGTGGTTTGTCCAAACTCATCAATGTATCTTAA-3'
```

This mixture was exposed to HeLa cells for 48 h in culture media containing serum. Cells were then washed with PBS and harvested to proceed with the T7E1 protocol assay as described in Example 13.4.

Figure 51I:
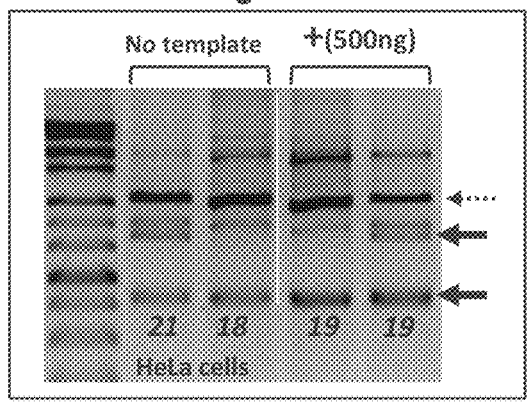
FIG. 51I shows the cleavage of the targeted HPRT genomic sequence by the CRISPR/Cas9-NLS complex transduced by FSD5, in the absence ("No template") or presence ("+500 ng") of a long linear DNA template (1631 bp). Thin dashed arrows indicate the bands corresponding to the target gene, and thick solid arrows indicate the bands corresponding to the CRISPR/Cas9-NLS-mediated cleavage products of this target gene, which indicate the successful transduction of fully functional genome editing complexes in the presence and absence of the DNA template. The numerical value in italics at the bottom of each lane is the sum of the relative signals (%) of only the two cleavage product bands (thick solid arrows).

FIG. 51I shows the cleavage of the targeted genomic HPRT genomic sequence by the CRISPR/Cas9 complex transduced by FSD5 (15 μM), in the absence ("No template") or presence ("+500ng") of the long DNA template. The cleavage products are indicated with thick solid arrows. These results show that FSD5 can transduce a functional CRISPR/Cas9 complex in the presence or absence of a long template DNA.

Figure 51J:
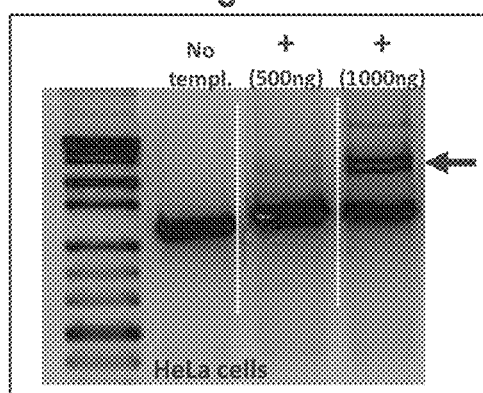
FIG. 51J shows the results of a PCR-amplification of the samples of FIG. 51I, using primers designed to amplify across the genomic cleavage site. Genomic insertion of the long DNA template sequence is visible by the presence of a larger band in the "+500 ng" (faint) and "+1000 ng" (darker) lanes see arrow in FIG. 51J.

To verify whether homologous-directed recombination occurred, we used the genomic DNA extracted from FSD5/CRISPR/long DNA template-treated cells to amplify the long DNA template sequence with specifically designed oligonucleotide primers flanking this sequence. The amplification of the long DNA template sequence confirmed the insertion of this template in the genome after the cutting of the HPRT gene by the CRISPR/Cas9-NLS genome editing complex. The PCR products were resolved by agarose gel electrophoresis and the results are shown in FIG. 51J. In the "No template" sample, a single band corresponding to the amplicon lacking the long DNA template insertion was detected. In contrast, additional larger bands (indicated with an arrow) were detected for the "+500 ng" (faint) and "+1000 ng" (darker) samples, indicating some insertion of the long DNA template into the genomic DNA had occurred. These results show that FSD5 can transduce CRISPR/Cas9 complex in the presence of a long DNA template, resulting in homologous-directed recombination.

G.2 CRISPR/Cpf1-NLS Complex Transduction by Rationally-Designed Shuttle Agents, Cleavage of Genomic Target Sequence in HeLa and NK Cells A mix composed of a Cpf1-NLS recombinant protein (2.5 μM) and crRNA (2 μM; see below) targeting a nucleotide sequence of the DNMT1 gene was co-incubated with different concentrations of FSD18 and incubated with HeLa or NK cells for 2 min in HeLa cells, or 90 sec in NK cells in PBS or in medium without serum using transduction protocols as described in Example 3.1a.

The sequence of the Cpf1-NLS recombinant protein produced was:

```
                                        [SEQ ID NO: 155]
MTQFEGFTNLYQVSKTLRFELIPQGKTLKHIQEQGFIEEDKARNDHYKEL

KPIIDRIYKTYADQCLOLVOLDWENLSAAIDSYRKEKTEETRNALIEEQA

TYRNAIHDYFIGRTDNLTDAINKRHAEIYKGLFKAELFNGKVLKQLGTVT

TTEHENALLRSFDKFTTYFSGFYENRKNVFSAEDISTAIPHRIVQDNFPK

FKENCHIFTRLITAVPSLREHFENVKKAIGIFVSTSIEEVFSFPFYNQLL

TQTQIDLYNQLLGGISREAGTEKIKGLNEVLNLAIQKNDETAHIIASLPH

RFIPLFKQILSDRNTLSFILEEFKSDEEVIQSFCKYKTLLRNENVLETAE

ALFNELNSIDLTHIFISHKKLETISSALCDHWDTLRNALYERRISELTGK

ITKSAKEKVQRSLKHEDINLQEIISAAGKELSEAFKOKTSEILSHAHAAL

DQPLPTTLKKQEEKEILKSQLDSLLGLYHLLDWFAVDESNEVDPEFSARL

TGIKLEMEPSLSFYNKARNYATKKPYSVEKFKLNFQMPTLASGWDVNKEK

NNGAILFVKNGLYYLGIMPKQKGRYKALSFEPTEKTSEGFDKMYYDYFPD

AAKMIPKCSTQLKAVTAHFQTHTTPILLSNNFIEPLEITKEIYDLNNPEK

EPKKFQTAYAKKTGDQKGYREALCKWIDFTRDFLSKYTKTTSIDLSSLRP

SSQYKDLGEYYAELNPLLYHISFQRIAEKEIMDAVETGKLYLFQIYNKDF

AKGHHGKPNLHTLYWTGLFSPENLAKTSIKLNGQAELFYRPKSRMKRMAH

RLGEKMLNKKLKDQKTPIPDTLYQELYDYVNHRLSHDLSDEARALLPNVI

TKEVSHEIIKDRRFTSDKFFFHVPITLNYQAANSPSKENORVNAYLKEHP

ETPIIGIDRGERNLIYITVIDSTGKILEQRSLNTIQQFDYQKKLDNREKE

RVAARQAWSVVGTIKDLKQGYLSQVIHEIVDLMIHYQAVVVLENLNFGFK

SKRTGIAEKAVYQQFEKMLIDKLNCLVLKDYPAEKVGGVLNPYQLTDQFT

SFAKMGTQSGFLFYVPAPYTSKIDPLTGFVDPFVWKTIKNHESRKHFLEG

FDFLHYDVKTGDFILHFKMNRNLSFQRGLPGEMPAWDIVFEKNETQFDAK

GTPFIAGKRIVPVIENHRFTGRYRDLYPANELIALLEEKGIVERDGSNIL

PKLLENDDSHAIDTMVALIRSVLQMRNSNAATGEDYINSPVRDLNGVCFD

SRFQNPEWPMDADANGAYHIALKGQLLLNHLKESKDLKLONGISNQDWLA

YIQELRNGGRSSDDEATADSQHAAPPKKKRKVGGSGGGSGGGSGGGRHHH

HHH
(MW = 155.7 kDa; pI = 8.34)
NLS sequence is underlined
Serine/glycine rich linkers are in bold
```

The sequences of the crRNA used was as follows:

```
- DNMT1 crRNA [SEQ ID NO: 157]:
5'- AAUUUCUACUGUUGUAGAUCUGAUGGUCCAUGUCUGUUACUC -3'
```

Figure 51K:
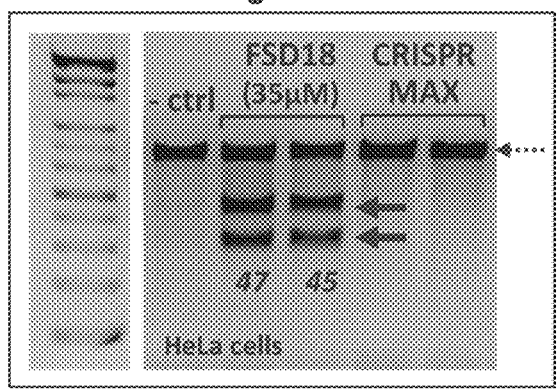
FIGS. 51K and 51L show the results of the cleavage of the targeted genomic DNMT1 DNA sequence with a CRISPR/Cpf1-NLS genome editing complex in the absence ("-ctrl") or presence of the shuttle agent FSD18 in HeLa (FIG. 51K) and NK cells (FIG. 51L), after PCR-amplification and separation by agarose gel electrophoresis. Thin dashed arrows indicate the bands corresponding to the target gene, and thick solid arrows indicate the bands corresponding to the CRISPR/Cpf1-NLS-mediated cleavage products of this target gene, which indicate the successful transduction of fully functional genome editing complexes. An imaging software was used to quantify the relative signal intensities of each of the different bands directly on gels. The sum of all the bands in a given lane corresponds to 100% of the signal, and the numerical value in italics at the bottom of each lane is the sum of the relative signals (%) of only the two cleavage product bands (thick solid arrows). No genomic DNA cleavage was observed using the lipofectamine-based transfection reagent CRISPRMAX™ to transduce the CRISPR/Cpf1-NLS genome editing complex.
Figure 51L:
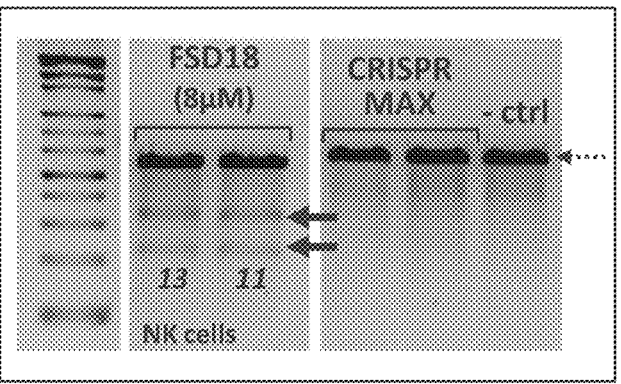

After 2 min (HeLa) or 90 sec (NK), cells were washed with PBS and harvested to proceed with the T7E1 protocol assay as described in Example 13.4. The PCR-amplified DNMT1 DNA sequence and the PCR-amplified cleavage product of this sequence were resolved on agarose gels and the results are shown in FIGS. 51K (HeLa cells) and 51L (NK cells). The negative control ("-ctrl") corresponds to cells that were exposed to CRISPR/Cpf1-NLS complex in the absence of the shuttle agent. Thin dashed arrows indicate the bands corresponding to the target gene, and thick solid arrows indicate the bands corresponding to the cleavage products of this target gene, which indicate the successful transduction of fully functional CRISPR/Cpf1-NLS genome editing complexes. The numerical value in italics at the bottom of each lane is the sum of the relative signals (%) of only the two cleavage product bands (thick solid arrows). These results show that FSD18 can transduce a functional CRISPR/Cpf1-NLS complex into the nucleus of these cells to effect cleavage of the target gene.

The CRISPRMAX™ technology is a commercially available lipofectamine-based transfection reagent optimized for CRISPR-Cas9 protein delivery. However, an equivalent reagent does not presently exist for the transduction of CRISPR-Cpf1. Interestingly, when we used the CRISPR-MAX™ reagent, it was unable to deliver the CRISPR/Cpf1-NLS complex in adherent and suspension cells. In contrast, FSD18 enabled a robust cleavage of the DNMT1 target in HeLa cells, and a lower but observable cleavage in NK cells.

These results show that the shuttle agent FSD18 successfully delivered a functional CRISPR/Cpf1-NLS complex to the nucleus of HeLa and NK cells, and that this delivery resulted in a CRISPR/Cpf1-NLS-mediated cleavage of genomic DNA.

Examples G.3-G.10

Rationally-Designed Peptide Shuttle Agents Enable Single or Multiple Gene Targeting, and/or Co-Delivery of Different CRISPR-Based Genome Editing Complexes These examples support the ability of rationally-designed peptide shuttle agents to enable the delivery and edition of multiple gene targets simultaneously. Functional CRISPR-based genome editing complexes were delivered to the nucleus of eukaryotic cells, and successful genome editing was evaluated using standard DNA cleavage assays. These assays were used to measure CRISPR/Cas9-mediated cleavage of cellular genomic DNA sequences HPRT (Hypoxanthine Phosphoribosyltransferase 1) and B2M (p2 microglobulin HLA subunit), and to measure CRISPR/Cpf1-mediated cleavage of cellular genomic DNA sequences NKG2A (Inhibitory NK cell receptor 2A), GSK3 (Glycogen Synthase Kinase 3), CBLB (E3 Ubiquitin-protein Ligase), DNMT1 (DNA (Cytosine-5-)-Methyltransferase 1) and B2M (p2 microglobulin HLA subunit). We also performed more complex genome editing approaches with the delivery of multiple CRISPR systems targeting one or two genes in the same cells. CRISPR/Cas9 and CRISPR/Cpf1 complexes were delivered together in HeLa cells to edit the HPRT and DNMT1 genes, respectively, or to edit the B2M gene in two different loci of exon 2. Finally, we co-delivered two CRISPR/Cpf1 complexes, each carrying a specific crRNA, to edit two exons in the B2M gene in NK cells.

G.3 Different Rationally-Designed Peptide Shuttle Agents Deliver CRISPR/Cas9-NLS and CRISPR/Cpf1 Complexes for B2M Gene Editing in HeLa, THP-1 and NK Cells Cas9-NLS recombinant protein was prepared as described in Example 13.1. Cpf1-NLS recombinant protein was prepared as described in Example G.2. A mix composed of a Cas9-NLS recombinant protein with its respective crRNAl-tracrRNA, or a Cpf1-NLS recombinant protein with its respective single guide crRNA(s) (see below) targeting a nucleotide sequence of the B2M gene, was co-incubated with different concentrations of the peptides FSD10, FSD18, FSD19, FSD21, FSD22, or FSD23 and incubated with HeLa, THP-1 or NK cells for 90 sec in PBS, or for 1 h in medium without serum, or for 48 h in medium with serum, using the transduction protocols as generally described in Example 3.1a. Cells were then washed with PBS and harvested to proceed with the T7E1 protocol assay as described in Example 13.4.

The sequences of the crRNAs and tracrRNAs constructed and their targets were:

```
- Feldan tracrRNA [SEQ ID NO: 77]:
5'- AAACAGCAUAGCAAGUUAAAAUAAGGCUAGUCCGUUAUCAACUU

GAAAAAGUGGCACCGAGUCGGUGCU -3'

- Cas9-flanked B2M-crRNA [SEQ ID NO: 160]:
5'- GAGTAGCGCGAGCACAGCTAGUUUUAGAGCUAUGCUGUUUUG -3'

- Cpf1-flanked B2M crRNA-1 [SEQ ID NO: 161]:
5'- AAUUUCUACUGUUGUAGAUAUCCAUCCGACAUUGAAGUU -3'

- Cpf1-flanked B2M crRNA-2 [SEQ ID NO: 162]:
5'- AAUUUCUACUCUUGUAGAUCCGAUAUUCCUCAGGUACUCCA -3'
```

Figure 52D:
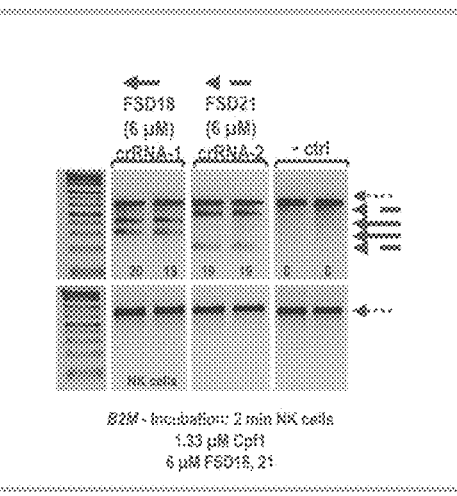
Figure 52E:
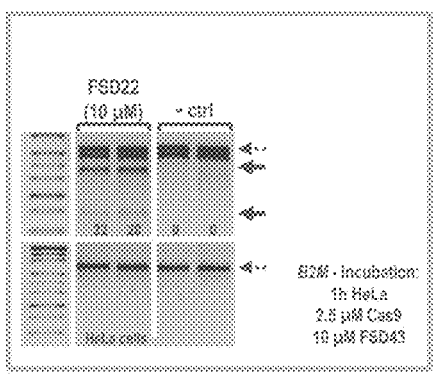
Figure 52J:
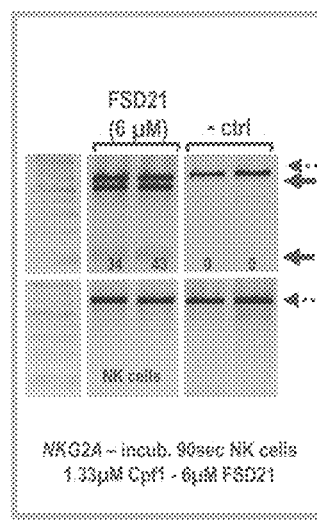
FIGS. 52J-52N show the results of the cleavage of a targeted genomic NKG2A DNA sequence with the CRISPR/Cpf1-NLS and a single guide crRNA in the absence ("-ctrl")
Figure 52K:
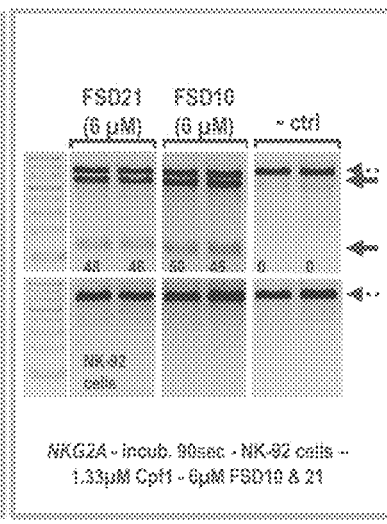
Figure 52L:
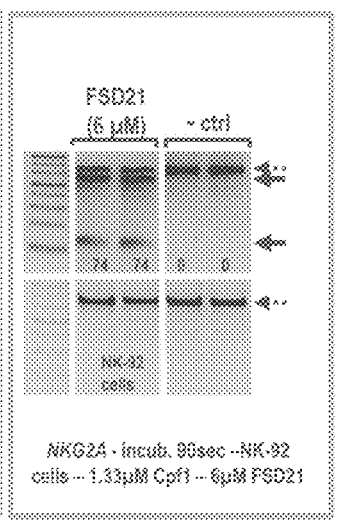
Figures 52M, 52N:
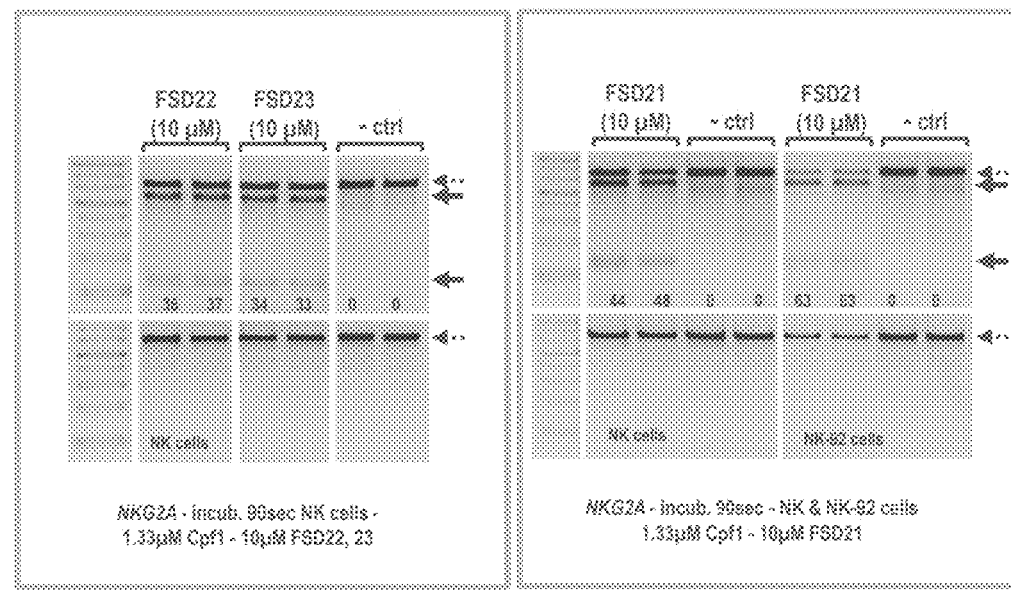

FIGS. 52A-52D show the results of the cleavage of the targeted genomic B2M DNA sequence after the delivery of CRISPR/Cpf1 (1.33 µM) with crRNA-1 or crRNA-2 (2 µM) in the absence ("-ctrl") or in the presence of the peptides FSD10, FSD18, FSD19, FSD21 or FSD23 used at different concentrations, exposure times, and in different types of cells: THP-1 (FIG. 52A), and NK (FIGS. 52B, 52C, 52D), after separation by agarose gel electrophoresis. FIG. 52D shows cleavage products of the genomic B2M exon 2 DNA sequence after the delivery of a CRISPR/Cpf1 complex carrying a specific single guide RNA (crRNA-1 or crRNA-2) in presence of FSD18 or FSD21, respectively. FIG. 52E shows the cleavage product of the genomic B2M exon 2 DNA sequence with CRISPR/Cas9 (2.5 µM) and crRNA (2 µM) in the absence ("-ctrl") or in the presence of the peptide FSD22 used at 10 µM for 1 h in HeLa cells, after separation by agarose gel electrophoresis. Gel lanes were loaded in duplicate. Thin dashed arrows indicate the bands corresponding to the target gene, and thick solid arrows indicate the bands corresponding to the cleavage products of this target gene, which indicate the successful transduction of fully functional CRISPR genome editing complexes. We used a Bio-Rad ImageLab™ software (Version 5.2.1, Bio-Rad, http://www.bio-rad.com/en-ca/product/image-lab-software?tab=Download) to quantify the relative signal intensities of each of the different bands directly on the gels. The sum of all the bands in a given lane corresponds to 100% of the signal, and the numerical value in italics at the bottom of each lane is the sum of the relative signals (%) of only the two cleavage product bands (thick solid arrows). No cleavage product bands were found in the negative controls ("-ctrl", i.e., to cells that were exposed to CRISPR system in the absence of FSD peptide). These results indicate the successful delivery of the CRISPR genome-editing complexes to the nucleus, resulting in cleavage of the target gene.

G.4 Different Rationally-Designed Peptide Shuttle Agents Deliver CRISPR/Cpf1 Systems for GSK3, CBLB and DNMT1 Gene Editing in NK, THP-1 and Primary Myoblasts Cells.

Cpf1-NLS recombinant protein was prepared as described in Example G.2. A mix composed of a Cpf1-NLS recombinant protein with a single guide crRNA (see below) targeting a nucleotide sequence of the GSK3, CBLB or DNMT1 genes was co-incubated with different concentrations of FSD10, FSD18, FSD19 or FSD23 and incubated with NK cells for 48 h in medium with serum, and in THP-1 or in primary myoblasts cells for 90 sec in PBS, using the transduction protocols as generally described in Example 3.a. Cells were then washed with PBS and harvested to proceed with the T7E1 protocol assay as described in Example 13.4.

The sequences of the crRNA constructed and their targets were:

```
- GSK3 crRNA [SEQ ID NO: 163]:
5'- AAUUUCUACUCUUGUAGAUCUUUCUUCCUUUAGGAGACA -3'

- CBLB crRNA [SEQ ID NO: 164]:
5'- AAUUUCUACUCUUGUAGAUAAGAACUAAAAUUCCAGAUG -3'

- DNMT1 crRNA [SEQ ID NO: 157]:
5'- AAUUUCUACUGUUGUAGAUCUGAUGGUCCAUGUCUGUUACUC -3'
```

FIGS. 52F-52I show the results of the cleavage of the targeted genomic GSK3, CBLB and DNMT1 DNA sequences with the CRISPR/Cpf1 (1.33 µM) and crRNA (2 µM) in absence ("-ctrl") or presence of the shuttle agents FSD10, FSD18, FSD19 or FSD23 used at different concentrations, exposure times, and in different types of cells: NK (FIGS. 52F and 52G), THP-1 (FIG. 52H) and primary myoblasts (FIG. 52I) after separation by agarose gel electrophoresis. Gel lanes were loaded in duplicate. Thin dashed arrows indicate the bands corresponding to the target gene, and thick solid arrows indicate the bands corresponding to the cleavage products of this target gene, which indicate the successful transduction of fully functional CRISPR genome editing complexes.

G.5 Different Rationally-Designed Peptide Shuttle Agents Deliver CRISPR/Cpf1 Systems for NKG2A Gene Editing in Nk Cells.

Cpf1-NLS recombinant protein was prepared as described in Example G.2. A mix composed of a Cpf1-NLS recombinant protein with a single guide crRNA (see below) targeting a nucleotide sequence of the NKG2A gene was co-incubated with different concentrations of FSD10, FSD21, FSD22 or FSD23 and incubated with NK and NK-92 cells for 90 sec in PBS, using the transduction protocols as generally described in Example 3.1a. Cells were then washed with PBS and harvested to proceed with the T7E1 protocol assay as described in Example 13.4.

The sequences of the crRNA constructed and their targets were:

```
- NKG2A crRNA [SEQ ID NO: 165]:
5'- AAUUUCUACUCUUGUAGAUGGGGCAGAUUCAGGUCUGAG -3'
```

FIGS. 52J-52N show the results of the cleavage of the targeted genomic NKG2A DNA sequence with the CRISPR/Cpf1 (1.33 µM) and crRNA (2 µM) in absence ("-ctrl") or presence of the shuttle agents FSD10, FSD21, FSD22 or FSD23 used at different concentrations, exposure times, and in NK and NK-92 cells after separation by agarose gel electrophoresis. Gel lanes were loaded in duplicate. Thin dashed arrows indicate the bands corresponding to the target gene, and thick solid arrows indicate the bands corresponding to the cleavage products of this target gene, which indicate the successful transduction of fully functional CRISPR genome editing complexes.

G.6 Different Rationally-Designed Peptide Shuttle Agents Co-Deliver CRISPR/Cas9 and CRISPR/Cpf1 Complexes for HPRT, DNMT1 and B2M Gene Editing in HeLa and NK Cells Cas9-NLS recombinant protein was prepared as described in Example 13.1. Cpf1-NLS recombinant protein was prepared as described in Example G.2. A mix composed of Cas9-NLS recombinant protein with its respective crRNA1-tracrRNA, or Cpf1-NLS recombinant protein with its respective single guide crRNA(s) (see below) targeting a nucleotide sequence of the DNMT1, HPRT and B2M genes, was co-incubated with different concentrations of FSD10, FSD18, FSD21 or FSD23, and incubated with HeLa or NK cells for 90 sec or 2 min in PBS using the transduction protocols as generally described in Example 3.1a. Cells were then washed with PBS and harvested to proceed with the T7E1 protocol assay as described in Example 13.4.

The sequences of the crRNA and tracrRNAs constructed and their targets were:

```
- Feldan tracrRNA [SEQ ID NO: 77]:
5'- AAACAGCAUAGCAAGUUAAAAUAAGGCUAGUCCGUUAUCAACUUG
AAAAAGUGGCACCGAGUCGGUGCU-3'

- HPRT crRNA [SEQ ID NO: 103]:
5'- AAUUAUGGGGAUUACUAGGAGUUUUAGAGCUAUGCU-3'

- DNMT1 crRNA [SEQ ID NO: 157]:
5'- AAUUUCUACUGUUGUAGAUCUGAUGGUCCAUGUCUGUUACUC -3'

- Cas9-flanked B2M-crRNA [SEQ ID NO: 160]:
5'- GAGUAGCGCGAGCACAGCTAGUUUUAGAGCUAUGCUGUUUUG -3'

- Cpf1-flanked B2M crRNA-1 [SEQ ID NO: 161]:
5'- AAUUUCUACUGUUGUAGAUAUCCAUCCGACAUUGAAGUU -3'

- Cpf1-flanked B2M crRNA-2 [SEQ ID NO: 162]:
5'- AAUUUCUACUCUUGUAGAUCCGAUAUUCCUCAGGUACUCCA -3'
```

Figures 53A, 53B:
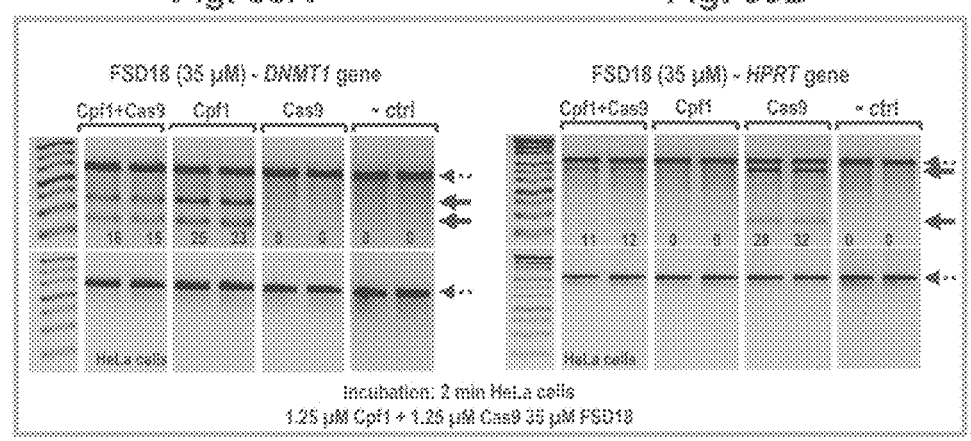
Figures 53C, 53D:
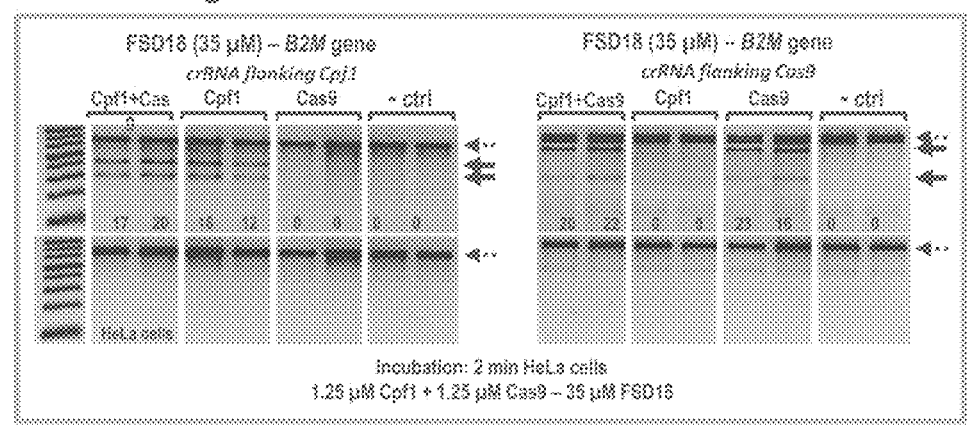
Figure 53E:
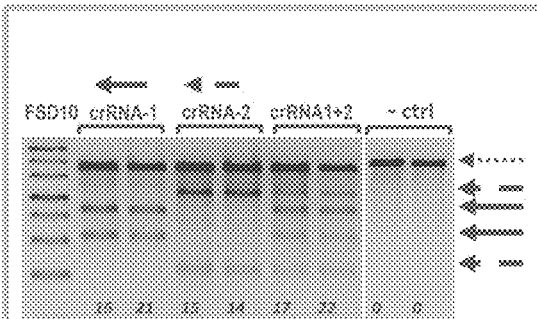

FIGS. 53A-53G show the results of the cleavage of the targeted genomic DNMT1, HPRT and B2M DNA sequences with different CRISPR systems in the absence ("-ctrl") or in the presence of the shuttle agents FSD10, FSD18, FSD21 or FSD23 used at different concentrations, exposure times, and in HeLa and NK cells after separation by agarose gel electrophoresis. FIG. 53A shows DNMT1 DNA cleavage products from the same genomic DNA extract after the co-delivery of a DNMT1-targeting CRISPR/Cpf1 (1.25 µM) complex and a HPRT-targeting CRISPR/Cas9 (1.25 µM) complex in HeLa cells. FIG. 53B shows HPRT DNA cleavage products from the same genomic DNA extract after the co-delivery of a DNMT1-targeting CRISPR/Cpf1 (1.25 µM) complex and a HPRT-targeting CRISPR/Cas9 (1.25 µM) complex in HeLa cells. FIG. 53C shows the cleavage products of the B2M exon 2 from the same genomic DNA extract after the co-delivery of a CRISPR/Cpf1 (1.25 µM) and a CRISPR/Cas9 (1.25 µM) in HeLa cells. Each complex targeted a different locus in the B2M exon 2 via a specific crRNA flanking Cpf1. FIG. 53D shows the cleavage products of the B2M exon 2 from the same genomic DNA extract after the co-delivery of a CRISPR/Cpf1 (1.25 µM) and a CRISPR/Cas9 (1.25 µM) in HeLa cells. Each complex targeted a different locus in the B2M exon 2 via a specific crRNA flanking Cas9.FIG. 53E shows the results of the cleavage of the B2M exon 2 from genomic extracts after the co-delivery of CRISPR/Cpf1 (1.33 µM) complexes, each one carrying a specific single guide crRNA-1 or crRNA-2 (2 µM) in presence of FSD10. For each experiment, NK cells were exposed to CRISPR/Cpf1 with crRNA-1 or CRISPR/

Figure 53F:
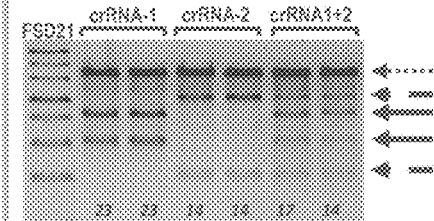
Figure 53G:
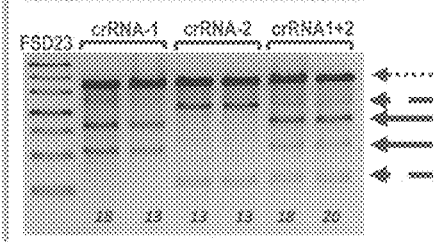

Cpf1 with crRNA-2, or both complexes. FIG. 53F shows the results of the cleavage of the B2M exon 2 from genomic extracts after the co-delivery of CRISPR/Cpf1 (1.33 µM) complexes, each one carrying a specific single guide crRNA-1 or crRNA-2 (2 µM) in presence of FSD21. For each experiment, NK cells were exposed to CRISPR/Cpf1 with crRNA-1 or CRISPR/Cpf1 with crRNA-2, or both complexes. FIG. 53G shows the results of the cleavage of the B2M exon 2 from genomic extracts after the co-delivery of CRISPR/Cpf1 (1.33 µM) complexes, each one carrying a specific single guide crRNA-1 or crRNA-2 (2 µM) in presence of FSD23. For each experiment, NK cells were exposed to CRISPR/Cpf1 with crRNA-1 or CRISPR/Cpf1 with crRNA-2, or both complexes.

G.7 Different Rationally-Designed Peptide Shuttle Agents Deliver CRISPR/Cpf1 Complexes for B2M Gene Editing in T Cells-Flow Cytometry Analysis Cpf1-NLS recombinant protein was prepared as described in Example G.2.

Unless otherwise specified, T cells used herein were obtained from healthy human blood collected in heparinized tubes. T cells were isolated using a Ficoll™ technique (Ficoll-Paque™ GE or Lymphoprep™ Stem Cell Technologies). Briefly, blood was mixed with the Ficoll™ solution in conical tubes (50 mL) and centrifuged at 2280 rpm for 20 minutes. Mononuclear cells were harvested and transferred in another conical tube (50 mL) before washing with PBS and centrifugation at 1100 rpm for 10 minutes. Cells were resuspended in 5 mL of PBS containing 20% FBS. Cells were counted and then incubated in a culture medium composed by RPMI advanced (cat: 12633012 ThermoFisher), 10% FBS, 1% Penstrep (15140122 ThermoFisher), 1% L-glutamine (25030081 ThermoFisher) IL-2 30U/ml). Next, T cells were enriched with a Human T cell Enrichment Kit (StemCell #cat: 19051) by negative selection following the manufacturer instructions. The enriched T cells were validated using a specific anti-CD3 antibody (Biolegend #cat: 300438). At this step, collected cells were typically around 99% T cells. T cells were activated by adding IL-2 at 30 U/mL and the anti-CD28 antibody (ThermoFisher #cat: 16-0289-85) in complete medium for 5 days prior to experimentation. The activation of T cell expansion was then double-checked with both anti-CD25 and anti-CD137 antibodies.

A mix composed of a Cpf1-NLS recombinant protein with respective single guide crRNA(s) targeting a nucleotide sequence of the B2M gene was co-incubated with different concentrations of FSD21 or FSD18 peptide shuttle agents and incubated with T cells for 90 seconds in PBS using the transduction protocols as generally described in Example 3.1a. Each of the B2M crRNAs were designed to mediate CRISPR/Cpf1-based cleavage of the B2M gene, the phenotypic effects of which can be seen by the disruption of cell surface HLA, which is detectable by flow cytometry using a fluorescent APC Mouse Anti-Human HLA-ABC antibody.

The cells were then resuspended in 100 µL PBS containing 1% FBS and 4 µL of APC Mouse Anti-Human HLA-ABC antibody before an incubation period of 20 minutes, in the dark, at ambient temperature. Then, 1 mL of PBS containing 1% FBS was added to the suspension followed by a 1200 rpm centrifugation of 5 minutes. Finally, the pellet was resuspended in 100 to 200 µL of PBS containing 1% FBS before flow cytometry analysis.

Flow cytometry results based on cell size and granularity using respectively the Forward Scatter (FSC) and the Side Scatter (SSC) parameters showed that viability of the transduced T cells was not substantially affected by the co-delivery of different tested concentrations of FSD21 or FSD18 peptide shuttle agents with CRISPR/Cpf1 systems (data not shown).

Figure 55A:
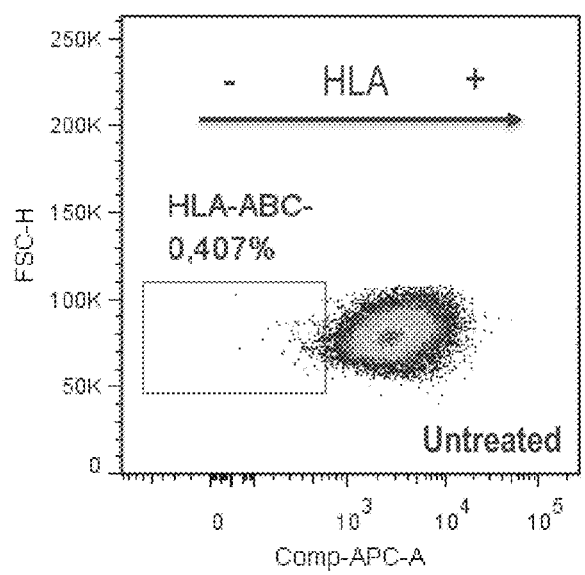
Figure 55B:
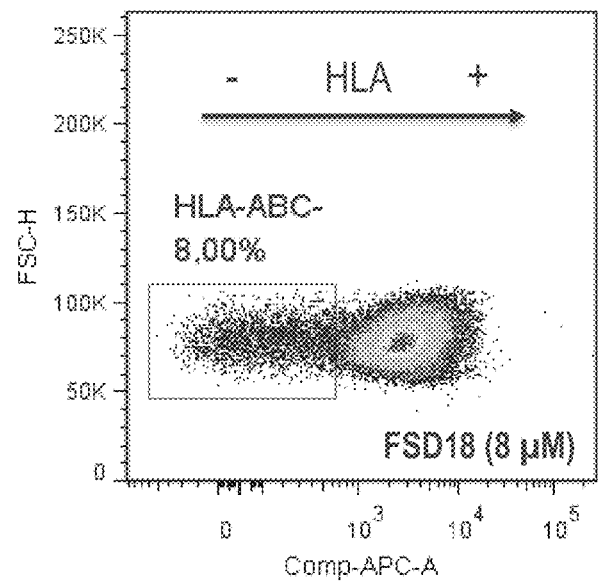
Figure 55C:
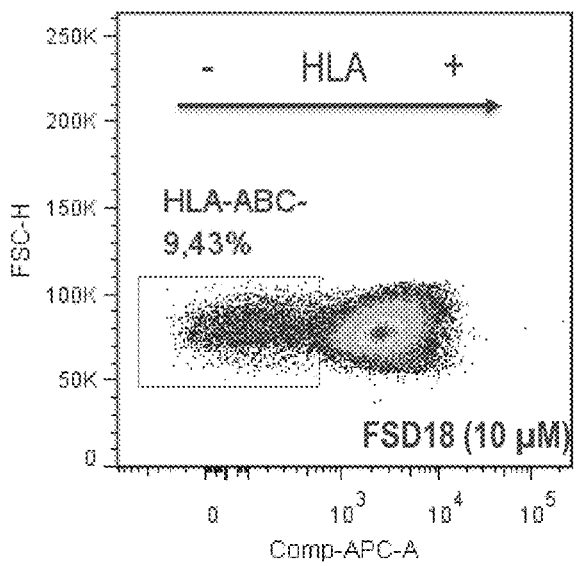
Figure 55D:
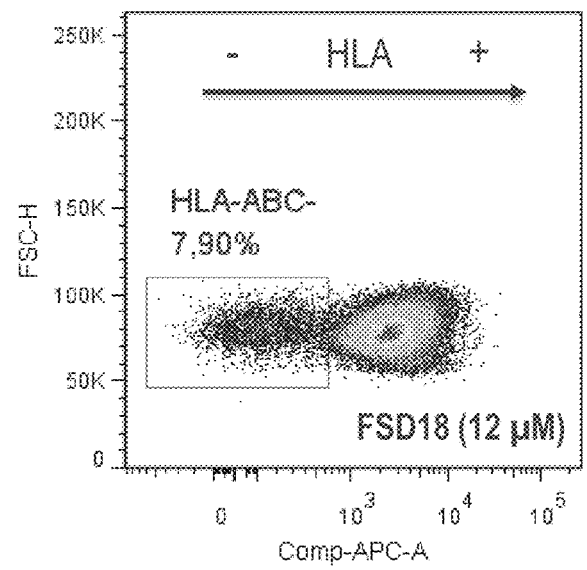

FIGS. 54A-54D and 55A-55D show delivery of CRISPR/Cpf1 genome editing complexes via the shuttle peptides FSD21 and FSD18, respectively. As seen in FIGS. 54A and 55A, "untreated" negative control cells, which were not exposed to CRISPR/Cpf1 or shuttle peptide, exhibited no significant genome editing (lack of HLA-negative cells). FIGS. 54B-54D show that FSD21 concentrations of 8, 10 and 12 µM resulted in 9.87%, 8.68%, and 12.2% of HLA-negative cells, indicating successful nuclear delivery of functional CRISPR/Cpf1 genome editing complexes and subsequent genome editing. FIGS. 55B-55D show that FSD18 concentrations of 8, 10 and 12 µM resulted in 8.0%, 9.43%, and 7.9% of HLA-negative cells, indicating successful nuclear delivery of functional CRISPR/Cpf1 genome editing complexes and subsequent genome editing.

G.8 Transduction of CRISPR/Cpf1 Complexes Containing Multiple Guide crRNA Targeting B2M in THP-1 Cell Lines Using a Single Rationally-Designed Peptide Shuttle Agent Cpf1-NLS recombinant protein was prepared as described in Example G.2. A mix composed of a Cpf1-NLS recombinant protein with a single guide crRNA (see below) targeting one of three chosen nucleotide sequences of the B2M gene was co-incubated with (3 µM) of FSD18 and incubated with THP-1 cells for 90 seconds in PBS, using the transduction protocols as generally described in Example 3.1a. The same experiments were performed using a mix composed of a Cpf1-NLS recombinant protein with three guide crRNA (see below), each targeting three different nucleotide sequences of the B2M gene. Flow cytometry experiments were performed as described in Example G.7. Also, to proceed with the T7E1 protocol assay as described in Example 13.4, cells were washed with PBS and harvested.

The sequences of the crRNA constructed and their targets were:

- B2M crRNA-E [SEQ ID NO: 166]:
5'- AAUUUCUACUCUUGUAGAUAUCCAUCCGACAUUGAAGUU -3'

- B2M crRNA-J [SEQ ID NO: 167]:
5'- AAUUUCUACUCUUGUAGAUCCGAUAUUCCUCAGGUACUCCA -3'

- B2M crRNA-G [SEQ ID NO: 168]:
5'- AAUUUCUACUCUUGUAGAUUUAGAGUCUCGUGAUGUUUAAG -3'

Flow cytometry results based on cell size and granularity using respectively the Forward Scatter (FSC) and the Side Scatter (SSC) parameters show that the viability of the transduced THP-1 cells was not substantially affected by the presence of CRISPR/Cpf1 systems comprising the guide crRNAs (RNA-E, RNA-G, RNA-J) used separately or in combination (data not shown).

As shown in FIG. 56A, "untreated" negative control cells, which were not exposed to CRISPR/Cpf1 or shuttle peptide, exhibited no significant genome editing (lack of HLA-negative cells). FIGS. 56B-56D show that each guide crRNA (RNA-E, RNA-G, RNA-J) used separately provided comparable HLA KO efficiencies, while FIG. 56E shows the combination the three guides crRNA enhanced the HLA KO efficiency by almost a factor of two. These observations were confirmed by performing a T7E1 cleavage assay as described in Example 13.4, followed by agarose gel electrophoresis (data not shown).

G.9 Increased Cytotoxicity of NK Cells Genome-Edited to Inactive the NKG2A Gene

Genome editing was performed in NK-92 cells to evaluate whether inactivation of the endogenous NKG2A gene could increase the cytotoxicity of the NK-92 cells. Briefly, one million NK-92 cells were incubated with Cpf1-NLS (1.5 µM) gRNA complex targeting the NKG2A gene and with FSD23 (6 µM) for 90 sec. After transduction, cells were incubated in complete medium with IL-2 (20 ng/mL) for 48 h at 37° C. NK-92 cells were then immunolabelled with a phycoerythrin (PE)-labelled anti-NKG2A antibody (Miltenyi Biotec #CD159a) following the manufacturer recommendations. NK-92 cells were then analyzed with FACS and scored as a function of their anti-NKG2A detection (PE fluorescence) level and the results are shown in FIG. 57A. As controls, unlabelled wild-type NK-92 cells ("unlabelled WT cells") had no antibody signal, and labelled wild-type NK-92 cells ("labelled WT cells") had full immunolabelling signal. For NKG2A-KO NK-92 cells, two cell populations (peaks) were observed: one with a complete knock-out of NKG2A receptor expression on the cell surface ("Complete NKG2A KO cells"), and the other with a partial lack of expression ("Partial NKG2A KO cells").

To study the effect of inactivation of the NKG2A gene on the cytotoxicity of the NK-92 cells, we evaluated the ability of WT and NKG2A KO NK-92 cells to kill target HeLa cells. The NKG2A receptor encoded by the NKG2A gene in NK cells normally binds HLA-E epitopes expressed on the surface of potential target cells, which inhibits the cytotoxic activity of the NK cells (effector). To improve this effector:target cell binding, HeLa cells were treated with interferons (50 ng/mL) to increase their HLA-E cell surface expression. Prior to being exposed to effector NK-92 cells, interferon-treated HeLa cells were exposed for 45 minutes at 37° C. to Calcein-AM (ThermoFisher #C3099), a non-fluorescent, hydrophobic compound that easily permeates intact live cells. The hydrolysis of Calcein-AM by intracellular esterases produces Calcein, a hydrophilic, strongly fluorescent compound that is well-retained in the cell cytoplasm. HeLa cells with intracellular Calcein were then centrifuged and incubated in complete medium before being exposed to WT or NKG2A-KO NK cells in a 96-well plate for 4 hrs at 37° C. Killing of the target HeLa cells by effector NK cells results in release of the intracellular Calcein into the extracellular medium. The 96-well plate was then centrifuged for 5 minutes at 1250 rpm and the Calcein signal in the supernatant was analyzed by spectrophotometry with excitation at 488 nm and detection at 510 nm. Results are shown in FIG. 57B, which presents the percentage of lysis of the target HeLa cells (measured by Calcein release) as a function of different ratios of effector NK cells to target HeLa cells (E:T ratio). The results indicate that the knock out of the NKG2A receptor expression on the surface of NK-92 cells ("NK92 NKG2A-KO") increased the cytotoxic activity of the effector cells as compared to wild-type NK-92 cells ("NK92-WT"). More specifically, NKG2A-KO NK-92 effector cells killed 10-15% more target HeLa cells than WT NK-92 cells at the different effector:target ratios (E:T ratios) tested.

G.10 Different Rationally-Designed Peptide Shuttle Agents Deliver CRISPR/Cpf1 Systems for B2M and NKG2A Gene Editing in HeLa and NK-92 Cells.

Cpf1-NLS recombinant protein was prepared as described in Example G.2. A mix composed of a Cpf1-NLS recombinant protein with a single guide crRNA (see below) targeting a nucleotide sequence of the B2M or the NKG2A genes was co-incubated with 20 NM or 6 µM of the indicated peptide and incubated with HeLa or NK-92 cells, respectively, for 1 min in PBS, using the transduction protocols as generally described in Example V.a. Cells were then washed with PBS and harvested to proceed with the T7E1 protocol assay as described in Example 13.4. The crRNA constructed and their targets were: B2M crRNA-G (SEQ ID NO: 168) and NKG2A crRNA (SEQ ID NO: 165).

Table G1 shows the percentage insertions and deletions (% INDELs) resulting from cleavage of the targeted genomic B2M and NKG2A DNA sequences with CRISPR/Cpf1 (1.33 µM) and crRNA (2 µM), which were transduced with the indicated peptides used at different concentrations in HeLa and NK-92 cells after T7E1 assay and direct quantification on agarose gel electrophoresis (n=2). The peptide FSD67, which failed to respect parameter (5) (low hydrophobic moment), failed to transduce CRISPR/Cpf1.

| Cells | Peptides | Gene target | % INDELs | Design parameters |
|---|---|---|---|---|
| HeLa | FSD43 | B2M | 50 | OK |
|  | FSD44 |  | 74 | OK |
|  | FSD45 |  | 45 | OK |
|  | FSD46 |  | 74 | OK |
|  | FSD47 |  | 55 | OK |
|  | FSD48 |  | 46 | OK |
|  | FSD49 |  | 27 | OK |
|  | FSD50 |  | 63 | OK |
|  | FSD51 |  | 65 | OK |
|  | FSD61 |  | 65 | OK |
|  | FSD62 |  | 65 | OK |
|  | FSD63 |  | 70 | OK |
|  | FSD99 |  | 49 | OK |
| NK-92 | FSD115 | B2M | 15 | OK |
|  | FSD99 | crRNA-G | 32 | OK |
|  | FSD44 |  | 19 | OK |
|  | FSD61 |  | 23 | OK |
|  | FSD63 |  | 10 | OK |
|  | FSD67 |  | 0 | Low hydrophobic moment (µH = 2.47) |
|  | FSD68 |  | 8 | No hydrophobic core |
|  | FSD69 |  | 23 | OK |
|  | FSD70 |  | 28 | OK |
|  | FSD71 |  | 15 | OK |
|  | FSD100 | NKG2A | 16 | OK |
|  | FSD101 |  | 17 | OK |

OK = peptide sequence respects parameters (1)-(15).

Example H

Rationally Designed Peptide Shuttle Agents Enable Transduction of Transcription Factor HOX64

Human HOXB4 recombinant protein (Example 14.1) was constructed, expressed and purified from a bacterial expression system as described in Example 1.4. THP-1 cells were cultured and tested in the protein transduction assay as generally described in Example 3.1b. Briefly, THP-1 cells were plated at 30 000 cells/well one day before transduction. HOXB4-WT recombinant protein (300 nM or 50 nM) was co-incubated with FSD10 or FSD18 (1 µM) and then exposed to THP-1 cells for 30 min in the presence of serum. The cells were subjected to real time-PCR analysis as described in Example 14.2 to measure the mRNA levels of a target gene as a marker for HOXB4 activity, which was then normalized to the target gene mRNA levels detected in the negative control cells (no treatment), to obtain a "Fold over control" value. Total RNA levels (ng/µL) were also measured as a marker for cell viability. Results are shown below.

TABLE H1

HOXB4-WT transduction by FSD10 and FSD18 in THP-1 cells

| Cells | Cargo/peptide | Conc. of peptide (µM) | Conc. of HOXB4-WT (µM) | Fold over control (mean ± St. Dev) | Total RNA in ng/µL (mean ± St. Dev) |
|---|---|---|---|---|---|
| THP-1 | No treatment | 0 | 0 | 1 ± 0.1 | 172 ± 9.21 |
| | HOXB4-WT alone | | 1.5 | 2.5 ± 0.2 | 175 ± 7.05 |
| | FSD10 alone | 1 | 0 | 1.1 ± 0.14 | 181 ± 10.7 |
| | FSD18 alone | | | 1.5 ± 0.09 | 157 ± 3.9 |
| | FSD10 + HOXB4-WT | | 0.3 | 17.5 ± 0.21 | 159 ± 12.5 |
| | | | 0.05 | 15.3 ± 0.3 | 176 ± 4.71 |
| | FSD18 + HOXB4-WT | | 0.3 | 15.8 ± 0.19 | 154 ± 11.24 |
| | | | 0.05 | 16.7 ± 15.61 | 154 ± 3.9 |

These results show that the shuttle agents FSD10 and FSD18 are able to deliver the transcription factor HOXB4-WT to the nucleus of THP-1 cells in the presence of serum, resulting in a dose-dependent increase in mRNA transcription of the target gene.

Example I

Co-Transduction with an Independent Fluorescent Protein Marker Enables Isolation of Successfully Transduced Cells The ability of domain-based and rationally-designed peptide shuttle agents described herein to co-transduce two different polypeptide cargos simultaneously is shown in Example 9.6 (i.e., co-transduction of the fluorescent proteins GFP-NLS and mCherry-NLS) and in Example G.6 (i.e., co-transduction of the genome editing complexes CRISPR/Cas9 and CRISPR/Cpf1).

The results presented in Example I demonstrate the successful co-transduction of a fluorescent protein marker (e.g., GFP-NLS) and a genome editing complex (e.g., CRISPR/Cpf1). Surprisingly, although co-transduction with the fluorescent protein marker was not found to significantly increase overall genome-editing efficiency per se, a strikingly high proportion of cells positive for genome-engineering were positive for the fluorescent protein marker. Isolating cells positive for the fluorescent protein marker resulted in a significant increase in the proportion of successfully genome-edited cells. Furthermore, the correlation was found to be concentration specific in that cell populations exhibiting the highest fluorescence of the protein marker also exhibited the highest proportion of successful genome-editing.

1.1 Enrichment of Genome-Edited T Cells by FACS Following Co-Transduction of CRIPSR/Cpf1-NLS and GFP-NLS Cpf1-NLS recombinant protein was prepared as described in Example G.2 and GFP-NLS recombinant protein was prepared as described in Example 5.1.

Unless otherwise specified, T cells used herein were obtained from healthy human blood collected in heparinized tubes. T cells were isolated using a Ficoll™ technique (Ficoll-Paque™ GE or Lymphoprep Stem Cell Technologies). Briefly, blood was mixed with the Ficoll™ solution in conical tubes (50 mL) and centrifuged at 2280 rpm for 20 minutes. Mononuclear cells were harvested and transferred in another conical tube (50 mL) before washing with PBS and centrifugation at 1100 rpm for 10 minutes. Cells were resuspended in 5 mL of PBS containing 20% FBS. Cells were counted and then incubated in a culture medium composed by RPMI advanced (cat: 12633012 ThermoFisher), 10% FBS, 1% Penstrep (15140122 ThermoFisher), 1% L-glutamine (25030081 ThermoFisher) IL-2 30U/ml). Next, T cells were enriched with a Human T cell Enrichment Kit (StemCell #cat: 19051) by negative selection following the manufacturer instructions. The enriched T cells were validated using a specific anti-CD3 antibody (Biolegend #cat: 300438). At this step, collected cells were typically around 99% T cells. T cells were activated by adding IL-2 at 30 U/mL and the anti-CD28 antibody (ThermoFisher #cat: 16-0289-85) in complete medium for 5 days prior to experimentation. The activation of T cell expansion was then double-checked with both anti-CD25 and anti-CD137 antibodies.

T cells were transduced with a CRISPR/Cpf1 complex comprising a guide RNA (B2M crRNA-E, SEQ ID NO: 166) designed to cleave and inactivate the B2M gene as generally described in Example G.2, resulting in the inactivation of cell surface HLA in genome-edited cells. Briefly, 4 million of activated T cells were used for each condition. In one experimental condition, cells were treated with a mix containing the peptide FSD18 at 15 µM and the CRISPR/Cpf1-NLS complex just before incubation with cells for 90 seconds. In a second experimental condition, GFP-NLS (20 µM) was added to the mix containing FSD18 at 15 µM and the CRISPR/Cpf1-NLS complex just before incubation with cells for 90 seconds. Untreated cells were used as negative control. After transduction, cells were washed and resuspended in culture media. Untreated cells and cells treated with the CRISPR/Cpf1-NLS complex were incubated in complete media for 48 hours before flow cytometry and T7E1 analysis. A first part of the cells treated with CRISPR/Cpf1-NLS and GFP-NLS complex were incubated for 48 hours in T cell medium before flow cytometry and T7E1 analysis. The second part of cells were centrifugated and resuspended in PBS with 1% serum. GFP positive (+) and GFP negative (−) cells were separated using cell sorters based on the fluorescence signal and fractions were collected and incubated for 48 hours in T cell medium before flow cytometry and T7E1 analysis.

Results are shown in FIGS. 58A-58F, in which quadrant 1 (Q1) represents cells that are HLA-positive (non-genome edited) and GFP-negative; quadrant 2 (Q2) represents cells that are HLA-positive (non-genome edited) and GFP-positive; quadrant 3 (Q3) represents cells that are HLA-negative (successfully genome edited) and GFP-positive; and quadrant 4 (Q4) represents cells that are HLA-negative (successfully genome edited) and GFP-negative. Flow cytometry results based on cell size and granularity using respectively the Forward Scatter (FSC) and the Side Scatter (SSC) parameters showed that co-delivery of GFP-NLS and CRISPR/Cpf1 systems under the tested conditions did not significantly affect the viability of the transduced T cells (data not shown).

As shown in FIG. 58A, "untreated" negative control cells not exposed to the peptide shuttle agent, GFP, nor CRISPR/Cpf1 resulted in 99% of cells in Q1 (non-genome edited, GFP-negative). FIG. 58B shows that cells exposed to the peptide FSD18 (15 µM) and CRISPR/Cpf1 in the absence of GFP-NLS resulted in 10.1% of cells in Q4—i.e., being HLA-negative (successfully genome-edited) and GFP-negative. FIG. 58C shows that cells exposed to both GFP-NLS and CRISPR/Cpf1 in the presence of the peptide FSD18, resulted in 65.7% (54.4%+11.3%) GFP-positive cells in Q2+Q3, and 11.7% (0.441%+11.3%) HLA-negative cells (successfully genome-edited) in Q3+Q4. Comparing FIGS. 58B and 58C, the presence or absence of GFP was not found to significantly increase overall genome editing efficiency (10.1% versus 11.7% of HLA-negative cells). Surprisingly, it was observed that over 96% of genome-edited cells (HLA-negative) were GFP-positive as well [FIG. 58C, Q3/(Q3+Q4)]. Fluorescence-activated cell sorting (FIG. 58D) of cells based on their GFP-fluorescence into a GFP-negative fraction (FIG. 58E) and a GFP-positive fraction (FIG. 58F) resulted in an increase in the proportion of genome-edited (HLA-negative) cells to 29.7% in the GFP-positive fraction (FIG. 58F). Strikingly, the proportion of genome-edited (HLA-negative) cells in the GFP-negative fraction (FIG. 58E) was less than 0.1%.

Each cell fraction was then subjected to the T7E1 cleavage assay as described in Example 13.4, and the different samples were subjected to agarose gel electrophoresis. The results are shown in FIG. 58G, wherein thin dashed arrows indicate the bands corresponding to the target gene, and thicker solid arrows indicate the bands corresponding to the CRISPR system-mediated cleavage products of this target gene, which indicate the successful transduction of fully functional CRISPR/Cpf1-NLS genome editing complexes. As can be seen in FIG. 58G, the GFP-positive cell fractions ("GFP+cells"; lane 4) had increased genome-editing efficiency as compared to cells before sorting ("no cell sorting"; lane 3). Peptide FSD18 and the CRISPR/Cpf1-NLS complex with GFP-NLS (lane 3) and without GFL-NLS (lane 2) showed the same genome editing level, indicating that the addition of GFP-NLS does not affect the transduction process. GFP-negative cell fractions (lane 5), and negative control ("untreated"; lane 1) demonstrated no detectable genome editing.

1.2 Further Enrichment of Genome-Edited T Cells by FACS Following Co-Transduction of CRIPSR/Cpf1-NLS and GFP-NLS The experiment described in Example 1.1 was repeated on activated T cells using 12 µM or 15 µM of the peptide FSD18. Since both concentrations of FSD18 produced similar results, only the results using 15 µM of FSD18 are shown herein. Flow cytometry results based on cell size and granularity using respectively the Forward Scatter (FSC) and the Side Scatter (SSC) parameters showed that co-delivery of GFP-NLS and CRISPR/Cpf1 systems under the tested conditions did not significantly affect the viability of the transduced T cells (data not shown).

FIGS. 59A and 59B, show the results of "untreated" negative control cells not exposed to the peptide shuttle agent, GFP, nor CRISPR/Cpf1, which were analyzed by flow cytometry for GFP fluorescence (FIG. 59A) and cell surface HLA expression (FIG. 59B). T cells were co-transduced with both GFP-NLS and CRISPR/Cpf1 via the peptide FSD18 (15 µM) and sorted based on their fluorescence signal, and cell fractions were collected and incubated for 48 hours. The resulting fraction of cells sorted for GFP fluorescence distribution is shown in FIG. 59C. The two gates in FIG. 59C indicate the fraction of cells that were considered to be GFP-positive ("GFP+"; 93.2%) and the sub-fraction of cells that were considered as exhibiting high GFP fluorescence ("GFP high"; 33.1%). Fluorescence-activated cell sorting analysis was performed to quantify the level of cell surface HLA expression in cells considered to be GFP-positive (FIG. 59D) as compared to cells considered as exhibiting high GFP fluorescence (FIG. 59E). As can be seen in FIG. 59D, 21.8% of GFP-positive cells were HLA-negative (successfully genome-edited), whereas this value rose to a striking 41.6% amongst cells exhibiting high GFP fluorescence (FIG. 59E). Thus, the proportion of successfully genome-edited (HLA-negative) cells increased with the fluorescence level of the fluorescent protein marker (GFP-NLS).

The above co-transduction experiment was repeated using 12 µM or 15 µM FSD18, followed by fluorescence-activated cell sorting into GFP-positive and GFP-negative cell fractions. Each fraction was subjected to the T7E1 cleavage assay as described in Example 13.4, and the different samples were subjected to agarose gel electrophoresis. Consistent with the results of the flow cytometry experiments described above, the results from T7E1 cleavage assays showed that the GFP-positive cell fractions had increased genome-editing efficiency as compared to in the GFP-negative cell fractions (data not shown).

1.3 Enrichment of Genome-Edited THP-1 Cells by FACS Following Co-Transduction of CRIPSR/Cpf1-NLS and GFP-NLS The experiments performed in Examples 1.1 and 1.2 were reproduced in THP-1 cells with similar results. Co-transduction of CRIPSR/Cpf1-NLS and GFP-NLS in the presence 2 µM FSD18, followed by fluorescence-activated cell sorting of GFP-positive cells resulted in a significant enrichment of genome edited cells (data not shown).

1.4 Successful Subsequent Transduction of Previously Sorted GFP-Negative Cells

This example shows that untransduced cells following a first round of transduction with a peptide shuttle agent are not necessarily refractory to subsequent transductions.

T cells obtained as described in Example 1.1 were subjected to a first transduction by co-incubation of FSD18 (10 µM) and GFP-NLS (20 µM) for 90 sec before washing and incubation at 37° C. The "untreated" negative control cells showed no GFP signal (FIG. 60A). Cell sorting was performed 18 h after GFP-NLS transduction. GFP-positive and GFP-negative cells were separated using cell sorters based on the fluorescence signal (see FIG. 60B), and GFP-negative cells were harvested and isolated (see FIG. 60C). A second GFP-NLS transduction was performed on the GFP-negative T cell population using the same protocol as the first transduction. GFP-NLS transduction was analyzed by flow cytometry as previously described 18 h later and GFP-positive cells were scored by flow cytometry. The results from this second transduction are shown in FIG. 60D, in which the GFP-NLS transduction efficiency was found to be 60.6%. These results indicate that untransduced cells following a first round of transduction with a peptide shuttle agent are not necessarily refractory to subsequent transductions, and that overall transduction efficiency in a starting cell population may be increased by repeated successive transduction experiments on the untransduced cell fraction. This method of repeated successive transduction experiments, along with the co-transduction results presented in Examples 1.1, 1.2 and 1.3, suggest an attractive method for increasing genome editing efficiency in valuable cell populations (e.g., patient-derived cells for cell therapy), and/or in cell populations that are inherently more difficult to transduce.

REFERENCES

Andreu, D., Ubach, J., Boman, A., Wahlin, B., Wade, D., Merrifield, R. B., and Boman, H. G. (1992) Shortened cecropin A-melittin hybrids. Significant size reduction retains potent antibiotic activity. FEBS letters 296, 190-194

Aguila, J. R., W. Liao, J. Yang, C. Avila, N. Hagag, L. Senzel and Y. Ma (2011). "SALL4 is a robust stimulator for the expansion of hematopoietic stem cells." Blood 118(3): 576-585.

Akinci, E., A. Banga, L. V. Greder, J. R. Dutton and J. M. Slack (2012). "Reprogramming of pancreatic exocrine cells towards a beta (beta) cell character using Pdx1, Ngn3 and MafA." Biochem J 442(3): 539-550.

Alford et al., (2009). "Toxicity of organic fluorophores used in molecular imaging: literature review." Mol Imaging. 8(6):341-54.

Amand, H. L., B. Norden and K. Fant (2012). "Functionalization with C-terminal cysteine enhances transfection efficiency of cell-penetrating peptides through dimer formation." Biochem Biophys Res Commun 418(3): 469-474.

Aoukaty, A. & Tan, R. (2005). Role for glycogen synthase kinase-3 in NK cell cytotoxicity and X-linked lymphoproliferative disease. J Immunol 174, 4551-8.

Barrangou, R. and Luciano A. Marraffini (2014). "CRISPR-Cas Systems: Prokaryotes Upgrade to Adaptive Immunity". Cell Volume 54, Issue 2, p234-244, 24 Apr. 2014.

Bejarano, L. A. and C. Gonzalez (1999). "Motif trap: a rapid method to clone motifs that can target proteins to defined subcellular localisations." J Cell Sci 112 (Pt 23): 4207-4211.

Bikard et al., Programmable repression and activation of bacterial gene expression using an engineered CRISPR-Cas system. Nucleic Acids Res. 41, 7429-7437.

Boman, H. G., Wade, D., Boman, I. A., Wahlin, B., and Merrifield, R. B. (1989) Antibacterial and antimalarial properties of peptides that are cecropin-melittin hybrids. FEBS letters 259,103-106.

Braud, V. M., Allan, D. S., O'Callaghan, C. A., Soderstrom, K., D'Andrea, A., Ogg, G. S., Lazetic, S., Young, N. T., Bell, J. I., Phillips, J. H., Lanier, L. L. & McMichael, A. J. (1998). HLA-E binds to natural killer cell receptors CD94/NKG2A, B and C. Nature 391, 795-9.

Buganim et al., (2014) "The Developmental Potential of iPSCs Is Greatly Influenced by Reprogramming Factor Selection". Cell stem cell. 15, 295-309.

Burstein et al., (2017), "New CRISPR-Cas systems from uncultivated microbes." Nature. 542(7640):237-241.

Chan, C. K. and D. A. Jans (1999). "Enhancement of polylysine-mediated transferrinfection by nuclear localization sequences: polylysine does not function as a nuclear localization sequence." Hum Gene Ther 10(10): 1695-1702.

Chan, C. K. and D. A. Jans (2001). "Enhancement of MSH receptor- and GAL4-mediated gene transfer by switching the nuclear import pathway." Gene Ther 8(2): 166-171.

Cong et al., (2013). Multiplex genome engineering using CRISPR/Cas systems. Science 339, 819-823.

Cooper, M. A., Fehniger, T. A. & Caligiuri, M. A. (2001). The biology of human natural killer-cell subsets. Trends Immunol 22, 633-40.

Cox et al. (2015). "Therapeutic genome editing: prospects and challenges". Nature medicine, 21:121-131.

de Kruijf, E. M., Sajet, A., van Nes, J. G., Natanov, R., Putter, H., Smit, V. T., Liefers, G. J., van den Eisen, P. J., van de Velde, C. J. & Kuppen, P. J. (2010). HLA-E and HLA-G expression in classical HLA class I-negative tumors is of prognostic value for clinical outcome of early breast cancer patients. J Immunol 185, 7452-9.

Delconte, R. B., Kolesnik, T. B., Dagley, L. F., Rautela, J., Shi, W., Putz, E. M., Stannard, K., Zhang, J. G., Teh, C., Firth, M., Ushiki, T., Andoniou, C. E., Degli-Esposti, M. A., Sharp, P. P., Sanvitale, C. E., Infusini, G., Liau, N. P., Linossi, E. M., Burns, C. J., Carotta, S., Gray, D. H., Seillet, C., Hutchinson, D. S., Belz, G. T., Webb, A. I., Alexander, W. S., Li, S. S., Bullock, A. N., Babon, J. J., Smyth, M. J., Nicholson, S. E. & Huntington, N. D. (2016). CIS is a potent checkpoint in NK cell-mediated tumor immunity. Nat Immunol 17, 816-24.

Denman, C. J., Senyukov, V. V., Somanchi, S. S., Phatarpekar, P. V., Kopp, L. M., Johnson, J. L., Singh, H., Hurton, L., Maiti, S. N., Huls, M. H., Champlin, R. E., Cooper, L. J. & Lee, D. A. (2012). Membrane-bound IL-21 promotes sustained ex vivo proliferation of human natural killer cells. PLoS ONE 7, e30264.

Dolfini, D., M. Minuzzo, G. Pavesi and R. Mantovani (2012). "The short isoform of NF-YA belongs to the embryonic stem cell transcription factor circuitry." Stem Cells 30(11): 2450-2459.

Drin, G., S. Cottin, E. Blanc, A. R. Rees and J. Temsamani (2003). "Studies on the internalization mechanism of cationic cell-penetrating peptides." J Biol Chem 278(33): 31192-31201.

Eisenberg et al., (1982). "The helical hydrophobic moment: a measure of the amphiphilicity of a helix". Nature 299, 371-374.

EI-Andaloussi, S., H. J. Johansson, T. Holm and U. Langel (2007). "A novel cell-penetrating peptide, M918, for efficient delivery of proteins and peptide nucleic acids." Mol Ther 15(10): 1820-1826.

EI-Sayed, A., S. Futaki and H. Harashima (2009). "Delivery of macromolecules using arginine-rich cell-penetrating peptides: ways to overcome endosomal entrapment." AAPS J 11(1): 13-22.

Elmquist, A., M. Lindgren, T. Bartfai and U. Langel (2001). "VE-cadherin-derived cell-penetrating peptide, pVEC, with carrier functions." Exp Cell Res 269(2): 237-244.

Erazo-Oliveras et al., (2014) "Protein delivery into live cells by incubation with an endosomolytic agent." Nat Methods. (8):861-7.

Fanara, P., M. R. Hodel, A. H. Corbett and A. E. Hodel (2000). "Quantitative analysis of nuclear localization signal (NLS)-importin alpha interaction through fluorescence depolarization. Evidence for auto-inhibitory regulation of NLS binding." J Biol Chem 275(28): 21218-21223.

Fasoli A et al., (2014) "Mechanistic insight into CM18-Tat11 peptide membrane-perturbing action by whole-cell patch-clamp recording." Molecules. 19(7):9228-39.

Fawell, S., J. Seery, Y. Daikh, C. Moore, L. L. Chen, B. Pepinsky and J. Barsoum (1994). "Tat-mediated delivery of heterologous proteins into cells." Proc Natl Acad Sci USA 91(2): 664-668.

Fominaya, J., C. Uherek and W. Wels (1998). "A chimeric fusion protein containing transforming growth factor-alpha mediates gene transfer via binding to the EGF receptor." Gene Ther 5(4): 521-530.

Fominaya, J. and W. Wels (1996). "Target cell-specific DNA transfer mediated by a chimeric multidomain protein. Novel non-viral gene delivery system." J Biol Chem 271(18): 10560-10568.

Fonoudi, H., M. Yeganeh, F. Fattahi, Z. Ghazizadeh, H. Rassouli, M. Alikhani, B. A. Mojarad, H. Baharvand, G. H. Salekdeh and N. Aghdami (2013). "ISL1 protein transduction promotes cardiomyocyte differentiation from human embryonic stem cells." PLoS One 8(1): e55577.

Gao et al., (2016) DNA-guided genome editing using the Natronobacterium gregoryi Argonaute. Nature Biotechnology 34, 768-773.

Giguere et al., Machine learning assisted design of highly active peptides for drug discovery. PLoS Comput Biol. 2015 Apr. 7; 11(4):e1004074.

Gilbert et al., CRISPR-mediated modular RNA-guided regulation of transcription in eukaryotes. Cell 154, 442-451.

Gilmore, T. D. and H. M. Temin (1988). "v-rel oncoproteins in the nucleus and in the cytoplasm transform chicken spleen cells." J Virol 62(3): 703-714.

Glover, D. J., S. M. Ng, A. Mechler, L. L. Martin and D. A. Jans (2009). "Multifunctional protein nanocarriers for targeted nuclear gene delivery in nondividing cells." FASEB J 23(9): 2996-3006.

Gordon, S. M., J. Chaix, L. J. Rupp, J. Wu, S. Madera, J. C. Sun, T. Lindsten and S. L. Reiner (2012). "The transcription factors T-bet and Eomes control key checkpoints of natural killer cell maturation." Immunity 36(1): 55-67.

Gottschalk, S., J. T. Sparrow, J. Hauer, M. P. Mims, F. E. Leland, S. L. Woo and L. C. Smith (1996). "A novel DNA-peptide complex for efficient gene transfer and expression in mammalian cells." Gene Ther 3(5): 448-457.

Gould, S. J., G. A. Keller, N. Hosken, J. Wilkinson and S. Subramani (1989). "A conserved tripeptide sorts proteins to peroxisomes." J Cell Biol 108(5): 1657-1664.

Green, M. and P. M. Loewenstein (1988). "Autonomous functional domains of chemically synthesized human immunodeficiency virus tat trans-activator protein." Cell 55(6): 1179-1188.

Grimes, M. L., J. Zhou, E. C. Beattie, E. C. Yuen, D. E. Hall, J. S. Valletta, K. S. Topp, J. H. LaVail, N. W. Bunnett and W. C. Mobley (1996). "Endocytosis of activated TrkA: evidence that nerve growth factor induces formation of signaling endosomes." J Neurosci 16(24): 7950-7964.

Guo, Z. Y., Lv, Y. G., Wang, L., Shi, S. J., Yang, F., Zheng, G. X., Wen, W. H. & Yang, A. G. (2015). Predictive value of HLA-G and HLA-E in the prognosis of colorectal cancer patients. Cell Immunol 293,10-6.

Hallbrink, M., A. Floren, A. Elmquist, M. Pooga, T. Bartfai and U. Langel (2001). "Cargo delivery kinetics of cell-penetrating peptides." Biochim Biophys Acta 1515(2): 101-109.

Herce, H. D. and A. E. Garcia (2007). "Molecular dynamics simulations suggest a mechanism for translocation of the HIV-1 TAT peptide across lipid membranes." Proc Nat Acad Sci USA 104(52): 20805-20810.

Ho et al., (2001). "Synthetic protein transduction domains: enhanced transduction potential in vivo." Cancer Research 61: 474-477.

Homg, T., Bezbradica, J. S. & Medzhitov, R. (2007). NKG2D signaling is coupled to the interleukin 15 receptor signaling pathway. Nat Immunol 8,1345-52.

Hurt, E. C., B. Pesold-Hurt, K. Suda, W. Oppliger and G. Schatz (1985). "The first twelve amino acids (less than half of the pre-sequence) of an imported mitochondrial protein can direct mouse cytosolic dihydrofolate reductase into the yeast mitochondrial matrix." EMBO J 4(8): 2061-2068.

Ichii, H., A. Sakamoto, Y. Kuroda and T. Tokuhisa (2004). "Bcl6 acts as an amplifier for the generation and proliferative capacity of central memory CD8+ T cells." J Immunol 173(2): 883-891.

Irie, Y., K. Yamagata, Y. Gan, K. Miyamoto, E. Do, C. H. Kuo, E. Taira and N. Miki (2000). "Molecular cloning and characterization of Amida, a novel protein which interacts with a neuron-specific immediate early gene product arc, contains novel nuclear localization signals, and causes cell death in cultured cells." J Biol Chem 275(4): 2647-2653.

Ishigami, S., Arigami, T., Okumura, H., Uchikado, Y., Kita, Y., Kurahara, H., Maemura, K., Kijima, Y., Ishihara, Y., Sasaki, K., Uenosono, Y. & Natsugoe, S. (2015). Human leukocyte antigen (HLA)-E and HLA-F expression in gastric cancer. Anticancer Res 35, 2279-85.

Kakudo, T., S. Chaki, S. Futaki, I. Nakase, K. Akaji, T. Kawakami, K. Maruyama, H. Kamiya and H. Harashima (2004). "Transferrin-modified liposomes equipped with a pH-sensitive fusogenic peptide: an artificial viral-like delivery system." Biochemistry 43(19): 5618-5628.

Kamiely, S. and O. Pines (2005). "Single translation—dual destination: mechanisms of dual protein targeting in eukaryotes." EMBO Rep 6(5): 420-425.

Kato, G. J., W. M. Lee, L. L. Chen and C. V. Dang (1992). "Max: functional domains and interaction with c-Myc." Genes Dev 6(1): 81-92.

Kichler, A., A. J. Mason and B. Bechinger (2006). "Cationic amphipathic histidine-rich peptides for gene delivery." Biochim Biophys Acta 1758(3): 301-307.

Kichler et al., (2003). "Histidine-rich amphipathic peptide antibiotics promote efficient delivery of DNA into mammalian cells". Proc Natl Acad Sci USA. 2003 Feb. 18; 100(4): 1564-1568.

Kira et al., (2011). "Unification of Cas protein families and a simple scenario for the origin and evolution of CRISPR-Cas systems". Biol Direct. 2011; 6: 38.

Kirwan, S. E. & Burshtyn, D. N. (2005). Killer cell Ig-like receptor-dependent signaling by Ig-like transcript 2 (ILT2/CD85j/LILRB1/LIR-1). J Immunol 175, 5006-15.

Kleinschmidt, J. A. and A. Seiter (1988). "Identification of domains involved in nuclear uptake and histone binding of protein N1 of Xenopus laevis." EMBO J 7(6): 1605-1614.

Kohler, M., D. Gorlich, E. Hartmann and J. Franke (2001). "Adenoviral E1A protein nuclear import is preferentially mediated by importin alpha3 in vitro." Virology 289(2): 186-191.

Kwon, et al., (2010). "A Truncated HGP Peptide Sequence That Retains Endosomolytic Activity and Improves Gene Delivery Efficiencies". Mol. Pharmaceutics, 7:1260-65.

Lamiable et al., (2016). "PEP-FOLD3: faster de novo structure prediction for linear peptides in solution and in complex" Nucleic Acids Res. 44(W1):W449-54.

Lanford, R. E., P. Kanda and R. C. Kennedy (1986). "Induction of nuclear transport with a synthetic peptide homologous to the SV40 T antigen transport signal." Cell 46(4): 575-582.

Lee, N., Llano, M., Carretero, M., Ishitani, A., Navarro, F., Lopez-Botet, M. & Geraghty, D. E. (1998). HLA-E is a major ligand for the natural killer inhibitory receptor CD94/NKG2A. Proc Natl Acad Sci USA 95, 5199-204.

Levy, E. M., Bianchini, M., Von Euw, E. M., Barrio, M. M., Bravo, A. I., Furman, D., Domenichini, E., Macagno, C., Pinsky, V., Zucchini, C., Valvassori, L. & Mordoh, J. (2008). Human leukocyte antigen-E protein is overexpressed in primary human colorectal cancer. Int J Oncol 32, 633-41.

Li, W., F. Nicol and F. C. Szoka, Jr. (2004). "GALA: a designed synthetic pH-responsive amphipathic peptide with applications in drug and gene delivery." Adv Drug Deliv Rev 56(7): 967-985.

Lin, M. H., F. C. Chou, L. T. Yeh, S. H. Fu, H. Y. Chiou, K. I. Lin, D. M. Chang and H. K. Sytwu (2013). "B lymphocyte-induced maturation protein 1 (BLIMP-1) attenuates autoimmune diabetes in NOD mice by suppressing Th1 and Th17 cells." Diabetologia 56(1): 136-146.

Liu, X., P. K. Tian, D. W. Ju, M. H. Zhang, M. Yao, X. T. Cao and J. R. Gu (2003). "Systemic genetic transfer of p21WAF-1 and GM-CSF utilizing of a novel oligopeptide-based EGF receptor targeting polyplex." Cancer Gene Ther 10(7): 529-539.

Loeser, S., Loser, K., Bijker, M. S., Rangachari, M., van der Burg, S. H., Wada, T., Beissert, S., Melief, C. J. & Penninger, J. M. (2007). Spontaneous tumor rejection by cbl-b-deficient CD8+ T cells. J Exp Med 204, 879-91.

London, E. (1992). "Diphtheria toxin: membrane interaction and membrane translocation." Biochim Biophys Acta 1113(1): 25-51.

Lord-Dufour et al., (2009) "Evidence for transcriptional regulation of the glucose-6-phosphate transporter by HIF-1alpha: Targeting G6PT with mumbaistatin analogs in hypoxic mesenchymal stromal cells". Stem cells 27:489-497.

Lorieau, J. L., J. M. Louis and A. Bax (2010). "The complete influenza hemagglutinin fusion domain adopts a tight helical hairpin arrangement at the lipid:water interface." Proc Natl Acad Sci USA 107(25): 11341-11346.

Lin, A., Yan, W. H., Xu, H. H., Gan, M. F., Cai, J. F., Zhu, M. & Zhou, M. Y. (2007). HLA-G expression in human ovarian carcinoma counteracts NK cell function. Ann Oncol 18,1804-9.

Liu, Q., Zhou, H., Langdon, W. Y. & Zhang, J. (2014). E3 ubiquitin ligase Cbl-b in innate and adaptive immunity. Cell Cycle 13,1875-84.

Lu, S. J., Q. Feng, Y. lvanova, C. Luo, T. Li, F. Li, G. R. Honig and R. Lanza (2007). "Recombinant HoxB4 fusion proteins enhance hematopoietic differentiation of human embryonic stem cells." Stem Cells Dev 16(4): 547-559.

Luan et al., (2015). "Peptide amphiphiles with multifunctional fragments promoting cellular uptake and endosomal escape as efficient gene vectors." J. Mater. Chem. B, 3:1068-1078.

Lutz-Nicoladoni, C., Wolf, D. & Sopper, S. (2015). Modulation of Immune Cell Functions by the E3 Ligase Cbl-b. Front Oncol 5, 58.

Mack, M., B. Luckow, P. J. Nelson, J. Cihak, G. Simmons, P. R. Clapham, N. Signoret, M. Marsh, M. Stangassinger, F. Borlat, T. N. Wells, D. Schlondorff and A. E. Proudfoot (1998). "Aminooxypentane-RANTES induces CCR5 internalization but inhibits recycling: a novel inhibitory mechanism of HN infectivity." J Exp Med 187(8): 1215-1224.

Maeng, C. H., J. H. Yi, J. Lee, J. Y. Hong, M. K. Choi, H. A. Jung, J. O. Park, S. H. Park, Y. S. Park, W. K. Kang and H. Y. Lim (2013). "Effects of single nucleotide polymorphisms on treatment outcomes and toxicity in patients treated with sunitinib." Anticancer Res 33(10): 4619-4626.

Mahlum, E., D. Mandal, C. Halder, A. Maran, M. J. Yaszemski, R. B. Jenkins, M. E. Bolander and G. Sarkar (2007). "Engineering a noncarrier to a highly efficient carrier peptide for noncovalently delivering biologically active proteins into human cells." Anal Biochem 365(2): 215-221.

Makarova et al., (2011) "Evolution and classification of the CRISPR-Cas systems". Nat Rev Microbiol. 9(6):467-77.

Makkerh, J. P., C. Dingwall and R. A. Laskey (1996). "Comparative mutagenesis of nuclear localization signals reveals the importance of neutral and acidic amino acids." Curr Biol 6(8): 1025-1027.

Martinez-Fong, D., I. Navarro-Quiroga, I. Ochoa, I. Alvarez-Maya, M. A. Meraz, J. Luna and J. A. Arias-Montano (1999). "Neurotensin-SPDP-poly-L-lysine conjugate: a nonviral vector for targeted gene delivery to neural cells." Brain Res Mol Brain Res 69(2): 249-262.

Matalon, O., Fried, S., Ben-Shmuel, A., Pauker, M. H., Joseph, N., Keizer, D., Piterburg, M. & Barda-Saad, M. (2016). Dephosphorylation of the adaptor LAT and phospholipase C-gamma by SHP-1 inhibits natural killer cell cytotoxicity. Sci Signal 9, raS4.

Maurer, M. and E. von Stebut (2004). "Macrophage inflammatory protein-1." Int J Biochem Cell Biol 36(10): 1882-1886.

McKay, T., P. Reynolds, S. Jezzard, D. Curiel and C. Coutelle (2002). "Secretin-mediated gene delivery, a specific targeting mechanism with potential for treatment of biliary and pancreatic disease in cystic fibrosis." Mol Ther 5(4): 447-454.

Midoux, P., A. Kichler, V. Boutin, J. C. Maurizot and M. Monsigny (1998). "Membrane permeabilization and efficient gene transfer by a peptide containing several histidines." Bioconjug Chem 9(2): 260-267.

Milenkovic, D., T. Ramming, J. M. Muller, L. S. Wenz, N. Gebert, A. Schulze-Specking, D. Stojanovski, S. Rospert and A. Chacinska (2009). "Identification of the signal directing Tim9 and Tim10 into the intermembrane space of mitochondria." Mol Biol Cell 20(10): 2530-2539.

Miyoshi, I., N. Kasai and Y. Hayashizaki (1994). "[Structure and regulation of human thyroid-stimulating hormone (TSH) gene]." Nihon Rinsho 52(4): 940-947.

Moede, T., B. Leibiger, H. G. Pour, P. Berggren and I. B. Leibiger (1999). "Identification of a nuclear localization signal, RRMKWKK, in the homeodomain transcription factor PDX-1." FEBS Lett 461(3): 229-234.

Montrose, K., Y. Yang, X. Sun, S. Wiles and G. W. Krissansen (2013). "Xentry, a new class of cell-penetrating peptide uniquely equipped for delivery of drugs." Sci Rep 3:1661.

Moreland, R. B., G. L. Langevin, R. H. Singer, R. L. Garcea and L. M. Hereford (1987). "Amino acid sequences that determine the nuclear localization of yeast histone 2B." Mol Cell Biol 7(11): 4048-4057.

Morris, M. C., L. Chaloin, M. Choob, J. Archdeacon, F. Heitz and G. Divita (2004). "Combination of a new generation of PNAs with a peptide-based carrier enables efficient targeting of cell cycle progression." Gene Ther 11(9): 757-764.

Morris, M. C., J. Depollier, J. Mery, F. Heitz and G. Divita (2001). "A peptide carrier for the delivery of biologically active proteins into mammalian cells." Nat Biotechnol 19(12): 1173-1176.

Nakanishi, A., D. Shum, H. Morioka, E. Otsuka and H. Kasamatsu (2002). "Interaction of the Vp3 nuclear localization signal with the importin alpha 2/beta heterodimer directs nuclear entry of infecting simian virus 40." J Virol 76(18): 9368-9377.

O'Keefe, D. O. (1992). "Characterization of a full-length, active-site mutant of diphtheria toxin." Arch Biochem Biophys 296(2): 678-684.

Paolino, M., Choidas, A., Wallner, S., Pranjic, B., Uribesalgo, I., Loeser, S., Jamieson, A. M., Langdon, W. Y., Ikeda, F., Fededa, J. P., Cronin, S. J., Nitsch, R., Schultz-Fademrecht, C., Eickhoff, J., Menninger, S., Unger, A., Torka, R., Gruber, T., Hinterleitner, R., Baier, G., Wolf, D., Ullrich, A., Klebl, B. M. & Penninger, J. M. (2014). The E3 ligase Cbl-b and TAM receptors regulate cancer metastasis via natural killer cells. Nature 507, 508-12.

Parente, R. A., S. Nir and F. C. Szoka, Jr. (1990). "Mechanism of leakage of phospholipid vesicle contents induced by the peptide GALA." Biochemistry 29(37): 8720-8728.

Parameswaran, R., Ramakrishnan, P., Moreton, S. A., Xia, Z., Hou, Y., Lee, D. A., Gupta, K., deLima, M., Beck, R. C. & Wald, D. N. (2016). Repression of GSK3 restores NK cell cytotoxicity in AML patients. Nat Commun 7, 11154.

Patel, P. & Woodgett, J. R. (2017). Glycogen Synthase Kinase 3: A Kinase for All Pathways?Curr Top Dev Biol 123, 277-302.

Paul, R. W., K. E. Weisser, A. Loomis, D. L. Sloane, D. LaFoe, E. M. Atkinson and R. W. Overell (1997). "Gene transfer using a novel fusion protein, GAL4/invasin." Hum Gene Ther 8(10): 1253-1262.

Perez, F., A. Joliot, E. Bloch-Gallego, A. Zahraoui, A. Triller and A. Prochiantz (1992). "Antennapedia homeobox as a signal for the cellular internalization and nuclear addressing of a small exogenous peptide." J Cell Sci 102 (Pt 4): 717-722.

Pimenta, D. C., V. C. Chen, J. Chao, M. A. Juliano and L. Juliano (2000). "Alpha1-antichymotrypsin and kallistatin hydrolysis by human cathepsin D." J Protein Chem 19(5): 411-418.

Poli, A., Michel, T., Theresine, M., Andres, E., Hentges, F. & Zimmer, J. (2009). CD56bright natural killer (NK) cells: an important NK cell subset. Immunology 126, 458-65.

Prieve, M. G. and M. L. Waterman (1999). "Nuclear localization and formation of beta-catenin-lymphoid enhancer factor 1 complexes are not sufficient for activation of gene expression." Mol Cell Biol 19(6): 4503-4515.

Rajagopalan, R., J. Xavier, N. Rangaraj, N. M. Rao and V. Gopal (2007). "Recombinant fusion proteins TAT-Mu, Mu and Mu-Mu mediate efficient non-viral gene delivery." J Gene Med 9(4): 275-286.

Riddell et al., (2014) "Reprogramming committed murine blood cells to induced hematopoietic stem cells with defined factors". Cell, 157:549-564

Salomone, F., F. Cardarelli, M. Di Luca, C. Boccardi, R. Nifosi, G. Bardi, L. Di Bari, M. Serresi and F. Beltram (2012). "A novel chimeric cell-penetrating peptide with membrane-disruptive properties for efficient endosomal escape." J Control Release 163(3): 293-303.

Salomone F., Cardarelli F, Signore G, Boccardi C, Beltram F. (2013) "In vitro efficient transfection by $CM_{18}$-$Tat_{11}$ hybrid peptide: a new tool for gene-delivery applications." PLoS One. 8(7):e70108.

Schneider, H., R. P. Harbottle, Y. Yokosaki, J. Kunde, D. Sheppard and C. Coutelle (1998). "A novel peptide, PLAEIDGIELTY, for the targeting of alpha9beta1-integrins." FEBS Lett 429(3): 269-273.

Schreiber, V., M. Molinete, H. Boeuf, G. de Murcia and J. Menissier-de Murcia (1992). "The human poly(ADP-ribose) polymerase nuclear localization signal is a bipartite element functionally separate from DNA binding and catalytic activity." EMBO J 11(9): 3263-3269.

Schuster, M. J., G. Y. Wu, C. M. Walton and C. H. Wu (1999). "Multicomponent DNA carrier with a vesicular stomatitis virus G-peptide greatly enhances liver-targeted gene expression in mice." Bioconjug Chem 10(6): 1075-1083.

Scott, M. S., F. M. Boisvert, M. D. McDowall, A. I. Lamond and G. J. Barton (2010). "Characterization and prediction of protein nucleolar localization sequences." Nucleic Acids Res 38(21): 7388-7399.

Shaw, P. A., I. R. Catchpole, C. A. Goddard and W. H. Colledge (2008). "Comparison of protein transduction domains in mediating cell delivery of a secreted CRE protein." Biochemistry 47(4): 1157-1166.

Shawe-Taylor J, Cristianini N (2004) Kemel methods for pattern analysis. Cambridge university press.

Shen et al., (2014) "Improved PEP-FOLD approach for peptide and miniprotein structure prediction". J. Chem. Theor. Comput. 10:4745-4758.

Shoya, Y., T. Kobayashi, T. Koda, K. Ikuta, M. Kakinuma and M. Kishi (1998). "Two proline-rich nuclear localization signals in the amino- and carboxyl-terminal regions of the Borna disease virus phosphoprotein." J Virol 72(12): 9755-9762.

Somasekaram, A., A. Jarmuz, A. How, J. Scott and N. Navaratnam (1999). "Intracellular localization of human cytidine deaminase. Identification of a functional nuclear localization signal." J Biol Chem 274(40): 28405-28412.

Stojanovski, D., M. Bohnert, N. Pfanner and M. van der Laan (2012). "Mechanisms of protein sorting in mitochondria." Cold Spring Harb Perspect Biol 4(10).

Sudbeck, P. and G. Scherer (1997). "Two independent nuclear localization signals are present in the DNA-binding high-mobility group domains of SRY and SOX9." J Biol Chem 272(44): 27848-27852.

Sung, M. S., J. Y. Mun, O. Kwon, K. S. Kwon and D. B. Oh (2013). "Efficient myogenic differentiation of human adipose-derived stem cells by the transduction of engineered MyoD protein." Biochem Biophys Res Commun 437(1): 156-161.

Takahashi, K. and S. Yamanaka (2006). "Induction of pluripotent stem cells from mouse embryonic and adult fibroblast cultures by defined factors." Cell 126(4): 663-676.

Takeda, A., C. Goolsby and N. R. Yaseen (2006). "NUP98-HOXA9 induces long-term proliferation and blocks differentiation of primary human CD34+hematopoietic cells." Cancer Res 66(13): 6628-6637.

Tan, Y., Z. Xie, M. Ding, Z. Wang, Q. Yu, L. Meng, H. Zhu, X. Huang, L. Yu, X. Meng and Y. Chen (2010). "Increased levels of FoxA1 transcription factor in pluripotent P19 embryonal carcinoma cells stimulate neural differentiation." Stem Cells Dev 19(9): 1365-1374.

Tan, Y. X., C. Chen, Y. L. Wang, S. Lin, Y. Wang, S. B. Li, X. P. Jin, H. W. Gao, F. S. Du, F. Gong and S. P. Ji (2012). "Truncated peptides from melittin and its analog with high lytic activity at endosomal pH enhance branched polyethylenimine-mediated gene transfection." J Gene Med 14(4): 241-250.

Thevenet et al., "PEP-FOLD: an updated de novo structure prediction server for both linear and disulfide bonded cyclic peptides." Nucleic Acids Res. 2012. 40, W288-293.

Uherek, C., J. Fominaya and W. Wels (1998). "A modular DNA carrier protein based on the structure of diphtheria toxin mediates target cell-specific gene delivery." J Biol Chem 273(15): 8835-8841.

Varkouhi, A. K., M. Scholte, G. Storm and H. J. Haisma (2011). "Endosomal escape pathways for delivery of biologicals." J Control Release 151(3): 220-228.

Veach, R. A., D. Liu, S. Yao, Y. Chen, X. Y. Liu, S. Downs and J. Hawiger (2004). "Receptor/transporter-independent targeting of functional peptides across the plasma membrane." J Biol Chem 279(12): 11425-11431.

Vives, E., P. Brodin and B. Lebleu (1997). "A truncated HIV-1 Tat protein basic domain rapidly translocates through the plasma membrane and accumulates in the cell nucleus." J Biol Chem 272(25): 16010-16017.

Wagstaff, K. M., D. J. Glover, D. J. Tremethick and D. A. Jans (2007). "Histone-mediated transduction as an efficient means for gene delivery." Mol Ther 15(4): 721-731.

Warr, M. R., M. Binnewies, J. Flach, D. Reynaud, T. Garg, R. Malhotra, J. Debnath and E. Passegue (2013). "FOX03A directs a protective autophagy program in haematopoietic stem cells." Nature 494(7437): 323-327.

Welch, K., J. Franke, M. Kohler and I. G. Macara (1999). "RanBP3 contains an unusual nuclear localization signal that is imported preferentially by importin-alpha3." Mol Cell Biol 19(12): 8400-8411.

Wiedenheft et al., (2011). RNA-guided complex from a bacterial immune system enhances target recognition through seed sequence interactions. Proc. Natl. Acad. Sci. USA 108,10092-10097.

Witzel, I., M. Graeser, T. Karn, M. Schmidt, R. Wirtz, D. Schutze, A. Rausch, F. Janicke, K. Milde-Langosch and V. Muller (2013). "Androgen receptor expression is a predictive marker in chemotherapy-treated patients with endocrine receptor-positive primary breast cancers." J Cancer Res Clin Oncol 139(5): 809-816.

Wu, J., L. Zhou, K. Tonissen, R. Tee and K. Artzt (1999). "The quaking I-5 protein (QKI-5) has a novel nuclear localization signal and shuttles between the nucleus and the cytoplasm." J Biol Chem 274(41): 29202-29210.

Wu, D., Kuiaste, I., Moreau, P., Carosella, E. & Yotnda, P. (2015). Rescuing lymphocytes from HLA-G immunosuppressive effects mediated by the tumor microenvironment. Oncotarget 6, 37385-97.

Wyman, T. B., F. Nicol, 0. Zelphati, P. V. Scaria, C. Plank and F. C. Szoka, Jr. (1997). "Design, synthesis, and characterization of a cationic peptide that binds to nucleic acids and permeabilizes bilayers." Biochemistry 36(10): 3008-3017.

Ye, S. R., Yang, H., Li, K., Dong, D. D., Lin, X. M. & Yie, S. M. (2007a). Human leukocyte antigen G expression: as a significant prognostic indicator for patients with colorectal cancer. Mod Pathol 20, 375-83.

Yie, S. M., Yang, H., Ye, S. R., Li, K., Dong, D. D. & Lin, X. M. (2007b). Expression of human leukocyte antigen G (HLA-G) correlates with poor prognosis in gastric carcinoma. Ann Surg Oncol 14, 2721-9.

Yie, S. M., Yang, H., Ye, S. R., Li, K., Dong, D. D. & Lin, X. M. (2007c). Expression of human leucocyte antigen G (HLA-G) is associated with prognosis in non-small cell lung cancer. Lung Cancer 58, 267-74.

Yie, S. M., Yang, H., Ye, S. R., Li, K., Dong, D. D. & Lin, X. M. (2007d). Expression of HLA-G is associated with prognosis in esophageal squamous cell carcinoma. Am J Clin Pathol 128,1002-9.

Yu, Z., C. H. Lee, C. Chinpaisal and L. N. Wei (1998). "A constitutive nuclear localization signal from the second zinc-finger of orphan nuclear receptor TR2." J Endocrinol 159(1): 53-60.

Zetsche et al., (2015). "Cpf1 Is a Single RNA-Guided Endonuclease of a Class 2 CRISPR-Cas System". Cell. 25. pii: S0092-8674(15)01200-3 [http://dx.doi.org/10.1016/j.cell.2015.09.038].

Zhen, Z. J., Ling, J. Y., Cai, Y., Luo, W. B. & He, Y. J. (2013). Impact of HLA-E gene polymorphism on HLA-E expression in tumor cells and prognosis in patients with stage Ill colorectal cancer. Med Oncol 30, 482.

Zhou, H., S. Wu, J. Y. Joo, S. Zhu, D. W. Han, T. Lin, S. Trauger, G. Bien, S. Yao, Y. Zhu, G. Siuzdak, H. R. Scholer, L. Duan and S. Ding (2009). "Generation of induced pluripotent stem cells using recombinant proteins." Cell Stem Cell 4(5): 381-384. The primary amino acid sequences of peptides FSD5, FSD16, FSD18, FSD19, FSD20, FSD22, and FSD23 are related, as shown in the alignment below.

Example C

Computer-Assisted Design of Synthetic Peptide Shuttle Agents

C.1 Machine-Learning-Assisted Design Approach

The peptides listed in Table C1 were designed using an algorithm described in an article by S6bastien Gigubre et al. entitled "*Machine Learning Assisted Design of Highly Active Peptides for Drug Discovery*" (Gigu6re et al., 2014). This computational prediction method is founded on the use of algorithms based on the Kernel and machine learning methods (Shawe-Taylor J. and Cristianini N., 2004). These algorithms aim to sort peptides with maximal bioactivity depending on a biological effect of interest. Here, we considered all the peptides that we tested to date in protein transduction assays, and separated them into three distinct groups. The composition of the groups was based on a "transduction score" calculated as described in Example A. Group 1 was composed of peptides demonstrating efficient cell delivery with low toxicity; Group 2 was composed of peptides demonstrating efficient cell delivery but with elevated toxicity; and Group 3 was composed of peptides that did not demonstrate any significant polypeptide cargo transduction ability.

The scores of the peptides in each group were used as starting data points for the generation of further peptide variants. The algorithm was programmed to use the peptide sequences and the scores of the peptides of Group 1 as the positive references for the prediction of peptide variants with efficient transduction ability. The sequences and the scores of Groups 2 and 3 were included as negative controls in the algorithm to delineate the search field. The peptide variants generated by the algorithm were limited to those having a length of 35 amino acids. After running, the prediction method generated sixteen sequences (FSD27 to FSD42). After analyzing the sequences of these sixteen sequences with respect to the design parameters set forth in Table Al, only peptides FSD27, FSD34 and FSD40 satisfied all of the design parameters (see Table C2). The other peptide variants had one or more parameters outside those set forth in Table Al.

SEQUENCE LISTING

The patent contains a lengthy sequence listing. A copy of the sequence listing is available in electronic form from the USPTO web site (https://seqdata.uspto.gov/?pageRequest=docDetail&DocID=US12286632B2). An electronic copy of the sequence listing will also be available from the USPTO upon request and payment of the fee set forth in 37 CFR 1.19(b)(3).

What is claimed is:

1. A method for synthesizing a peptide having protein transduction activity, the method comprising:
   (a) designing a peptide which is:
      (1) a peptide soluble in aqueous solution having an overall length of between 20 and 150 amino acids comprising
      (2) an amphipathic alpha-helical motif having
      (3) a positively-charged hydrophilic outer face comprising: (a) at least two adjacent positively-charged K and/or R residues upon helical wheel projection; and/or (b) a segment of six adjacent residues comprising three to five K and/or R residues upon helical wheel projection, based on an alpha helix having angle of rotation between consecutive amino acids of 100 degrees and/or an alpha-helix having 3.6 residues per turn; and
      (4) a hydrophobic outer face comprising a highly hydrophobic core consisting of spatially adjacent L, I, F, V, W, and/or M amino acids representing 12 to 50% of the amino acids of the peptide, based on an open cylindrical representation of the alpha-helix having 3.6 residues per turn;
   wherein at least five of the following parameters (5) to (15) are respected:
      (5) the peptide has a hydrophobic moment ($\mu$) of 3.5 to 11;
      (6) the peptide has a predicted net charge of at least +4 at physiological pH, calculated from amino acid residues having charged side chains;
      (7) the peptide has an isoelectric point (pI) of 8 to 13;
      (8) the peptide is composed of 35% to 65% of any combination of the amino acids: A, C, G, I, L, M, F, P, W, Y, and V;
      (9) the peptide is composed of 0% to 30% of any combination of the amino acids: N, Q, S, and T;
      (10) the peptide is composed of 35% to 85% of any combination of the amino acids: A, L, K, or R;
      (11) the peptide is composed of 15% to 45% of any combination of the amino acids: A and L, provided there being at least 5% of L in the peptide;
      (12) the peptide is composed of 20% to 45% of any combination of the amino acids: K and R;
      (13) the peptide is composed of 0% to 10% of any combination of the amino acids: D and E;
      (14) the difference between the percentage of A and L residues in the peptide (% A+L), and the percentage of K and R residues in the peptide (% K+R), is less than or equal to 10%; and
      (15) the peptide is composed of 10% to 45% of any combination of the amino acids: Q, Y, W, P, I, S, G, V, F, E, D, C, M, N, T and H,
   (b) chemically synthesizing the peptide in (a),
   wherein said peptide is deemed to have protein transduction activity when target eukaryotic cells contacted for five minutes with an independent polypeptide cargo in the presence of at least 2.5 $\mu$M of the peptide results in an increase transduction efficiency and cytosolic delivery of the independent polypeptide cargo, as compared to in the absence of the peptide, wherein the peptide and the independent polypeptide cargo comprise independent polypeptide backbones or are not covalently bound, and
   wherein the peptide lacks a cell penetrating domain.

2. The method of claim 1, wherein said amphipathic alpha-helical motif comprises a positively-charged hydrophilic outer face comprising: (a) at least three or four adjacent positively-charged K and/or R residues upon helical wheel projection.

3. The method of claim 1, wherein said amphipathic alpha-helical motif comprises a hydrophobic outer face comprising: (a) at least two adjacent L residues upon helical wheel projection; and (b) a segment of ten adjacent residues comprising at least five hydrophobic residues selected from: L, I, F, V, W, and M, upon helical wheel projection, based on an alpha helix having angle of rotation between consecutive amino acids of 100 degrees and/or an alpha-helix having 3.6 residues per turn.

4. The method of claim 1, wherein said amphipathic alpha-helical motif has a hydrophobic moment ($\mu$) between a lower limit of 3.5 and an upper limit of 11.0.

5. The method of claim 1, wherein said hydrophobic outer face comprises a highly hydrophobic core consisting of spatially adjacent L, I, F, V, W, and/or M amino acids representing from 12% to 45% of the amino acids of the peptide.

6. The method of claim 1, wherein said hydrophobic outer face comprises a highly hydrophobic core consisting of spatially adjacent L, I, F, V, W, and/or M amino acids representing from 12% to 40% of the amino acids of the peptide.

7. The method of claim 1, wherein said peptide has an overall length of between 25 and 150 amino acids.

8. The method of claim 1, wherein said peptide has an overall length of between 20 and 125 amino acids.

9. The method of claim 1, wherein said peptide has an overall length of between 20 and 100 amino acids.

10. The method of claim 1, wherein said peptide has a hydrophobic moment ($\mu$) between a lower limit of 4.0 and an upper limit of 10.5.

11. The method of claim 1, wherein said peptide has a predicted net charge of between +4 to +15.

12. The method of claim 1, wherein said peptide has an isoelectric point (pI) of 8 to 13.

13. The method of claim 1, wherein said peptide has an isoelectric point (pI) of 9 to 13.

14. The method of claim 1, wherein said peptide has an isoelectric point (pI) of 10 to 13.

15. The method of claim 1, wherein said peptide respects at least six of parameters (5) to (15).

16. The method of claim 1, wherein said peptide respects at least seven of parameters (5) to (15).

17. The method of claim 1, wherein said peptide respects at least eight of parameters (5) to (15).

18. The method of claim 1, wherein said peptide further comprises a flexible linker domain rich in serine and/or glycine residues.

19. The method of claim 1, wherein said peptide further comprises a histidine-rich domain positioned towards the N terminus and/or towards the C terminus of the peptide, wherein said histidine-rich domain is a stretch of at least 3, at least 4, at least 5, or at least 6 amino acids comprising at least 50%, at least 55%, at least 60%, at least 65%, at least 70%, at least 75%, at least 80%, at least 85%, or at least 90% histidine residues; and/or comprises at least 2, at least 3, at least 4, at least 5, at least 6, at least 7, at least 8, or at least 9 consecutive histidine residues.

20. The method of claim 1, wherein said peptide comprises or consists of the amino acid sequence of:
  (a) [X1]-[X2]-[linker]-[X3]-[X4](Formula 1);
  (b) [X1]-[X2]-[linker]-[X4]-[X3](Formula 2);
  (c) [X2]-[X1]-[linker]-[X3]-[X4](Formula 3);
  (d) [X2]-[X1]-[linker]-[X4]-[X3](Formula 4);
  (e) [X3]-[X4]-[linker]-[X1]-[X2](Formula 5);
  (f) [X3]-[X4]-[linker]-[X2]-[X1](Formula 6);
  (g) [X4]-[X3]-[linker]-[X1]-[X2](Formula 7); or
  (h) [X4]-[X3]-[linker]-[X2]-[X1](Formula 8),
  wherein:
    [X1] is selected from: 2[ζ]-1[+]-2[ζ]-1[ζ]-1[+]-; 2[ζ]-1[+]-2[ζ]-2[+]-; 1[+]-1[ζ]-1[+]-2[ζ]-1[ζ]-1[+]-; and 1[+]-1[ζ]-1[+]-2[D]-2[+]-;
    [X2] is selected from: -2[(D)]-1[+]-2[(D)-2[ζ]-; -2[ζ]-1[+]-2[ζ]-2[+]-; -2[ζ]-1[+]-2[ζ]-1[+[ζ];- 2[ζ]-1[+]-2[ζ]-1[ζ]-1 [+]-; -2[ζ]-2[+]-1[ζ]-2 [+]-; -2[ζ]-2[+]-1[ζ]-2[ζ]-; -2[ζ]-2[+]-1 [ζ]-1 [+]-1 [ζ]-; and -2[(D)-2[+]-1 [ζ]-1[ζ]-1 [+]-;
    [X3] is selected from: -4[+]-A-; -3[+]-G-A-; -3[+]-A-A-; -2[+]-1[ζ]-1[+]-A-; -2[+]-1[ζ]-G-A-; -2[+]-1[ζ]-A-A-; or -2[+]-A-1[+]-A; -2[+]-A-G-A; -2[+]-A-A-A-; -1[ζ]-3[+]-A-; -1[ζ]-2 [+]-G-A-; -1[ζ]-2[+]-A-A-; -1[ζ]-1[+]-1[ζ]-1 [+]-A; -1[Φ]-1[+]-1[ζ]-G-A; -1[ζ]-1[+]-1[ζ]- A-A; -1[(D)]-1[+]-A-1[+]-A; -1[(D)]-1[+]-A-G-A; -1[ζ]-1[+]-A-A-A; -A-1[+]-A-1[+]-A; -A-1[+]-A-G-A; and -A-1[+]-A-A-A;
    [X4] is selected from: -1[ζ]-2A-1[+]-A; -1[ζ]-2A-2 [+]; -1[+]-2A-1[+]-A; -1[ζ]-2A-1[+]-1[Φ]-A-1 [+]; and -1[ζ]-A-1-[+]; -2[+]-A-1[+]-A; -2[+]- A-1[+]-1 [ζ]-A-1[+]; —Gn-; 1]-A-1 [; (GnSn) [Φ]-n1-[+]; -([Φ]n-[Φ]; -A 1[+]-1[(]-A-1 [Φ]- [+]-1]-A-1 [+]; -1 [+]-]-A-1 [+]-; -1 [+]-]-2[+]; -1+-[ ]1 [+]-A; -1 [+]-2[ζ]-1 [+]-1 [ζ]-A-1 [+]; -1 [+]-2[ζ]-1 [ζ]-A-1 [+]; -3 [ζ]-2[+]; -3[ ]1[+- A-3(]-[+1[Φ]-A1[+;-1 [ζ]-2A-1 [+]-A; -1 [ζ]- 2A-2[+]; -1 [ζ]-2A-1 [+]-1 [ζ]-A-1 [+]; -2[+]- A-1 [+]-A; -2[+]-1 [ζ]-1 [+]-A; -1 [+]-1 [ζ]- A-1 [+]-A; -1 [+]-2A-1 [+]-1 [ζ]-A-1 [+]; and -[Φ]A1-[Φ]; and [linker] is selected from: —Gn—; —Sn—; —(GnSn)n—; —(GnSn)nGn—; —(GnSn) nSn—; -(GnSn)nGn(GnSn)n—; and (GnSn)nSn (GnSn)n—;

wherein:
  [Φ] is an amino acid which is: Leu, Phe, Trp, Ile, Met, Tyr, or Val;
  [+] is an amino acid which is: Lys or Arg;
  [ζ] is an amino acid which is: Gln, Asn, Thr, or Ser;
  A is the amino acid Ala;
  G is the amino acid Gly;
  S is the amino acid Ser; and
  n is an integer from 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, or 1 to 3.

* * * * *